United States Patent
Ramos et al.

(10) Patent No.: US 10,500,265 B2
(45) Date of Patent: Dec. 10, 2019

(54) GENERATION OF HPV-SPECIFIC T-CELLS

(71) Applicant: BAYLOR COLLEGE OF MEDICINE, Houston, TX (US)

(72) Inventors: Carlos A. Ramos, Houston, TX (US); Cliona M. Rooney, Bellaire, TX (US); Sandhya Sharma, Houston, TX (US); Benjamin Hyun Joon Shin, Houston, TX (US); Alex Salyer, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 15/885,197

(22) Filed: Jan. 31, 2018

(65) Prior Publication Data

US 2018/0250379 A1   Sep. 6, 2018

Related U.S. Application Data

(63) Continuation-in-part of application No. PCT/EP2017/073274, filed on Sep. 15, 2017, and a continuation of application No. 15/331,659, filed on Oct. 21, 2016, now Pat. No. 9,642,906, application No. 15/885,197, filed on Jan. 31, 2018, which is a continuation of application No. PCT/US2017/051284, filed on Sep. 13, 2017.

(60) Provisional application No. 62/395,440, filed on Sep. 16, 2016, provisional application No. 62/395,438, filed on Sep. 16, 2016.

(51) Int. Cl.
| | |
|---|---|
| *C07K 14/025* | (2006.01) |
| *A61K 39/12* | (2006.01) |
| *C12N 5/0783* | (2010.01) |
| *C12N 5/0784* | (2010.01) |
| *A61K 39/00* | (2006.01) |
| *A61P 35/00* | (2006.01) |

(52) U.S. Cl.
CPC .......... *A61K 39/12* (2013.01); *C12N 5/0636* (2013.01); *C12N 5/0639* (2013.01); *A61K 39/0011* (2013.01); *A61K 2039/5158* (2013.01); *A61K 2039/55527* (2013.01); *A61K 2039/80* (2018.08); *A61P 35/00* (2018.01); *C12N 5/0638* (2013.01); *C12N 2501/02* (2013.01); *C12N 2501/05* (2013.01); *C12N 2501/051* (2013.01); *C12N 2501/056* (2013.01); *C12N 2501/22* (2013.01); *C12N 2501/2301* (2013.01); *C12N 2501/2304* (2013.01); *C12N 2501/2306* (2013.01); *C12N 2501/2307* (2013.01); *C12N 2501/2312* (2013.01); *C12N 2501/2315* (2013.01); *C12N 2501/24* (2013.01); *C12N 2501/25* (2013.01); *C12N 2501/999* (2013.01); *C12N 2502/1107* (2013.01); *C12N 2502/1114* (2013.01); *C12N 2502/1121* (2013.01); *C12N 2710/20034* (2013.01)

(58) Field of Classification Search
None
See application file for complete search history.

(56) References Cited

U.S. PATENT DOCUMENTS

| 2017/0028052 A1 | 2/2017 | Ramos et al. |
| 2018/0250379 A1 | 9/2018 | Ramos et al. |

FOREIGN PATENT DOCUMENTS

| WO | WO 2008/147187 | 12/2008 |
| WO | WO 2013/088114 | 6/2013 |
| WO | WO 2018/052947 | 3/2018 |

OTHER PUBLICATIONS

Ramos et al. Human Papillomavirus Type 16 E6/E7-specific Cytotoxic T Lymphocytes for Adoptive Immunotherapy of HPV-associated Malignancies. J Immunother 2013;36:66-76.*

Sili et al. Large-Scale Expansion of Dendritic Cell-Primed Polyclonal Human Cytotoxic T-Lymphocyte Lines Using Lymphoblastoid Cell Lines for Adoptive Immunotherapy. J Immunother. 26(3):241-256, 2003.*

Torikai et al. Toward eliminating HLA class I expression to generate universal cells from allogeneic donors. Blood. 2013; 122(8):1341-1349.*

Santin et al. Induction of Human Papillomavirus-Specific CD41 and CD81 Lymphocytes by E7-Pulsed Autologous Dendritic Cells in Patients with Human Papillomavirus Type 16- and 18-Positive Cervical Cancer. J. Virol., 1999, 73: 5402-5410.*

* cited by examiner

*Primary Examiner* — Nianxiang Zou
(74) *Attorney, Agent, or Firm* — Adsero IP

(57) ABSTRACT

Embodiments of the disclosure concern methods and compositions for immunotherapy for human papillomavirus infection and diseases associated therewith. In specific embodiments, methods concern production of immune cells that target one or more antigens of HPV16 and/or HPV18, including methods with stimulation steps that employ IL-7 and IL-15, but not IL-6 and/or IL-12. Other specific embodiments utilize stimulations in the presence of certain cells, such as costimulatory cells and certain antigen presenting cells.

22 Claims, 75 Drawing Sheets

GENERATION OF HPV-SPECIFIC T-CELLS

RELATED APPLICATIONS

This application is a continuation-in-part application of International Application Serial No. PCT/EP2017/073274, filed 15 Sep. 2017. International Application Serial No. PCT/EP2017/073274 claims priority to U.S. Provisional Patent Application Ser. No. 62/395,440, filed 16 Sep. 2016 and U.S. Utility application Ser. No. 15/331,659, filed 21 Oct. 2016. U.S. Utility application Ser. No. 15/331,659 also claims priority to U.S. Provisional Patent Application Ser. No. 62/395,440. This application also claims priority to International Application Serial No. PCT/US17/51284, filed 13 Sep. 2017. International Application Serial No. PCT/US17/51284 claims priority to U.S. Provisional Patent Application Ser. No. 62/395,438, filed 16 Sep. 2016. All of the referenced applications are incorporated herein by reference.

STATEMENT REGARDING FEDERALLY SPONSORED RESEARCH OR DEVELOPMENT

This invention was made with government support under P50 CA097007 and PO1 CA94237 awarded by National Cancer Institute. The government has certain rights in the invention.

TECHNICAL FIELD

The present disclosure concerns at least the fields of immunology, cell biology, molecular biology, and medicine, including cancer medicine.

BACKGROUND

Human papillomavirus (HPV) is a DNA virus that establishes productive infections in keratinocytes of the skin or mucous membranes. There are over 170 types of HPV, a subset of which HPV types are carcinogenic, including high-risk sexually transmitted types that can develop into genital neoplasias, including cervical intraepithelial neoplasia (CIN), vulvar intraepithelial neoplasia (VIN), penile intraepithelial neoplasia (PIN), and/or anal intraepithelial neoplasia (AIN), for example. HPV—induced cancers arise when viral sequences are integrated into the cellular DNA of host cells. Some of the HPV "early" genes, such as E6 and E7, act as oncogenes that promote tumor growth and malignant transformation.

Ramos et al., (J Immunother 2013; 36:66-76) describes a method for stimulating peripheral blood mononuclear cells to generate T-cells specific for HPV16 E6 and E7. In brief, the method comprises stimulation of peripheral blood mononuclear cells with dendritic cells in which cells are cultured in CTL medium with or without the combination of cytokines IL-6, IL-7, IL-12 and IL-15, a second stimulation in which co-cultures are supplemented with IL-2, and weekly stimulation with pepmix-loaded accessory antigen presenting cells (e.g., B-blasts) in the presence of IL-15. This reference teaches the combination of cytokines IL-6, IL-7, IL-12 and IL-15 is required for expansion of the HPV-specific T-cells from patient samples, for detectable T-cell responses.

The present disclosure provides relief for a long-felt need in the art to treat HPV-associated diseases, including at least for those associated with HPV16 and HPV18, for example.

BRIEF SUMMARY

The present disclosure is directed to methods and compositions that concern immune system cells that are modified to immunogenically recognize particular targets. In some embodiments, the present disclosure concerns the development of immune cells (including cytotoxic T-lymphocytes (CTLs), also referred to as cytotoxic T-cells)) that target a biological moiety that elicits an immune response in an individual. In specific embodiments, the present disclosure concerns the development of cytotoxic T-cells that target a HPV antigen, including a HPV disease-associated antigen. In some cases, a mixture of cytotoxic T-cells is produced, and the mixture targets more than one HPV antigen, including more than one antigen of more than one HPV type, in some cases.

Embodiments of the disclosure concern methods and compositions for providing therapy to individuals infected with HPV or that have HPV-associated diseases, including cancers, for example. A "HPV-associated disease" may be a disease which is caused or exacerbated by HPV infection, a disease for which HPV infection is a risk factor and/or a disease for which HPV infection is positively associated with disease onset, development, progression or severity. A HPV-associated disease may be a disease in which the methods and compositions of the present invention provide therapeutic effect (e.g. inhibition of the development/progression of the disease, delayed/prevented onset of the disease, reduced severity of the symptoms of the disease, reversal of disease symptoms, and/or increased survival). It will be clear to the person skilled in the art that the therapeutic utility of the methods and compositions of the present invention extends to essentially any disease/condition which would benefit from a reduction in the number of HPV-infected cells. In specific embodiments, the disclosure regards methods and compositions for adoptive cellular immunotherapy that can target HPV-associated, e.g., HPV16-associated, HPV18-associated, HPV1-associated, HPV2-associated and/or HPV3-associated medical conditions (including cancer) and are therapeutic therefor.

In certain aspects, the present disclosure concerns the development of a plurality of T-cells that target antigens from HPV, e.g., HPV16, HPV18, HPV1, HPV2 and/or HPV3. The present disclosure provides significant and non-obvious improvements on methods for generating T cell lines with specificity against HPV, e.g., HPV16, HPV18, HPV1, HPV2 and/or HPV3 antigens.

In some embodiments of the disclosure, an individual is in need of the methods and/or compositions of the disclosure. In certain embodiments, an individual has been exposed to HPV, e.g., HPV16, HPV18, HPV1, HPV2 and/or HPV3 (the presence of which may or may not be known for the individual), or the individual is suspected of having been exposed to or at risk for being exposed to HPV, e.g., HPV16, HPV18, HPV1, HPV2 and/or HPV3. In certain embodiments, the individual has or is suspected of having or is at risk for having HPV-associated disease, e.g., HPV16-associated, HPV18-associated, HPV1-associated, HPV2-associated and/or HPV3-associated disease, including cancer.

In specific embodiments of part of the method, certain HPV, e.g., HPV16, HPV18, HPV1, HPV2 and/or HPV3, antigen(s) are presented to antigen-presenting cells (APCs) in the form of one or more peptides that span some or all of certain antigen(s). The antigenic peptides may be provided to the antigen-presenting cells in a library of peptide mixtures, which may be referred to as pepmixes. In certain aspects of the disclosure, there is pooling of a variety of pepmixes for exposure to the APCs. APCs that express the antigens may be exposed to peripheral blood T-cells under certain conditions to result in stimulation of T-cells specific for the certain HPV antigen(s).

Some aspects and embodiments of the present disclosure concern the generation and/or expansion of HPV-specific T-cells.

In a first aspect, the present disclosure provides a method for stimulating peripheral blood cells, preferably peripheral blood T-cells, wherein the method comprises stimulating peripheral blood T-cells with antigen presenting cells in the presence of interleukin (IL)-7 and IL-15 and, in at least some cases, in the absence of IL-6 and/or IL-12, wherein the antigen presenting cells were previously exposed to one or more peptides, wherein the peptides comprise sequence that corresponds to at least part of the sequence of one or more proteins of HPV. In accordance with various aspects disclosed herein, where a stimulation/culture is performed in the "presence of" a given cytokine, the relevant cytokine (e.g. recombinant and/or exogenous cytokine) may have been added to the stimulation/culture. Where a stimulation/culture is performed in the "absence of" a given cytokine, the relevant cytokine (e.g. recombinant and/or exogenous cytokine) will not have been added to the stimulation/culture.

In some embodiments a method of producing therapeutic T-cells for human papillomavirus (HPV)-associated disease(s) is provided, the method comprising the step of stimulating peripheral blood T-cells with antigen presenting cells in the presence of one or more of interleukin IL-7 and IL-15 and, in at least some cases, in the absence of IL-6 and/or IL-12, wherein the antigen presenting cells were previously exposed to one or more peptides, wherein the peptides comprise sequence that corresponds to at least part of the sequence of one or more proteins of HPV, wherein the stimulating produces T-cells therapeutic for HPV-associated diseases.

In some embodiments, the peripheral blood T-cells being stimulated are obtained from a prior stimulation of peripheral blood cells. The prior stimulation may comprise stimulating peripheral blood cells with antigen presenting cells in the presence of IL-7 and IL-15, and in at least some cases in the presence of IL-6 and/or IL-12, wherein the antigen presenting cells were previously exposed to one or more peptides, wherein the peptides comprise sequence that corresponds to at least part of the sequence of one or more proteins of HPV.

As such, prior to stimulating the peripheral blood T-cells, the methods may further comprise stimulating peripheral blood cells with antigen presenting cells in the presence of IL-7 and IL-15, and in at least some cases in the presence of IL-6 and/or IL-12, wherein the antigen presenting cells were previously exposed to one or more peptides, wherein the peptides comprise sequence that corresponds to at least part of the sequence of one or more proteins of HPV, to produce peripheral blood T-cells.

In some embodiments the one or more peptides comprise sequence that corresponds to at least part of the sequence of one or more proteins of HPV16; one or more proteins of HPV18; or both of one or more proteins of HPV16 and one or more proteins of HPV18. In some embodiments the one or more peptides comprise sequence that corresponds to at least part of the sequence of one or more proteins of HPV1; one or more proteins of HPV2; one or more proteins of HPV3; or one or more proteins of HPV1, HPV2 and/or HPV3. In some embodiments the one or more peptides comprise sequence that corresponds to one or more of proteins E5, E6, E7, L1 and L2. In some embodiments the one or more peptides may be a library of peptides, including E1, E2, E3, E4, E5, E6, E7, L1, and/or L2 peptides.

In some embodiments the method may produce immune cells, such as T-cells, specific for HPV or for an HPV antigen. In some embodiments the method may expand a population of T-cells present in the peripheral blood T-cells that are specific for HPV or for at least one HPV antigen Immune cells other than T cells that may be produced by methods of the disclosure including NK cells and NKT cells.

In some embodiments the antigen presenting cells are activated T-cells, dendritic cells (DC), B-Blasts (BB), or PBMCs, for example.

In some embodiments stimulation of peripheral blood T-cells in the presence of IL-7 and IL-15 occurs in the absence of at least IL-2. In some embodiments stimulation of peripheral blood T-cells in the presence of IL-7 and IL-15 occurs in the absence of at least IL-4. In some embodiments stimulation of peripheral blood T-cells in the presence of IL-7 and IL-15 occurs in the absence of at least IL-6. In some embodiments stimulation of peripheral blood T-cells in the presence of IL-7 and IL-15 occurs in the absence of at least IL-12. In some embodiments stimulation of peripheral blood T-cells in the presence of IL-7 and IL-15 occurs in the absence of at least IL-21. In some embodiments stimulation of peripheral blood T-cells in the presence of IL-7 and IL-15 occurs in the absence of IL-6 and IL-12.

In some particular embodiments stimulation of cells in the method of the first aspect of the present invention occurs in the absence of IL-6 and IL-12.

In some embodiments, peripheral blood T-cells may be present in a population of peripheral blood mononuclear cells (PBMCs) or are obtained or isolated therefrom. The PBMCs in the population may be non-adherent PBMCs. The antigen presenting cells may be activated T-cells, dendritic cells, B-blasts, or PBMCs, for example.

In a second aspect, the present disclosure provides a method for stimulating T-cells specific for HPV or for an HPV antigen, wherein the method comprises stimulating T-cells specific for HPV or for an HPV antigen with antigen presenting cells in the presence of IL-7 and IL-15, and optionally in the presence of co-stimulatory cells, wherein the antigen presenting cells were previously exposed to one or more peptides, wherein the peptides comprise sequence that corresponds to at least part of the sequence of one or more proteins of HPV.

In some embodiments a method of producing therapeutic T-cells for human papillomavirus (HPV)-associated diseases is provided, the method comprising the step of stimulating T-cells specific for HPV or for an HPV antigen with antigen presenting cells in the presence of one or more of interleukin IL-7 and IL-15, and optionally in the presence of co-stimulatory cells, wherein the antigen presenting cells were previously exposed to one or more peptides, wherein the peptides comprise sequence that corresponds to at least part of the sequence of one or more proteins of HPV, wherein the stimulating produces T-cells therapeutic for one or more HPV-associated diseases.

In some embodiments the antigen presenting cells are activated T-cells, dendritic cells (DC), B-Blasts (BB) or PBMCs. In particular embodiments the antigen presenting cells are activated T-cells.

In some embodiments the co-stimulatory cells are one or more cell types selected from the group consisting of CD80+ cells, CD86+ cells, CD83+ cells, 4-1BBL+ cells, CD40+ cells, OX40+ cells, and a combination thereof. The co-stimulatory cells may be CD80+/CD86+/CD83+/4-1BBL+ cells.

In some embodiments the stimulation of T-cells specific for HPV or for an HPV antigen is not a first stimulation step. The T-cells being stimulated cells may be the product of a prior stimulation, e.g. using the method of the first aspect of the present disclosure.

In some embodiments the one or more peptides comprise sequence that corresponds to at least part of the sequence of one or more proteins of HPV16; one or more proteins of HPV18; or one or more proteins of HPV16 and one or more proteins of HPV18. In some embodiments the one or more peptides comprise sequence that corresponds to at least part of the sequence of one or more proteins of HPV1; one or more proteins of HPV2; one or more proteins of HPV3; or one or more proteins of HPV1, HPV2 and/or HPV3. In some embodiments the one or more peptides comprise sequence that corresponds to one or more of proteins E5, E6, E7, L1 and L2. In some embodiments the one or more peptides may be a library of peptides, including E1, E2, E3, E4, ES, E6, E7, L1, and/or L2 peptides.

In some embodiments the method may produce T-cells specific for HPV or for an HPV antigen. In some embodiments the method may expand a population of T-cells specific for HPV or for an HPV antigen.

In certain embodiments stimulation of T-cells specific for HPV or for an HPV antigen comprises stimulating T-cells specific for HPV or for an HPV antigen with antigen presenting cells in the presence of IL-7, IL-15, and in the presence of one or more types of co-stimulatory cells.

In some embodiments stimulation of T-cells in the presence of IL-7 and IL-15 is in the absence of IL-2. In some embodiments stimulation of T-cells in the presence of IL-7 and IL-15 is in the absence of IL-4. In some embodiments stimulation of T-cells in the presence of IL-7 and IL-15 is in the absence of IL-6. In some embodiments stimulation of T-cells in the presence of IL-7 and IL-15 is in the absence of IL-7. In some embodiments stimulation of T-cells in the presence of IL-7 and IL-15 is in the absence of IL-12. In some embodiments stimulation of T-cells in the presence of IL-7 and IL-15 is in the absence of IL-21. In some embodiments stimulation of T-cells in the method of the first aspect of the present invention is in the absence of IL-6 and IL-12.

Methods according to the first and second aspect of the present disclosure may be methods of producing therapeutic T-cells for HPV-associated diseases. The stimulation of cells may produce T-cells that are therapeutic for HPV-associated diseases.

In a third aspect, the methods of the first and second aspects may be combined to provide a method of producing therapeutic T-cells for HPV-associated diseases, the method comprising:

stimulating peripheral blood cells, preferably peripheral blood T-cells, wherein the method comprises stimulating peripheral blood T-cells with antigen presenting cells in the presence of interleukin (IL)-7 and IL-15, and optionally in the absence of IL-6 and/or IL-12, wherein the antigen presenting cells were previously exposed to one or more peptides, wherein the peptides comprise sequence that corresponds to at least part of the sequence of one or more proteins of HPV;

stimulating T-cells obtained from (i) with antigen presenting cells in the presence of interleukin (IL)-7 and IL-15, and optionally in the presence of one or more types of co-stimulatory cells, wherein the antigen presenting cells were previously exposed to one or more peptides, wherein the peptides comprise sequence that corresponds to at least part of the sequence of one or more proteins of HPV.

In some embodiments prior to step (ii), T-cells obtained from (i) may be re-stimulated in the presence of IL-7 and IL-15 but not in the presence of co-stimulatory cells, and optionally in the absence of IL-6 and/or IL-12. Such re-stimulation may occur for one, two, three, four, five or more rounds, as required.

In some embodiments the antigen presenting cells used in (i) are dendritic cells (DC), B-Blasts (BB) or PBMCs. In some embodiments the antigen presenting cells used in (ii) are activated T-cells, dendritic cells (DC), B-Blasts (BB) or PBMCs. In some embodiments the antigen presenting cells used in (i) are different to the antigen presenting cells used in (ii), although they may be the same in certain cases. In particular embodiments the antigen presenting cells used in (ii) are activated T-cells.

In some embodiments the co-stimulatory cells are one or more cell types selected from the group consisting of CD80+ cells, CD86+ cells, CD83+ cells, 4-1BBL+ cells, CD40+ cells, OX40+ cells, and a combination thereof. The co-stimulatory cells may be CD80+/CD86+/CD83+/4-1BBL+ cells.

In some embodiments stimulation of cells in the presence of IL-7 and IL-15 is in the absence of IL-2. In some embodiments stimulation of cells in the presence of IL-7 and IL-15 is in the absence of IL-4. In some embodiments stimulation of cells in the presence of IL-7 and IL-15 is in the absence of IL-6. In some embodiments stimulation of cells in the presence of IL-7 and IL-15 is in the absence of IL-12. In some embodiments stimulation of cells in the presence of IL-7 and IL-15 is in the absence of IL-21. In some embodiments stimulation of cells in the presence of IL-7 and IL-15 is in the absence of IL-6 and IL-12.

In some preferred embodiments stimulation of cells in step (i) is in the absence of IL-6 and IL-12.

In some embodiments stimulation of cells in step (ii) is in the absence of IL-6 and IL-12.

Accordingly, in some embodiments a method of producing therapeutic T-cells for HPV-associated diseases is provided, the method comprising:

(i) stimulating peripheral blood cells, wherein the method comprises stimulating peripheral blood T-cells with antigen presenting cells in the presence of interleukin (IL)-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of HPV;

(ii) stimulating T-cells obtained from (i) with antigen presenting cells in the presence of interleukin (IL)-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of HPV, wherein (ii) is optionally repeated one or more times; and (iii) stimulating T-cells obtained from (ii) with antigen presenting cells in the presence of IL-7 and IL-15, and optionally in the presence of co-stimulatory cells, wherein the antigen presenting cells were previously exposed to one or more peptides, wherein the peptides comprise sequence that corresponds to at least part of the sequence of one or more proteins of HPV, wherein (iii) is optionally repeated one or more times.

In some embodiments the antigen presenting cells used in (i) and (ii) are dendritic cells (DC) B-Blasts (BB) or PBMCs.

In some embodiments the antigen presenting cells used in (iii) are activated T-cells, dendritic cells (DC), B-Blasts (BB) or PBMCs. In some embodiments the antigen presenting cells used in (iii) are different to the antigen presenting cells used in (i) and/or (ii). In preferred embodiments the antigen presenting cells used in (iii) are activated T-cells.

In preferred embodiments the stimulation in (iii) is in the presence of co-stimulatory cells. In some embodiments the co-stimulatory cells are one or more cell types selected from the group consisting of CD80+ cells, CD86+ cells, CD83+ cells, 4-1BBL+ cells, CD40+ cells, OX40+ cells, and a combination thereof. The co-stimulatory cells may be CD80+/CD86+/CD83+/4-1BBL+ cells.

In some embodiments stimulation of cells in the presence of IL-7 and IL-15 is in the absence of IL-2. In some embodiments stimulation of cells in the presence of IL-7 and IL-15 is in the absence of IL-4. In some embodiments stimulation of cells in the presence of IL-7 and IL-15 is in the absence of IL-6. In some embodiments stimulation of cells in the presence of IL-7 and IL-15 is in the absence of IL-12. In some embodiments stimulation of cells in the presence of IL-7 and IL-15 is in the absence of IL-21. In some embodiments stimulation of cells in the presence of IL-7 and IL-15 is in the absence of IL-6 and IL-12.

In some embodiments stimulation of cells in step (i) is in the absence of IL-6 and IL-12. In some other embodiments stimulation of cells in step (i) is in the presence of IL-6 and IL-12.

In some particular embodiments stimulation of cells in step (ii) is in the absence of IL-6 and IL-12. In some particular embodiments stimulation of cells in step (iii) is in the absence of IL-6 and IL-12.

In some particular embodiments methods of the present disclosure are for producing T-cells specific for HPV16 and/or HPV18. In some particular embodiments methods of the present invention are for producing T-cells specific for HPV16-associated and/or HPV18-associated diseases.

In some embodiments, peripheral blood T-cells may be obtained from an individual that is known to be infected or suspected of being infected with HPV; HPV16 or HPV18; both HPV16 and HPV18; HPV1, HPV2 and/or HPV3.

In some embodiments, antigen presenting cells may be obtained from an individual that is known to be infected or suspected of being infected with HPV; HPV16 or HPV18; both HPV16 and HPV18; HPV1, HPV2 and/or HPV3.

In some embodiments, the method may occur in the absence of exposing the T-cells produced by the method to activated B cells that were previously exposed to a library of peptides.

In some embodiments, antigen presenting cells may be autologous or allogeneic to an individual intended to be treated with the therapeutic T-cells obtained.

In some embodiments, the one or more peptides comprise sequence that corresponds to at least part of the sequence of one or more proteins of HPV16; one or more proteins of HPV18; or one or more proteins of HPV16 and one or more proteins of HPV18. In some embodiments the one or more peptides comprise sequence that corresponds to at least part of the sequence of one or more proteins of HPV1; one or more proteins of HPV2; one or more proteins of HPV3; or one or more proteins of HPV1, HPV2 and/or HPV3. In some embodiments the one or more peptides comprise sequence that corresponds to one or more of proteins E1, E2, E3, E4, E5, E6, E7, L1, and/or L2 that come from HPV16, HPV18, or HPV16 and HPV18.

In embodiments of the present disclosure the peptides may comprise sequence that corresponds to one or more of HPV proteins E1, E2, E3, E4, E5, E6, E7, L1, and/or L2. In some embodiments, the peptides may comprise sequence that corresponds to one or more HPV proteins which are expressed following proviral integration (e.g. E1, E2, E3, E4, E5, E6 and/or E7), e.g. in a cell infected HPV. In some embodiments, the peptides may comprise sequence that corresponds to one or more transforming HPV proteins (e.g. E6, and/or E7). The peptides may correspond to a contiguous amino acid sequence present within said HPV protein. A peptide may have a length of at least or no more than 8, 9, 10, 11, 12, 13, 14, 15, 16, 17, 18, 19, or 20 amino acids in length, or of 15 amino acids in length. The collection of peptides may form a library and peptides in the library may overlap in sequence with other peptides by any suitable amount, including 3, 4, 5, 6, 7, 8, 9, 10, 11, 12, 13, or 14 amino acids, for example. The peptides may comprise sequence that corresponds to: a) the HPV18 E6 protein and/or the HPV18 E7 protein, and/or b) the HPV16 E6 protein and/or the HPV16 E7 protein.

In embodiments of the present disclosure the HPV may be HPV16 or HPV18, or both. In embodiments concerned with treatment of an HPV-associated disease, the disease may be cancer and the peptides may comprise a sequence that corresponds to one or both of E6 and E7. When the HPV-associated disease is a pre-cancerous lesion, the peptides may comprise sequence that corresponds to one, some, or all of E1, E2, E3, E4, E5, E6, E7, L1, and L2.

T-cells produced by the methods of the present disclosure may be isolated and/or purified, e.g., isolated/purified from other cells.

In some embodiments, a therapeutically effective amount of T-cells produced by the methods of the present disclosure are provided to an individual that has been exposed to HPV, or that has HPV-associated disease. In a related aspect T-cells produced by the method of the present disclosure are provided for use in the treatment of HPV-associated disease. In another related aspect the use of T-cells produced by the method of the present disclosure are provided for use in the manufacture of a medicament for use in the treatment of HPV-associated disease.

In one aspect of the present invention T-cells for use in a method of adoptive cellular immunotherapy are provided, wherein the T-cells are obtained by, obtainable by, or are the product of, a method for stimulating peripheral blood or T-cells or a method of producing therapeutic T-cells described herein, the method of adoptive cellular immunotherapy comprising administering the T-cells to the subject.

In one aspect of the present invention the use of T-cells in the manufacture of a medicament for use in a method of adoptive cellular immunotherapy comprising administering the T-cells to the subject is provided, wherein the T-cells are obtained by, obtainable by, or are the product of, a method for stimulating peripheral blood or T-cells or a method of producing therapeutic T-cells described herein.

In one aspect of the present invention a method of preparing a pharmaceutical composition, medicament or vaccine is provided, the method comprising stimulating peripheral blood or T-cells according to a method described herein, or producing therapeutic T-cells according to a method described herein, and mixing the cells obtained, with a pharmaceutically acceptable carrier, adjuvant, diluent or excipient.

The disease to be treated may be a neoplasm. The neoplasm may be a cancer. The cancer may be an HPV-positive cancer, e.g. a HPV16-positive cancer and/or HPV18-positive cancer.

The individual to be treated may be a human. The individual may be a patient. The individual may have been exposed to HPV, such as HPV16, HPV18, or both HPV16 and HPV18, or has an HPV-, HPV16- and/or HPV18-associated disease. The HPV-, HPV16- and/or HPV18-associated disease may be a neoplasm. The neoplasm may be a cancer.

A cancer may be of any kind. In some embodiments the cancer is a cervical cancer, anal cancer, vulvar cancer, vaginal cancer, penile cancer, or oropharyngeal cancer. In some embodiments the cancer may be a HPV-associated cancer. A "HPV-associated cancer" may be a cancer which is caused or exacerbated by HPV infection, a cancer for which HPV infection is a risk factor and/or a cancer for which HPV-infection is positively associated with onset, development, progression, severity or metastasis. A HPV-associated cancer may be a cancer in which the methods and compositions of the present invention provide therapeutic effect (e.g. inhibition of the development/progression of the cancer, delayed/prevented onset of the cancer, reduced/delayed/prevented metastasis, reduced severity of the symptoms of the cancer, reduction in number of cancer cells, reduction in tumour size, and/or increased survival). In some embodiments the cancer is a HPV-related carcinoma, HPV-positive oropharyngeal carcinoma, HPV-positive cervical carcinoma, HPV-positive anal carcinoma, HPV-positive vulvar carcinoma, nasopharyngeal carcinoma, HPV-positive penile carcinoma, HPV-positive dysplasias of any site, or laryngeal papillomatosis.

The individual or subject may have received, be receiving, or will receive an additional cancer therapy. The additional cancer therapy may be surgery, radiation, hormone therapy, chemotherapy, immunotherapy, or a combination thereof.

The individual or subject may be determined as having HPV-associated cancer or HPV-positive cancer. The individual may be determined as having HPV16-associated cancer or HPV16-positive cancer. The individual may be determined as having HPV18-associated cancer or HPV18-positive cancer. The individual or subject may be any animal or human. The individual or subject is preferably mammalian, more preferably human. The individual or subject may be a non-human mammal, but is more preferably human. The individual or subject may be male or female. The individual or subject may be a patient.

Methods according to the present disclosure that involve steps of cell stimulation may be performed in vitro or ex vivo. The term "in vitro" is intended to encompass studies with materials, biological substances, cells and/or tissues in laboratory conditions or in culture. "Ex vivo" refers to something present or taking place outside an organism, e.g. outside the human or animal body, which may be on tissue (e.g. whole organs) or cells taken from the organism.

In one embodiment, there is a method for stimulating peripheral blood cells, the method comprising stimulating peripheral blood T-cells with antigen presenting cells in the presence of interleukin (IL)-7 and IL-15 and in the absence of IL-6 and/or IL-12, wherein the antigen presenting cells were previously exposed to one or more peptides, wherein the peptides comprise sequence that corresponds to at least part of the sequence of one or more proteins of human papillomavirus (HPV). The peripheral blood T-cells may be obtained from a prior stimulation of peripheral blood cells, such as wherein the prior stimulation of peripheral blood cells comprises stimulating peripheral blood cells with antigen presenting cells in the presence of IL-7 and IL-15, and in the presence of IL-6 and/or IL-12, wherein the antigen presenting cells were previously exposed to one or more peptides, wherein the peptides comprise sequence that corresponds to at least part of the sequence of one or more proteins of HPV. In specific cases, prior to stimulating the peripheral blood T-cells, the method further comprises stimulating peripheral blood cells with antigen presenting cells in the presence of IL-7 and IL-15, and in the presence of IL-6 and/or IL-12, wherein the antigen presenting cells were previously exposed to one or more peptides, wherein the peptides comprise sequence that corresponds to at least part of the sequence of one or more proteins of HPV, to produce peripheral blood T-cells.

In an embodiment, there is a method of producing therapeutic T-cells for HPV-associated diseases, the method comprising the step of: stimulating peripheral blood T-cells with antigen presenting cells in the presence of one or more of IL-7 and IL-15 and in the absence of IL-6 and/or IL-12, wherein the antigen presenting cells were previously exposed to one or more peptides, wherein the peptides comprise sequence that corresponds to at least part of the sequence of one or more proteins of HPV, wherein the stimulating produces T-cells therapeutic for HPV-associated diseases. The peripheral blood T-cells may be obtained from a prior stimulation of peripheral blood cells, such as wherein the prior stimulation of peripheral blood cells comprises stimulating peripheral blood cells with antigen presenting cells in the presence of IL-7 and IL-15, and in the presence of IL-6 and/or IL-12, wherein the antigen presenting cells were previously exposed to one or more peptides, wherein the peptides comprise sequence that corresponds to at least part of the sequence of one or more proteins of HPV. In specific cases, prior to stimulating the peripheral blood T-cells, the method further comprises stimulating peripheral blood cells with antigen presenting cells in the presence of IL-7 and IL-15, and in the presence of IL-6 and/or IL-12, wherein the antigen presenting cells were previously exposed to one or more peptides, wherein the peptides comprise sequence that corresponds to at least part of the sequence of one or more proteins of HPV, to produce peripheral blood T-cells.

In embodiments of methods encompassed by the disclosure, antigen presenting cells are activated T-cells, dendritic cells, B-blasts, or PBMCs. Peripheral blood T-cells may be present in a population of peripheral blood mononuclear cells (PBMCs) or are obtained or isolated therefrom, in at least some cases, and the PBMCs in the population may be non-adherent PBMCs. When employed, co-stimulatory cells may be CD80+, CD86+, CD83+, 4-1BBL+, CD40+ cells, OX40+ cells, or a combination thereof.

In a particular embodiment, there is a method for stimulating T-cells specific for HPV or for an HPV antigen, the method comprising stimulating T-cells specific for HPV or for an HPV antigen with antigen presenting cells in the presence of IL-7 and IL-15 and in the presence of co-stimulatory cells, wherein the antigen presenting cells were previously exposed to one or more peptides, wherein the peptides comprise sequence that corresponds to at least part of the sequence of one or more proteins of HPV.

In certain embodiments, there is a method of producing therapeutic T-cells for HPV-associated diseases, the method comprising the step of stimulating T-cells specific for HPV or for an HPV antigen with antigen presenting cells in the presence of one or more of IL-7 and IL-15 and in the presence of co-stimulatory cells, wherein the antigen presenting cells were previously exposed to one or more peptides, wherein the peptides comprise sequence that corresponds to at least part of the sequence of one or more proteins of HPV, wherein the stimulating produces T-cells therapeutic for HPV-associated diseases.

In one embodiment, there is a method of producing therapeutic T-cells for HPV-associated diseases, the method comprising: (i) stimulating peripheral blood cells, wherein the method comprises stimulating peripheral blood T-cells with antigen presenting cells in the presence of IL-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of HPV; and (ii) stimulating T-cells obtained from (i) with antigen presenting cells in the presence of IL-7 and IL-15, and in the presence of co-stimulatory cells, wherein the antigen presenting cells were previously exposed to one or more peptides, wherein the peptides comprise sequence that corresponds to at least part of the sequence of one or more proteins of HPV. In specific embodiments, prior to step (ii) T-cells obtained from (i) may be re-stimulated in the presence of IL-7 and IL-15 but not in the presence of co-stimulatory cells.

In an embodiment, a method of producing therapeutic T-cells for HPV-associated diseases is provided, the method comprising: (i) stimulating peripheral blood cells, wherein the method comprises stimulating peripheral blood T-cells with antigen presenting cells in the presence of interleukin (IL)-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of HPV; (ii) stimulating T-cells obtained from (i) with antigen presenting cells in the presence of interleukin (IL)-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of HPV, wherein (ii) is optionally repeated one or more times; and (iii) stimulating T-cells obtained from (ii) with antigen presenting cells in the presence of interleukin (IL)-7 and IL-15, and in the presence of co-stimulatory cells, wherein the antigen presenting cells were previously exposed to one or more peptides, wherein the peptides comprise sequence that corresponds to at least part of the sequence of one or more proteins of HPV, wherein (iii) is optionally repeated one or more times.

In any method of the disclosure, the HPV may be HPV16, HPV18, HPV1, HPV2 and HPV3. Peptides comprising sequence that corresponds to one or more of E1, E2, E3, E4, E5, E6, E7, L1, and L2 may be utilized in any method of the disclosure. The peptides may comprise sequence that corresponds to: a) the HPV18 E6 protein and/or the HPV18 E7 protein, and/or b) the HPV16 E6 protein and/or the HPV16 E7 protein. In some cases, an individual being provided with an effective amount of cells as described herein has an HPV-associated disease, such as cancer, and the peptides comprise sequence that corresponds to one or both of E6 and E7. In specific aspects, the one or more peptides comprises peptides of at least or no more than 8, 9, 10, 11, 12, 13, 14, 15, 16, 17, 18, 19, or 20 amino acids in length, and in particular the one or more peptides comprises peptides of 15 amino acids in length. In specific embodiments, one or more peptides form a library and peptides in the library overlap in sequence with other peptides by 11 amino acids.

In particular embodiments, a therapeutically effective amount of T-cells produced by the method are provided to an individual that has been exposed to HPV or that has HPV-associated disease. In specific embodiments, an HPV-associated disease comprises a neoplasm.

A therapeutically effective amount of T-cells produced by a method of the disclosure may be provided to an individual that has been exposed to HPV16, HPV18, or both, or that has HPV16-associated and/or HPV18-associated disease, including a neoplasm such as cancer.

In particular embodiments, the cancer is a cervical cancer, anal cancer, vulvar cancer, vaginal cancer, penile cancer, oropharyngeal cancer, nasopharyngeal carcinoma, laryngeal papillomatosis, laryngeal cancer, head and neck cancer, or a dysplasia of any site thereof.

In some cases, an individual that has received and/or will receive cells of the disclosure has also received, is receiving, or will receive an additional cancer therapy, such as surgery, radiation, hormone therapy, chemotherapy, immunotherapy, or a combination thereof.

In certain aspects, an individual that has received and/or will receive cells of the disclosure is determined as having HPV-associated cancer, such as HPV16-associated cancer or HPV18-associated cancer.

The following numbered paragraphs contain statements of broad combinations of the inventive technical features herein disclosed:

1. A method for stimulating peripheral blood cells, the method comprising stimulating peripheral blood T-cells with antigen presenting cells in the presence of interleukin (IL)-7 and IL-15 and in the absence of IL-6 and/or IL-12, wherein the antigen presenting cells were previously exposed to one or more peptides, wherein the peptides comprise sequence that corresponds to at least part of the sequence of one or more proteins of human papillomavirus (HPV).

2. A method of producing therapeutic T-cells for HPV-associated diseases, the method comprising the step of: stimulating peripheral blood T-cells with antigen presenting cells in the presence of one or more of IL-7 and IL-15 and in the absence of IL-6 and/or IL-12, wherein the antigen presenting cells were previously exposed to one or more peptides, wherein the peptides comprise sequence that corresponds to at least part of the sequence of one or more proteins of HPV, wherein the stimulating produces T-cells therapeutic for HPV-associated diseases.

3. The method of paragraph 1 or 2, wherein the peripheral blood T-cells are obtained from a prior stimulation of peripheral blood cells.

4. The method of paragraph 3, wherein the prior stimulation of peripheral blood cells comprises stimulating peripheral blood cells with antigen presenting cells in the presence of IL-7 and IL-15, and in the presence of IL-6 and/or IL-12, wherein the antigen presenting cells were previously exposed to one or more peptides, wherein the peptides comprise sequence that corresponds to at least part of the sequence of one or more proteins of HPV.

5. The method of paragraph 1 or 2, wherein prior to stimulating said peripheral blood T-cells, the method further comprises stimulating peripheral blood cells with antigen presenting cells in the presence of IL-7 and IL-15, and in the presence of IL-6 and/or IL-12, wherein the antigen presenting cells were previously exposed to one or more peptides, wherein the peptides comprise sequence that corresponds to at least part of the sequence of one or more proteins of HPV, to produce peripheral blood T-cells.

6. The method of any one of paragraphs 1-7, wherein the antigen presenting cells are dendritic cells, B-blasts, or PBMCs.

7. The method of any one of paragraphs 1-6, wherein the peripheral blood T-cells are present in a population of peripheral blood mononuclear cells (PBMCs) or are obtained or isolated therefrom.

8. The method of paragraph 7, wherein the PBMCs in the population are non-adherent PBMCs.

9. A method for stimulating T-cells specific for HPV or for an HPV antigen, the method comprising stimulating T-cells specific for HPV or for an HPV antigen with antigen presenting cells in the presence of IL-7 and IL-15 and in the presence of co-stimulatory cells, wherein the antigen presenting cells were previously exposed to one or more peptides, wherein the peptides comprise sequence that corresponds to at least part of the sequence of one or more proteins of HPV.

10. A method of producing therapeutic T-cells for HPV-associated diseases, the method comprising the step of stimulating T-cells specific for HPV or for an HPV antigen with antigen presenting cells in the presence of one or more of IL-7 and IL-15 and in the presence of co-stimulatory cells, wherein the antigen presenting cells were previously exposed to one or more peptides, wherein the peptides comprise sequence that corresponds to at least part of the sequence of one or more proteins of HPV, wherein the stimulating produces T-cells therapeutic for HPV-associated diseases.

11. The method of paragraph 9 or 10, wherein the antigen presenting cells are activated T cells, dendritic cells, B-blasts, or PBMCs.

12. The method of any one of paragraphs 9 to 11, wherein the co-stimulatory cells are CD80+, CD86+, CD83+, 4-1BBL+, CD40+ cells, OX40+ cells, or a combination thereof.

13. A method of producing therapeutic T-cells for HPV-associated diseases, the method comprising:
 (i) stimulating peripheral blood cells, wherein the method comprises stimulating peripheral blood T-cells with antigen presenting cells in the presence of IL-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of HPV; and
 (ii) stimulating T-cells obtained from (i) with antigen presenting cells in the presence of IL-7 and IL-15, and in the presence of co-stimulatory cells, wherein the antigen presenting cells were previously exposed to one or more peptides, wherein the peptides comprise sequence that corresponds to at least part of the sequence of one or more proteins of HPV.

14. The method of paragraph 13, wherein prior to step (ii) T-cells obtained from (i) may be re-stimulated in the presence of IL-7 and IL-15 but not in the presence of co-stimulatory cells.

15. The method of paragraph 13 or 14, wherein the antigen presenting cells used in (i) are dendritic cells (DC), B-Blasts (BB) or PBMCs.

16. The method of any one of paragraphs 13 to 15, wherein the antigen presenting cells used in (ii) are activated T cells, dendritic cells (DC) or B-Blasts (BB).

17. The method of any one of paragraphs 13 to 16, wherein the co-stimulatory cells are CD80+, CD86+, CD83+, 4-1BBL+, CD40+ cells, OX40+ cells, or a combination thereof.

18. A method of producing therapeutic T-cells for HPV-associated diseases is provided, the method comprising:
 (i) stimulating peripheral blood cells, wherein the method comprises stimulating peripheral blood T-cells with antigen presenting cells in the presence of interleukin (IL)-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of HPV;
 (ii) stimulating T-cells obtained from (i) with antigen presenting cells in the presence of interleukin (IL)-7 and IL-15 and optionally in the absence of IL-6 and/or IL-12, wherein the antigen presenting cells were previously exposed to one or more peptides, wherein the peptides comprise sequence that corresponds to at least part of the sequence of one or more proteins of HPV, wherein (ii) is optionally repeated one or more times; and
 (iii) stimulating T-cells obtained from (ii) with antigen presenting cells in the presence of interleukin (IL)-7 and IL-15, and in the presence of co-stimulatory cells, wherein the antigen presenting cells were previously exposed to one or more peptides, wherein the peptides comprise sequence that corresponds to at least part of the sequence of one or more proteins of HPV, wherein (iii) is optionally repeated one or more times.

19. The method of paragraph 18, wherein the antigen presenting cells used in (i) and (ii) are DC, BB, or PBMCs.

20. The method of paragraph 18 or 19, wherein the antigen presenting cells used in (iii) are activated T cells, DC, BB, or PBMCs.

21. The method of any one of paragraphs 18 to 20, wherein the co-stimulatory cells are CD80+, CD86+, CD83+, 4-1BBL+, CD40+ cells, OX40+ cells or a combination thereof.

22. The method of any one of paragraphs 1-21, wherein the HPV is HPV16 or HPV18.

23. The method of any one of paragraphs 1-22, wherein the peptides comprise sequence that corresponds to one or more of E1, E2, E3, E4, E5, E6, E7, L1, and L2.

24. The method of any one of paragraphs 1-23, wherein the HPV-associated disease is cancer and the peptides comprise sequence that corresponds to one or both of E6 and E7.

25. The method of any one of paragraphs 1-25, wherein the peptides comprise sequence that corresponds to:
 a) the HPV18 E6 protein and/or the HPV18 E7 protein, and/or
 b) the HPV16 E6 protein and/or the HPV16 E7 protein.

26. The method of any one of paragraphs 1-25, wherein the one or more peptides comprises peptides of at least or no more than 8, 9, 10, 11, 12, 13, 14, 15, 16, 17, 18, 19, or 20 amino acids in length.

27. The method of any one of paragraphs 1-26, wherein the one or more peptides comprises peptides of 15 amino acids in length.

28. The method of any one of paragraphs 1-27, wherein one or more peptides form a library and peptides in the library overlap in sequence with other peptides by 11 amino acids.
29. The method of any one of paragraphs 1-28, wherein a therapeutically effective amount of T-cells produced by the method are provided to an individual that has been exposed to HPV or that has HPV-associated disease.
30. The method of paragraph 29, wherein the HPV-associated disease comprises a neoplasm.
31. The method of any one of paragraphs 1 to 30, wherein a therapeutically effective amount of T-cells produced by the method are provided to an individual that has been exposed to HPV16, HPV18 or both, or that has HPV16-associated and/or HPV18-associated disease.
32. The method of paragraph 31, wherein the HPV16-associated and/or HPV18-associated disease comprises a neoplasm.
33. The method of paragraph 31 or 32, wherein the neoplasm is cancer.
34. The method of paragraph 33, wherein the cancer is cervical cancer, anal cancer, vulvar cancer, vaginal cancer, penile cancer, oropharyngeal cancer, nasopharyngeal carcinoma, laryngeal papillomatosis, laryngeal cancer, head and neck cancer, or a dysplasia of any of site thereof.
35. The method of paragraph 33 or 34, wherein the individual has received, is receiving, or will receive an additional cancer therapy.
36. The method of paragraph 35, wherein the additional cancer therapy is surgery, radiation, hormone therapy, chemotherapy, immunotherapy, or a combination thereof.
37. The method of any one of paragraphs 33 to 36, wherein the individual is determined as having HPV-associated cancer.
38. The method of any one of paragraphs 33 to 37, wherein the individual is determined as having HPV16-associated cancer.
39. The method of any one of paragraphs 33 to 38, wherein the individual is determined as having HPV18-associated cancer.
40. T-cells for use in a method of adoptive cellular immunotherapy, wherein the T-cells are obtained by, obtainable by, or are the product of, a method for stimulating peripheral blood or T-cells or a method of producing therapeutic T-cells according to any one of paragraphs 1 to 39, wherein the method of adoptive cellular immunotherapy comprises administering the T-cells to the subject.
41. Use of T-cells in the manufacture of a medicament for use in a method of adoptive cellular immunotherapy comprising administering the T-cells to the subject, wherein the T-cells are obtained by, obtainable by, or are the product of, a method for stimulating peripheral blood or T-cells or a method of producing therapeutic T-cells according to any one of claims 1 to 39.
42. A method of preparing a pharmaceutical composition, medicament or vaccine, the method comprising stimulating peripheral blood or T-cells or producing therapeutic T-cells according to any one of claims 1 to 39, and mixing the cells obtained with a pharmaceutically acceptable carrier, adjuvant, diluent or excipient.
43. A method of treating a cancer in a subject, the method comprising:
    (1) isolating T cells from a subject;
    (2) generating or expanding a population of T cells specific for a human papillomavirus (HPV) by a method comprising: stimulating the T-cells with antigen presenting cells in the presence of interleukin (IL)-7 and IL-15 and in the absence of IL-6 and/or IL-12, wherein the antigen presenting cells were previously exposed to one or more peptides, wherein the peptides comprise sequence that corresponds to at least part of the sequence of one or more proteins of HPV; and
    (3) administering the generated or expanded population of T cells to a subject.
44. The method of paragraph 43, wherein the T-cells stimulated in (2) are obtained from a prior stimulation of peripheral blood cells or T-cells.
45. The method of paragraph 43, wherein prior to stimulating said T-cells, the method comprises stimulating peripheral blood cells or T-cells with antigen presenting cells in the presence of IL-7 and IL-15, and in the presence of IL-6 and/or IL-12, wherein the antigen presenting cells were previously exposed to one or more peptides, wherein the peptides comprise sequence that corresponds to at least part of the sequence of one or more proteins of HPV.
46. The method of paragraph 43, wherein after (2) and before (3) the method comprises stimulating the T-cells obtained from (2) with antigen presenting cells in the presence of IL-7 and IL-15, and in the presence of co-stimulatory cells, wherein the antigen presenting cells were previously exposed to one or more peptides, wherein the peptides comprise sequence that corresponds to at least part of the sequence of one or more proteins of HPV.
47. The method of paragraph 46 wherein the co-stimulatory cells are CD80+, CD86+, CD83+, 4-1BBL+, CD40+ cells, OX40+ cells, or a combination thereof.
48. The method of paragraph 43, wherein after (2) and before (3) the method comprises (i) re-stimulating the T-cells obtained from (2) in the presence of IL-7 and IL-15 but not in the presence of co-stimulatory cells, and (ii) stimulating the T-cells obtained after (i) with antigen presenting cells in the presence of IL-7 and IL-15, and in the presence of co-stimulatory cells, wherein the antigen presenting cells were previously exposed to one or more peptides, wherein the peptides comprise sequence that corresponds to at least part of the sequence of one or more proteins of HPV.
49. The method of paragraph 43, wherein the antigen presenting cells are dendritic cells (DC), B-blasts (BB), or peripheral blood mononuclear cells (PBMCs).
50. The method of paragraph 43, wherein in (1) the T-cells are isolated from a population of peripheral blood mononuclear cells (PBMCs).
51. The method of paragraph 43, wherein the cancer is cervical cancer, anal cancer, vulvar cancer, vaginal cancer, penile cancer, oropharyngeal cancer, nasopharyngeal carcinoma, laryngeal papillomatosis, laryngeal cancer, head and neck cancer, or a dysplasia of any of site thereof.
52. The method of paragraph 43, wherein the cancer is HPV-positive.
53. The method of paragraph 43, wherein the subject is determined as having HPV-associated cancer.

54. A method of treating a cancer in a subject, the method comprising:
   (1) isolating T cells from a subject;
   (2) generating or expanding a population of T cells specific for a human papillomavirus (HPV) by a method comprising:
      (i) stimulating the T-cells with antigen presenting cells in the presence of interleukin (IL)-7 and IL-15, wherein the antigen presenting cells were previously exposed to one or more peptides, wherein the peptides comprise sequence that corresponds to at least part of the sequence of one or more proteins of HPV;
      (ii) stimulating T-cells obtained from (i) with antigen presenting cells in the presence of interleukin (IL)-7 and IL-15 and in the absence of IL-6 and/or IL-12, wherein the antigen presenting cells were previously exposed to one or more peptides, wherein the peptides comprise sequence that corresponds to at least part of the sequence of one or more proteins of HPV, wherein (ii) is optionally repeated one or more times; and
      (iii) stimulating T-cells obtained from (ii) with antigen presenting cells in the presence of interleukin (IL)-7 and IL-15, and in the presence of co-stimulatory cells, wherein the antigen presenting cells were previously exposed to one or more peptides, wherein the peptides comprise sequence that corresponds to at least part of the sequence of one or more proteins of HPV, wherein (iii) is optionally repeated one or more times.
   (3) administering the generated or expanded population of T cells to a subject.
55. The method of paragraph 54, wherein stimulation of T-cells in (i) is in the presence of IL-6 and/or IL-12.
56. The method of paragraph 54, wherein the antigen presenting cells used in (i) and (ii) are dendritic cells (DC), B-blasts (BB), or peripheral blood mononuclear cells (PBMCs).
57. The method of paragraph 54, wherein the antigen presenting cells used in (iii) are activated T cells, dendritic cells (DC), B-blasts (BB), or peripheral blood mononuclear cells (PBMCs).
58. The method of paragraph 54, wherein the co-stimulatory cells are CD80+, CD86+, CD83+, 4-1BBL+, CD40+ cells, OX40+ cells or a combination thereof.
59. A method of treating a cancer in a subject, the method comprising:
   (1) isolating T cells from a subject;
   (2) generating or expanding a population of T cells specific for a human papillomavirus (HPV) by a method comprising: stimulating T-cells specific for HPV or for an HPV antigen with antigen presenting cells in the presence of IL-7 and IL-15 and in the presence of co-stimulatory cells, wherein the antigen presenting cells were previously exposed to one or more peptides, wherein the peptides comprise sequence that corresponds to at least part of the sequence of one or more proteins of HPV; and
   (3) administering the generated or expanded population of T cells to a subject.
60. The method of paragraph 59, wherein the antigen presenting cells are activated T cells, dendritic cells (DC), B-blasts (BB), or peripheral blood mononuclear cells (PBMCs).
61. The method of paragraph 59, wherein the co-stimulatory cells are CD80+, CD86+, CD83+, 4-1BBL+, CD40+ cells, OX40+ cells, or a combination thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

BRIEF DESCRIPTION OF THE DRAWINGS

FIG. 1A is a bar chart showing production of spot forming colonies (SFC) on stimulation of PBMCs from three HPV-associated cancer patients (identified as OCV, HND and HNC) with autologous DCs loaded with no pepmix (Neg), HPV16 E6 pepmix (HPV16 E6) or HPV16 E7 pepmix (HPV16 E7). For patient OCV the three bars present from left to right are Neg, HPV16 E6 and HPV16 E7. For patients HND and HNC the two bars present from left to right are HPV16 E6 and HPV16 E7.

FIG. 1B is a bar chart showing production of spot forming colonies (SFC) on stimulation of PBMCs from three HPV-associated cancer patients (identified as OCV, PCV and HND). For patient OCV the five bars present from left to right are no pepmix (Neg), HPV16 E6 pepmix (HPV16 E6), HPV16 E7 pepmix (HPV16 E7), HPV18 E6 pepmix (HPV18 E6), and HPV18 E7 pepmix (HPV18 E7). For patient PCD the two bars present from left to right are HPV16 E6 and HPV16 E7. For patient HND the four bars present from left to right are HPV16 E6, HPV16 E7, HPV18 E6 and HPV18 E7.

FIG. 17C shows the proportions of CD80+CD83− cells, FIG. 17D shows the proportions of CD80+CD83+ cells, and FIG. 17E shows the proportions of PD-L1+ cells.

DETAILED DESCRIPTION

Figure 1A:
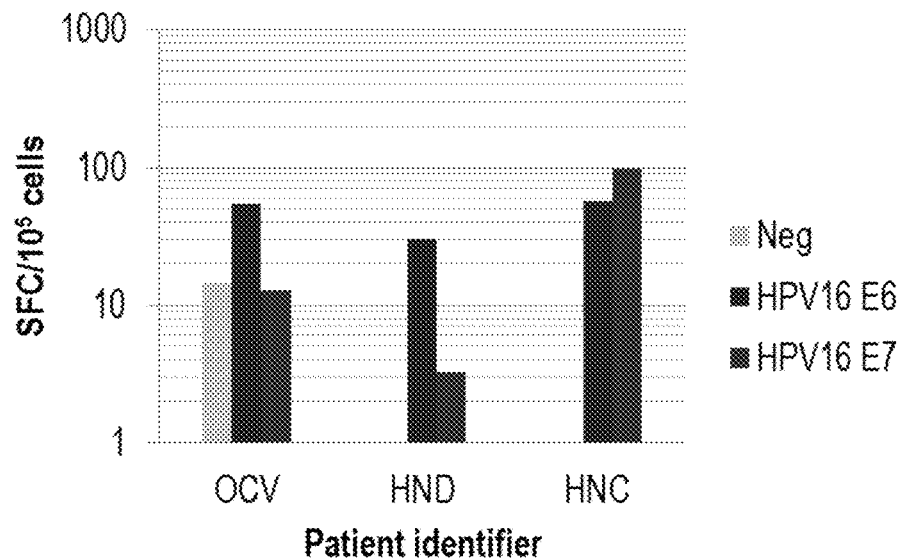
FIG. 1A demonstrates a method in the art that utilizes certain conditions for the production of HPV16-specific T-cells.

The scope of the present application is not intended to be limited to the particular embodiments of the process, machine, manufacture, composition of matter, means, methods and steps described in the specification.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The present disclosure concerns the production and use of therapeutic T-cells for individuals that are in need of HPV-specific T-cells, e.g., HPV16- and/or HPV18-specific T-cells, including for treating HPV infection and HPV-associated medical conditions. In particular embodiments, the methods and compositions are useful for treating neoplasms that are indirectly or directly related to HPV infection, and such neoplasms may be benign or malignant. Between 13 and 18 HPV strains have been characterized as conferring a high oncogenic risk, with 12 of these strains belonging to the HPV species 7 (HPV-18, -39, -45, -59, -68) and species 9 (HPV-16, -31, -33, -35, -52, -58, -67). HPV Types 6 and 11 cause laryngeal papillomatisis.

I. HPV Antigen(s) and Generation of Pepmixes

Methods of the disclosure utilize antigen-presenting cells that present mixtures of peptides to T-cells. Such "loaded" APCs are generated prior to exposure to peripheral blood T-cells for stimulation of the peripheral blood T-cells, and the generation of the loaded APCs may or may not be performed by the individual or entity that performs the stimulation step for the peripheral blood T-cells. Thus, in some embodiments, an effective amount of a library of peptides is provided to APCs as part of methods that ultimately generate therapeutic CTLs. In methods of the disclosure, prior to a stimulation step, APCs are exposed to a sufficient amount of the library of peptides. The library, in particular cases, comprises a mixture of peptides ("pepmixes") that span part or all of the same antigen, although in some cases the library comprises pepmixes that span part or all of one or more antigens, and the one or more antigens may or may not be from the same HPV. In particular embodiments, peptides for the APCs are non-natural, and they may or may not be chemically synthesized or produced by recombinant means.

In utilizing a library of mixtures of peptides from one or more HPV antigens, the various peptides may come from any part of a given protein, but in specific cases the peptides collectively span the length of the majority or all of the protein, wherein the sequence of the peptides overlap at least in part to facilitate coverage of the entire desired region of the specific antigen(s). In some cases the peptides span the length of one or more known epitopes or domains of the respective antigen to which the peptides correspond. Certain regions may be covered by peptides that span the length of the region, including a region such as a N-terminal domain, C-terminal domain, extracellular domain, or intracellular domain, for example.

The antigens from which the peptides are derived may be antigens for HPVs that may be of any kind, but in specific embodiments the antigens are such that they allow for direction of cytotoxic T-cells to neoplasms, including cancers, associated with HPV infection. In particular embodiments, the peptides are derived from, or have sequence that corresponds to, at least part of one or more antigens of at least one HPV type, including HPV16 and/or HPV18. For example, in late stage cervical cancer, the HPV virus integrates into a tumor cell genome and loses all of its other genes except E6 and E7, so in some cases these antigens are targeted. In embodiments wherein one would treat an earlier stage of cancer, such as before the virus integrated, one could utilize peptides from antigens other than E6 and E7, including E5 and L1 and L2, for example. However, given that the two primary oncoproteins of high risk HPV types are E6 and E7, in specific embodiments the sequence of the peptides are obtained from E6 and/or E7 from any HPV, but HPV16 and/or HPV18, in particular. Peptides from any of antigens E1, E2, E3, E4, E5, E6, E7, L1, and/or L2 may be utilized in methods of the disclosure.

In some cases, a pepmix library includes peptides corresponding to one or more antigens from a single type of HPV virus, and those peptides may or may not provide sequence coverage across the entire antigen(s) in question. In other cases, a pepmix library includes peptides corresponding to one or more antigens from more than one HPV virus, and those peptides may or may not provide sequence coverage across the entire antigen(s) in question. The pepmix may or may not be enriched for peptides corresponding to one or more certain regions of one or more certain antigens or corresponding to the entirety of one or more certain antigens.

Pepmixes utilized in the disclosure may be from commercially available peptide libraries or may be synthetically generated, for example. Examples of available libraries include those from JPT Technologies (Springfield, Va.) or Miltenyi Biotec (Auburn, Calif.). The skilled artisan, based on known sequences of HPV16 E6, HPV16 E7, HPV18 E6, and HPV18 E7, for example, would have sufficient information to be able to generate peptides that correspond to their exemplary, respective sequences. An example of sequence of the HPV16 E6 protein is available at the National Center for Biotechnology Information's GenBank® database at GenBank® Accession No. AIQ82776.1 GI:688010703. An example of sequence of the HPV16 E7 protein is at GenBank® Accession No. AIQ82814.1 GI:688010789. An example of sequence of the HPV18 E6 protein is at GenBank® Accession No. AGU90423.1 GI:537801975. An example of sequence of the HPV18 E7 protein is at GenBank® Accession No. AGU90424.1 GI:537801976.

In particular embodiments, a library is comprised of peptides of a certain length that correspond to their respective antigens, although in some cases a library is comprised of a mixture of peptides with two or more different lengths. The peptides may be of a certain length(s) and they may overlap in sequence of a certain amount, although there may be variability of length of overlap in some libraries. In particular embodiments, the peptides are at least 9, 10, 11, 12, 13, 14, 15, 16, 17, 18, 19, 20, 21, 22, 23, 24, 25, 26, 27, 28, 29, 30, 31, 32, 33, 34, or 35 or more amino acids in length, for example. In particular embodiments, there is overlap among the peptides of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acids in length, for example. In specific embodiments, the peptides are 15 amino acids long and overlap one another by 11 amino acids. A mixture of different peptides may include any ratio of the different peptides, although in some embodiments each particular peptide is present at substantially the same numbers in the mixture as another particular peptide. Although coverage of an antigen in sequence for the peptides may be random and substantially even over a given region of an antigen, in some embodiments a library may be enriched for one or more particular peptides, such as one or more peptides that are known to encode an epitope or a part thereof, for example.

In particular embodiments, the pepmix for a particular antigen protein comprise all possible HLA class I epitopes that are 8 to 10 amino acids long, for example. In specific embodiments, longer peptides are utilized to cover all class II epitopes for a particular peptide. In certain aspects, the peptides are at a maximum of 30 amino acids in length with overlapping of 25 amino acids.

II. Methods of Producing and Using Therapeutic T-Cells

A. Producing Therapeutic T-Cells

In certain aspects, the present disclosure concerns the development of immune cells, such as cytotoxic T-cells, that target one or more antigens from at least one HPV virus.

Methods disclosed herein may involve the stimulation and/or expansion of immune cells. The methods may involve the stimulation and/or expansion of peripheral blood cells, such as peripheral blood mononuclear cells. The methods may involve expansion of an immune cell population (e.g. a population of T-cells) from within a population of immune cells (e.g. PBMCs). For example, a population of T-cells may be expanded from within a population of PBMCs, by stimulation of the T-cells within the population of PBMCs. Accordingly, in embodiments of the methods disclosed herein, stimulation and/or expansion of T cells may involve stimulation of a population of PBMCs. In some embodiments, a population of T-cells may be expanded from within a population of tumor-infiltrating lymphocytes, by stimulation of the T-cells within the population of tumor-infiltrating lymphocytes. Accordingly, in embodiments of the methods disclosed herein, stimulation and/or expansion of T cells may involve stimulation of a population of tumor-infiltrating lymphocytes. In some embodiments, a population of T-cells may be expanded from within a population of T-cells (e.g. a population of T cells of heterogeneous specificity), which may have been obtained from a blood sample, a population of PBMCs, or from a population of tumor-infiltrating lymphocytes. The stimulations/expansions may result in an increase the number HPV-specific immune cells (e.g. HPV-specific T cells, such as HPV-specific CTLs), and/or result in an increased proportion of such cells in the cell population at the end of the stimulation/expansion. The methods may involve the stimulation and/or expansion of T cells. The cells may have been obtained from the patient to be treated (i.e., autologous cells), or from another individual (i.e., allogeneic cells). The methods involve stimulation and/or expansion of isolated immune cells, in certain embodiments. That is, specific methods may be performed on a population of cells that contains substantially no non-immune cells, such as erythrocytes. In some cases, the immune cells are isolated PBMCs, or isolated T cells. The cells may have been obtained from a sample of blood, such as a sample of blood obtained from the patient or individual. The cells may have been obtained from tissue sample or biopsy. The cells may have been obtained from a tumor (e.g. tumor-infiltrating lymphocytes). Certain methods disclosed herein involve a step of obtaining PBMCs and/or T cells from a sample obtained from the patient. Certain embodiments of methods do not involve the step of obtaining a sample of blood or cells from the patient or individual, but instead are performed on a sample or cells that have been previously obtained. The method may involve processing the sample, such as enriching the sample for immune cells, such as PBMCs and/or T cells. Such methods may involve removing or substantially reducing the amount of, erythrocytes, platelets, serum and/or plasma in a sample. This may result in a population of immune cells containing substantially no other cells, such as erythrocytes. Methods disclosed herein may be performed on isolated immune cells, or a sample containing immune cells in addition to other cells.

In methods of producing the T-cells, peripheral blood T-cells may be initially stimulated with APCs that have been exposed to one or more peptides that span some or all of at least one HPV antigen. The antigenic peptides may be provided to the APCs in a library of peptide mixtures, and multiple libraries of pepmixes may be provided to the same collection of APCs. In some embodiments, the collection includes both immunodominant and subdominant antigens.

In embodiments of the disclosure, therapeutic T-cells are generated and may be provided to an individual that has an HPV infection or is at risk of having an HPV-associated medical condition that results indirectly or directly from an HPV infection. In methods of producing the therapeutic T-cells, under certain conditions peripheral blood T-cells are mixed with APCs that are loaded with a library of peptides that span part or all of one or more antigens, including part or all of a HPV16 and/or HPV18 antigen, including E6 and/or E7, for example. In specific embodiments, for the stimulating step the T-cells reside within a population of PBMCs.

In some embodiments, the APCs used in certain steps may be dendritic cells (DCs). Methods for generation of DCs are well known in the art, e.g. see Ramos et al., supra. Monocytes may be isolated from PBMCs by CD14 selection and cultured in DC medium and 2 mM alanyl-glutamine with 800 U/ml granulocyte/macrophage colony stimulating factor (GM-CSF) and 1000 U/ml interleukin 4 (IL-4) for 5 days. GM-CSF and IL-4 may be replenished on day 3. On day 5, DCs are matured in DC media with 10 ng/ml interleukin-1β(IL-1β), 100 ng/ml interleukin 6 (IL-6), 10 ng/ml prostaglandin E2, 800 U/ml GM-CSF and 1000 U/ml IL-4. DC maturation may be assessed by flow cytometry to detect upregulation of CD80. CD83, CD86 and HLA-DR.

In some embodiments, the APCs used in certain steps are activated T-cells. Activated T-cells may be polyclonal T-cells (T-APCs) generated using a portion of the autologous PBMC isolated from the venesected blood. The cells may be activated by culturing in cell culture plates that are coated with anti-CD3 and anti-CD28 antibodies. The cells are then cultured to expand in the presence of IL-2 for 2 weeks. The expanded T-APC can be cryopreserved for later use. 2-3 days prior to using T-APC for stimulation (e.g., for the 3rd cycle of stimulation and optionally for subsequent stimulations), cryopreserved cells are thawed and re-stimulated in anti-CD3 and anti-CD28 antibody-coated cell culture plates. On the day of stimulation, the T-APC cells are harvested and pulsed with the HPV E6/E7 peptides, followed by adding to the on-going culture of HPV stimulated T-cells at 1:1 ratio.

In some embodiments, the APCs used in certain steps and/or methods may be B-blasts (BBs). B-blasts may be generated from a patient's autologous PBMC, for example. The B lymphocytes within the PBMCs are activated by co-culturing with an irradiated allogeneic CD40L-expressing MRCS epithelial cell line and expanded in media containing 100 U/ml IL-4 and 1 microgram/ml cyclosporin A.

In some embodiments, there is a method of generating T-cells that target at least one antigen from one or both of HPV16 and HPV18, and this occurs generally by contacting a plurality of PBMCs with a plurality of APCs loaded for peptides from a library of peptides that correspond to one or more particular HPV16 and/or HPV18 viral antigens. In specific embodiments, the exposure of the two populations of cells allows for expansion of the T-cells. In particular embodiments, the stimulation step(s) occurs in the presence of one or more particular cytokines, which may be mammalian (e.g. murine, human) or human cytokines. In certain embodiments, the one or more cytokines are IL-7 and IL-15, although in alternative embodiments the cytokine(s) are selected from the group consisting of IL-15, IL-7, IL-21, IL-12, IL-6, IL-4, and a combination thereof. In specific embodiments, one or more steps of the methods do not occur in the presence of IL-2, IL-4, IL-6, IL-7, IL-12, and/or IL-21, although alternatively IL-2, IL-4, IL-6, IL-7, IL-12, and/or IL-21 may be utilized. Reference to the presence of a cytokine is to presence of exogenously added cytokine, i.e. excluding any cytokine present within or secreted by the culture of cells. In some embodiments, the peptides are further defined as peptides that overlap in sequence to span part or all of a HPV antigen. For example, in certain aspects the peptides overlap by at least 10 amino acids, and particularly 11, and in some embodiments the peptides are at least 12 or more amino acids in length, and particularly 15 amino acids in length.

The selection of an appropriate amount or concentration of a given cytokine for inclusion in a cell culture is within the ability of the person or ordinary skill in the art. By way of example, the following is a list of certain interleukins and examples of appropriate concentrations that may be used:

Interleukin 6 (IL-6): 50 to 150 ng/ml, one of about 50 ng/ml, 60 ng/ml, 70 ng/ml, 80 ng/ml, 90 ng/ml, 100 ng/ml, 110 ng/ml, 120 ng/ml, 130 ng/ml, 140 ng/ml or 150 ng/ml;

Interleukin 7 (IL-7): 5 to 15 ng/ml, one of about 5 ng/ml, 6 ng/ml, 7 ng/ml, 8 ng/ml, 9 ng/ml, 10 ng/ml, 11 ng/ml, 12 ng/ml, 13 ng/ml, 14 ng/ml or 15 ng/ml;

Interleukin 12 (IL-12): 5 to 15 ng/ml, one of about 5 ng/ml, 6 ng/ml, 7 ng/ml, 8 ng/ml, 9 ng/ml, 10 ng/ml, 11 ng/ml, 12 ng/ml, 13 ng/ml, 14 ng/ml or 15 ng/ml;

Interleukin 15 (IL-15): 5 to 15 ng/ml, one of about 5 ng/ml, 6 ng/ml, 7 ng/ml, 8 ng/ml, 9 ng/ml, 10 ng/ml, 11 ng/ml, 12 ng/ml, 13 ng/ml, 14 ng/ml or 15 ng/ml.

Table 1 below provides examples of certain embodiments of methods of the disclosure.

TABLE 1

Examples of Elements of a Method

| Embodiments | | Examples for Embodiments |
|---|---|---|
| First Stimulation | Source of T-cells | Peripheral blood mononuclear cells (PBMC) |
| | | Non-adherent PBMC |
| | Antigen-presenting cells (APC) | Dendritic cells (DC)s, PBMCs or B-blasts |
| | Cytokines | Combinations of IL-15 and IL-7, optionally with IL-6 and/or IL-12 and/or IL-21 and/or IL-4 |
| | Antigen | Viral pepmixes for HPV |
| Second stimulation | Source of T-cells | Product of first stimulation |
| | APCs | DC |
| | | PBMCs |
| | | Autologous activated T-cells (AATC) |

TABLE 1-continued

Examples of Elements of a Method

| Embodiments | | Examples for Embodiments |
|---|---|---|
| | Cytokines | IL-15 and IL-7, preferably no IL-6 or IL-12 and optionally IL-15 and IL-7 are the only interleukins |
| | Antigen | Viral pepmixes for HPV |
| Third stimulation (and subsequent stimulations as desired) | Source of T-cells | Product of second stimulation |
| | APCs | Pepmix-loaded AATCs + costimulatory cells |
| | Cytokines | IL-15 and IL-7, preferably no IL-6 or IL-12 and optionally IL-15 and IL-7 are the only interleukins |
| | Costimulatory cells | Cells expressing CD86, 4-1BB, and CD83, e.g., K562 cells |

Thus, in particular embodiments, a population of T-cells (wherein the population may comprise substantially all T-cells or wherein the population of T-cells is within another population of cells, such as within PBMCs) is exposed to a population of APCs to generate T cell lines having particular characteristics, including at least: a) effectiveness at targeting HPV16 E6 and/or E7 and/or effectiveness at targeting HPV18 E6 and/or E7; b) polyclonality; c) TH1 bias; or d) a combination thereof. The generated T cell lines may be produced to be effective at targeting HPV species 7 (HPV-18, -39, -45, -59, -68) and species 9 (HPV-16, -31, -33, -35, -52, -58, -67), and types 6 and 11, and this may be the results of pepmixes directed to any one or more of the following antigens: E1, E2, E3, E4, E5, E6, E7, L1, and/or L2.

In some cases, T-cells are stimulated more than once, and different stimulation steps may or may not expose the population of cells to the same conditions. In specific embodiments, a first stimulation has conditions different from a subsequent stimulation, including a second stimulation and/or a third stimulation. In specific embodiments, a first stimulation step of the method utilizes APCs that are pepmix-loaded DCs or pepmix-loaded PBMCs and utilizes IL-7 and IL-15. This stimulation step may optionally be repeated one or more times.

In certain embodiments of the methods, between days 8 and 10 following an initial exposure of the peripheral blood T-cells (or PBMCs) to the pepmix or APCs, there may be a re-stimulation of the PBMCs on day 8, day 9, or day 10, but not later, and then a subsequent re-stimulation may occur on day 15, day 16, or day 17.

In a stimulation step that is subsequent to the first stimulation step (including optional repeats of the first stimulation step), the resultant T-cells obtained after the first stimulation (and which may be in a heterogeneous population of cells) are exposed to pepmix-loaded DCs or pepmix-loaded PBMCs and/or autologous activated T-cells. In a stimulation that is subsequent to first and second stimulation steps, T-cells obtained after the second or later stimulation (and which may reside in a heterogeneous population of cells) are exposed to pepmix-autologous activated T-cells. Costimulatory cells that may be utilized in any stimulation step include at least cells that express CD86, 4-1BB, CD83, CD40, OX40, and/or CD80. In specific cases, the costimulatory cells may be K562 cells.

In some embodiments, during the steps of the method the cells in culture are modified. In specific embodiments, the cells are modified to harbor a polynucleotide that expresses a gene product that renders the cells effective or more effective for a specific purpose or function, such as effective or more effective for targeting a particular target and/or enhanced in function for T-cell-mediated cytotoxicity, and/or modified to resist tumor antigen-specific cellular immunity, for example.

In some embodiments, the cells are modified to express a certain non-natural receptor that allows the T-cells to effectively or more effectively target a desired target cell, such as one that expresses a certain antigen. The cells may be modified to express a chimeric antigen receptor (CAR), an αβ T-cell receptor, and so forth. The cells may be modified to express an expression vector (that may be viral (including retroviral, lentiviral, adenoviral, adeno-associated viral, and so forth) or non-viral) during the method at specific time points, such as the vector being introduced between day 2 and 5 of culture, for example. In some embodiments the cells are exposed to the expression vector within about 3 days after each stimulation, but in such cases the modification occurs in more differentiated T-cells that have less long term potential (which in specific circumstances is desirable).

In specific embodiments, the cells are modified to express a CAR that targets a cancer antigen, such as EphA2, HER2, GD2, Glypican-3, 5T4, 8H9, $a_v\beta_6$integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor α, GD2, GD3, HLA-AI MAGE A1, HLA-A2, IL11Ra, IL13Ra2, KDR, Lambda, Lewis-Y, MCSP, Mesothelin, Mucl, Muc16, NCAM, NKG2D ligands, NY-ESO-1, PRAME, PSCA, PSC1, PSMA, ROR1, Sp17, SURVIVIN, TAG72, TEM1, TEM8, VEGRR2, carcinoembryonic antigen, HMW-MAA, VEGF receptors, and/or other exemplary antigens that are present with in the extracellular matrix of tumors, such as oncofetal variants of fibronectin, tenascin, or necrotic regions of tumors and other tumor-associated antigens or actionable mutations that are identified through genomic analysis and or differential expression studies of tumors, for example.

In some embodiments the cells are modified to resist tumor antigen-specific cellular immunity, e.g. mediated by transforming growth factor beta (TGF-β). For example, the cells may be modified to express a dominant negative receptor for TGF-beta (DNRII), e.g. as described in Foster et al., (Antitumor activity of EBV-specific T lymphocytes transduced with a dominant negative TGF-beta receptor. *J Immunother.* 2008; 31:500-505, incorporated herein by reference). This may comprise transfecting the cells with a retroviral expression vector encoding a dominant negative TGF-β type II receptor (DNRII) modified by removal of the immunogenic hemagglutinin tag. Such modified T-cells have been shown to have a functional advantage over unmodified T-cells in the presence of TGF-β-secreting tumor, including enhanced antitumor activity (Foster et al., supra).

Methods according to the present invention may improve the rate of expansion for populations of virus-specific T-cells as compared to prior art methods. The rate of expansion for a T-cell population can be analysed by methods well known to the skilled person. Methods include measuring the number of T-cells at one or more time points. For example, the number of T-cells can be determined after performing a method according to the invention and compared to the number of T-cells at the beginning of the method; fold expansion in the number of T-cells can then be calculated.

Rates of expansion can also be determined by analysing cell division by T-cells over a period of time. Cell division for a given population of T-cells can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety.

The improvement in the rate of expansion achieved by the methods according to the present invention can be determined by performing a method according to the invention, and comparing the expansion for T-cells in that method to a comparable, control method, e.g. as per the method of Ramos et al., (J Immunother 2013; 36:66-76).

In some embodiments, the rate of expansion for a population of T-cells in a method according to the present invention is one of at least 1.001 times, 1.002 times, 1.003 times, 1.004 times, 1.005 times, 1.006 times, 1.007 times, 1.008 times, 1.009 times, 1.01 times, 1.02 times, 1.03 times, 1.04 times, 1.05 times, 1.06 times, 1.07 times, 1.08 times, 1.09 times, 1.1 times, 1.2 times, 1.3 times, 1.4 times, 1.5 times, 1.6 times, 1.7 times, 1.8 times, 1.9 times, or 2 times the rate of expansion in a comparable control method.

The rate of expansion may be of the virus-specific T-cell population, or the total T-cell population.

The virus-specific T-cells generated/expanded according to the method of the present invention may at least retain the same functional properties as virus-specific T-cells generated/expanded according to prior art methods. That is, the accelerated rate of expansion does not negatively influence the functional properties of the expanded T-cells.

For example, in embodiments wherein the methods generate/expand a population of virus-specific T-cells, the T-cells display similar cytotoxicity to cells infected with or comprising/expressing a peptide of the virus as virus-specific T-cells expanded according to prior art methods.

Cytotoxicity of expanded T-cells can be analysed e.g. by culturing the expanded T-cell population with APCs presenting a peptide of the virus for which the T-cell is specific at different effector (i.e. T-cell) to target (i.e. APC) ratios, and measuring specific lysis of the APCs. For example, cytotoxicity of an HPV-specific CTL population can be analysed by measuring specific lysis of HPV-transformed LCL cells at different effector to target ratios.

B. Using Therapeutic T-Cells

In certain embodiments, cells produced by methods of the disclosure are provided to an individual in need thereof for treatment of a medical condition, including one caused by a viral infection, or to target a viral infection in which no symptoms of a medical condition are detectable or have manifested. As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

In the methods encompassed by the disclosure, the therapeutic T-cells are utilized to treat viral-associated disease caused directly or indirectly by a single non-HPV virus or are otherwise provided to an individual that is seropositive for a single non-HPV virus. In other cases, the therapeutic T-cells are utilized to treat viral-associated disease(s) caused directly or indirectly by more than one virus or are otherwise provided to an individual that is seropositive for more than one virus. In the collection of therapeutic T-cells, each T-cell and its progeny has specificity for only one peptide in one antigen from one virus, and upon production of the collection of therapeutic T-cells, one expands a population of T-cell clones that together have multi-specificity, such as for multiple epitopes in each viral antigen, for example.

In at least some methods of the disclosure, a therapeutically effective amount of the CTLs generated thereby are administered to an individual, for example, an individual known to have or suspected of having or susceptible to having HPV16 and/or HPV18-associated disease. In specific embodiments, the cells are administered by injection, such as intravenous, intramuscular, intradermal, subcutaneous, intraperitoneal injection, and so forth, for example. In some embodiments, the CTLs are further defined as polyclonal CD4+ and CD8+ CTLs. The PBMCs may be allogeneic to the individual or may be autologous to the individual.

In certain cases, neoplasms are treated with cells of the disclosure, and the neoplasm may be benign, malignant, or a premalignant lesion that can lead to cancer. Thus, an individual may be treated with cells produced by methods of the disclosure at the premalignant lesion stage and/or after the lesion becomes malignant. The individual may have early or late stage cancer, and the skilled artisan is aware that the methods of producing the cells may be tailored for such different stages of cancer, such as by utilizing peptides for the APCs that are from antigens associated with early vs. late stage cancer. In specific embodiments, the cancer may be primary, metastatic, recurrent, refractory, and so forth.

In certain cases, premalignant lesions that can lead to cancers, such as premalignant lesions of the cervix, vulva, vagina, penis, larynx, oropharynx anus, and other upper aerodigestive areas, for example, are treated with cells produced by methods of the disclosure. Thus, an individual may be treated with cells produced by methods of the disclosure at the premalignant lesion stage and/or after the lesion becomes malignant. HPV-associated medical conditions that may be treated with cells produced by methods of the disclosure include at least dysplasias of the genital area(s), cervical intraepithelial neoplasia, vulvar intraepithelial neoplasia, penile intraepithelial neoplasia, anal intraepithelial neoplasia, cervical cancer, anal cancer, vulvar cancer, vaginal cancer, penile cancer, genital cancers, oropharyngeal cancer, nasopharyngeal carcinoma, oral papillomas and other upper aerodigestive lesions.

In some cases, one can determine the serotype that is associated with a cancer before administration of the cells, although in some cases the serotype is not determined. In specific embodiments, HPV16-specific or HPV18-specific cells have activity for tumors that are HPV16 or HPV18-positive, respectively, although in some cases there is cross-reactivity with different HPV serotypes. The ability to cross-react may or may not be known, and in certain cases, for example, an individual with HPV16 infection or HPV16-associated medical condition is administered HPV18-specific T-cells, and vice versa. In such cases, an individual may be treated with cells specific for a serotype in which it is unknown if the individual has that serotype, yet the cells still are therapeutically effective because of cross-reactivity.

In cases wherein the APCs of the stimulation steps of the method are loaded with HPV16 and HPV18 pepmixes together, the outcome of administration of T-cells expanded through such APCs is determined by whether the individual has been exposed to the virus in question. For example, if an individual is infected with HPV18 and not HPV16, only HPV18-specific T-cells will respond, and this is because the infection will initially have stimulated a T-cell response to HPV 18. Those T-cells will expand in the individual and then become memory T-cells and would be at higher numbers than T-cells specific for HPV16 that have never been activated, for example.

The individual being treated may be known to have cancer, suspected of having cancer, or at risk for having cancer (such as personal or family history; being sexual active, including sexually promiscuous; and/or having a genetic predisposition, including one or more specific markers). An individual being treated may have the presence of the HPV virus but there are not yet any deleterious symptoms of a HPV-related medical condition. The individual may have a benign or malignant neoplasm. The individual may have early or late stage cancer, and the skilled artisan is aware that the methods of producing the cells may be tailored for such different stages of cancer, such as by utilizing peptides for the APCs that are from antigens associated with early vs. late stage cancer. In specific embodiments, the HPV-associated disease is malignant cancer of the mouth or genital region. In specific embodiments, the cancer may be primary, metastatic, recurrent, refractory, and so forth. The individual may be infected with HPV16 and/or HPV18 as a result of sexual acts of any kind or intimate physical contact of any kind.

Any stage of HPV infection may be treated with cells encompassed by the disclosure. The individual with established HPV-associated cancer being treated with methods of the disclosure include Carcinoma in Situ (Stage 0), Stage I, Stage II, Stage III, or Stage IV (which may be determined by MRI, CT scan, PET scan, etc.). Additionally, individuals with pre-cancer lesions (dysplasia) may also be treated.

In some embodiments, one or more administrations of the cells produced by methods of the disclosure are provided to an individual in need thereof. The length of time between different administrations may be of any suitable duration, including on the order of 1-7 days, 1-4 weeks, 1-12 months, or 1, 2, 3, 4, 5, 6, 7, 8, 9, 10, or more years. Multiple infusions within about a year may be employed, in some cases. In cases wherein more than one administration of cells are provided to the individual, the antigen to which the cells are targeted may or may not be the same antigen that was targeted with the cells utilized in earlier administration(s). For example, in a first administration of cells, the cells may target HPV18 E6, whereas in another administration of cells, the cells target HPV18 E7, or vice versa. Additional administration(s) may be required in cancers that become refractory, for example. Additional stimulations may be employed in conjunction with one or more other types of cancer treatments.

In some cases, an individual is optionally determined to have HPV infection by any suitable means in the art. Because HPV cannot be cultured in cell cultures, one may utilize HPV infection diagnosis methods such as DNA tests utilizing PCR, Southern blot hybridization, and/or in situ hybridization, and these methods may or may not be used in conjunction with colposcopy; acetic acid test; biopsy; physical examination; and/or Pap smear, for example.

In specific embodiments, a male individual is provided an effective amount of cells produced by methods of the disclosure to target HPV with which he is infected, and in such a case the individual thereafter has a reduced chance of infecting another, such as a female individual through sexual activity. The male individual may or may not be determined to be infected with HPV prior to exposure to the cells of the methods of the disclosure. In some cases, if an individual is shown to be infected with an oncogenic HPV, it would be worth treating him with cells to eliminate his risk. If the cells were effective, they would also reduce the chances of him transmitting the virus to his partner.

In specific embodiments, the individual is immunocompromised (which for example, may be defined as an individual whose ability to fight infectious disease or cancer with the immune system is compromised or entirely absent). In specific embodiments, the immunocompromised individual has had a stem cell transplant (including hematopoietic stem cell transplantation), has had an organ transplant and/or has received one or more cancer treatments, including chemotherapy or radiation, for example. In some cases, the individual has acquired or inherited immune deficiency disorder. In some embodiments, those that are immunocompromised by their disease and/or its treatment are provided methods and/or compositions of the disclosure.

Methods of medical treatment may involve treatment of cancer by a method of ameliorating, treating, or preventing a malignancy in a human subject wherein the steps of the method assist or boost the immune system in eradicating cancerous cells. Such methods may include the administration of cells, according to the present invention that invoke an active (or achieve a passive) immune response to destroy cancerous cells. Methods of treatment may optionally include the co-administration of biological adjuvants (e.g., interleukins, cytokines, Bacillus Comette-Guerin, monophosphoryl lipid A, etc.) in combination with conventional therapies for treating cancer such as chemotherapy, radiation, or surgery. Methods of treatment may involve administering a composition according to the present invention as a vaccine that works by activating the immune system to prevent or destroy cancer cell growth. Methods of medical treatment may also involve in vivo, ex vivo, and adoptive immunotherapies, including those using autologous and/or heterologous cells or immortalized cell lines.

III. Pharmaceutical Compositions

In accordance with this disclosure, the term "pharmaceutical composition" relates to a composition for administration to an individual. In a particular embodiment, the pharmaceutical composition comprises a composition comprising therapeutic immune cells for parenteral, transdermal, intraluminal, intra-arterial, intrathecal or intravenous administration or for direct injection into a neoplasm, such as a cancer. It is in particular envisaged that the pharmaceutical composition is administered to the individual via infusion or injection. Administration of the suitable compositions may be effected by different ways, e.g., by intravenous, subcutaneous, intraperitoneal, intramuscular, topical or intradermal administration.

The pharmaceutical composition of the present disclosure may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well-known conventional methods. These pharmaceutical compositions can be administered to the subject at a suitable dose.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. A particular dosage for administration might be in the range of $2 \times 10^7$ cells per $m^2$ to $1 \times 10^{10}$ cells per $m^2$ of body surface area. Progress can be monitored by periodic assessment.

The compositions of the disclosure may be administered locally or systemically. In a preferred embodiment, the pharmaceutical composition is administered subcutaneously and in an even more preferred embodiment intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present disclosure might comprise proteinaceous carriers, like, e.g., serum albumin or immunoglobulin, preferably of human origin. It is envisaged that the pharmaceutical composition of the disclosure might comprise, in addition to the cells as described in this disclosure, further biologically active agents, depending on the intended use of the pharmaceutical composition.

IV. Combination Therapy

In certain embodiments of the disclosure that concern CTLs generated against HPV antigen(s), methods of the present disclosure for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions may be provided in a combined amount effective to kill or inhibit proliferation of the cell. This may be achieved by contacting the cancer cell with a single composition or pharmacological formulation that includes both agents, or by contacting the cancer cell with two distinct compositions or formulations, at the same time, wherein one composition includes the expression construct and the other includes the second agent(s). In other cases, administration of the cells and a second composition may be separate and may have separate administration routes and/or carriers.

Tumor cell resistance to chemotherapy and radiotherapy agents represents a major problem in clinical oncology. One goal of current cancer research is to find ways to improve the efficacy of chemo- and/or radiotherapy by combining it with additional therapy. In the context of the present disclosure, it is contemplated that cell therapy could be used similarly in conjunction with chemotherapeutic, radiotherapeutic, and/or immunotherapeutic intervention, for example.

Alternatively, the present inventive therapy may precede or follow the other agent treatment by intervals ranging from minutes to weeks, months, or years. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

Examples of HPV-associated cancer treatments (as an example) that may be used in conjunction with cells produced from methods of the disclosure include at least the following: 1) surgery (tumor resection, neck dissection, conization, hysterectomy, and so forth.); 2) drug therapy that may include Avastin® (Bevacizumab); Blenoxane (Bleomycin); Hycamtin® (Topotecan Hydrochloride); or a combination thereof; 3) radiotherapy; 4) immunotherapy other than that of the disclosure; 5) hormone therapy; or 6) a combination thereof.

V. Kits of the Disclosure

Any of the compositions described herein may be comprised in a kit. In a non-limiting example, a library of pepmixes may be comprised in a kit, any type of cells may be provided in the kit, and/or reagents for manipulation of pepmixes and/or cells may be provided in the kit. Cytokine(s) or means of producing them (such as vectors that encode them) may be included in the kit. Cell culture reagents and/or apparatus(es) may be included. The component(s) are provided in suitable container means.

In one embodiment a kit may comprise a container comprising a quantity of T-cells obtained by a method of the present invention formulated for administration to a subject (e.g. by admixture with a suitable carrier, excipient, diluent, or adjuvant) preferably by infusion, more preferably for administration by infusion in a method of autologous adoptive cellular immunotherapy. The kit may be maintained at a predetermined temperature, e.g. less than about 4° C., less than about −2° C. or less than about −50° C. The kit may further comprise instructions for the storage and/or transport of the kit and/or for the administration of the T-cells.

The kits may comprise a suitably aliquoted compositions of the present invention. The components of the kits may be packaged either in aqueous media or in lyophilized form.

The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

However, the components of the kit may be provided as dried powder(s). When reagents and/or components are provided as a dry powder, the powder can be reconstituted by the addition of a suitable solvent. It is envisioned that the solvent may also be provided in another container means.

In some cases, reagents and/or devices to detect HPV infection may be included in the kit. Examples include swabs, spatulas, cytobrushes, slides, cover slips, cytology sample collection receptacle(s), and so forth. Additional drugs for HPV infection or cancer may be included in the kit, such as Bevacizumab; Bleomycin; Topotecan Hydrochloride; or a combination thereof.

VI. High IL-15

In some embodiments of aspects of the present disclosure stimulations are performed in the presence of IL-15. In some embodiments stimulations are performed in the presence of IL-7 and IL-15. In some embodiments stimulations are performed in the presence of IL-7 and IL-15 only. In some embodiments stimulations are performed in the presence of IL-7 and IL-15 and in the absence of IL-6 and/or IL-12).

In embodiments of the present disclosure where stimulations are performed in the presence of IL-15, the IL-15 may be present in the culture at a final concentration greater than 15 ng/ml. Final IL-15 concentrations greater than 15 ng/ml may be referred to herein as high IL-15. In some embodiments, the IL-15 may be present in the culture at a final concentration of one of 20-1000 ng/ml, 20-900 ng/ml, 20-800 ng/ml, 20-700 ng/ml, 20-600 ng/ml, 20-500 ng/ml, 30-500 ng/ml, 40-500 ng/ml, 50-500 ng/ml, 50-400 ng/ml, 50-300 ng/ml, 50-200 ng/ml, 50-175 ng/ml, 50-150 ng/ml, 75-150 ng/ml, 75-125 ng/ml, 80-120 ng/ml, 90-110 ng/ml or 100 ng/ml. Stimulations using high IL-15 are contemplated in particular in connection with methods in which the populations of HPV-specific immune cells are generated/expanded from within a population of cells (e.g. blood cells, immune cells or PBMCs) depleted of CD45RA+ cells.

Stimulations using high IL-15 may be provided with advantageous properties. For example, methods comprising stimulations using high IL-15 may be useful to generate/expand populations of immune cells specific for HPV with improved efficiency (e.g. greater fold expansion within the same period of time). Methods comprising stimulations using high IL-15 may be useful for generating/expanding populations of immune cells specific for HPV comprising a reduced number/frequency of undesirable immune cell subsets (e.g. NK cells, regulatory T cells (Tregs) and/or naïve T cells), an increased proportion/frequency of desirable immune cell subsets (e.g. CD8+ T cells, CD8+ cytotoxic T lymphocytes, CD4+ T cells, CD4+ T helper cells, IFNγ-producing cells, memory T cells, central memory T cells, antigen-experienced T cells, CD45RO+ T cells), and/or an increased proportion/frequency of virus- and/or antigen-specific cells in the generated/expanded population, as compared to populations generated/expanded in accordance with prior art methods.

VII. HLA-Negative LCLs

In aspects of the present disclosure the costimulatory cells used in a stimulation step described herein may be cells of a lymphoblastoid cell line (LCL) lacking gene and/or protein expression of MHC class I and/or MHC class II. In some embodiment LCLs may lack surface expression of MHC class I and MHC class II; such LCLs may be referred to herein as "HLA-negative LCLs", "universal LCLs" or "ULCLs".

LCLs can be prepared by viral transformation of B cells. LCLs are typically produced by transformation of B cells with Epstein-Barr virus (EBV). Generation and characteristics of LCLs is described in detail, for example, in Hui-Yuen et al., J Vis Exp (2011) 57: 3321, and Hussain and Mulherkar, Int J Mol Cell Med (2012) 1(2): 75-87, both hereby incorporated by reference in their entirety. Briefly, LCLs can be produced by incubation of PBMCs with concentrated cell culture supernatant of cells producing EBV, for example B95-8 cells, in the presence of cyclosporin A.

HLA-negative LCLs may lack surface expression of an MHC class I polypeptide and an MHC class II polypeptide. An "MHC class I polypeptide" refers to a constituent polypeptide of an MHC class I molecule (i.e. a polypeptide complex of an MHC class I α chain polypeptide and a B2M polypeptide). An "MHC class II polypeptide" refers to a constituent polypeptide of an MHC class II molecule (i.e. a polypeptide complex of an MHC class II α chain polypeptide and a MHC class II β chain polypeptide). Surface expression refers to expression of the relevant polypeptide/polypeptide complex which is detectable at the cell surface (i.e. in or at the cell membrane). Surface expression can be analyzed e.g. on intact cells using an antigen-binding molecule specific for a region of the polypeptide/polypeptide complex which is extracellular to the cell when the polypeptide/polypeptide complex is expressed at the cell surface.

In some embodiments the HLA-negative LCLs display substantially no gene/protein expression of MHC class I and MHC class II, e.g. as determined by an appropriate method for detecting gene and/or protein expression. In some embodiments the HLA-negative LCLs display substantially no surface expression of MHC class I and MHC class II, e.g. as determined by analysis by flow cytometry using an antibody capable of binding to MHC class I and an antibody capable of binding to MHC class II. In such assays, the level of staining of the HLA-negative LCLs by the relevant antibodies may not be significantly greater than the level of staining of the cells by appropriate negative control antibodies of the same isotype.

HLA-negative LCLs may have been obtained by modification (e.g. to a nucleic acid, e.g. by insertion, substitution or deletion of one or more nucleotides) to reduce/prevent gene and/or protein expression of one or more polypeptides of an MHC class I molecule and an MHC class I molecule (e.g. B2M polypeptide, MHC class I α chain polypeptide (e.g. HLA-A, HLA-B or HLA-C), MHC class II α chain polypeptide (e.g. HLA-DPA1, HLA-DQA1, HLA-DQA2 or HLA-DRA) and/or MHC class II β chain polypeptide (e.g. HLA-DPB1, HLA-DQB1, HLA-DQB2, HLA-DRB1, HLA-DRB3, HLA-DRB4 or HLA-DRB5)). In some embodiments the HLA-negative LCLs comprise modification to reduce/prevent gene and/or protein expression of an MHC class I polypeptide (e.g. B2M) and modification to reduce/prevent gene and/or protein expression of one or more MHC class II polypeptides (e.g. HLA-DR, HLA-DQ, and HLA-DP) as compared to gene and/or protein expression by an unmodified LCL. In some embodiments the HLA-negative LCLs comprise modification to reduce/prevent gene and/or protein expression of B2M, HLA-DRA, HLA-DQA1, HLA-DQA2, and HLA-DP. In some embodiments the HLA-negative LCLs may be obtained by targeted knockout of genes encoding B2M, HLA-DRA, HLA-DQA1, HLA-DQA2, and HLA-DP, e.g. using sequence specific nucleases (SSNs); gene editing using SSNs is reviewed e.g. in Eid and Mahfouz, Exp Mol Med. 2016 October; 48(10): e265, which is hereby incorporated by reference in its entirety. In some embodiments modification to reduce/prevent gene and/or protein expression of an MHC class I polypeptide (e.g. B2M) and/or modification to reduce/prevent gene and/or protein expression of one or more MHC class II polypeptides (e.g. HLA-DR, HLA-DQ, and HLA-DP) is achieved using CRISPR/Cas-9 systems comprising crRNA targeting nucleic acid encoding the relevant polypeptide(s). In some embodiments the HLA-negative LCLs are obtained by sequential knockout of genes encoding B2M, HLA-DRA, HLA-DQA1, HLA-DQA2, and HLA-DP. [0232] In some embodiments the HLA-negative LCLs additionally comprise modification to nucleic acid encoding one or more polypeptides necessary for EBV replication/infection. LCLs comprising modification to reduce/prevent EBV replication/infection may be described herein as being EBV replication defective. Accordingly, in some embodiments the HLA-negative LCLs are EBV replication defective. In some embodiments the HLA-negative LCLs comprise modification to nucleic acid (e.g. by insertion, substitution or deletion of one or more nucleotides) encoding one or more of BFLF1, BFLF2, BFRF1, BFRF2 and BFRF3 e.g. using SSNs. In some embodiments the HLA-negative LCLs comprise modification to nucleic acid encoding BFLF1 and/or nucleic acid encoding BFRF1. In some embodiments modification is achieved using CRISPR/Cas-9 systems comprising crRNA targeting nucleic acid encoding the relevant polypeptide(s). In some embodiments the HLA-negative LCLs are obtained by a method comprising culture in the presence of an agent suppressing viral replication (e.g. acyclovir). In some embodiments the EBV replication defective HLA-negative LCLs stimulate less proliferation of B cells from within a population of PBMCs following co-culture with the PBMCs as compared to the level of proliferation of B cells from within a population of PBMCs following co-culture of the PBMCs with LCLs described in the prior art. In some embodiments the EBV replication defective HLA-negative LCLs lack the ability to promote outgrowth of B cells in a co-culture with PBMCs. HLA-negative LCLs modified to reduce/prevent gene and/or protein expression of one or more polypeptides necessary for EBV replication may have an improved safety profile as compared to LCLs lacking modification to reduce/prevent gene and/or protein expression of one or more polypeptides necessary for EBV replication.

The HLA-negative LCLs of the present disclosure are employed as costimulatory cells in the manner in which costimulatory cells are typically employed in methods for generating/expanding virus-specific T cells. For example, the HLA-negative LCLs may be provided as an irradiated cell population, and at appropriate ratios to responder cells and antigen presenting cells (APCs). In some embodiments the HLA-negative LCLs are irradiated or treated with a substance (e.g. mitomycin C) to prevent their proliferation, prior to use in stimulations. Irradiation of LCLs in accordance with the present methods is typically at 6000 to 12000 rads. In some embodiments the HLA-negative LCLs are present in a stimulation comprising responder cells, APCs and HLA-negative LCLs at a ratio of responder cells:APCs: HLA-negative LCLs of one of 1:1:1 to 1:1:10, e.g. about 1:1:5.

HLA-negative LCLs described herein may be provided with advantageous properties relevant to their use as costimulatory cells in methods for generating/expanding populations of HPV-specific immune cells. For example, the HLA-negative LCLs may be useful to generate/expand populations of immune cells specific for HPV with improved efficiency (e.g. greater fold expansion within the same period of time). The HLA-negative LCLs may be useful in methods for generating/expanding populations of immune cells specific for HPV comprising a reduced number/frequency of undesirable immune cell subsets (e.g. NK cells, regulatory T cells (Tregs) and/or naïve T cells), an increased proportion/frequency of desirable immune cell subsets (e.g. CD8+ T cells, CD8+ cytotoxic T lymphocytes, CD4+ T cells, CD4+ T helper cells, IFNγ-producing cells, memory T cells, central memory T cells, antigen-experienced T cells, CD45RO+ T cells), and/or an increased proportion/frequency of virus- and/or antigen-specific cells in the generated/expanded population, as compared to populations generated/expanded in accordance with prior art methods.

HLA-negative LCLs are useful for generating/expanding populations of HPV-specific immune cells having reduced alloreactivity as compared to prior art methods for generating/expanding populations of HPV-specific immune cells. Accordingly, HLA-negative LCLs are useful for generating/expanding populations of HPV-specific immune cells for use in both autologous and allogeneic applications. In some embodiments the HLA-negative LCLs stimulate less proliferation of PBMCs in a coculture comprising the HLA-negative LCLs and PBMCs obtained from an allogeneic donor as compared to HLA-positive LCLs (i.e. LCLs described in the prior art). In some embodiments the HLA-negative LCLs stimulate less proliferation of PBMCs in a coculture comprising the HLA-negative LCLs and PBMCs obtained from a HLA-matched donor as compared to HLA-positive LCLs.

VIII. Dendritic Cells

In aspects of the present disclosure the dendritic cells used in a stimulation step described herein may be derived from cells within a population of blood cells obtained from a subject. In some embodiments the dendritic cells are derived from cells within a population of peripheral blood mononuclear cells (PBMCs). In some embodiments the dendritic cells are derived from CD14+ positive cells within a population of PBMCs. In some embodiments the dendritic cells are monocyte-derived dendritic cells (also referred to herein as moDCs).

In some embodiments the dendritic cells are obtained by a process comprising separating CD14+ cells from other cells (i.e. CD14− cells), e.g. from within a population of PBMCs. Separation may be performed by appropriate positive or negative selection. In some embodiments, CD14+ positive cells may be positively selected from within a population of cells using beads coated with antibody capable of binding specifically to CD14. For example, CD14+ cells may be isolated by MACS cell separation using CD14 MicroBeads (Miltenyi Biotec).

In some embodiments the dendritic cells are obtained by a process comprising culturing cells in the presence of factors promoting differentiation of immature dendritic cells (also referred to herein as iDCs) from CD14+ cells. The cells cultured in the presence of factors promoting differentiation of iDCs may be e.g. PBMCs, or CD14+ cells isolated from a population of PBMCs. Cells may be cultured at any suitable density, e.g. one of $0.1 \times 10^6$ to $1 \times 10^6$ cells/ml, $0.2 \times 10^6$ to $0.9 \times 10^6$ cells/ml, $0.3 \times 10^6$ to $0.8 \times 10^6$ cells/ml, $0.4 \times 10^6$ to $0.7 \times 10^6$ cells/ml or $0.5 \times 10^6$ cells/ml. Factors promoting differentiation of immature dendritic cells may include IL-4 and/or GM-CSF. In some embodiments the culture comprises IL-4 and GM-CSF. The IL-4 may be present in the culture at a final concentration of one of 50-1000 IU/ml, 100-800 IU/ml, 150-700 IU/ml, 200-600 IU/ml, 250-500 IU/ml, 300-500 IU/ml or 400 IU/ml. The GM-CSF may be present in the culture at a final concentration of one of 100-1500 IU/ml, 200-1400 IU/ml, 300-1300 IU/ml, 400-1200 IU/ml, 500-1100 IU/ml, 600-1000 IU/ml, 700-900 IU/ml or 800 IU/ml. The culture may be for any suitable period of time for differentiation of immature DCs, e.g. one of 1 day, 2 days, 3 days, 4 days, 5 days, 6 days, 7 days, 8 days, 9 days or 10 days.

In some embodiments the dendritic cells used in a stimulation step described herein are obtained by a process comprising culturing cells (i.e. precursor cells of mature dendritic cells, e.g. immature dendritic cells) to mature dendritic cells. In some embodiments the process comprises culturing the cells in the presence of factors promoting differentiation of mature DCs (e.g. moDCs). The cells cultured in the presence of factors promoting differentiation of mature DCs may be e.g. PBMCs, CD14+ cells isolated (i.e. separated and/or purified) from a population of PBMCs, or immature dendritic cells (iDCs). Cells may be cultured at any suitable density, e.g. one of $0.1 \times 10^6$ to $1 \times 10^6$ cells/ml, $0.2 \times 10^6$ to $0.9 \times 10^6$ cells/ml, $0.3 \times 10^6$ to $0.8 \times 10^6$ cells/ml, $0.4 \times 10^6$ to $0.7 \times 10^6$ cells/ml or $0.5 \times 10^6$ cells/ml. Factors promoting differentiation of immature dendritic cells to mature DCs may be one or more of GM-CSF, IL-4, IL-1β, IL-6, TNFα, PGE-1, CD40L, Poly (I:C), MPLA, Resiquimod, IFNα, IFNγ or AmpB In some embodiments the culture comprises IL-4 and GM-CSF. In some embodiments the culture comprises GM-CSF, IL-4, IL-1β, IL-6, TNFα and PGE-1. In some embodiments the culture comprises GM-CSF, IL-4, IL-1β, IL-6 and TNFα. In some embodiments the culture comprises GM-CSF, IL-4, IL-1β, IL-6, TNFα, PGE-1 and CD40L. In some embodiments the culture comprises GM-CSF, IL-4, IL-1β, IL-6, TNFα and CD40L. In some embodiments the culture comprises GM-CSF, IL-4, IL-1β, IL-6, TNFα, PGE-1 and Poly (I:C). In some embodiments the culture comprises GM-CSF, IL-4, IL-1β, IL-6, TNFα and Poly (I:C). In some embodiments the culture comprises GM-CSF, IL-4, IL-1β, IL-6, TNFα, PGE-1 and MPLA. In some embodiments the culture comprises GM-CSF, IL-4, IL-1β, IL-6, TNFα and MPLA. In some embodiments the culture comprises GM-CSF, IL-4, IL-1β, IL-6, TNFα, PGE-1 and Resiquimod. In some embodiments the culture comprises GM-CSF, IL-4, IL-1β, IL-6, TNFα and Resiquimod. In some embodiments the culture comprises GM-CSF, IL-4, IL-1β, IL-6, TNFα, PGE-1 and IFNα. In some embodiments the culture comprises GM-CSF, IL-4, IL-1β, IL-6, TNFα and IFNα. In some embodiments the culture comprises GM-CSF, IL-4, IL-1β, IL-6, TNFα, PGE-1 and IFNγ. In some embodiments the culture comprises GM-CSF, IL-4, IL-1β, IL-6, TNFα and IFNγ. In some embodiments the culture comprises GM-CSF, IL-4, IL-1β, IL-6, TNFα, PGE-1, IFNα and IFNγ. In some embodiments the culture comprises GM-CSF, IL-4, IL-1β, IL-6, TNFα, IFNα and IFNγ. In some embodiments the culture comprises GM-CSF, IL-4, IL-1β, IL-6, TNFα, PGE-1, Poly (I:C) and MPLA. In some embodiments the culture comprises GM-CSF, IL-4, IL-1β, IL-6, TNFα, Poly (I:C) and MPLA. In some embodiments the culture comprises GM-CSF, IL-4, MPLA and IFNγ. In some embodiments the culture comprises GM-CSF and IFNα. In some embodiments the culture comprises GM-CSF, IL-4, IFNγ and AmpB. The IL-4 may be present in the culture at a final concentration of one of 50-1000 IU/ml, 100-800 IU/ml, 150-700 IU/ml, 200-600 IU/ml, 250-500 IU/ml, 300-500 IU/ml or 400 IU/ml. The GM-CSF may be present in the culture at a final concentration of one of 100-1500 IU/ml, 200-1400 IU/ml, 300-1300 IU/ml, 400-1200 IU/ml, 500-1100 IU/ml, 600-1000 IU/ml, 700-900 IU/ml or 800 IU/ml. The IL-1β may be present in the culture at a final concentration of one of 1-100 pg/ml, 1-75 pg/ml, 5-50 pg/ml, 5-40 pg/ml, 5-30 pg/ml, 5-25 pg/ml, 5-20 pg/ml, 5-15 pg/ml or 10 pg/ml. The IL-6 may be present in the culture at a final concentration of one of 10-1000 pg/ml, 10-750 pg/ml, 50-500 pg/ml, 50-400 pg/ml, 50-300 pg/ml, 50-250 pg/ml, 50-200 pg/ml, 50-150 pg/ml or 100 pg/ml. The TNFα may be present in the culture at a final concentration of one of 1-100 pg/ml, 1-75 pg/ml, 5-50 pg/ml, 5-40 pg/ml, 5-30 pg/ml, 5-25 pg/ml, 5-20 pg/ml, 5-15 pg/ml or 10 pg/ml. The PGE-1 may be present in the culture at a final concentration of one of 0.1-10 ng/ml, 0.1-7.5 ng/ml, 0.5-5 ng/ml, 0.5-4 ng/ml, 0.5-3 ng/ml, 0.5-2.5 ng/ml, 0.5-2 ng/ml, 0.5-1.5 ng/ml or 1 ng/ml. The CD40L may be present in the culture at a final concentration of one of 10-1000 pg/ml, 10-750 pg/ml, 50-500 pg/ml, 50-400 pg/ml, 50-300 pg/ml, 50-250 pg/ml, 50-200 pg/ml, 50-150 pg/ml or 100 pg/ml. The Poly (I:C) may be present in the culture at a final concentration of one of 0.1-10 μg/ml, 0.1-7.5 μg/ml, 0.5-5 μg/ml, 0.5-4 μg/ml, 0.5-3 μg/ml, 0.5-2.5 μg/ml, 0.5-2 μg/ml, 0.5-1.5 μg/ml or 1 μg/ml. The MPLA may be present in the culture at a final concentration of one of 0.1-10 μg/ml, 0.1-7.5 μg/ml, 0.5-5 μg/ml, 0.5-4 μg/ml, 0.5-3 μg/ml, 0.5-2.5 μg/ml, 0.5-2 μg/ml, 0.5-1.5 μg/ml or 1 μg/ml. The Resiquimod may be present in the culture at a final concentration of one of 0.1-10 μg/ml, 0.1-7.5 μg/ml, 0.5-5 pg/ml, 0.5-4 μg/ml, 0.5-3 μg/ml, 0.5-2.5 μg/ml, 0.5-2 μg/ml, 0.5-1.5 μg/ml or 1 μg/ml. The IFNα may be present in the culture at a final concentration of one of 10-1000 ng/ml, 10-750 ng/ml, 50-500 ng/ml, 50-400 ng/ml, 50-300 ng/ml, 50-250 ng/ml, 50-200 ng/ml, 50-150 ng/ml or 100 ng/ml. The IFNγ may be present in the culture at a final concentration of one of 10-1000 ng/ml, 10-750 ng/ml, 50-500 ng/ml, 50-400 ng/ml, 50-300 ng/ml, 50-250 ng/ml, 50-200 ng/ml, 50-150 ng/ml or 100 ng/ml. The AmpB may be present in the culture at a final concentration of one of 0.1-10 μg/ml, 0.1-7.5 μg/ml, 0.5-5 μg/ml, 0.5-4 μg/ml, 0.5-3 μg/ml, 0.5-2.5 μg/ml, 0.5-2 μg/ml, 0.5-1.5 μg/ml or 1 μg/ml. The culture may be for any suitable period of time for differentiation of mature DCs, e.g. one of 6 hours to 5 days, 12 hours to 4 days, 12 hours to 72 hours, 12 hours to 48 hours, 12 hours to 36 hours, or 24 hours. In some embodiments the dendritic cells used in stimulations are obtained by a process comprising culturing immature DCs in the presence of GM-CSF, IL-4, IL-1β, IL-6, TNFα and CD40L. In some embodiments the dendritic cells used in stimulations are obtained by a process comprising culturing immature DCs in the presence of GM-CSF, IL-4, MPLA and IFNγ.

Dendritic cells obtained by culture according to the methods described herein may display higher surface expression of CD80 and/or CD83 as compared to dendritic cells obtained by culture according to methods disclosed in the prior art. Populations of dendritic cells obtained by culture according to the methods described herein may comprise a higher proportion of cells displaying surface expression of CD80 and/or CD83 as compared to populations of dendritic cells obtained by culture according to methods disclosed in the prior art.

Dendritic cells obtained by culture according to the methods described herein may be provided with advantageous properties relevant to their use as antigen-presenting cells (APCs) in methods for expanding HPV-specific immune cells. For example, the DCs may be useful to generate/expand populations of immune cells specific for HPV with improved efficiency (e.g. greater fold expansion within the same period of time). The DCs obtained by culture according to the methods described herein may be useful in methods for generating/expanding populations of immune cells specific for HPV comprising a reduced number/frequency of undesirable immune cell subsets (e.g. NK cells, regulatory T cells (Tregs) and/or naïve T cells), an increased proportion/frequency of desirable immune cell subsets (e.g. CD8+ T cells, CD8+ cytotoxic T lymphocytes, CD4+ T cells, CD4+ T helper cells, IFNγ-producing cells, memory T cells, central memory T cells, antigen-experienced T cells, CD45RO+ T cells), and/or an increased proportion/frequency of virus- and/or antigen-specific cells in the generated/expanded population, as compared to populations generated/expanded in accordance with prior art methods.

VIII. CD45RA+ Cell Depletion

In aspects of the present disclosure, populations of HPV-specific immune cells are generated/expanded from a population of cells (e.g. blood cells, immune cells or PBMCs) depleted of CD45RA+ cells (i.e. a CD45RA− cell population). In some embodiments the populations of HPV-specific immune cells are generated/expanded from a population of PBMCs depleted of CD45RA+ cells. In some embodiments the depletion of CD45RA+ cells may be achieved by separation of CD45RA− cells from other cells (i.e. CD45RA+ cells). Separation may be performed by appropriate positive or negative selection. In some embodiments, CD45RA− cells may be separated from CD45RA+ cells using beads coated with antibody capable of binding specifically to CD45RA. For example, CD45RA− cells may be separated from CD45RA+ cells by MACS cell separation using CD45RA MicroBeads (Miltenyi Biotec). In some embodiments the population of cells may additionally be depleted of CD14+ cells.

Depletion of CD45RA+ cells may remove NK cells, Tregs and/or naïve T cells, preventing substantial outgrowth of these cell types during stimulations according to the present disclosure. Depletion of CD45RA+ cells may also enrich the initial population of cells for CD45RO+ cells and/or antigen-experienced T cells, promoting preferential expansion of these desirable cell types in stimulations according to the present disclosure.

In some embodiments depletion of CD45RA+ cells is contemplated especially in methods employing IL-7 and IL-15 in one or more stimulations, and in particular where high concentrations of IL-15 are used (i.e. concentrations greater than 15 ng/ml, e.g. ~100 ng/ml), because such methods may be particularly susceptible to the problem of NK cell outgrowth. Depletion of CD45RA+ cells from the starting population of cells used in expansions is also contemplated in particular in methods employing K562cs costimulatory cells in methods for generating/expanding populations of HPV-specific immune cells, and/or methods in which HPV-specific immune cells are expanded from populations of immune cells (e.g. PBMCs) obtained from a patient, e.g. a patient having an HPV-associated disease.

Generation/expansion of populations of HPV-specific immune cells from within a population of cells (e.g. blood cells, immune cells or PBMCs) depleted of CD45RA+ cells may be provided with advantages over prior art methods for generating/expanding populations of HPV-specific immune cells. For example, the immune cell populations depleted of CD45RA+ cells may be useful to generate/expand populations of immune cells specific for HPV with improved efficiency (e.g. greater fold expansion within the same period of time) Immune cell populations depleted of CD45RA+ cells (e.g. PBMCs depleted of CD45RA+ cells) may be useful in methods for generating/expanding populations of immune cells specific for HPV comprising a reduced number/frequency of undesirable immune cell subsets (e.g. NK cells, regulatory T cells (Tregs) and/or naïve T cells), an increased proportion/frequency of desirable immune cell subsets (e.g. CD8+ T cells, CD8+ cytotoxic T lymphocytes, CD4+ T cells, CD4+ T helper cells, IFNγ-producing cells, memory T cells, central memory T cells, antigen-experienced T cells, CD45RO+ T cells), and/or an increased proportion/frequency of virus- and/or antigen-specific cells in the generated/expanded population, as compared to populations generated/expanded in accordance with prior art methods.

IX. Allogeneic and Autologous Applications

The methods disclosed herein are contemplated in the context of generating/expanding HPV-specific immune cells for use in both autologous and allogeneic applications, e.g. cellular immunotherapies. Populations of immune cells specific for HPV prepared in accordance with the methods disclosed herein may be used after their generation/expansion, or may be frozen for use at a later date.

In some embodiments the generated/expanded populations of immune cells specific for HPV are prepared for use in the subject from which the initial population of immune cells from which the population is generated/expanded was obtained/derived. In some embodiments the generated/expanded populations of immune cells specific for HPV are prepared for use with any subject, e.g. a different subject to the subject from which the initial population of immune cells from which the population is generated/expanded was obtained/derived.

Accordingly, in some embodiments the generated/expanded populations of immune cells specific for HPV are adoptively transferred to the subject from which the initial population of immune cells from which the population is generated/expanded was obtained/derived. In some embodiments the generated/expanded populations of immune cells specific for HPV are adoptively transferred to a different subject from the subject from which the initial population of immune cells from which the population is generated/expanded was obtained/derived.

EXAMPLES

The following examples are presented in order to more fully illustrate the preferred embodiments of the invention. They should in no way, however, be construed as limiting the broad scope of the invention.

Example 1

Production of Therapeutic T-Cells

In some embodiments of the disclosure, there is a mechanism by which one can rapidly generate a single preparation of T-cells, including polyclonal (for example, CD4+ and CD8+) CTLs, that are consistently specific for a variety of antigens derived from one or more human papillomaviruses that can prove fatal. The disclosure is readily adaptable to clinical implementation and can be used as an "off the shelf" HPV antiviral agent. The methods and compositions are readily adaptable to clinical implementation and are useful as a safe and effective HPV antiviral agent for individuals.

In specific embodiments, peripheral blood T-cells were stimulated with monocyte-derived dendritic cells loaded with pepmixes [peptide libraries of 15-mers overlapping by 11 amino acids (aa)] spanning E6/E7, in the presence or absence of specific accessory cytokines. The resulting T-cell lines were further expanded with pepmix-loaded activated B-cell blasts. There was successfully reactivation and expansion (>1200-fold) of E6-specific/E7-specific T-cells from 8/16 cervical and 33/52 oropharyngeal cancer patients.

The presence of the cytokines interleukin (IL)-6, IL-7, IL-12, and IL-15 is useful in the method, in specific embodiments of the methods. The produced T-cell lines possess the desirable characteristics of polyclonality, multiple T-cell subset representation (including the memory compartment) and a TH1 bias, and eliminate E6/E7 targets. The disclosure has shown that it is possible to robustly generate HPV16 E6/E7-directed T-cell lines from patients with HPV16-associated cancers. Because the technique is scalable and good-manufacturing procedures-compliant, these lines are useful for adoptive cellular immunotherapy of patients with HPV16 cancers and may be applied to HPV18 cancers also.

Figure 1B:
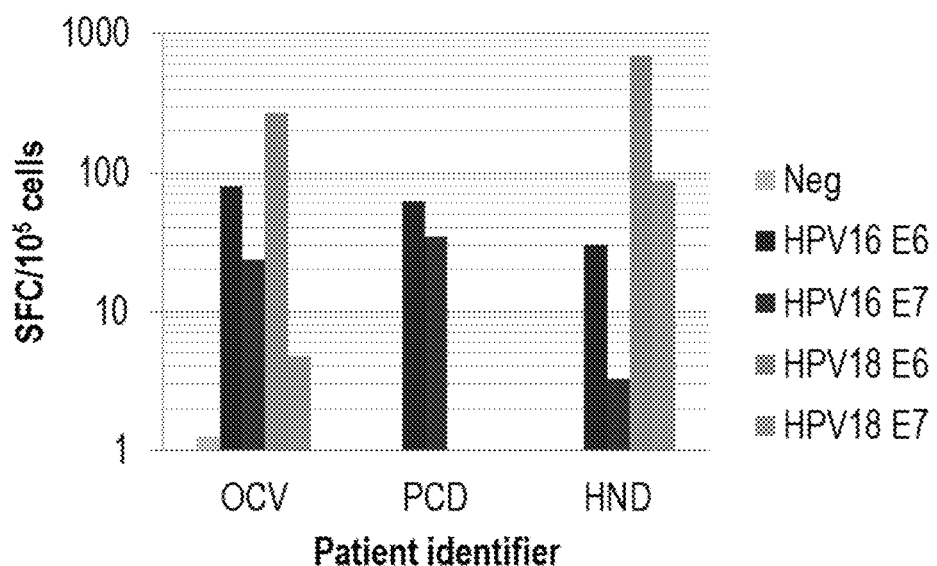
FIG. 1B demonstrates a method of the disclosure that utilizes, under certain novel conditions, the production of a mixture of T-cells specific for HPV16 or HPV18 by stimulation of T-cells in the presence of IL-7 and IL-15 and in the absence of IL-6 and IL-12.

Known methods for producing T-cells for HPV16 are demonstrated in FIG. 1A, showing results for 3 HPV-associated cancer patients (γIFN ELISpot assay obtained in cell lines obtained after stimulation of PBMCs by DCs loaded with only HPV16-pepmix). In FIG. 1B, results are shown for 2 of the patients whose results are also demonstrated in FIG. 1A, in addition to a third individual. FIG. 1B shows results of γIFN ELISpot assay for cell lines obtained after stimulation of PBMCs by DCs loaded with HPV16-pepmix and HPV18-pepmix. Reactivity against both HPV16 and HPV18 antigens can be detected (not all patients will have reactivity against both serotypes).

Turning to specifics of the methods, in certain cases DCs are loaded with HPV16-E6/E7 and HPV18-E6/E7 pepmix libraries. In such cases, the cell lines are able to recognize both HPV16 and HPV18 E6 and E7 antigens (instead of only HPV16 antigens, for example). In at least certain cases, expansion of the T-cells occurs in the presence of IL-7 and IL-15 but not IL-2. The presence of IL-7 and IL-15 in conditions for the method may or may not be at each step of stimulation and expansion. In some embodiments, expansion of the HPV-specific T-cells after initial generation/expansion with DCs occurs not with autologous B-blasts loaded with pepmixes in the presence of IL-15 but instead utilizes autologous, polyclonal activated T-cells loaded with pepmix, in the presence of costimulatory cells (CD80/CD86/CD83/4-1BBL), and IL-7 and IL-15. Employing these conditions, T-cell expansion occurs at a more rapid rate, at least 10-fold as that obtained by known methods, with successful demonstration having occurred after 3 rounds of stimulation and without loss of specificity.

Summary of fold cellular expansion using the known method with 3 HPV-associated cancer patients is provided in Table 2.

TABLE 2

Fold expansion at the end of each stimulation with known method

| Patient ID | After 1st stimulation (with DC and IL-2/15) | After 2nd stimulation (with DC and IL-2/15) | After 3rd stimulation (with B-blasts and IL-2/15) |
|---|---|---|---|
| OPA | 3.38 | 2.63 | 4.96 |
| OPE | 1.59 | 4.60 | 1.60 |
| OPY | 2.20 | 2.50 | 0.38 |

A summary of fold cellular expansion using a novel method of the disclosure with 3 HPV-associated cancer patients is shown in Table 3. Fold expansion after 3 rounds of stimulation is on average approximately 50 times higher than using a known method. Specificity is maintained (illustrated in #1).

TABLE 3

Fold expansion at the end of each stimulation with a method of the disclosure

| Patient ID | After 1st stimulation (with DC and IL-7/15) | After 2nd stimulation (with DC and IL-7/15) | After 3rd stimulation (with activated T-cells, costim cells and IL-7/15) |
|---|---|---|---|
| PDC | 2.60 | 5.35 | 151.20 |
| PGD | 5.00 | 6.36 | 120.00 |
| PJK | 3.58 | 5.53 | 60.00 |

Example 2

Protocol for the Expansion of HPV T-Cells

HPV stimulated T-cells (HPVST) are first activated by HPV E6/E7 peptide-pulsed autologous dendritic cells (DCs) at 10-20:1 PBMC:DC ratio, and cultured for 8 days in culture medium containing IL-6 (100 ng/ml), IL-7 (10 ng/ml), IL-12 (10 ng/ml), IL-15 (10 ng/ml) (e.g. per the first stimulation step described by Ramos et al., (J Immunother 2013;36:66-76)).

A second stimulation step on day 9 is carried out using peptide-pulsed DCs at 5-10:1 PBMC:DC ratio in media containing IL-7 (10 ng/ml) and IL-15 (100 ng/ml).

Subsequent weekly stimulation/expansion steps are then carried to achieve a desired number of HPVSTs out using HPV E6/E7 peptide-pulsed autologous T-APC at 1:1 ratio, in the presence of equal number of irradiated allogeneic K562-cs co-stimulatory cells, and in media containing IL-7 (10 ng/ml) and IL-15 (100 ng/ml). The polyclonal T cells (T-APCs) are generated using a portion of the autologous PBMC isolated from the venesected blood. The cells are activated by culturing in cell culture plates that are coated with anti-CD3 and anti-CD28 antibodies. The cells are then cultured to expand in the presence of IL-2 for 2 weeks. The expanded T-APC can be cryopreserved for later use. 2-3 days prior to using T-APC for HPVST re-stimulation (3rd cycle of HPVST re-stimulation and onward), cryopreserved cells are thawed and re-stimulated in anti-CD3 and anti-CD28 antibody-coated cell culture plates. On the day of HPVST re-stimulation, the T-APC cells are harvested and pulsed with the HPV E6/E7 peptides, followed by adding to the on-going culture of HPVST at 1:1 ratio.

Example 3

In Vivo Expansion and Persistence of Infused HPVSTs in Human Patients

HPVSTs obtained from Example 2 were transduced with a dominant negative receptor for TGF-beta (DNRII) [see Foster et al., Antitumor activity of EBV-specific T lymphocytes transduced with a dominant negative TGF-beta receptor. *J Immunother.* 2008; 31:500-505].

The HPVSTs were administered to two human patients and tested for in vivo expansion and persistence. Patient #1 had widely metastatic oropharyngeal cancer and had discontinued prior therapy. Patient #2 had oropharyngeal cancer metastatic to the neck and was receiving concomitant nivolumab treatment, without prior response to nivolumab alone.

In vivo expansion and persistence of infused HPVSTs was assessed by qPCR for the DNRII gene performed in PBMCs isolated from peripheral blood from the patient. Data points in FIGS. 2 and 3 represent critical post-infusion intervals after the infusion of HPVSTs.

Figure 2:
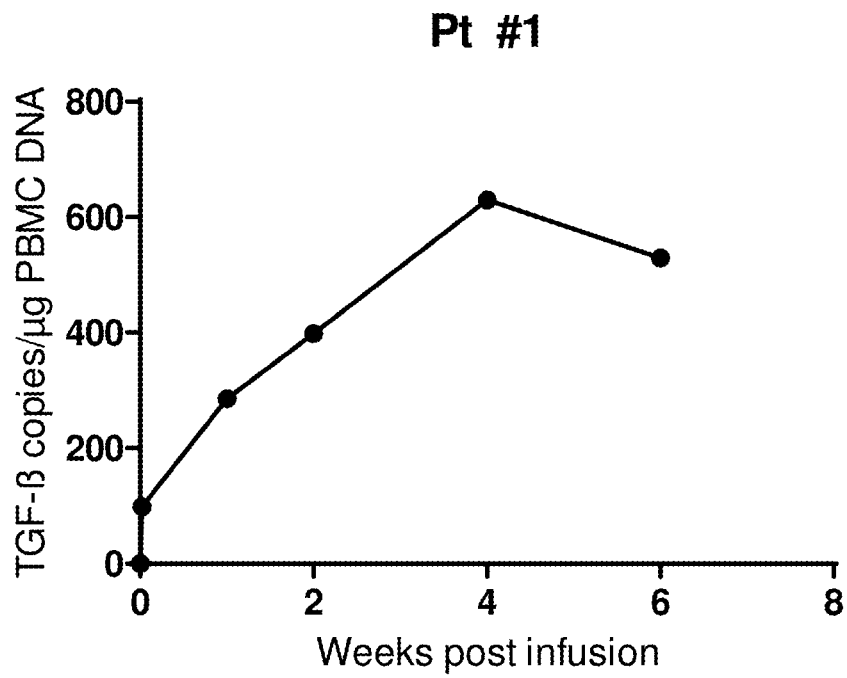
FIG. 2 is a chart showing in vivo expansion and persistence of infused HPV stimulated T-cells transduced with a dominant negative receptor for TGF-beta (DNRII) in patient #1 at time points post infusion.
Figure 3:
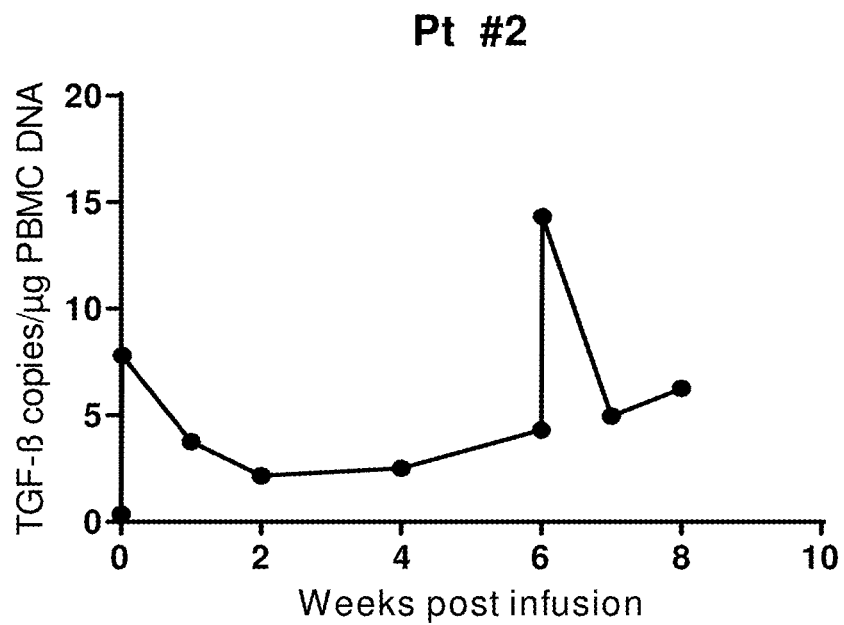
FIG. 3 is a chart showing in vivo expansion and persistence of infused HPV stimulated T cells transduced with a dominant negative receptor for TGF-beta (DNRII) in patient #2 at time points post infusion.
Figure 4:
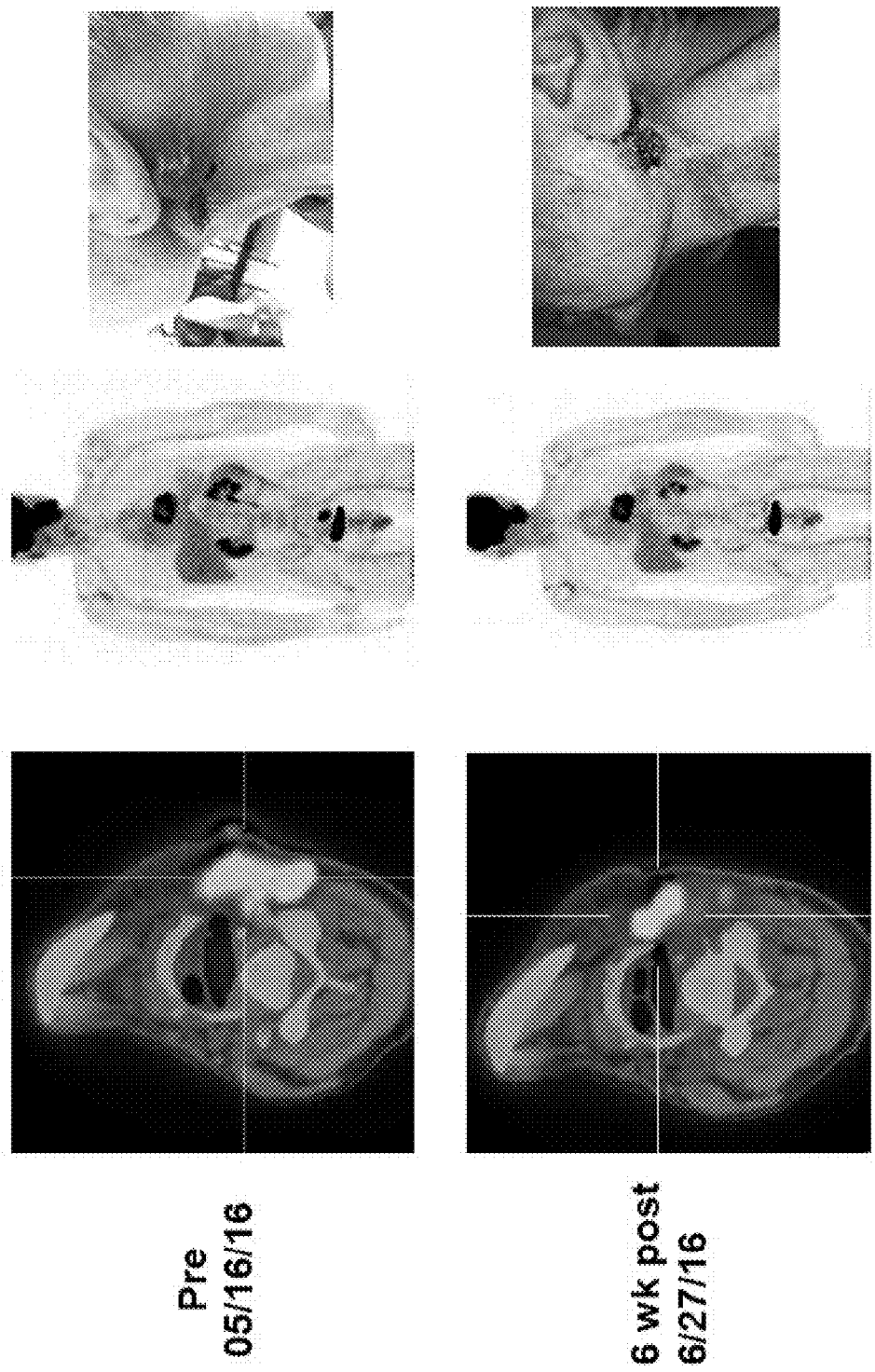
FIG. 4 shows PET scans (left and center) and photographs of physical examination (right) for patient #2. Top row: pre-treatment. Bottom row: 6 weeks after treatment with HPV stimulated T cells produced according to the present invention.

In patient #1 progressive expansion was observed (FIG. 2). In patient #2 although expansion was limited (FIG. 3), with a peak at 6 weeks coinciding with re-infusion of HPVSTs, the patient had a partial clinical response. Six weeks after HPVST infusion patient #2 exhibited a decrease in disease burden measured by PET scan and physical examination compared to a pre-treatment baseline (FIG. 4).

Example 4

Optimization of DC Maturation

Blood samples were collected from EBV-reactive donors in heparin vacutainers and PBMCs were isolated from the blood samples by Ficoll density gradient centrifugation. CD14 MicroBeads (Miltenyi Biotec) were then used to isolate CD14+ cells from within the PBMCs by positive selection. The number of cells was counted, and the CD14− cell population was frozen and stored. The CD14+ cells were then differentiated to immature dendritic cells (iDCs). Briefly, CD14+ cells were cultured in wells of a 24-well plate at a concentration of $0.5 \times 10^6$ cells/ml in DC cell culture medium containing 400 IU/ml IL-4 and 800 IU/ml GM-CSF, for 5 days.

The iDCs were then matured to mature DCs by culture for 24 hours in DC cell culture medium according to the conditions shown in one of 1 to 20 in Table 4 below:

TABLE 4

| | DC Maturation Culture Conditions |
|---|---|
| Condition No. | Conditions |
| 1 | 800 U/ml GM-CSF, 400 U/ml IL-4 |
| 2 | 800 U/ml GM-CSF, 400 U/ml IL-4, 10 pg/ml IL-1β, 100 pg/ml IL-6, 10 pg/ml TNFα, 1 ng/ml PGE-1 |
| 3 | 800 U/ml GM-CSF, 400 U/ml IL-4, 10 pg/ml IL-1β, 100 pg/ml IL-6, 10 pg/ml TNFα |
| 4 | 800 U/ml GM-CSF, 400 U/ml IL-4, 10 pg/ml IL-1β, 100 pg/ml IL-6, 10 pg/ml TNFα, 1 ng/ml PGE-1, 100 pg/ml CD40L |
| 5 | 800 U/ml GM-CSF, 400 U/ml IL-4, 10 pg/ml IL-1β, 100 pg/ml IL-6, 10 pg/ml TNFα, 100 pg/ml CD40L |
| 6 | 800 U/ml GM-CSF, 400 U/ml IL-4, 10 pg/ml IL-1β, 100 pg/ml IL-6, 10 pg/ml TNFα, 1 ng/ml PGE-1, 1 µg/ml Poly (I:C) |
| 7 | 800 U/ml GM-CSF, 400 U/ml IL-4, 10 pg/ml IL-1β, 100 pg/ml IL-6, 10 pg/ml TNFα, 1 µg/ml Poly (I:C) |
| 8 | 800 U/ml GM-CSF, 400 U/ml IL-4, 10 pg/ml IL-1β, 100 pg/ml IL-6, 10 pg/ml TNFα, 1 ng/ml PGE-1, 1 µg/ml MPLA |
| 9 | 800 U/ml GM-CSF, 400 U/ml IL-4, 10 pg/ml IL-1β, 100 pg/ml IL-6, 10 pg/ml TNFα, 1 µg/ml MPLA |
| 10 | 800 U/ml GM-CSF, 400 U/ml IL-4, 10 pg/ml IL-1β, 100 pg/ml IL-6, 10 pg/ml TNFα, 1 ng/ml PGE-1, 1 µg/ml Resiquimod |
| 11 | 800 U/ml GM-CSF, 400 U/ml IL-4, 10 pg/ml IL-1β, 100 pg/ml IL-6, 10 pg/ml TNFα, 1 µg/ml Resiquimod |
| 12 | 800 U/ml GM-CSF, 400 U/ml IL-4, 10 pg/ml IL-1β, 100 pg/ml IL-6, 10 pg/ml TNFα, 1 ng/ml PGE-1, 100 ng/ml IFNα |
| 13 | 800 U/ml GM-CSF, 400 U/ml IL-4, 10 pg/ml IL-1β, 100 pg/ml IL-6, 10 pg/ml TNFα, 100 ng/ml IFNα |
| 14 | 800 U/ml GM-CSF, 400 U/ml IL-4, 10 pg/ml IL-1β, 100 pg/ml IL-6, 10 pg/ml TNFα, 1 ng/ml PGE-1, 100 ng/ml IFNγ |
| 15 | 800 U/ml GM-CSF, 400 U/ml IL-4, 10 pg/ml IL-1β, 100 pg/ml IL-6, 10 pg/ml TNFα, 100 ng/ml IFNγ |
| 16 | 800 U/ml GM-CSF, 400 U/ml IL-4, 10 pg/ml IL-1β, 100 pg/ml IL-6, 10 pg/ml TNFα, 1 ng/ml PGE-1, 100 ng/ml IFNα, 100 ng/ml IFNγ |
| 17 | 800 U/ml GM-CSF, 400 U/ml IL-4, 10 pg/ml IL-1β, 100 pg/ml IL-6, 10 pg/ml TNFα, 100 ng/ml IFNα, 100 ng/ml IFNγ |
| 18 | 800 U/ml GM-CSF, 400 U/ml IL-4, 10 pg/ml IL-1β, 100 pg/ml IL-6, 10 pg/ml TNFα, 1 ng/ml PGE-1, 1 µg/ml Poly (I:C), 1 µg/ml MPLA |
| 19 | 800 U/ml GM-CSF, 400 U/ml IL-4, 10 pg/ml IL-1β, 100 pg/ml IL-6, 10 pg/ml TNFα, 1 µg/ml Poly (I:C), 1 µg/ml MPLA |
| 20 | 800 U/ml GM-CSF, 400 U/ml IL-4, 1 µg/ml MPLA, 100 ng/ml IFNγ |

The mature DCs were then analyzed by flow cytometry for expression of CD80, CD83, CCR7 and PD-L1. The previously frozen CD14− fraction was thawed and rested in cell culture medium for 24 hours.

Immature and mature DCs were then pulsed with individual EBV antigen pepmixes (LMP1, LMP2, BRAF1 or EBNA1), and the peptide-pulsed DCs were used to stimulate the autologous CD14− cells by coculture for 9 days in the presence of IL-7 (10 ng/ml) and IL-15 (100 ng/ml). The expanded T cell populations were then analyzed by flow cytometry for expression of CCR7, CD45RO, EBV peptide reactivity and intracellular staining for IFNγ.

Figure 5A:
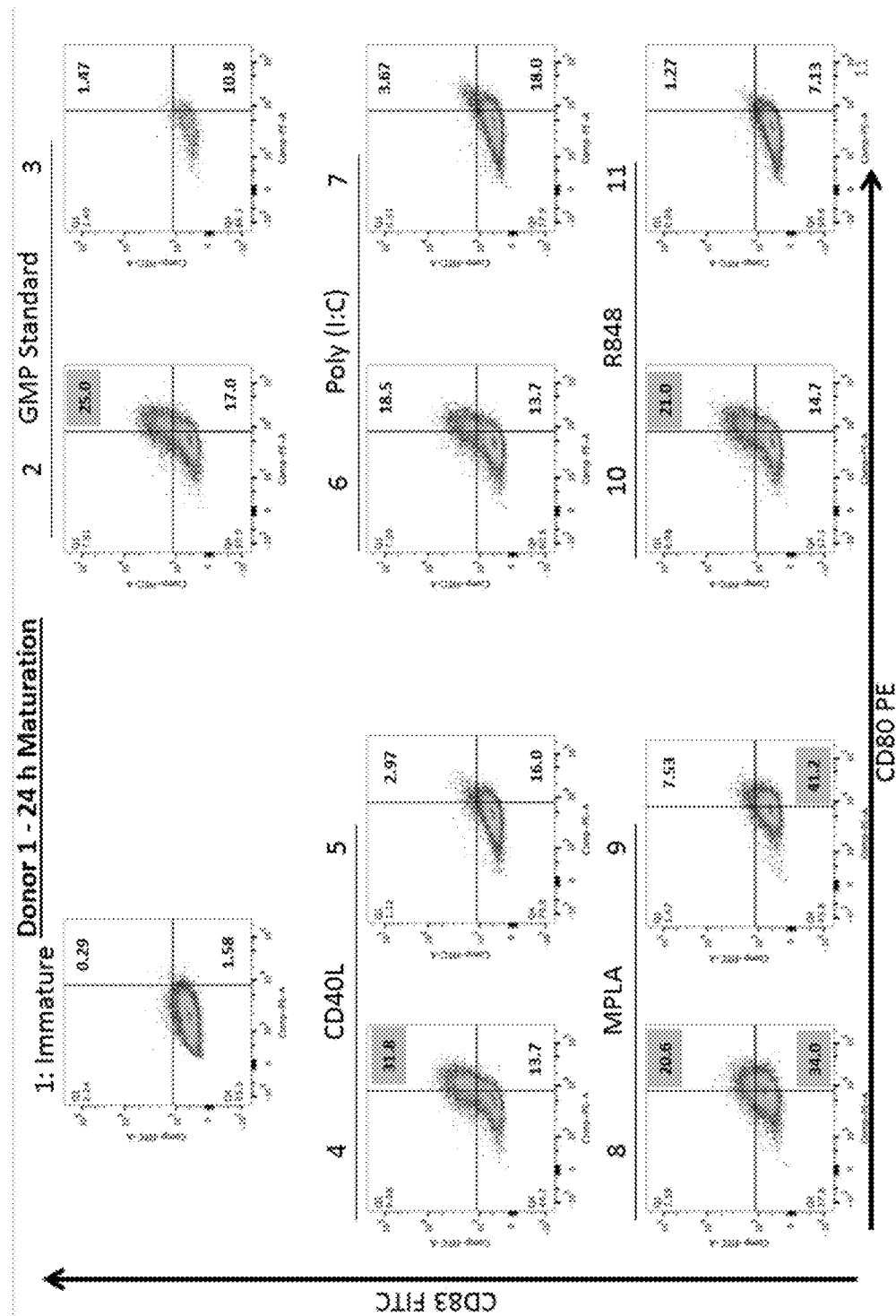
FIGS. 5A and 5B are scatterplots showing surface expression of (FIG. 5A) CD83 and CD80, and (FIG. 5B) CCR7 and PD-L1 expression by monocyte-derived DCs derived from Donor 1 CD14+ PBMCs following culture according to experimental conditions 1, 2, 3, 4, 5, 6, 7, 8, 9, 10 or 11 (see Table 4).
Figure 5B:
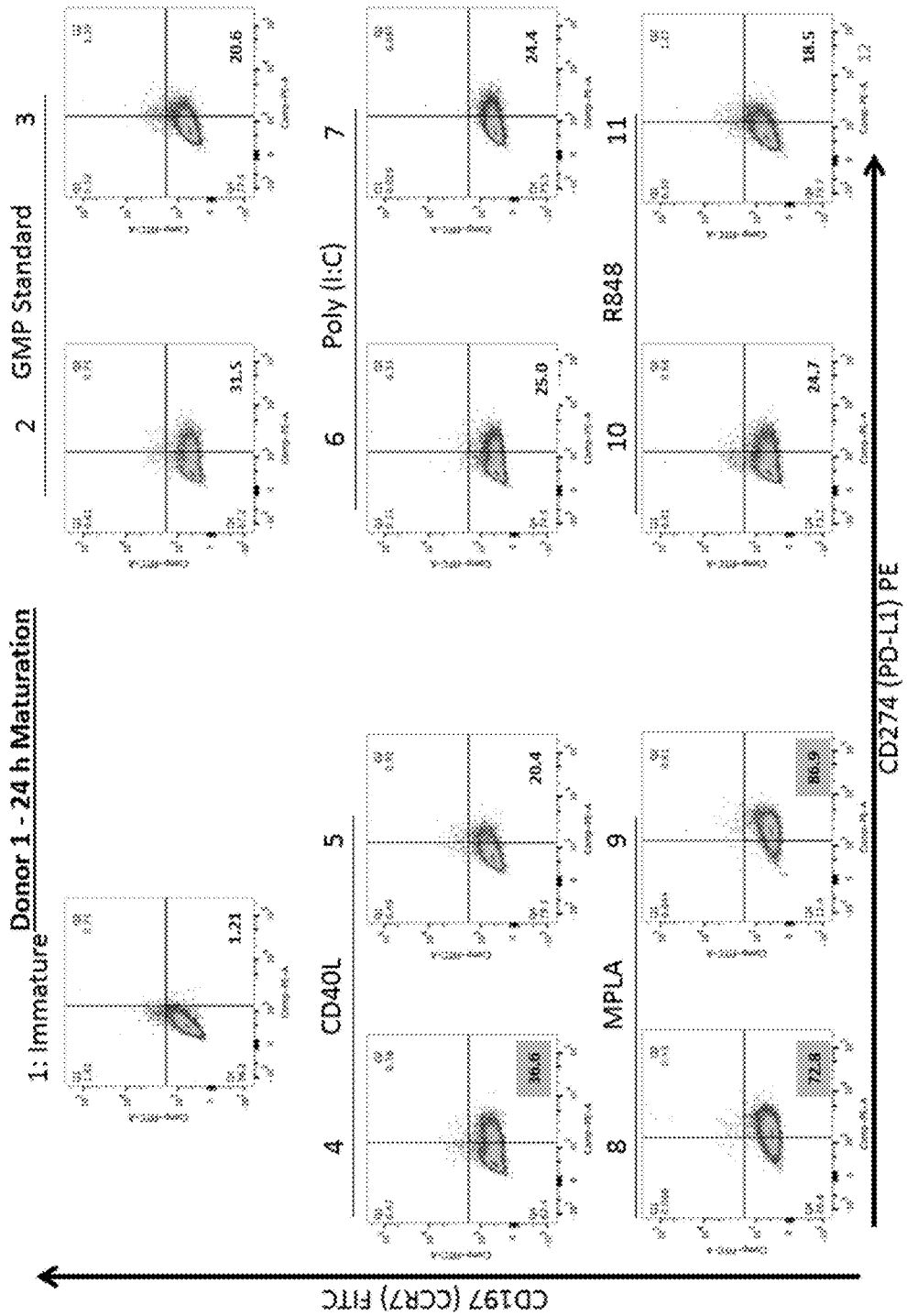

FIGS. 5A and 5B show CD83, CD80, CCR7 and PD-L1 expression by monocyte-derived DCs derived from Donor 1 CD14+ PBMCs following culture according to experimental conditions 1, 2, 3, 4, 5, 6, 7, 8, 9, 10 or 11 (see Table 4).

Figure 6A:
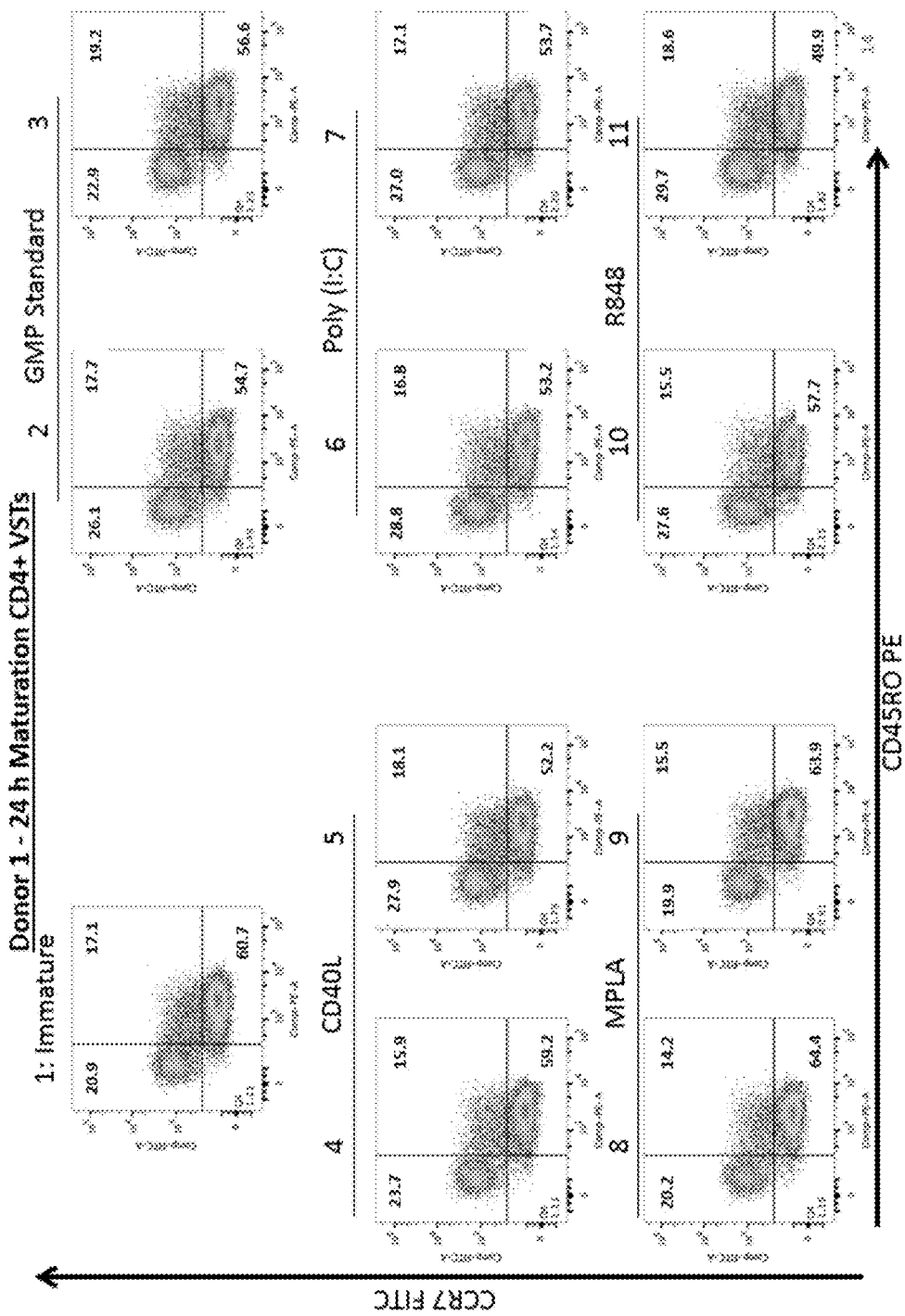
FIGS. 6A and 6B are scatterplots showing surface expression of CCR7 and CD4SRO by (FIG. 6A) CD4+ T cells, and (FIG. 6B) CD8+ T cells obtained following stimulation of autologous CD14− PBMCs derived from Donor 1 for 9 days with EBV peptide-pulsed mature DCs cultured according to experimental conditions 1, 2, 3, 4, 5, 6, 7, 8, 9, 10 or 11 (see Table 4).
Figure 6B:
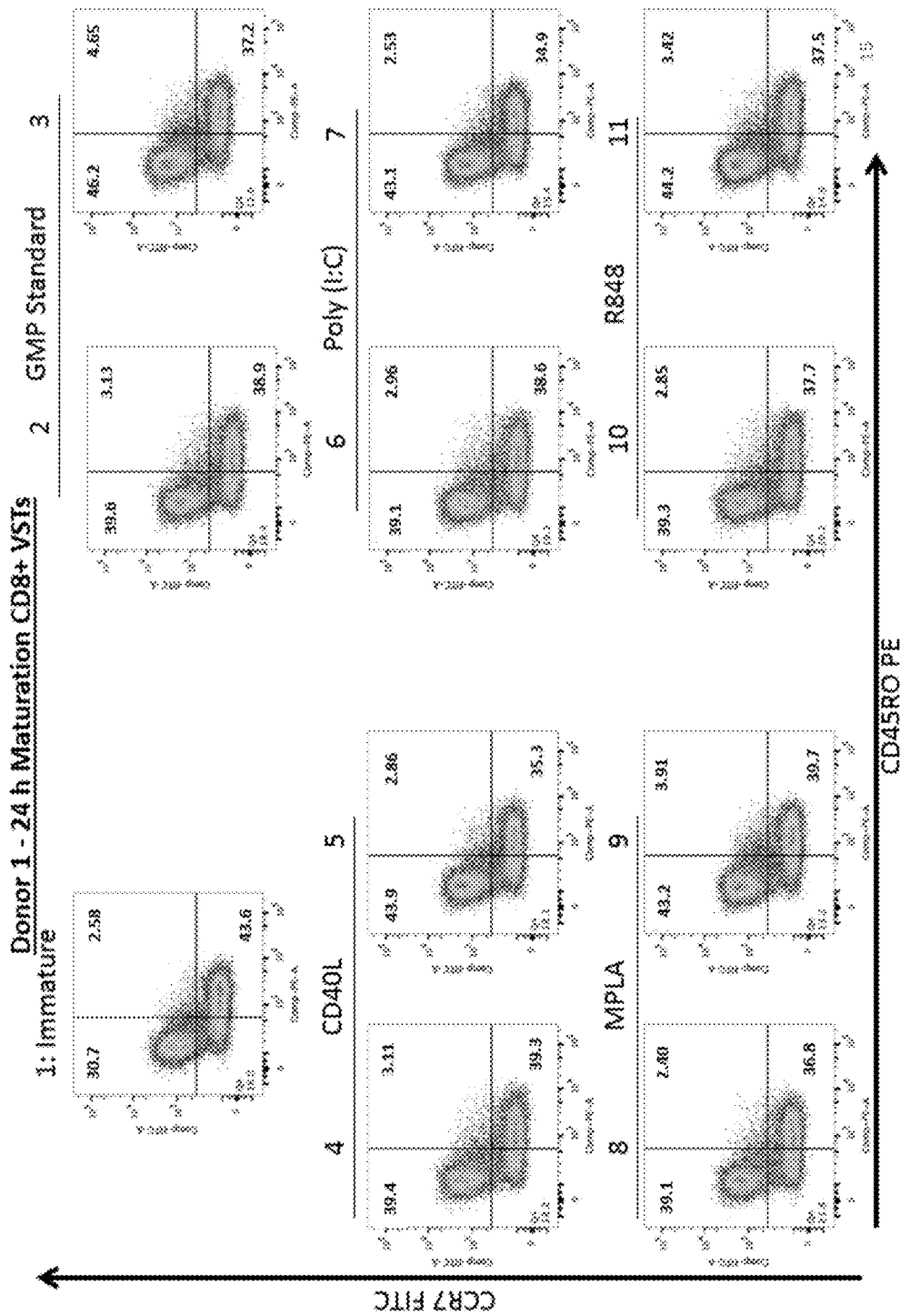

FIGS. 6A and 6B show CCR7 and CD45RO expression by CD4+ T cell and CD8+ T cells obtained following stimulation of autologous CD14− PBMCs derived from Donor 1 for 9 days with EBV peptide-pulsed mature DCs cultured according to experimental conditions 1, 2, 3, 4, 5, 6, 7, 8, 9, 10 or 11. No major differences in T cell memory phenotype were observed for the expanded T cell populations.

Figure 7:
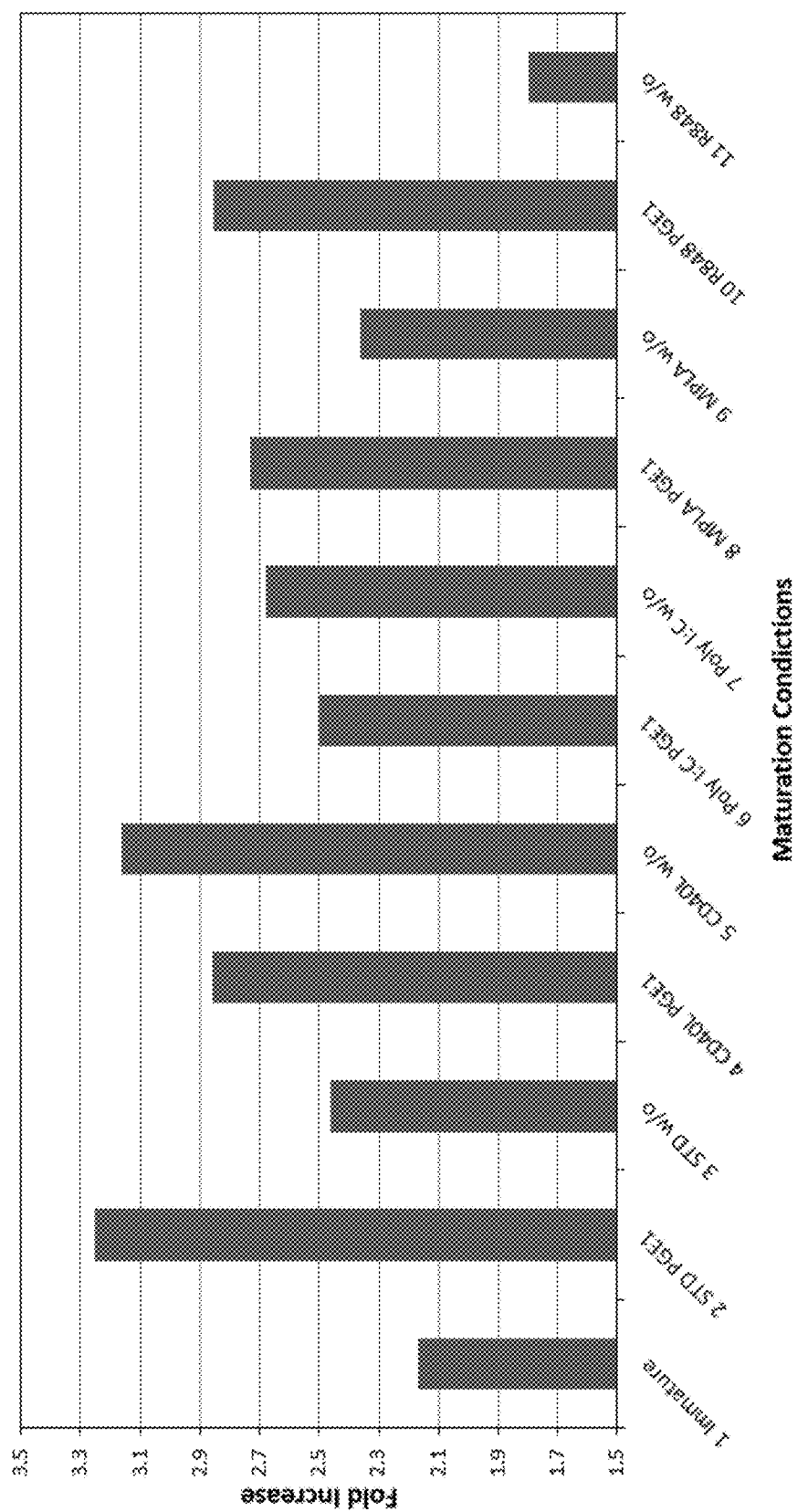
FIG. 7 is a bar chart showing the total number of virus-specific T cells obtained following stimulation of autologous CD14- PBMCs derived from Donor 1 for 9 days with EBV peptide-pulsed mature DCs cultured according to experimental conditions 1, 2, 3, 4, 5, 6, 7, 8, 9, 10 or 11 (see Table 4).

FIG. 7 shows the total number of virus-specific T cells obtained following stimulation of autologous CD14− PBMCs derived from Donor 1 for 9 days with EBV peptide-pulsed mature DCs cultured according to experimental conditions 1, 2, 3, 4, 5, 6, 7, 8, 9, 10 or 11.

Figure 8:
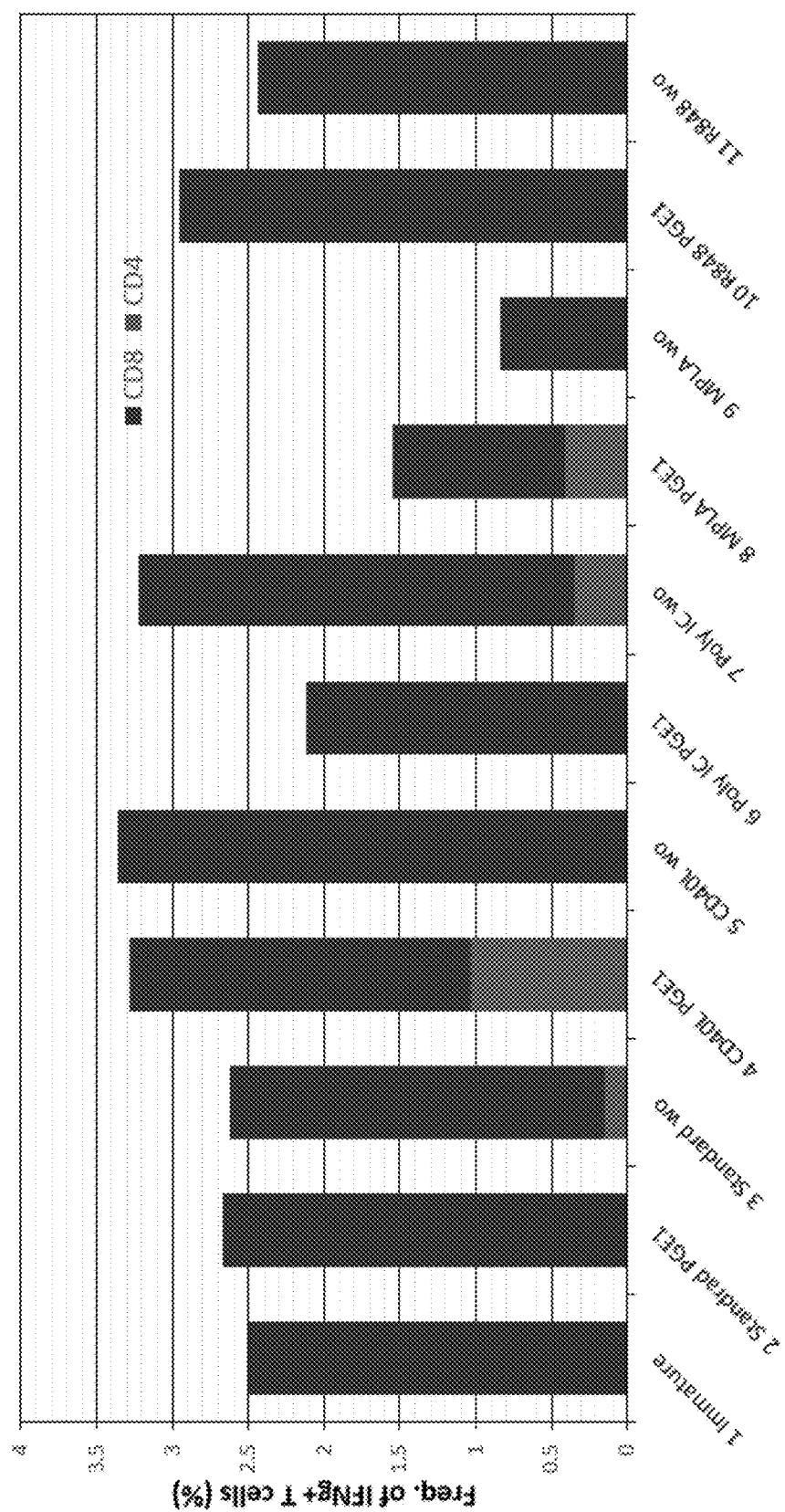
FIG. 8 is a bar chart shows the proportions of IFNγ+CD8+ CTLs and IFNγ+CD4+ Th cells (background subtracted) obtained following stimulation of autologous CD14− PBMCs derived from Donor 1 for 9 days with EBV peptide-pulsed mature DCs cultured according to experimental conditions 1, 2, 3, 4, 5, 6, 7, 8, 9, 10 or 11 (see Table 4).

FIG. 8 shows the proportions of IFNγ+CD8+ CTLs and IFNγ+CD4+ Th cells obtained following stimulation of autologous CD14− PBMCs derived from Donor 1 for 9 days with EBV peptide-pulsed mature DCs cultured according to experimental conditions 1, 2, 3, 4, 5, 6, 7, 8, 9, 10 or 11, as determined by ELISPOT analysis. Frequencies shown are subtracted for background signal obtained in control conditions performed in the absence of EBV peptide stimulation.

Figure 9:
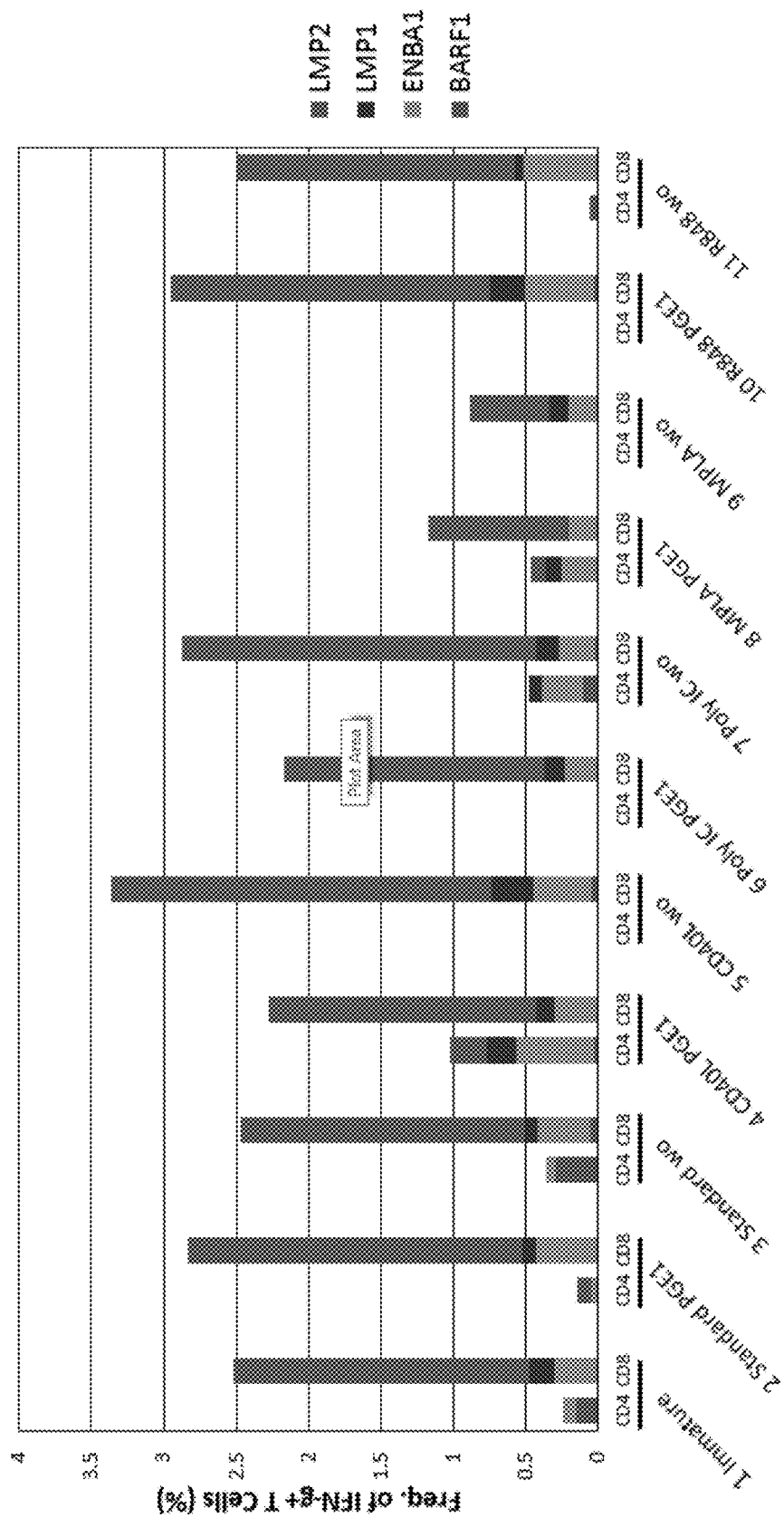
FIG. 9 is a bar chart showing the proportions of EBV antigen-reactive IFNγ+CD8+ CTLs and IFNγ+CD4+ Th cells (background subtracted) obtained following stimulation of autologous CD14− PBMCs derived from Donor 1 for 9 days with EBV peptide-pulsed mature DCs cultured according to experimental conditions 1, 2, 3, 4, 5, 6, 7, 8, 9, 10 or 11 (see Table 4).

FIG. 9 shows the proportions of EBV antigen-reactive IFNγ+CD8+ CTLs and IFNγ+CD4+ Th cells obtained following stimulation of autologous CD14− PBMCs derived from Donor 1 for 9 days with EBV peptide-pulsed mature DCs cultured according to experimental conditions 1, 2, 3, 4, 5, 6, 7, 8, 9, 10 or 11, as determined by ELISPOT analysis. Frequencies shown are subtracted for background signal obtained in control conditions performed in the absence of EBV peptide stimulation. Donor 1 was strongly responsive to LMP2.

Figure 10:
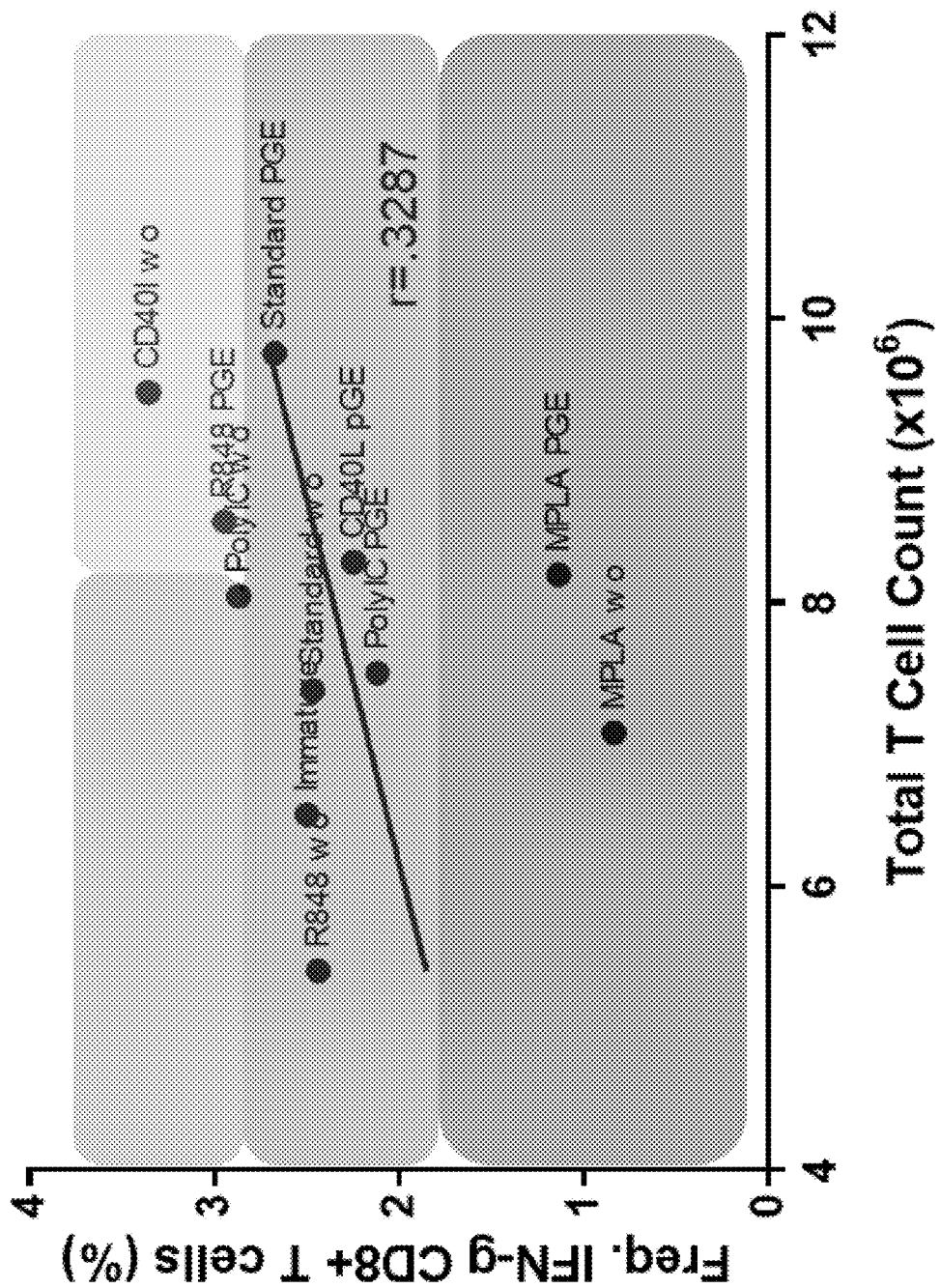
FIG. 10 is a graph showing the total number of virus-specific T cells plotted against the proportion of IFNγ+CD8+ CTLs obtained following stimulation of autologous CD14− PBMCs derived from Donor 1 for 9 days with EBV peptide-pulsed mature DCs cultured under different experimental conditions (see Table 4).

FIG. 10 shows the total number of virus-specific T cells and the proportion of IFNγ+CD8+ CTLs obtained following stimulation of autologous CD14− PBMCs derived from Donor 1 for 9 days with EBV peptide-pulsed mature DCs cultured under different experimental conditions. Condition number 5 ('CD40L wo') was identified as a promising candidate for further evaluation because it was shown to perform better than condition 2 ('Standard PGE').

Figure 11A:
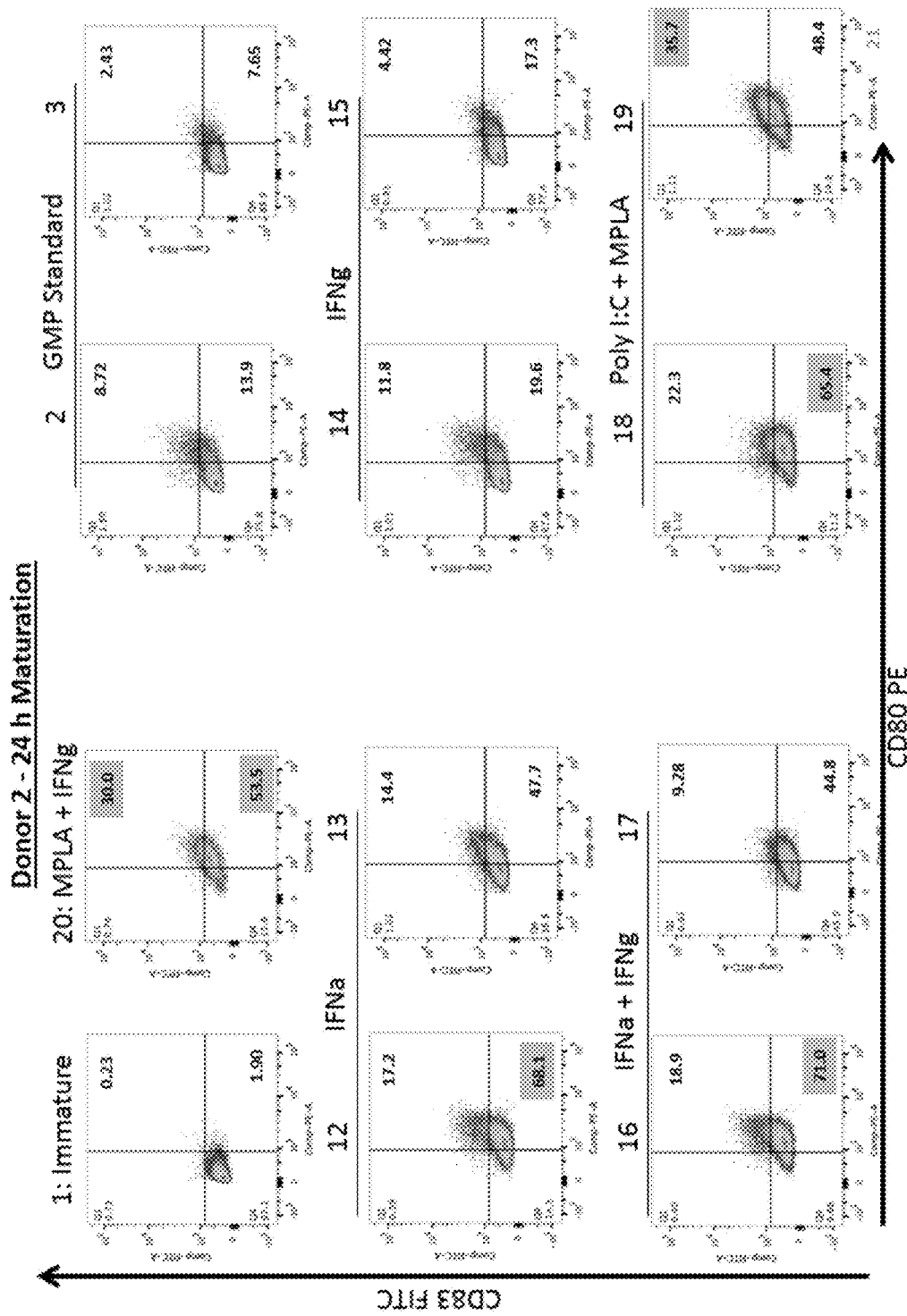
FIGS. 11A and 11B are scatterplots showing surface expression of (FIG. 11A) CD83 and CD80, and (FIG. 11B) CCR7 and PD-L1 expression by monocyte-derived DCs derived from Donor 2 CD14+ PBMCs following culture according to experimental conditions 1, 2, 3, 12, 13, 14, 15, 16, 17, 18, 19 or 20 (see Table 4).
Figure 11B:
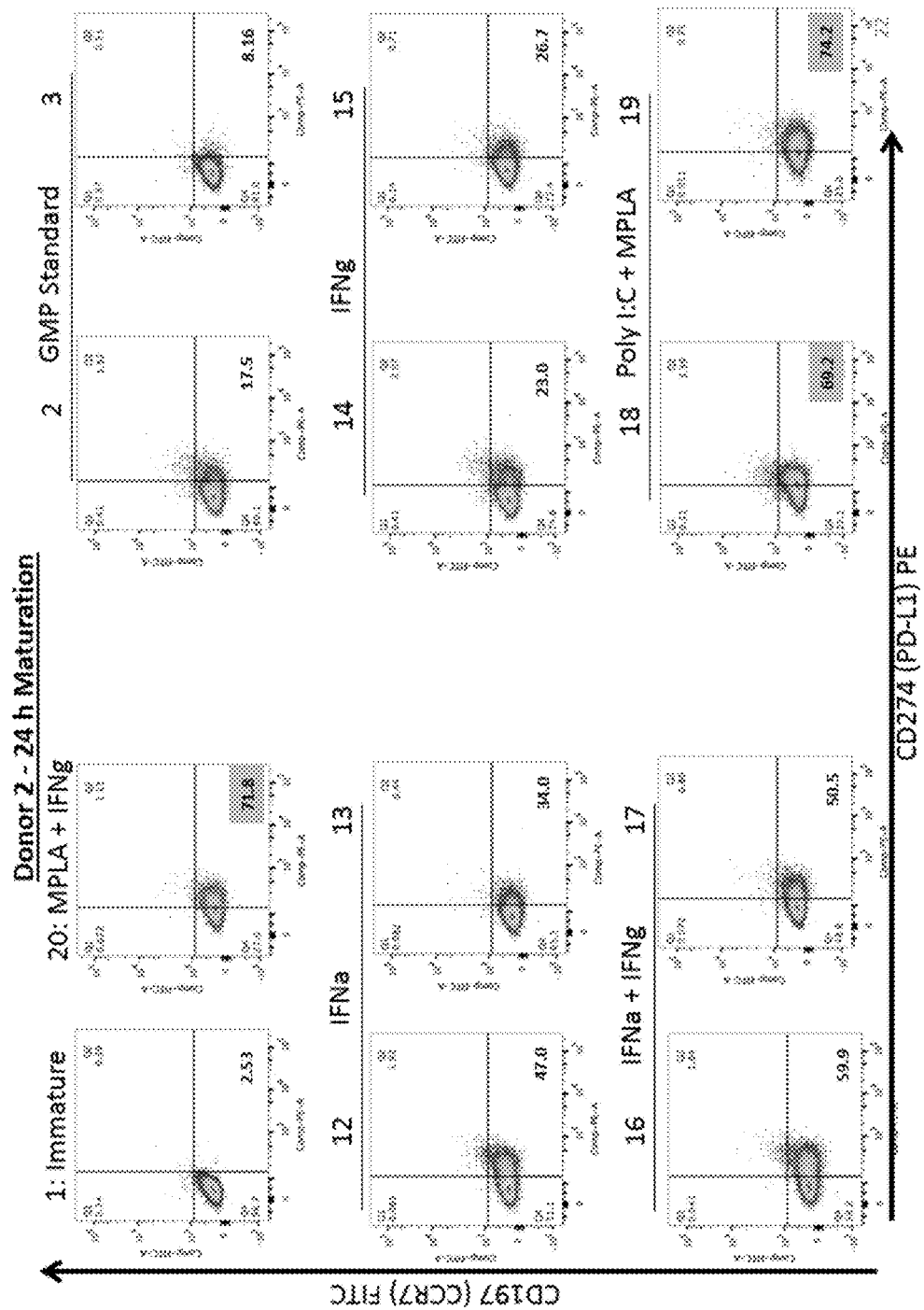

FIGS. 11A and 11B show CD83, CD80, CCR7 and PD-L1 expression by monocyte-derived DCs derived from Donor 2 CD14+ PBMCs following culture according to experimental conditions 1, 2, 3, 12, 13, 14, 15, 16, 17, 18, 19 or 20.

Figure 12A:
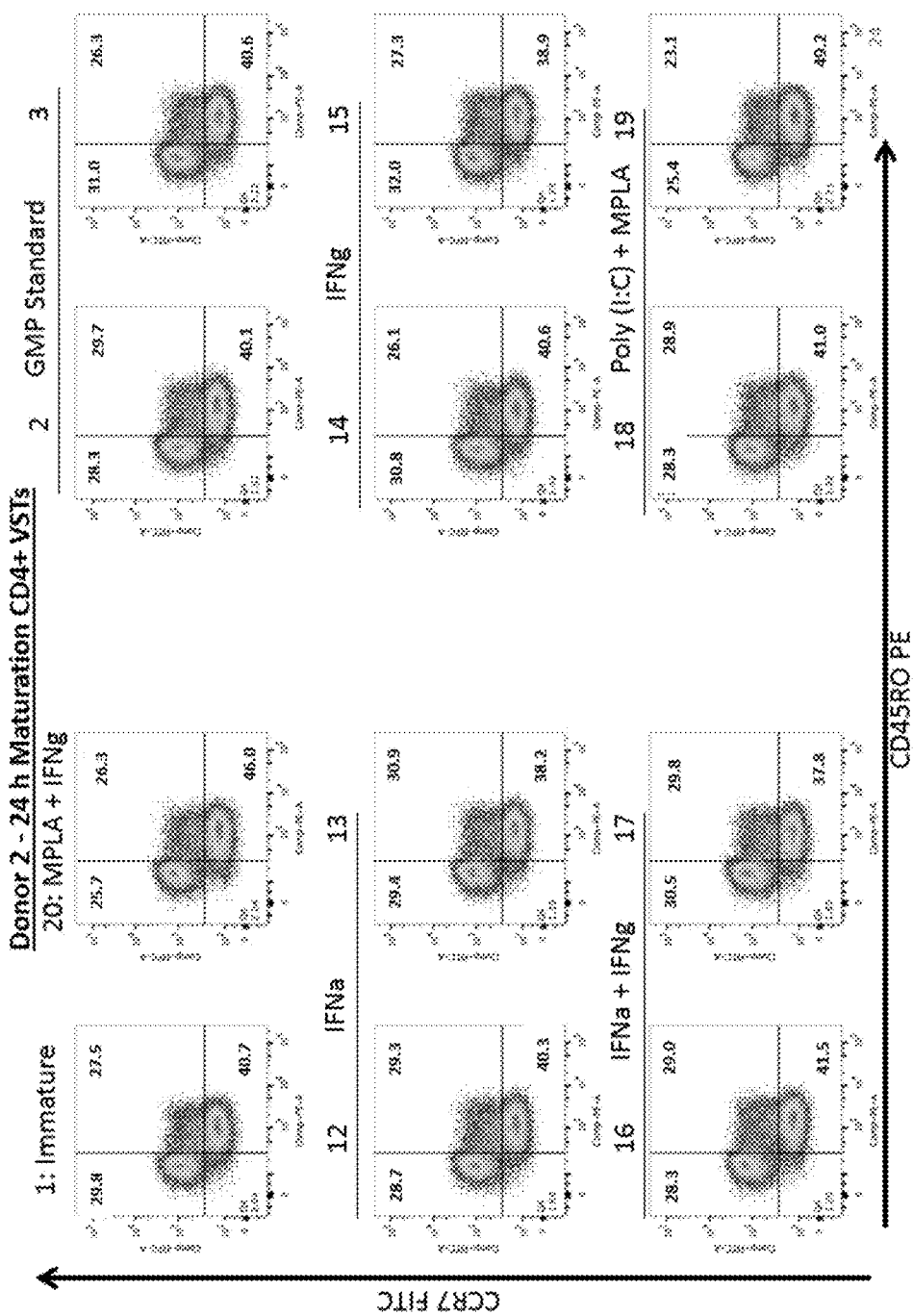
FIGS. 12A and 12B are scatterplots showing surface expression of CCR7 and CD45RO by (FIG. 12A) CD4+ T cells, and (FIG. 12B) CD8+ T cells obtained following stimulation of autologous CD14− PBMCs derived from Donor 2 for 9 days with EBV peptide-pulsed mature DCs cultured according to experimental conditions 1, 2, 3, 12, 13, 14, 15, 16, 17, 18, 19 or 20 (see Table 4).
Figure 12B:
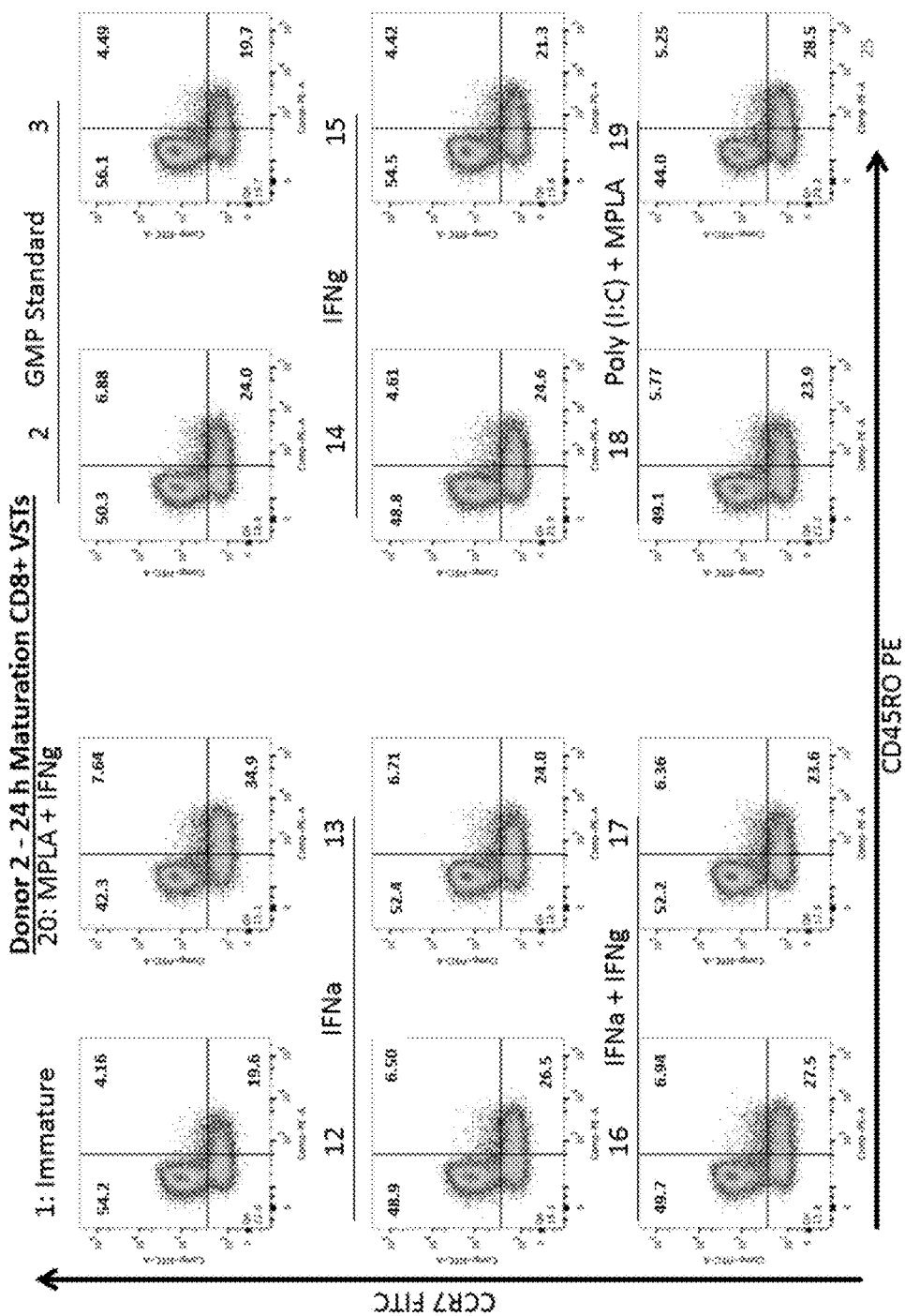

FIGS. 12A and 12B show CCR7 and CD45RO expression by CD4+ T cell and CD8+ T cells obtained following stimulation of autologous CD14− PBMCs derived from Donor 2 for 9 days with EBV peptide-pulsed mature DCs cultured according to experimental conditions 1, 2, 3, 12, 13, 14, 15, 16, 17, 18, 19 or 20. No major differences in T cell memory phenotype were observed for the expanded T cell populations.

Figure 13:
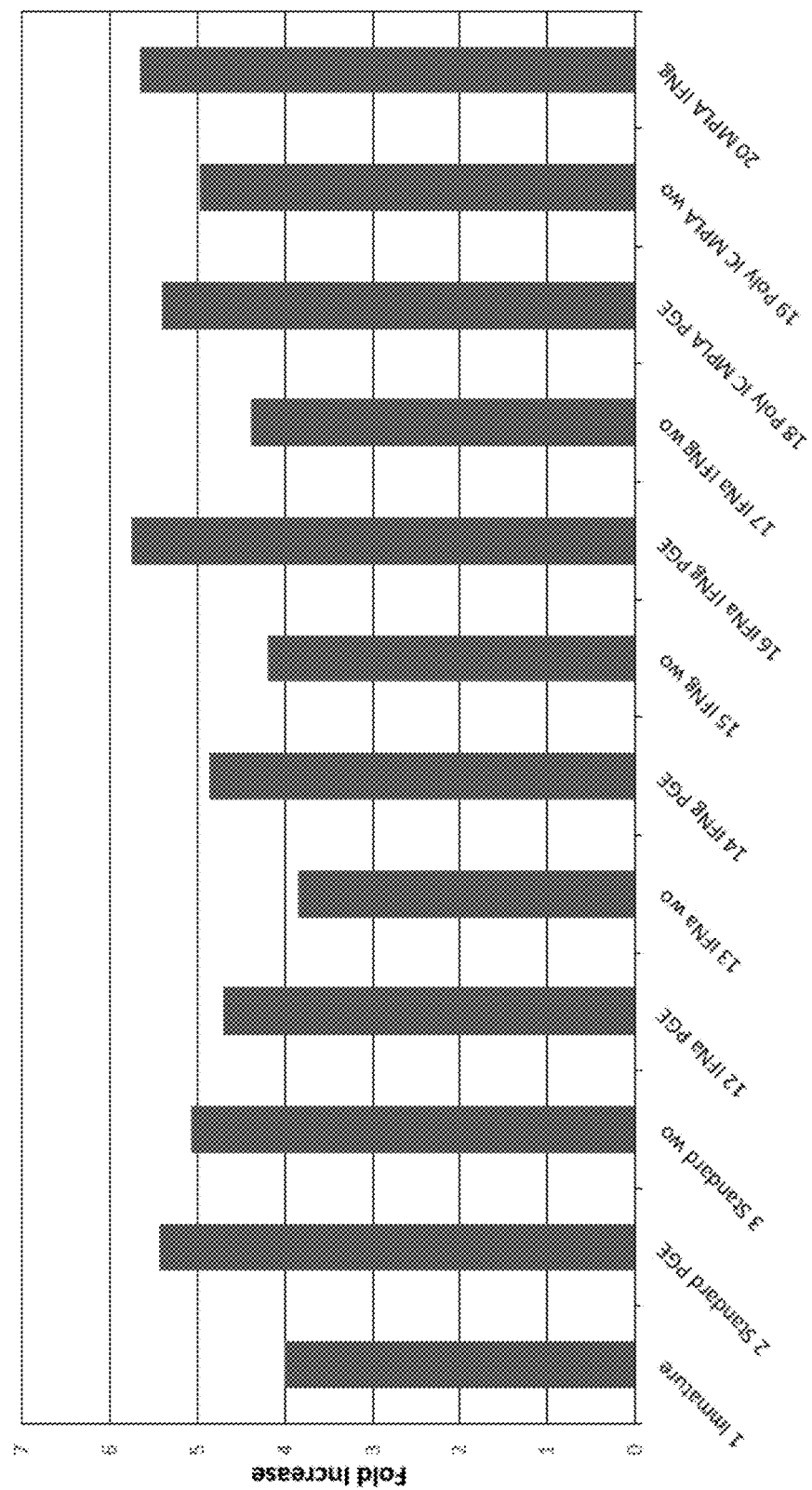
FIG. 13 is a bar chart showing the total number of virus-specific T cells obtained following stimulation of autologous CD14− PBMCs derived from Donor 2 for 9 days with EBV peptide-pulsed mature DCs cultured according to experimental conditions 1, 2, 3, 12, 13, 14, 15, 16, 17, 18, 19 or 20 (see Table 4).

FIG. 13 shows the total number of virus-specific T cells obtained following stimulation of autologous CD14− PBMCs derived from Donor 2 for 9 days with EBV peptide-pulsed mature DCs cultured according to experimental conditions 1, 2, 3, 12, 13, 14, 15, 16, 17, 18, 19 or 20.

Figure 14:
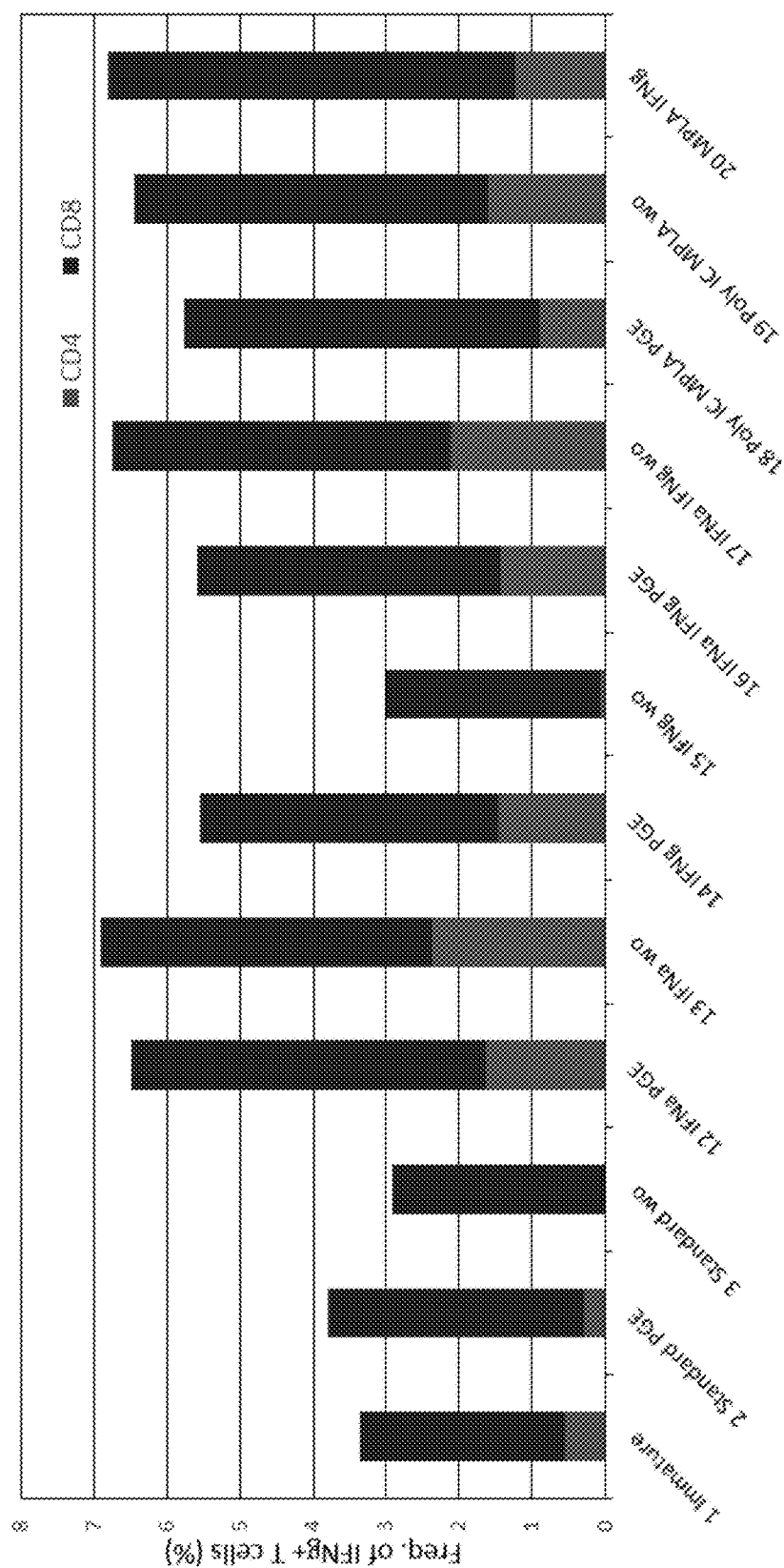
FIG. 14 is a bar chart shows the proportions of IFNγ+CD8+ CTLs and IFNγ+CD4+ Th cells (background subtracted) obtained following stimulation of autologous CD14− PBMCs derived from Donor 2 for 9 days with EBV peptide-pulsed mature DCs cultured according to experimental conditions 1, 2, 3, 12, 13, 14, 15, 16, 17, 18, 19 or 20 (see Table 4).

FIG. 14 shows the proportions of IFNγ+CD8+ CTLs and IFNγ+CD4+ Th cells obtained following stimulation of autologous CD14− PBMCs derived from Donor 2 for 9 days with EBV peptide-pulsed mature DCs cultured according to experimental conditions 1, 2, 3, 12, 13, 14, 15, 16, 17, 18, 19 or 20, as determined by ELISPOT analysis. Frequencies shown are subtracted for background signal obtained in control conditions performed in the absence of EBV peptide stimulation.

Figure 15:
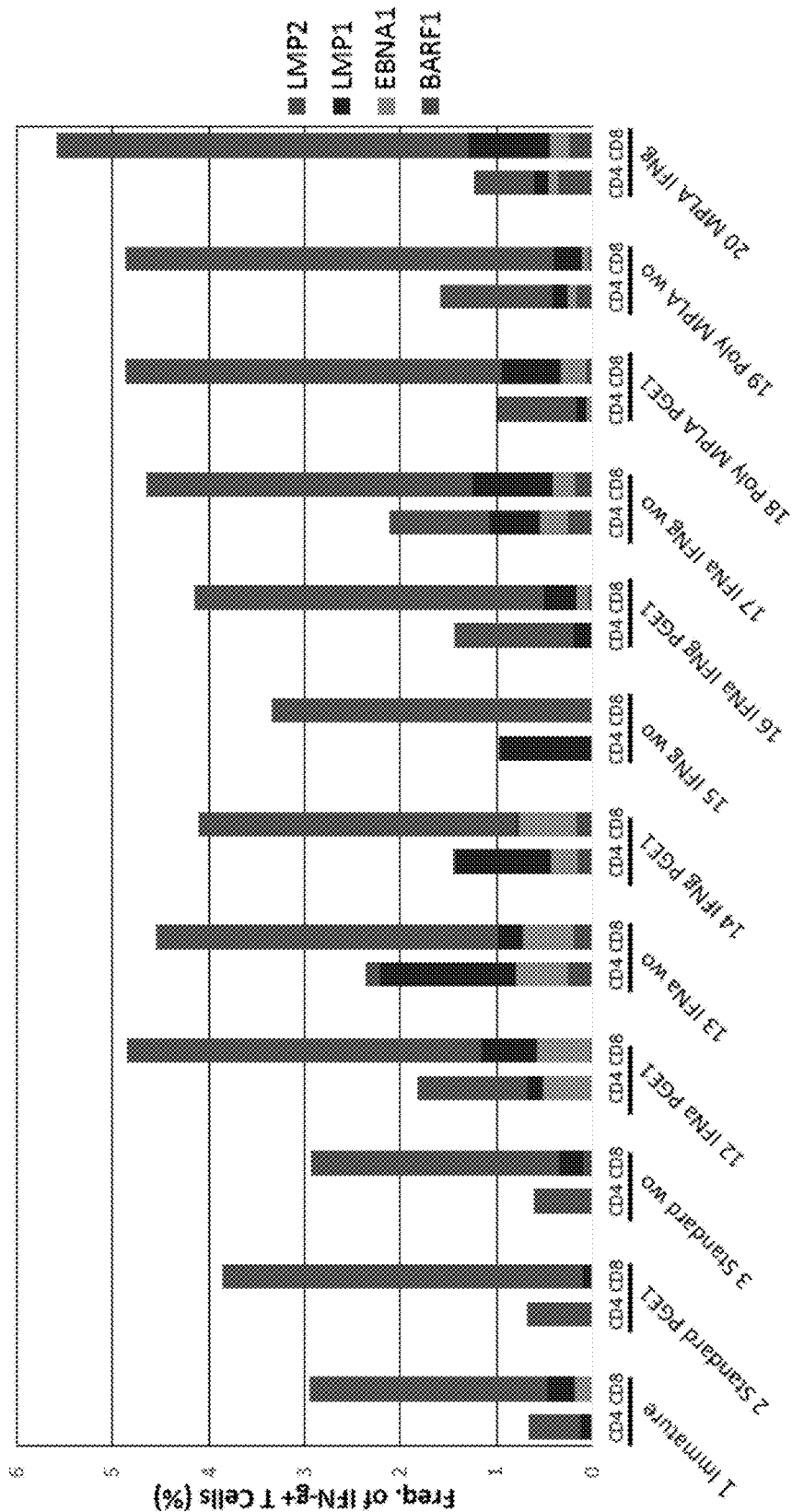
FIG. 15 is a bar chart showing the proportions of EBV antigen-reactive IFNγ+CD8+ CTLs and IFNγ+CD4+ Th cells (background subtracted) obtained following stimulation of autologous CD14− PBMCs derived from Donor 2 for 9 days with EBV peptide-pulsed mature DCs cultured according to experimental conditions 1, 2, 3, 12, 13, 14, 15, 16, 17, 18, 19 or 20 (see Table 4).

FIG. 15 shows the proportions of EBV antigen-reactive IFNγ+CD8+ CTLs and IFNγ+CD4+ Th cells obtained following stimulation of autologous CD14− PBMCs derived from Donor 2 for 9 days with EBV peptide-pulsed mature DCs cultured according to experimental conditions 1, 2, 3, 12, 13, 14, 15, 16, 17, 18, 19 or 20, as determined by ELISPOT analysis. Frequencies shown are subtracted for background signal obtained in control conditions performed in the absence of EBV peptide stimulation. Donor 2 was strongly responsive to LMP2.

Figure 16:
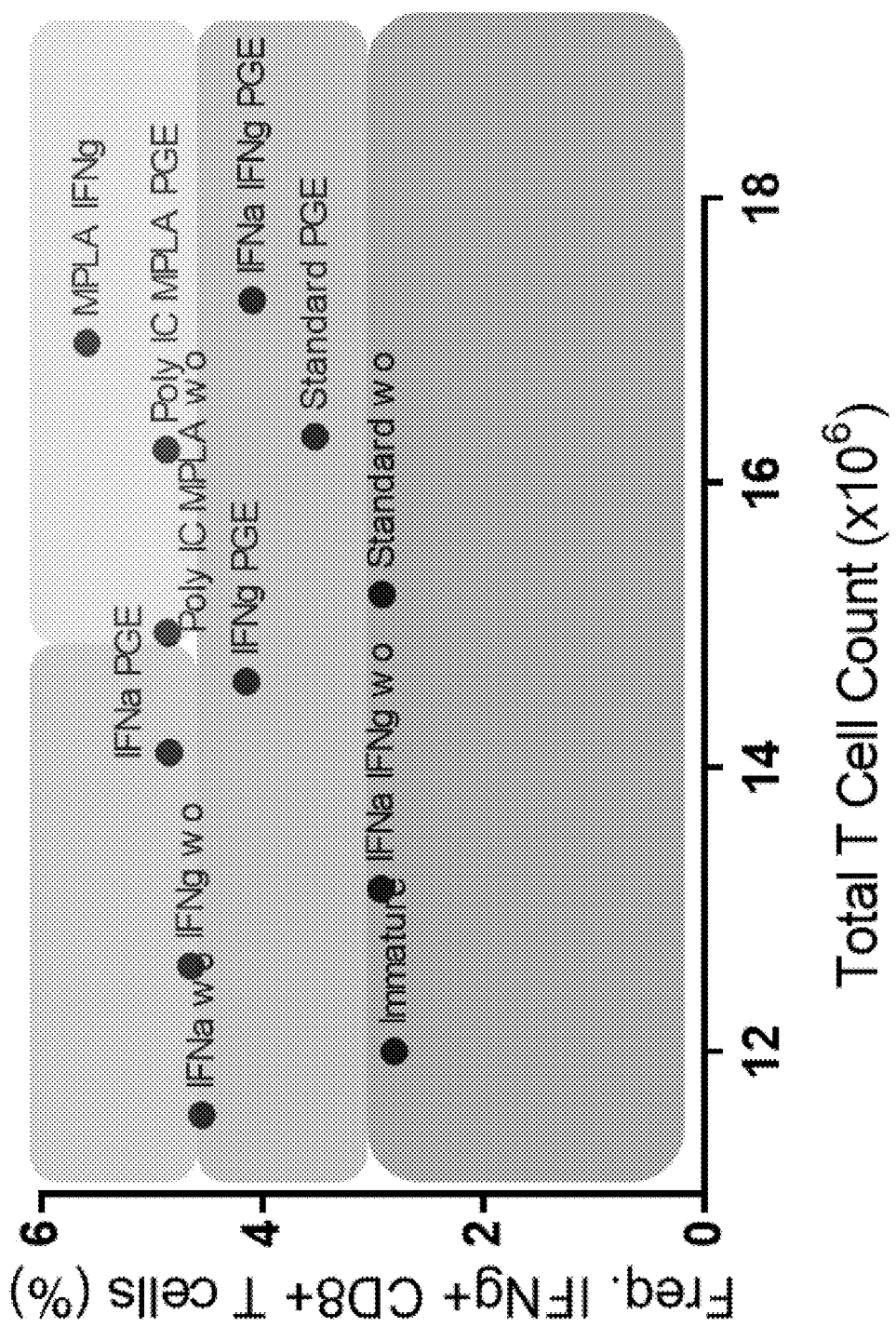
FIG. 16 is a graph showing the total number of virus-specific T cells plotted against the proportion of IFNγ+CD8+ CTLs obtained following stimulation of autologous CD14− PBMCs derived from Donor 2 for 9 days with EBV peptide-pulsed mature DCs cultured under different experimental conditions (see Table 4).

FIG. 16 shows the total number of virus-specific T cells and the proportion of IFNγ+CD8+ CTLs obtained following stimulation of autologous CD14− PBMCs derived from Donor 2 for 9 days with EBV peptide-pulsed mature DCs cultured under different experimental conditions. Condition numbers 18, 19 and 20 ('PolyIC MPLA wo', 'PolyIC MPLA PGE' and 'MPLA IFNγ') were identified as promising candidates for further evaluation as they were shown to perform better than condition 2 ('Standard PGE').

The inventors then undertook further investigation of the four most promising DC maturation conditions 5, 18, 19 and 20 (see Table 4), extending the characterization to cells derived from three different donors.

Figure 17A:
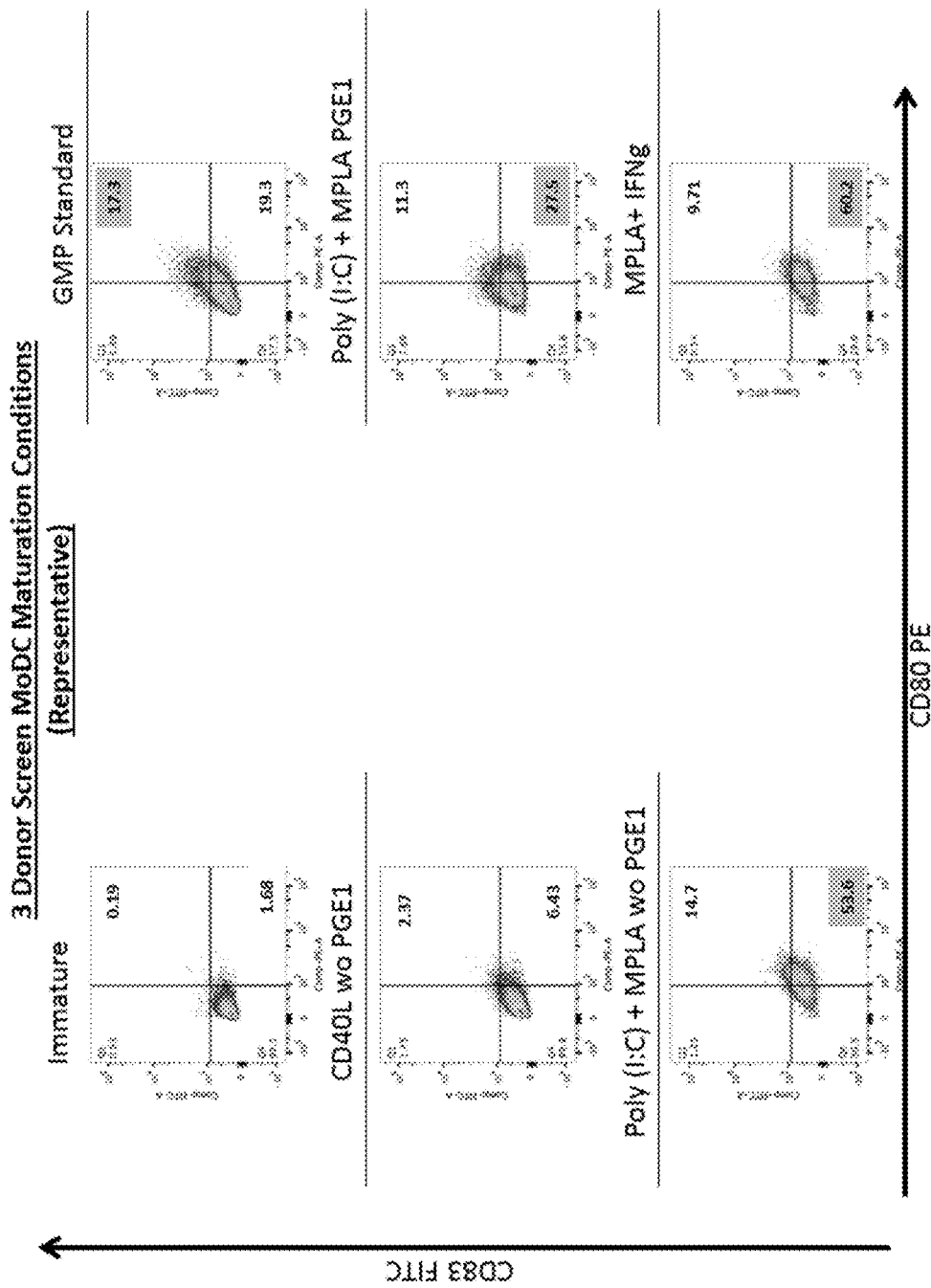
FIGS. 17A, 17B, 17C, 17D and 17E are scatterplots and bar charts showing surface expression of (FIGS. 17A) CD80 and CD83, and (FIG. 17B) CCR7 and PD-L1 by monocyte-derived DCs derived from three different donors following culture according to the experimental conditions 1, 2, 5, 18, 19 and 20 (see Table 4).
Figure 17B:
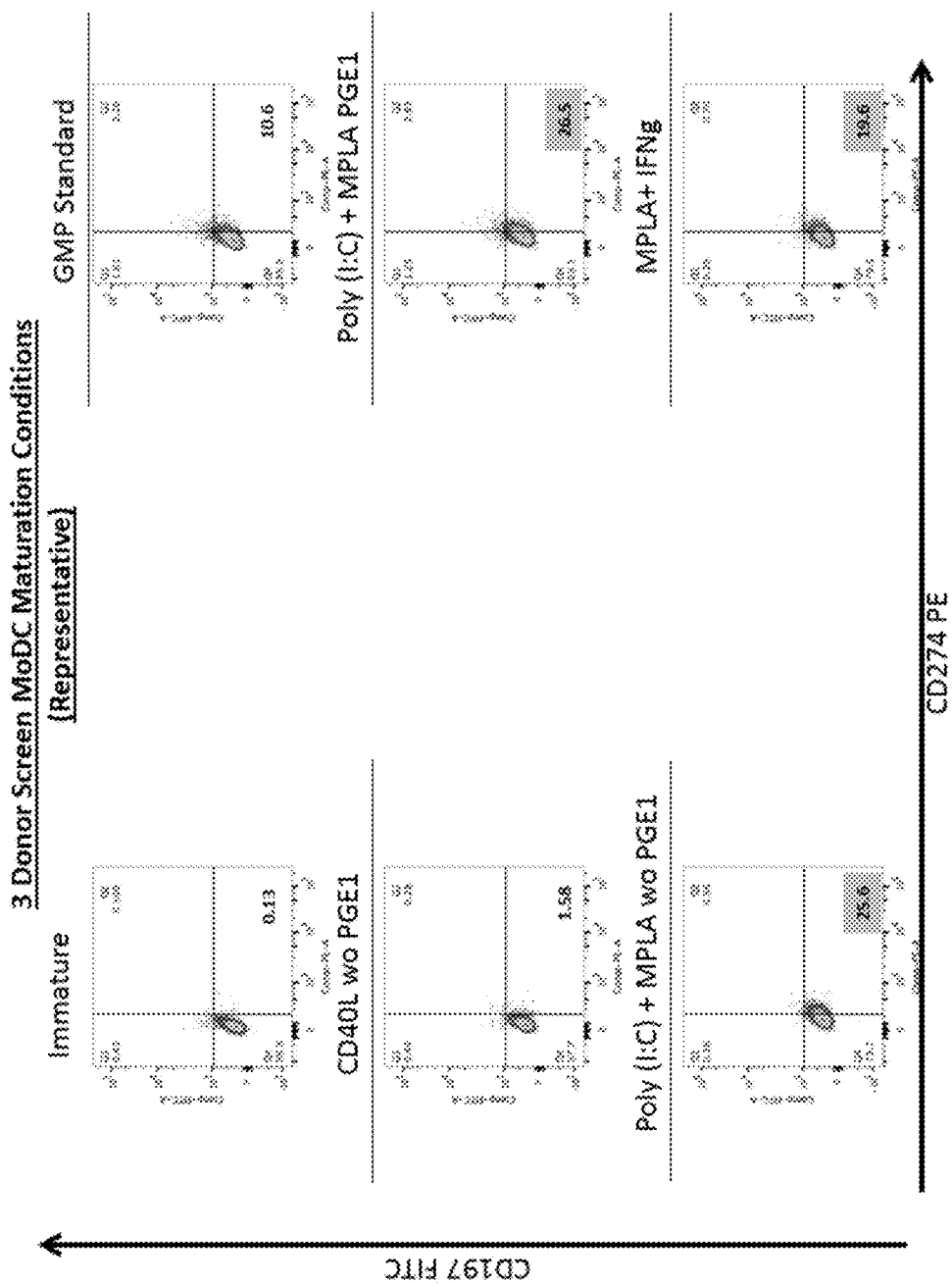
Figure 17C:
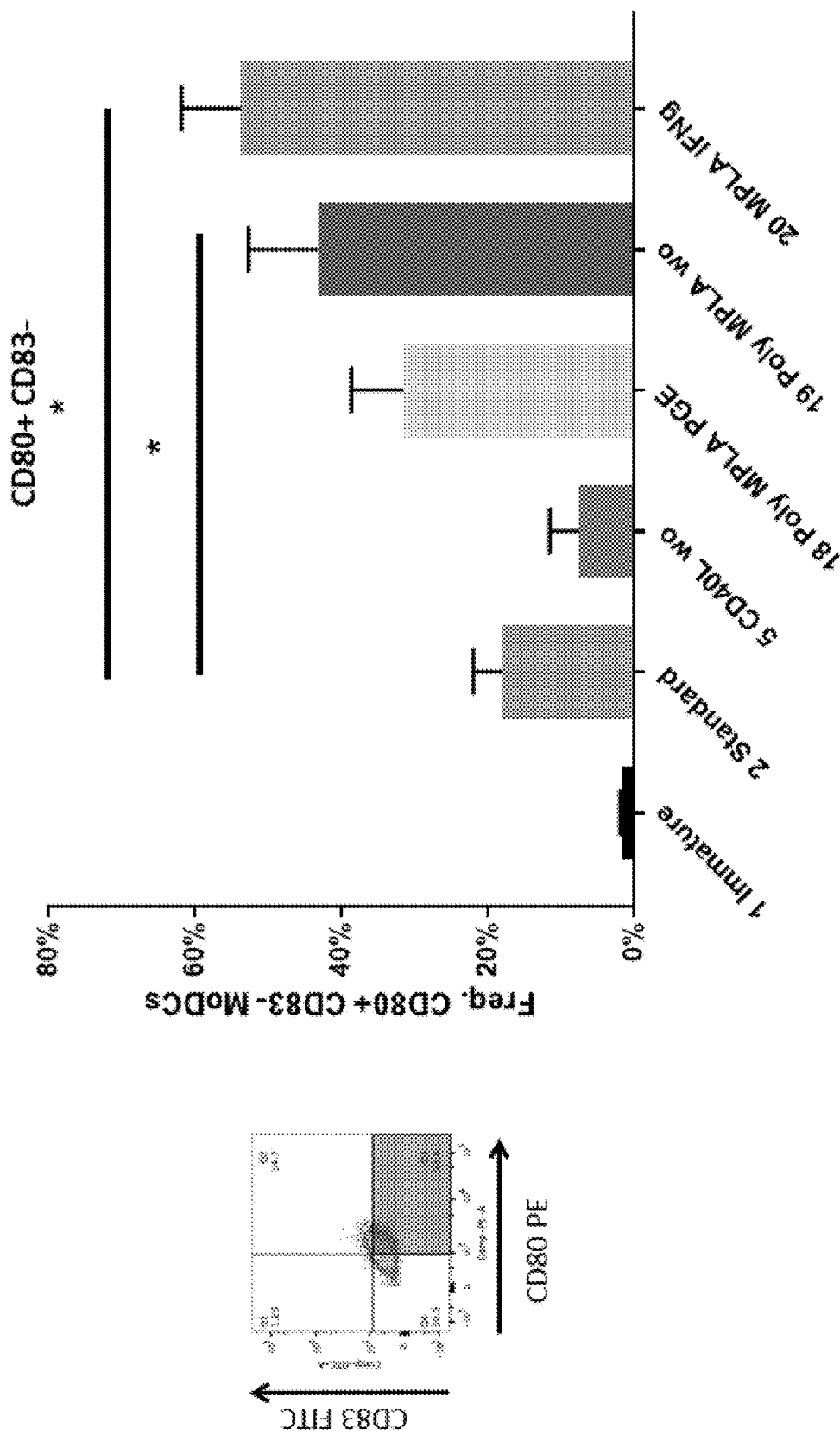
Figure 17D:
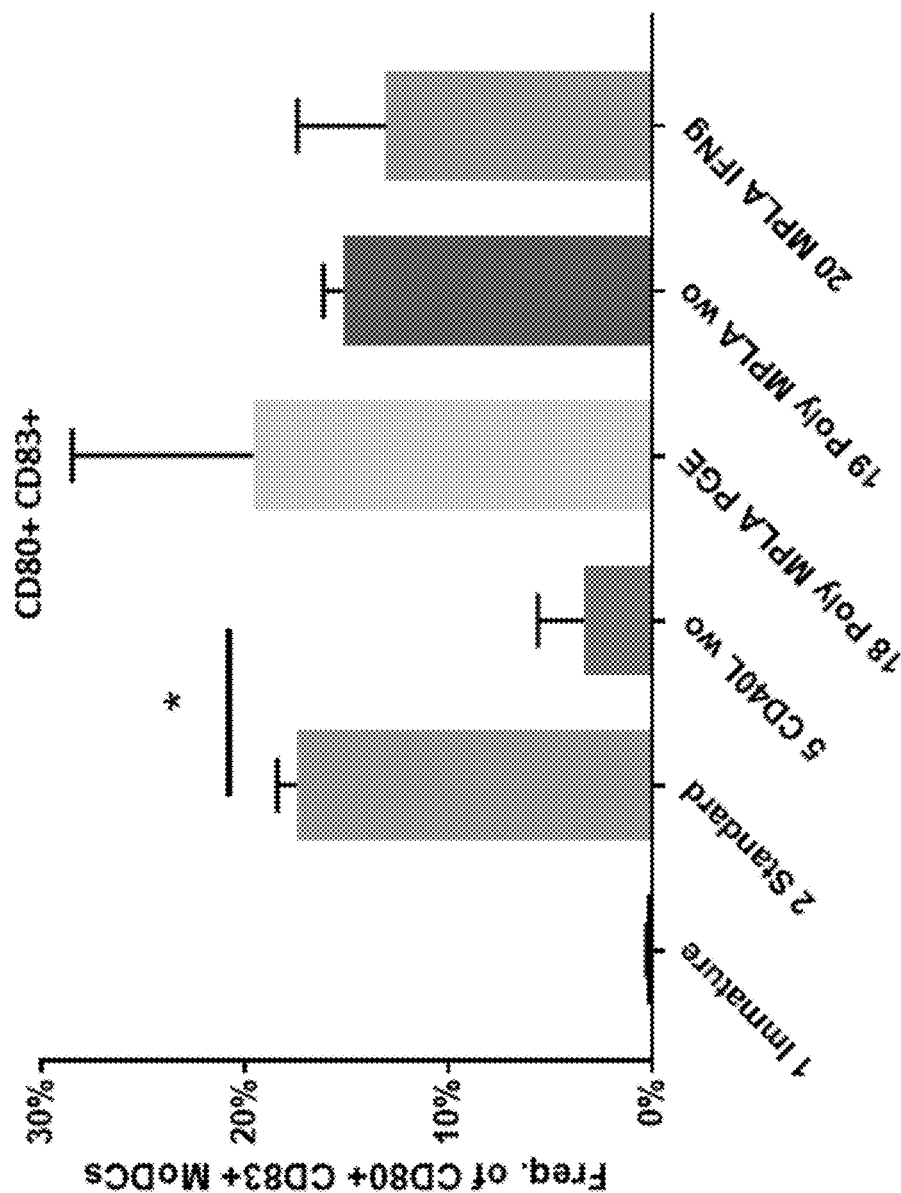
Figure 17D:
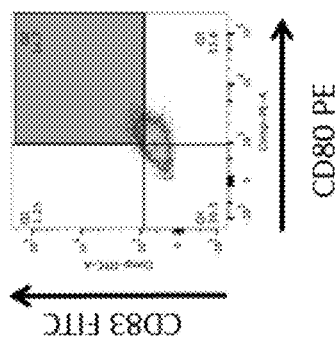
Figure 17E:
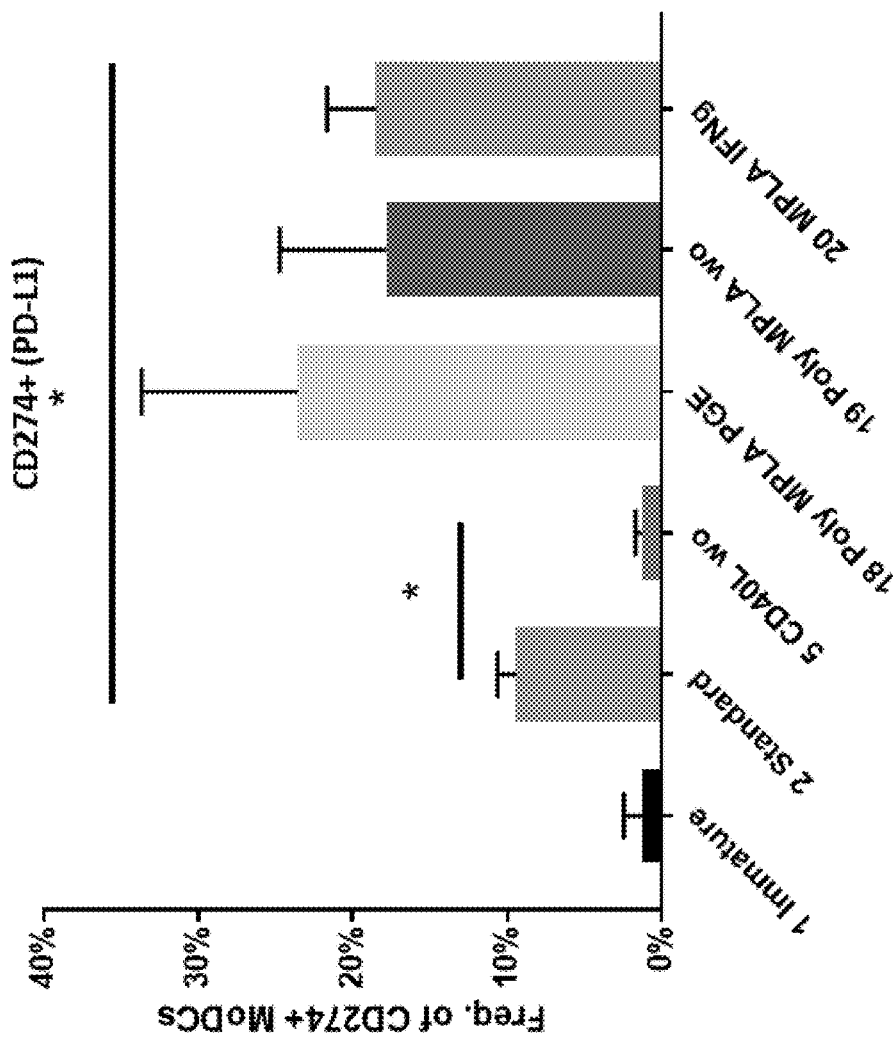
Figure 17E:
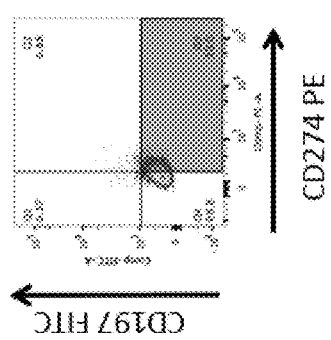

FIGS. 17A and 17B show representative CD83, CD80, CCR7 and PD-L1 expression by monocyte-derived DCs derived from three different donors following culture according to the experimental conditions 1, 2, 5, 18, 19 and 20. FIG. 17C shows the proportions of CD80+CD83− DCs, FIG. 17D shows the proportions of CD80+CD83+ DCs and 17E shows the proportions of PD-L1+ DCs.

Figure 18:
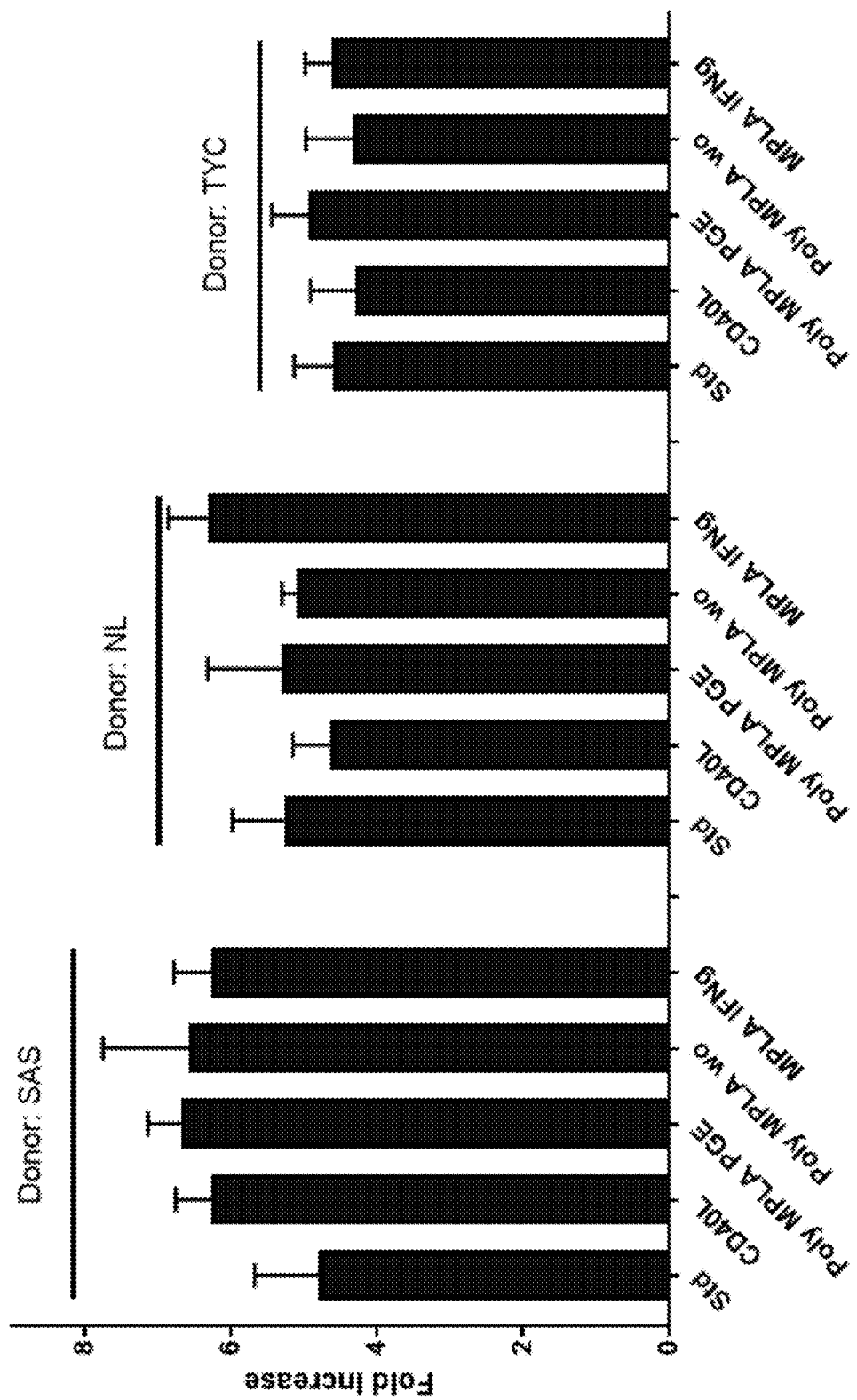
FIG. 18 is a bar chart showing the total number of virus-specific T cells obtained following stimulation of autologous CD14− PBMCs derived from the three different donors for 9 days with EBV peptide-pulsed mature DCs cultured according to the experimental conditions 2, 5, 18, 19 and 20 (see Table 4).

FIG. 18 shows the total number of virus-specific T cells obtained following stimulation of autologous CD14− PBMCs derived from the three different donors for 9 days with EBV peptide-pulsed mature DCs cultured according to the experimental conditions 2, 5, 18, 19 and 20. Mature DCs expanded under the different conditions had similar overall levels of expansion.

Figure 19:
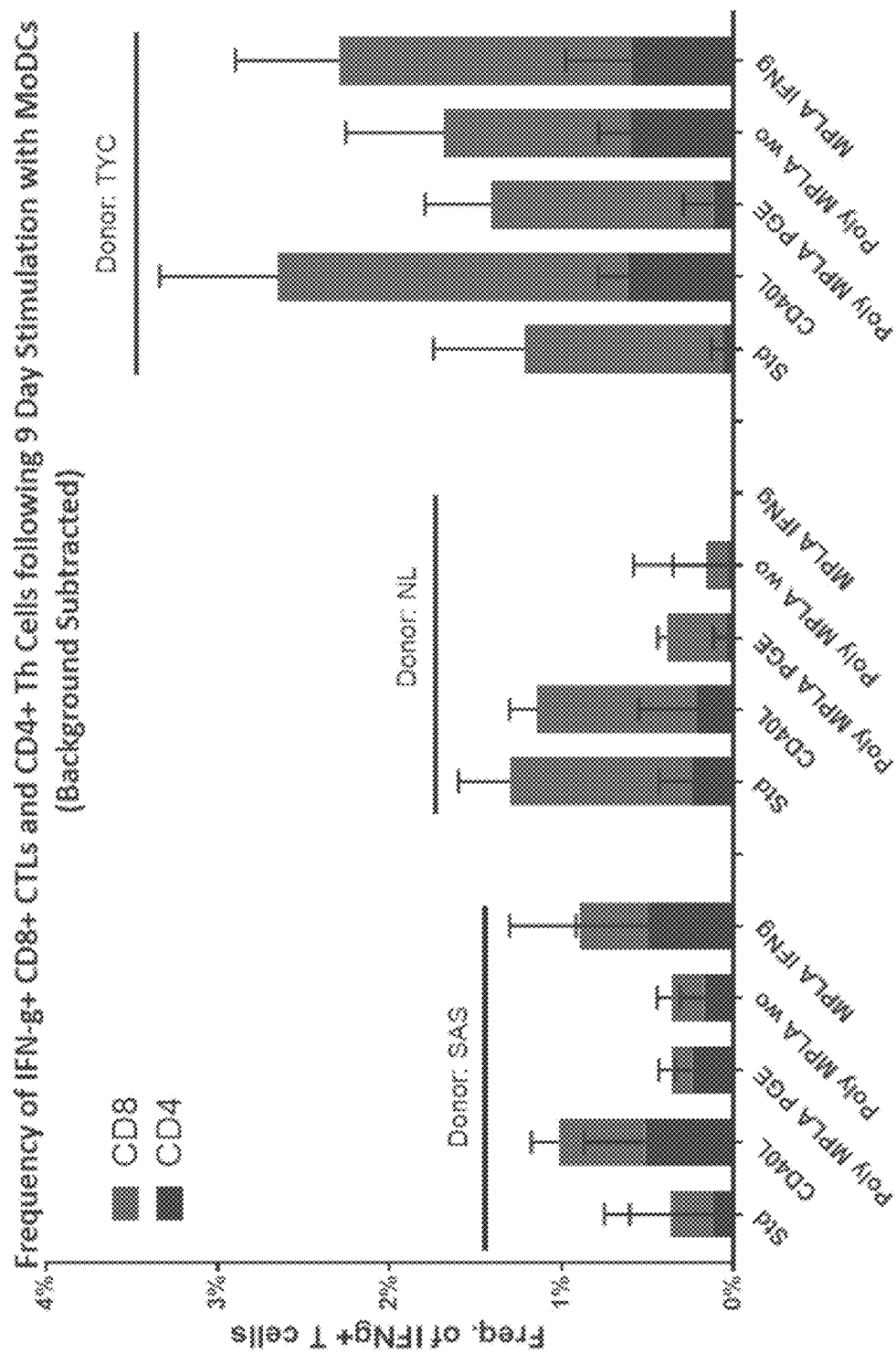
FIG. 19 is a bar chart showing the proportions of IFNγ+CD8+ CTLs and IFNγ+CD4+ Th cells (background subtracted) obtained following stimulation of autologous CD14− PBMCs derived from the different donors for 9 days with EBV peptide-pulsed mature DCs cultured according to the experimental conditions 2, 5, 18, 19 and 20 (see Table 4).

FIG. 19 shows the proportions of IFNγ+CD8+ CTLs and IFNγ+CD4+ Th cells obtained following stimulation of autologous CD14− PBMCs derived from the different donors for 9 days with EBV peptide-pulsed mature DCs cultured according to the experimental conditions 2, 5, 18, 19 and 20, as determined by ELISPOT analysis. Frequencies shown are subtracted for background signal obtained in control conditions performed in the absence of EBV peptide stimulation.

Figure 20:
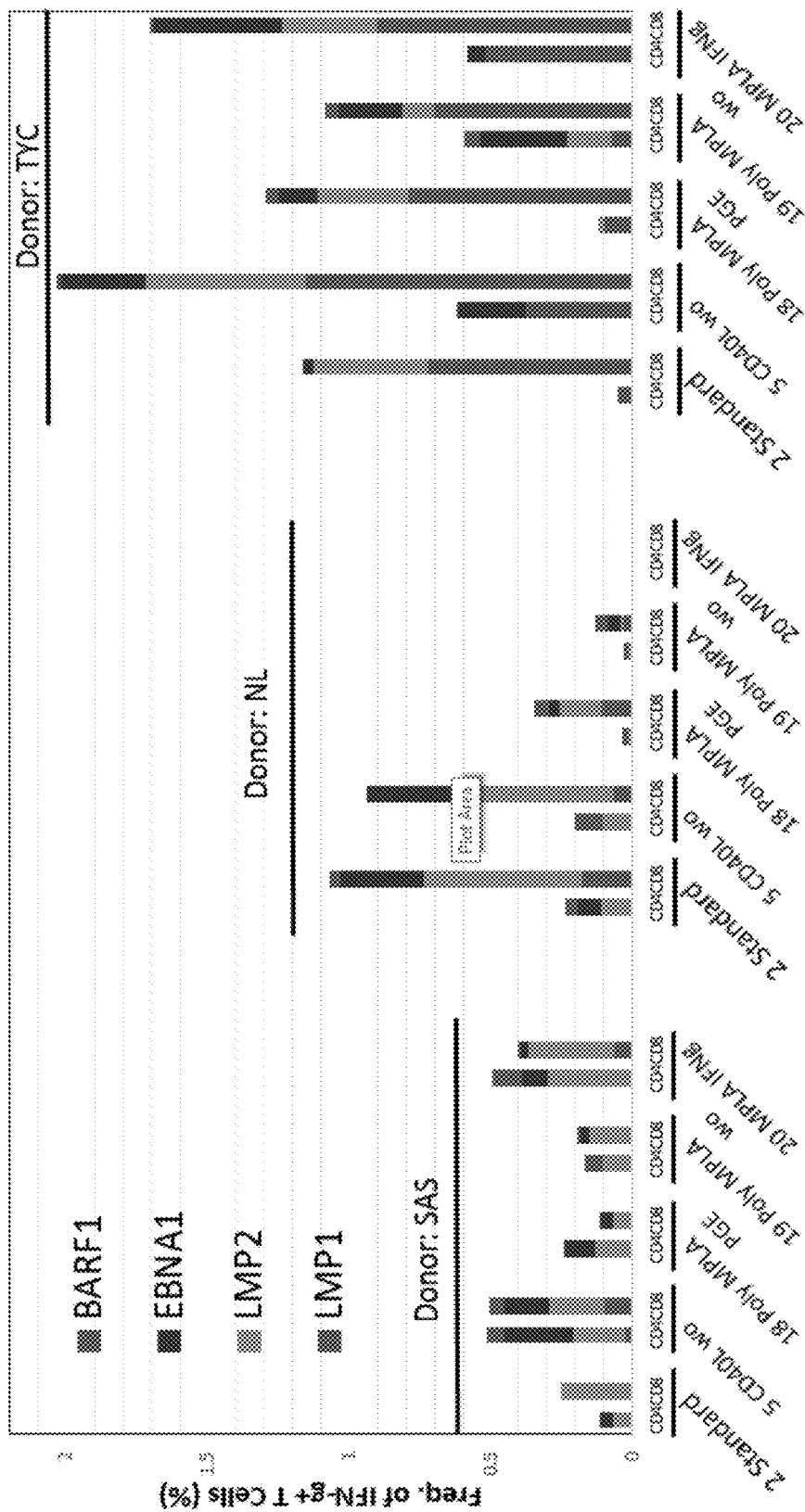
FIG. 20 shows the proportions of EBV antigen-reactive IFNγ+CD8+ CTLs and IFNγ+CD4+ Th cells (background subtracted) obtained following stimulation of autologous CD14− PBMCs derived from the different donors for 9 days with EBV peptide-pulsed mature DCs cultured according to the experimental conditions 2, 5, 18, 19 and 20 (see Table 4).

FIG. 20 shows the proportions of EBV antigen-reactive IFNγ+CD8+ CTLs and IFNγ+CD4+ Th cells obtained following stimulation of autologous CD14− PBMCs derived from the different donors for 9 days with EBV peptide-pulsed mature DCs cultured according to the experimental conditions 2, 5, 18, 19 and 20 as determined by ELISPOT analysis. Frequencies shown are subtracted for background signal obtained in control conditions performed in the absence of EBV peptide stimulation.

Figure 21:
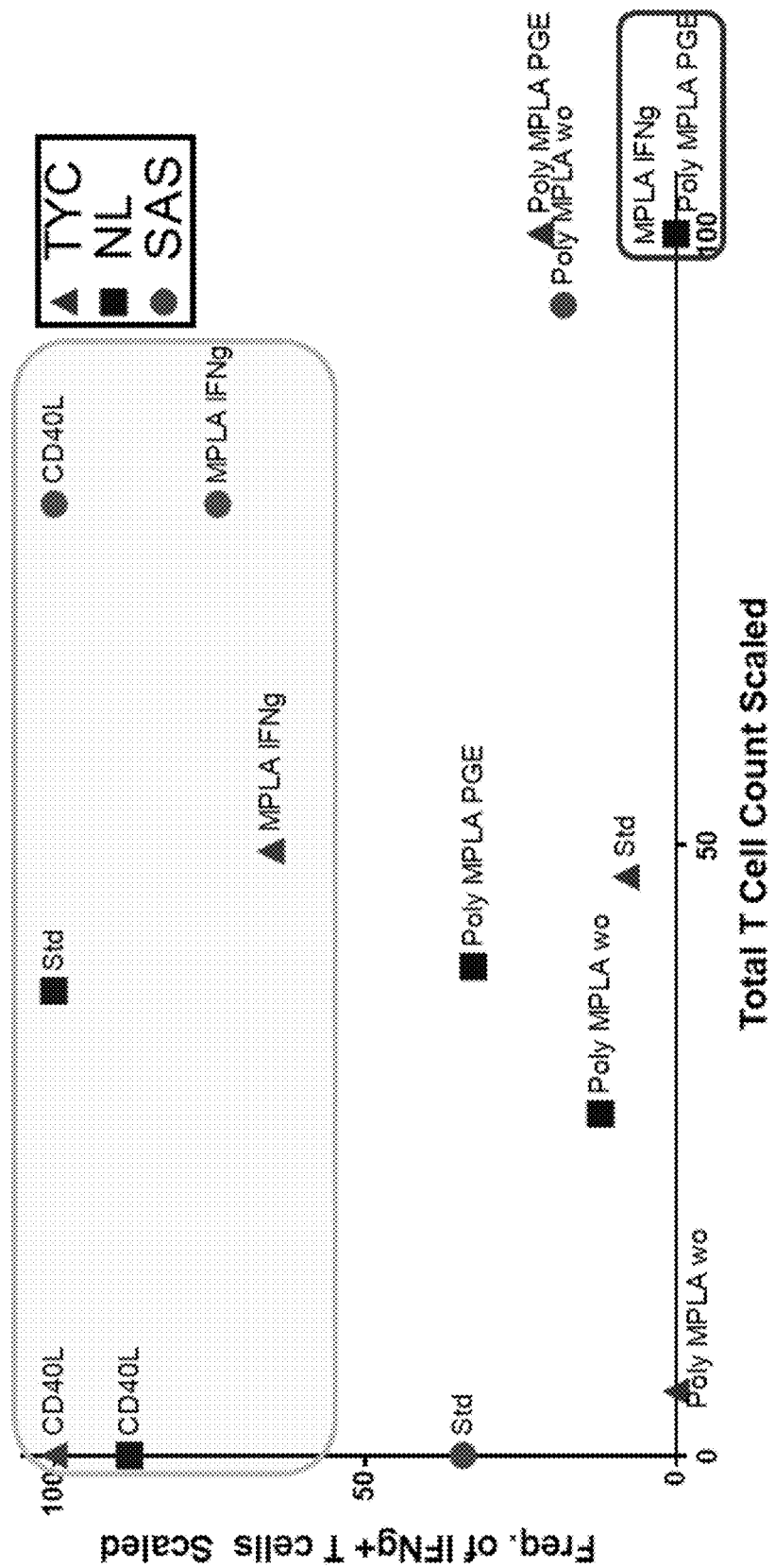
FIG. 21 is a graph showing the scaled total number of virus-specific T cells and the scaled frequency of IFNγ+ T cells obtained following stimulation of autologous CD14- PBMCs derived from the three donors for 9 days with EBV peptide-pulsed mature DCs cultured under different experimental conditions (see Table 4).

FIG. 21 shows the scaled total number of virus-specific T cells and the scaled frequency of IFNγ+ T cells obtained following stimulation of autologous CD14− PBMCs derived from the three donors for 9 days with EBV peptide-pulsed mature DCs cultured under different experimental conditions.

Overall, the results suggested that the best condition for DC maturation is culture in the presence of GM-CSF, IL-4, IL-1β, IL-6, TNFα and CD40L. Another good condition is culture in the presence of GM-CSF, IL-4, MPLA and IFNγ.

Example 5

Further Optimization of DC Maturation

Blood samples are collected from EBV-reactive donors in heparin vacutainers and PBMCs are isolated from the blood samples by Ficoll density gradient centrifugation. CD14+ microbeads are then used to isolate CD14+ cells from within the PBMCs by positive selection. The number of cells is counted, and the CD14− cell population is frozen and stored.

The CD14+ cells are then differentiated to immature dendritic cells (iDCs). Briefly, CD14+ cells are cultured in wells of a 24-well plate at a concentration of $0.5 \times 10^6$ cells/ml in DC cell culture medium containing 400 IU/ml IL-4 and 800 IU/ml GM-CSF, for 5 days.

The iDCs are then matured to mature DCs by culture for 24 hours in DC cell culture medium according to the conditions shown in one of 1, 2, 21 or 25 in Table 5 below:

TABLE 5

DC Maturation Culture Conditions

| Condition No. | Conditions |
|---|---|
| 1 | 800 U/ml GM-CSF, 400 U/ml IL-4 |
| 2 | 800 U/ml GM-CSF, 400 U/ml IL-4, 10 pg/ml IL-1β, 100 pg/ml IL-6, 10 pg/ml TNFα, 1 ng/ml PGE-1 |
| 21 | 800 U/ml GM-CSF, 100 ng/ml IFNα |
| 22 | 800 U/ml GM-CSF, 400 U/ml IL-4, 100 ng/ml IFNγ, 1 µg/ml AmpB |

The mature DCs are then analyzed by flow cytometry for expression of CD80, CD83, CCR7 and PD-L1. The previously frozen CD14− fraction is thawed and rested in cell culture medium for 24 hours.

Immature and mature DCs are then pulsed with individual EBV antigen pepmixes (LMP1, LMP2, BRAF1 or EBNA1), and the peptide-pulsed DCs are used to stimulate the autologous CD14− cells by coculture for 3 days or 9 days in the presence of IL-7 (10 ng/ml) and IL-15 (100 ng/ml). The expanded T cell populations are then analyzed by flow cytometry for expression of CCR7, CD45RO, EBV peptide reactivity and intracellular staining for IFNγ.

DCs matured according to conditions 21 and 22 are expected to be associated with advantageous properties as compared to DCs matured according to condition 2.

Example 6

Characterization of Virus-Specific T Cells Expanded by Stimulation Culture in the Presence of Different Costimulatory Cells The inventors next investigated the use of K562cs cells and HLA-negative LCLs (also referred to herein as universal LCLs (ULCLs)) as costimulatory cells in stimulations in methods for generating/expanding populations of virus-specific T cells. Briefly, PBMCs were harvested, and pulsed with EBV pepmixes corresponding to EBV antigens (EBNA-1, LMP-1, LMP-2 and BARF-1) in the presence of IL-7 (10 ng/ml) and IL-15 (100 ng/ml) to stimulate the expansion of EBV-specific T cells. On day 9, and every 7 days thereafter, restimulation steps were performed either with (i) EBV pepmix-pulsed, irradiated autologous ATCs, in the presence of IL-7 (10 ng/ml) and IL-15 (100 ng/ml), and in the presence of irradiated K562-cs co-stimulatory cells, at a ratio of responder cells:ATCs:K562-cs of 1:1:5, or (ii) EBV pepmix-pulsed, irradiated autologous ATCs, in the presence of IL-7 (10 ng/ml) and IL-15 (100 ng/ml), and in the presence of irradiated ULCLs, at a ratio of responder cells:ATCs:ULCLs of 1:1:5.

LCLs lacking surface expression of HLA class I and HLA class II (i.e. HLA-negative LCLs) were obtained by targeted knockout of genes encoding HLA class I and HLA class II molecules. The HLA-negative LCLs were further modified to knockout genes necessary for EBV replication. Three different ULCL clones (#4, #5 and #13) were analyzed.

Figure 22A:
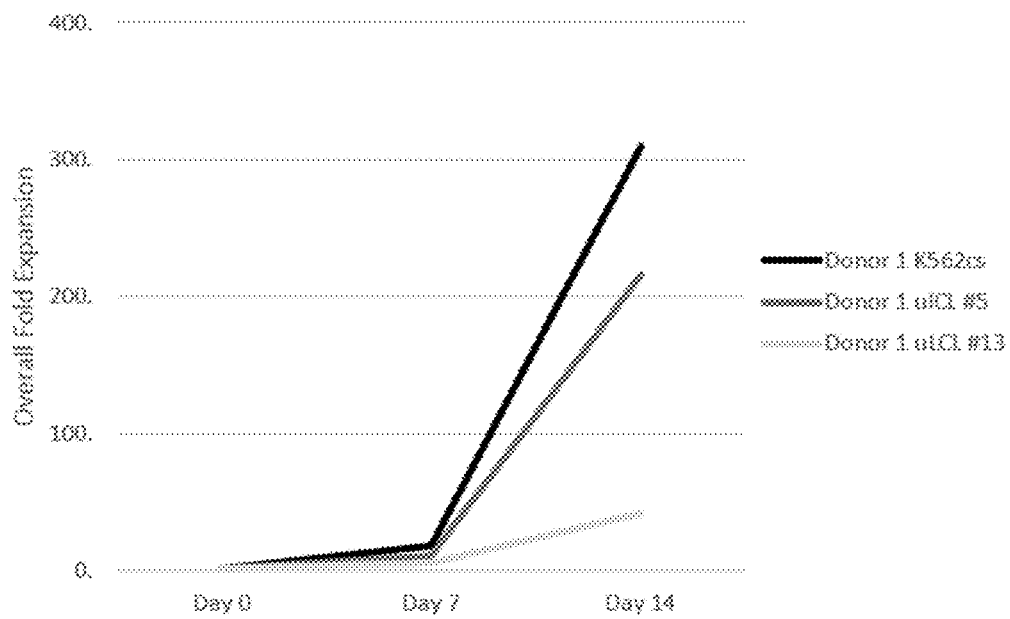
FIGS. 22A and 22B are graphs showing the results of two separate experiments investigating overall fold expansion of cells following stimulations using K562-cs cells as costimulatory cells as compared to ULCL clones #5 and #13.
Figure 22B:
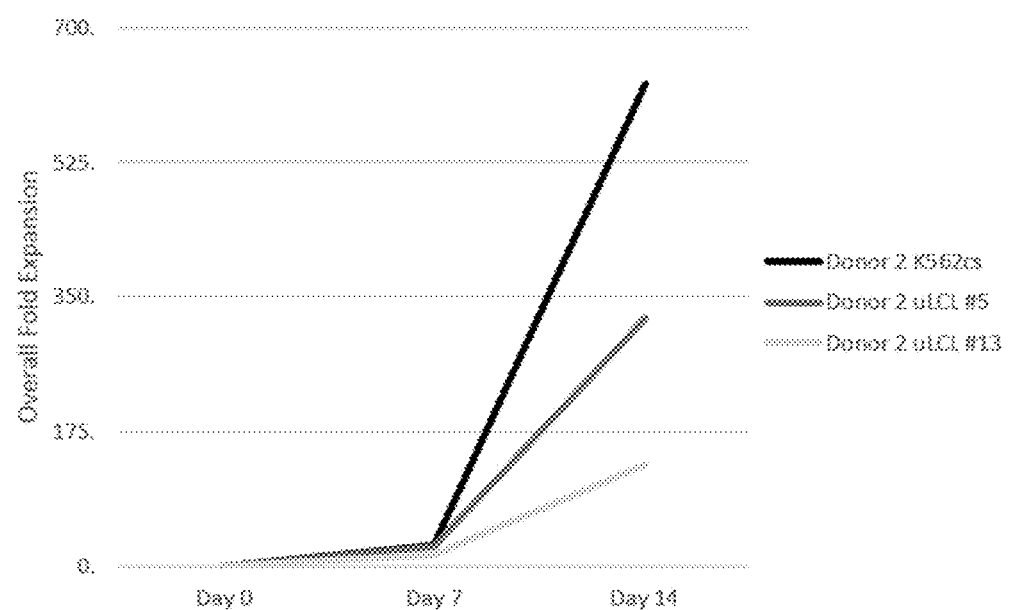
Figure 23A:
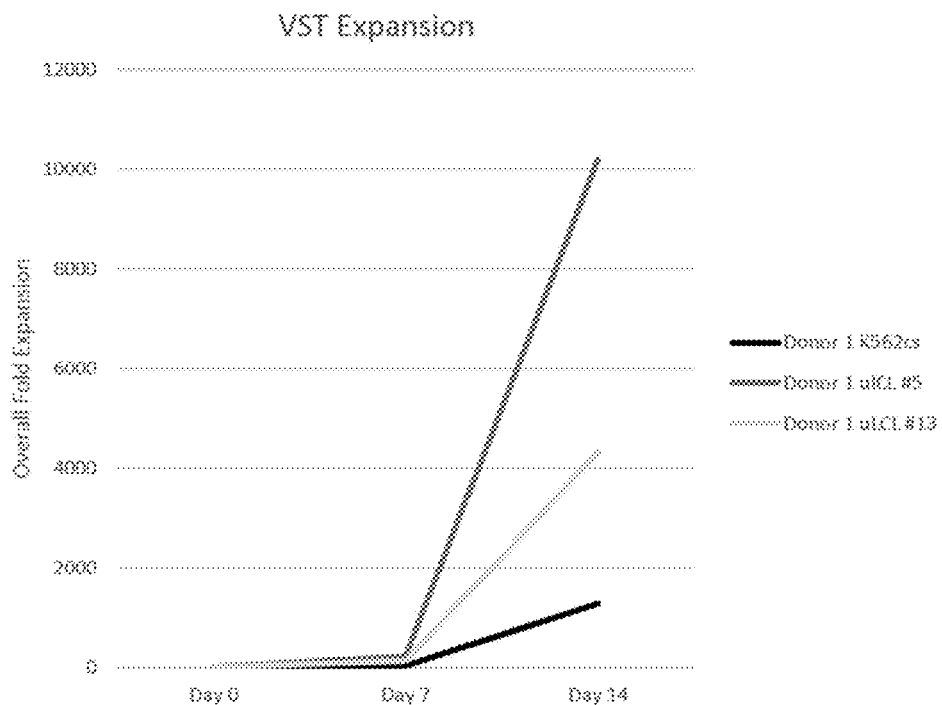
FIGS. 23A and 23B are graphs showing the results of two separate experiments investigating overall fold expansion of virus-specific T cells following stimulations using K562-cs cells as costimulatory cells as compared to ULCL clones #5 and #13, as determined by ELISPOT analysis of the number of IFNγ producing cells.
Figure 23B:
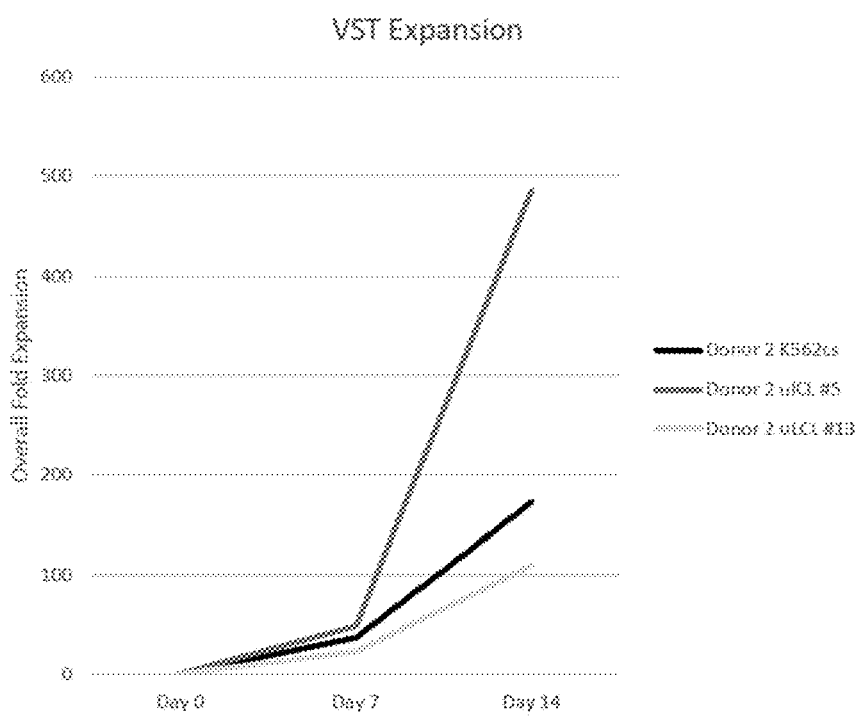

FIGS. 22A and 22B show the results of two separate experiments, demonstrating that the overall fold expansion of the cells in culture was higher for cells expanded using K562-cs cells as costimulatory cells as compared to ULCLs. However, as shown in FIGS. 23A and 23B, ULCL clone #5 was found to expand greater numbers of virus-specific T cells, as determined by ELISPOT analysis of the number of IFNγ producing cells.

Figure 24A:
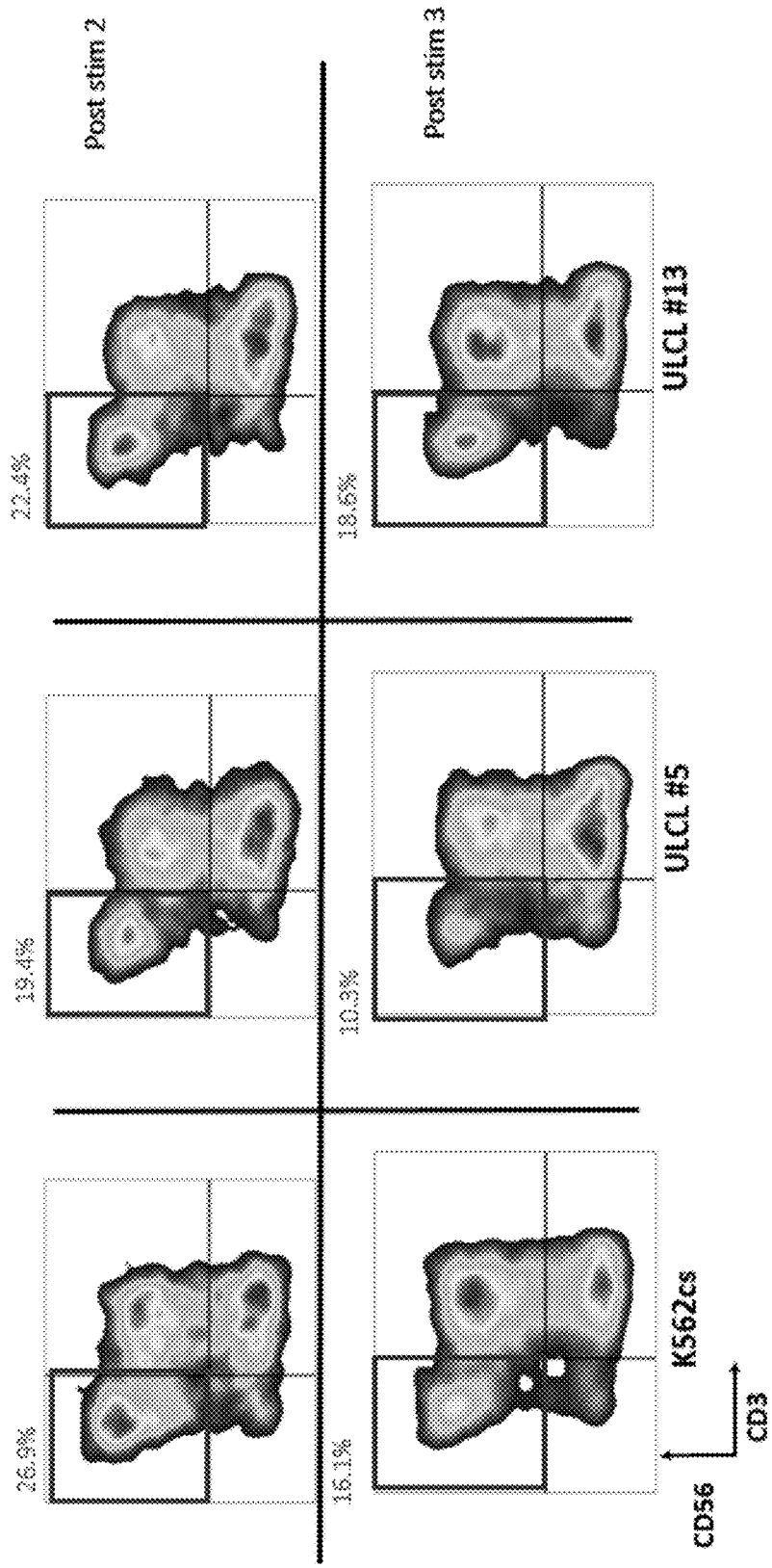
FIGS. 24A, 24B and 24C provide scatterplots from a representative donor (n=7) showing the proportions of (FIG. 24A) CD3-CD56+ NK cells, (FIG. 24B) CD4+ T cells and CD8+ T cells, and (FIG. 24C) gamma delta T cells and alpha beta T cells in populations expanded using K562-cs cells or ULCL clones #5 and #13 as costimulatory cells.
Figure 24B:
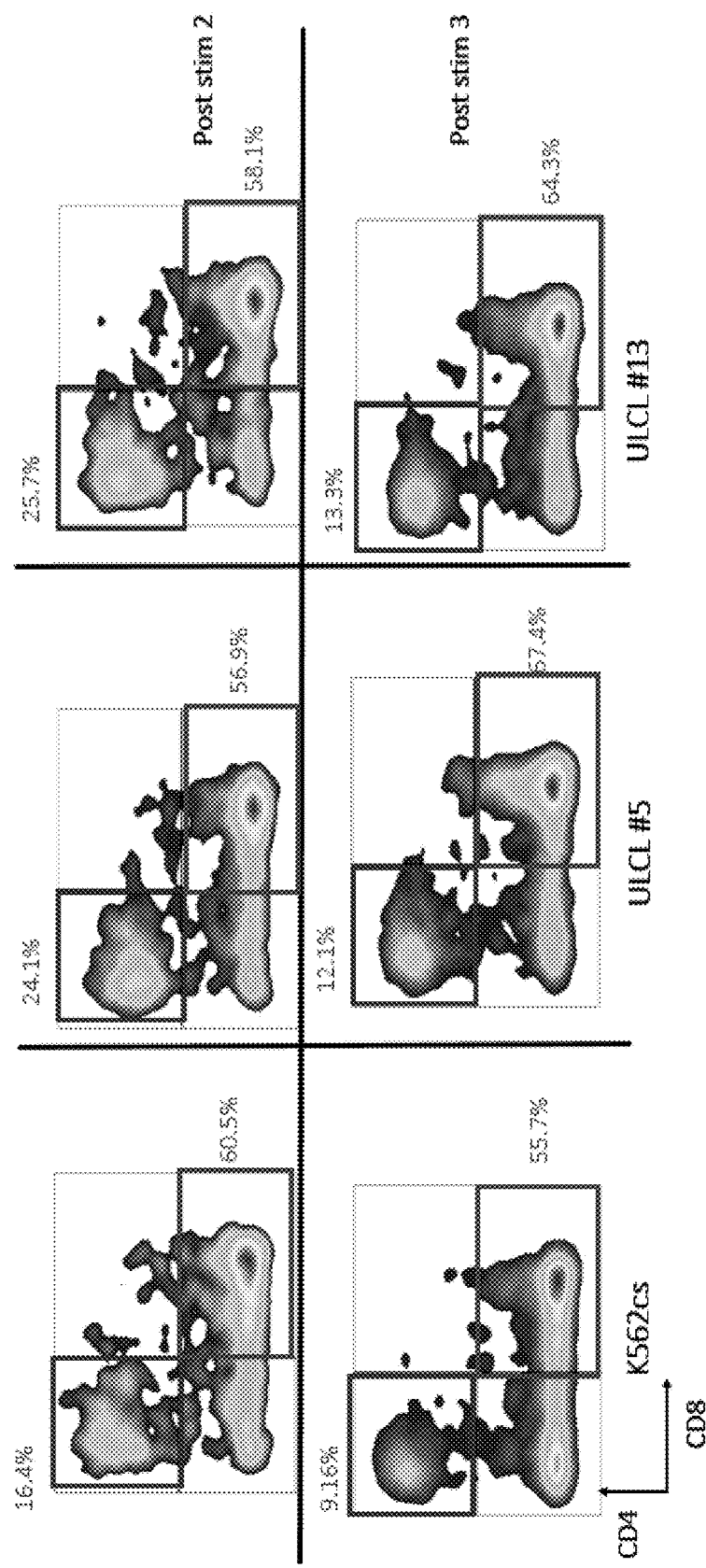
Figure 24C:
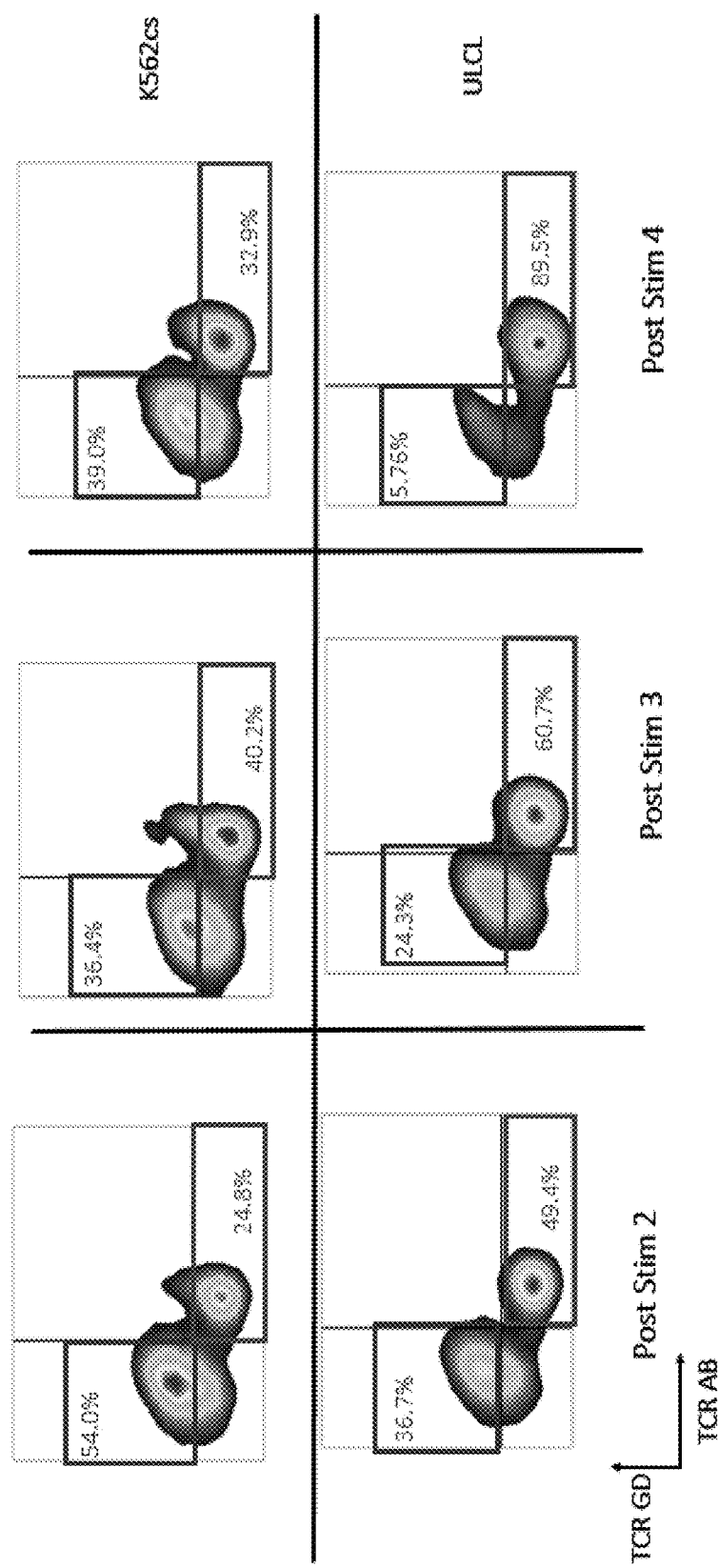
Figure 25:
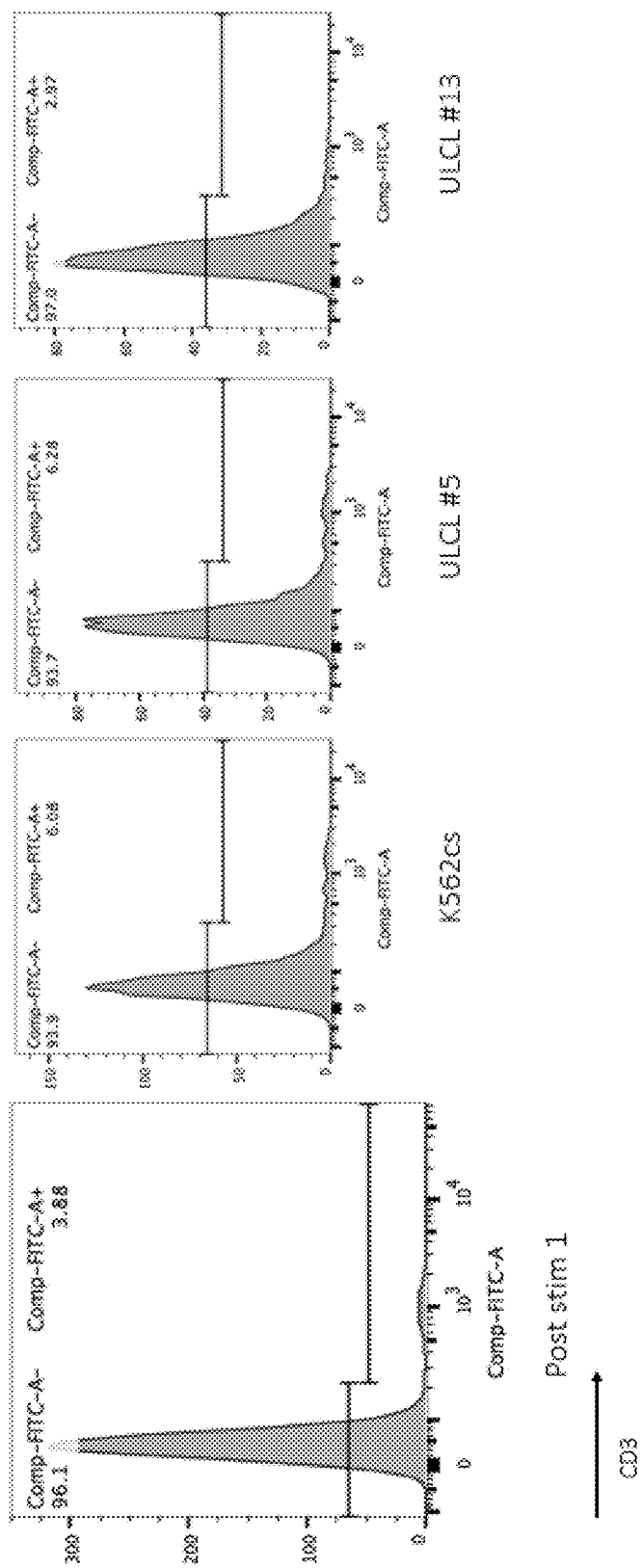
FIG. 25 provides histograms showing representative results of characterization of gamma delta TCR expression by ULCL clones #5 and #13, as compared to expression by K562cs cells.

The inventors next analyzed the proportions of different cell types expanded after the indicated number of stimulations using K562-cs or ULCLs as costimulatory cells, by flow cytometry using antibodies specific for cell surface markers. FIGS. 32A to 32C show scatterplots from a representative donor (n=7) showing the proportions of CD3-CD56+ NK cells, CD4+ T cells, CD8+ T cells, gamma delta T cells and alpha beta T cells in the expanded populations. Similar proportions of CD3-CD56+ NK cells were found in the expanded populations (FIG. 24A), whilst populations obtained by stimulations using K562cs cells tended to have a reduced proportion of CD4+ T cells in the expanded populations (FIG. 24B), and populations obtained by stimulations using ULCLs tended to have an increased proportion of alpha beta T cells in the expanded populations (FIG. 24C). FIG. 25 shows representative results of characterization of gamma delta TCR expression by ULCL clones #5 and #13, as compared to expression by K562cs cells.

Figure 26A:
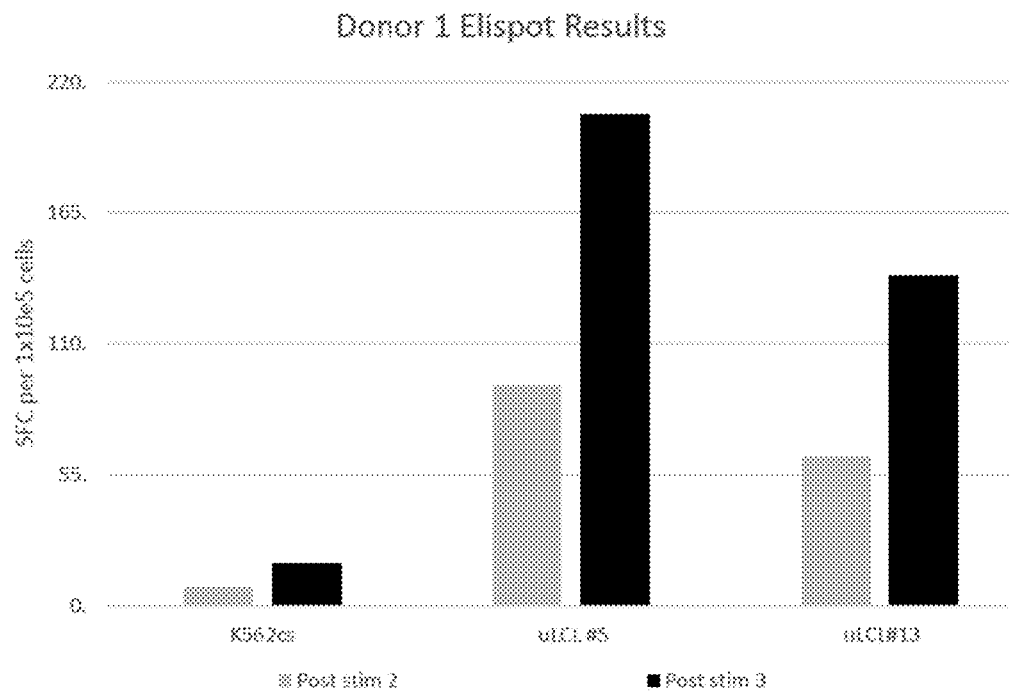
FIGS. 26A and 26B are bar charts for two different donors showing the frequency of virus-specific T cells in populations expanded using K562-cs cells or ULCL clones #5 and #13 as costimulatory cells, after the indicated number of stimulations, as determined by ELISPOT analysis of the number of IFNγ producing cells.
Figure 26B:
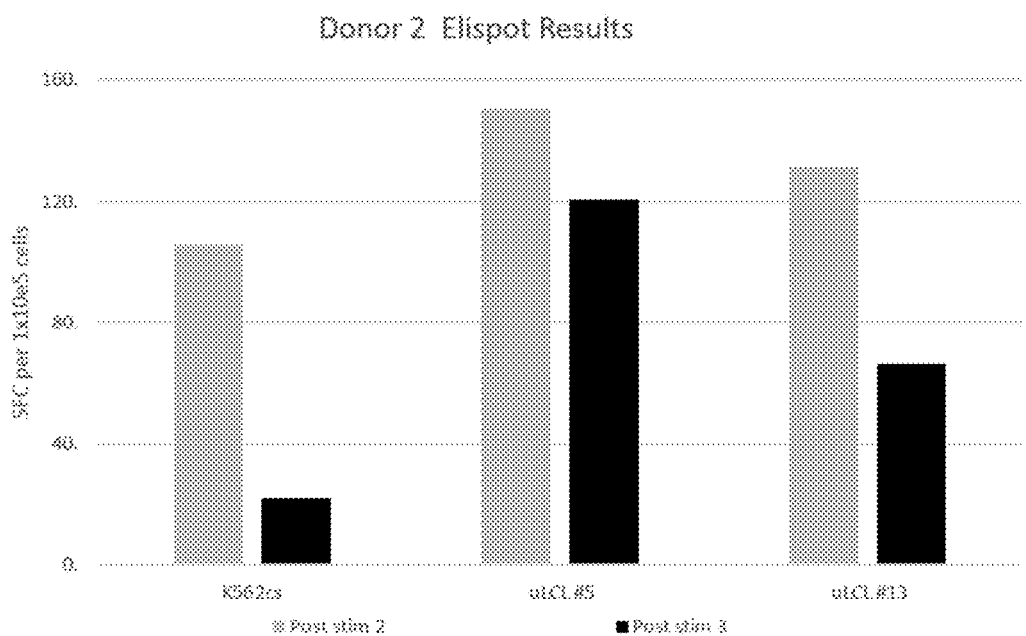
Figure 27A:
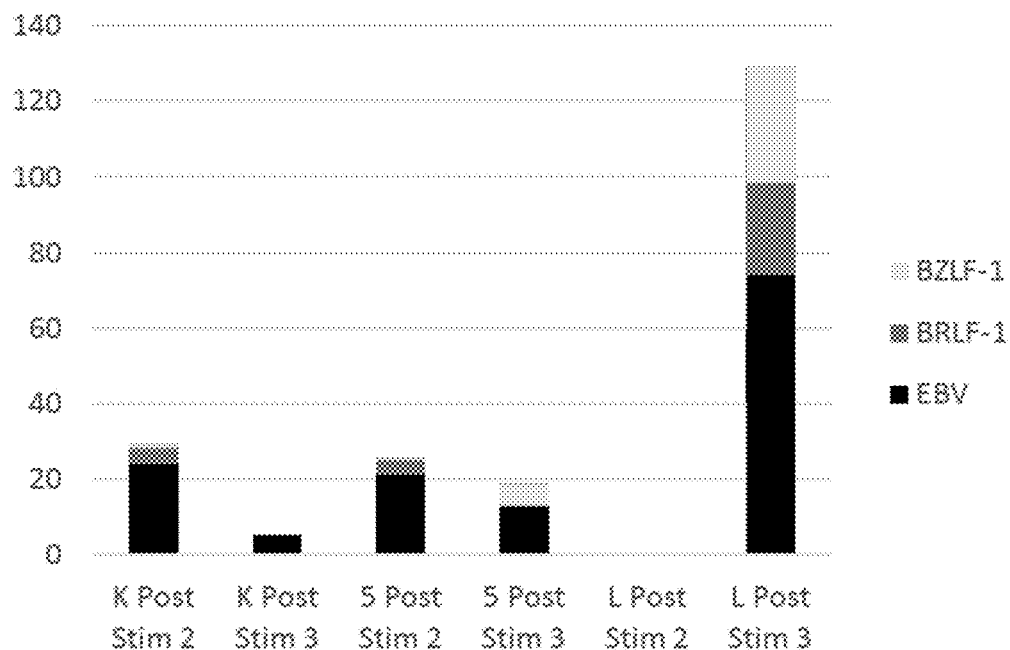
FIGS. 27A, 27B, 27C and 27D are bar charts for four different donors showing the frequency of T cells specific for the indicated EBV antigens, after the indicated number of stimulations using K562cs cells (K), ULCL clone #5 (5) or LCLs (L) as costimulatory cells, as determined by ELISPOT analysis of the number of IFNγ producing cells.
Figure 27B:
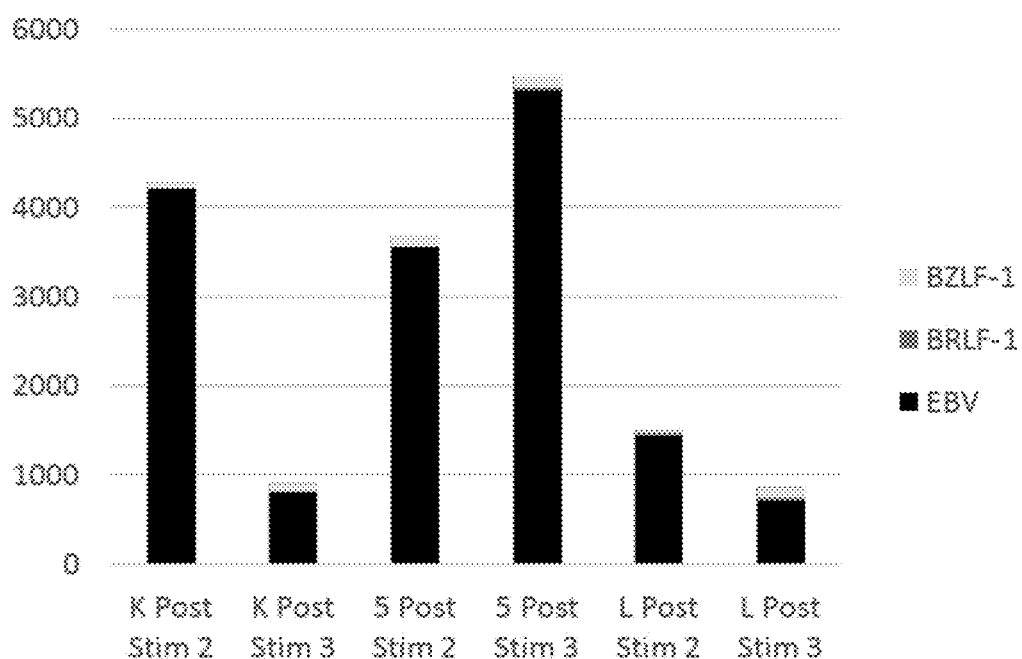
Figure 27C:
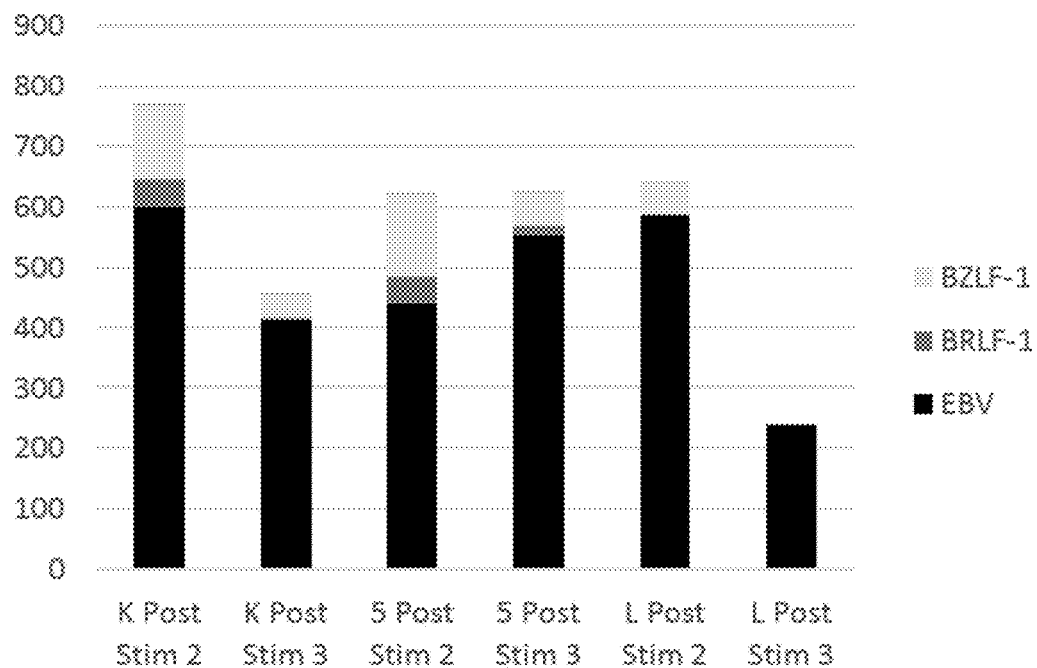
Figure 27D:
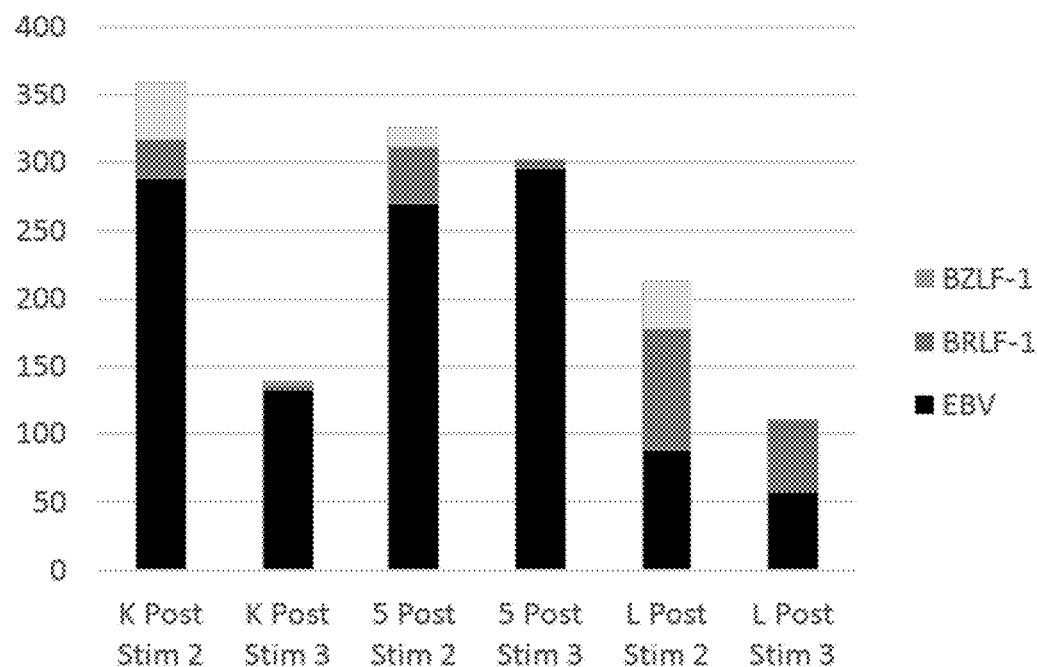
Figure 28A:
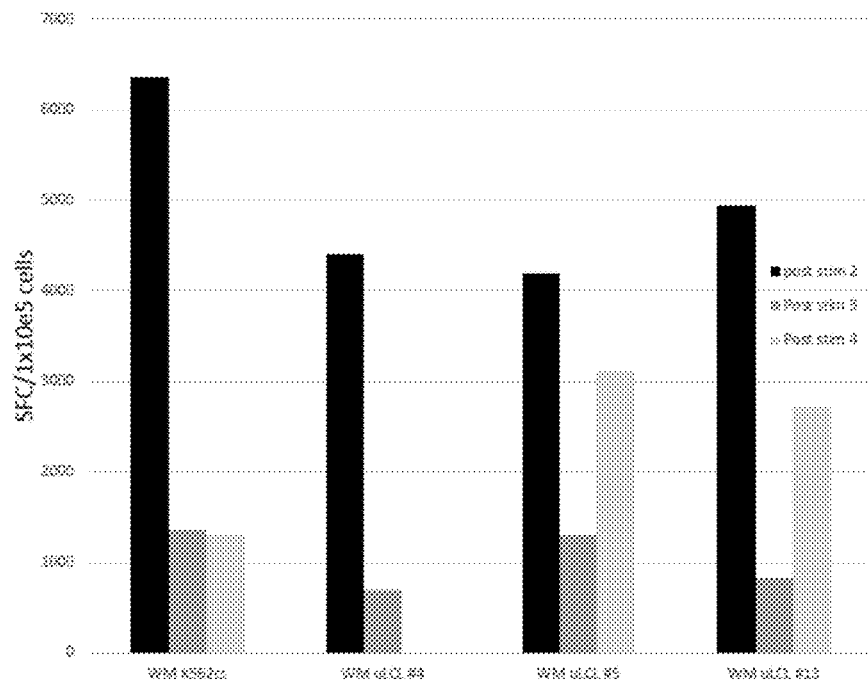
FIGS. 28A, 28B, 28C and 28D are bar charts and graphs showing the frequency and fold expansion of virus-specific T cells in populations expanded using K562-cs cells or ULCL clones #4, #5 and #13 as costimulatory cells, after the indicated number of stimulations, as determined by ELISPOT analysis of the number of IFNγ producing cells.
Figure 28B:
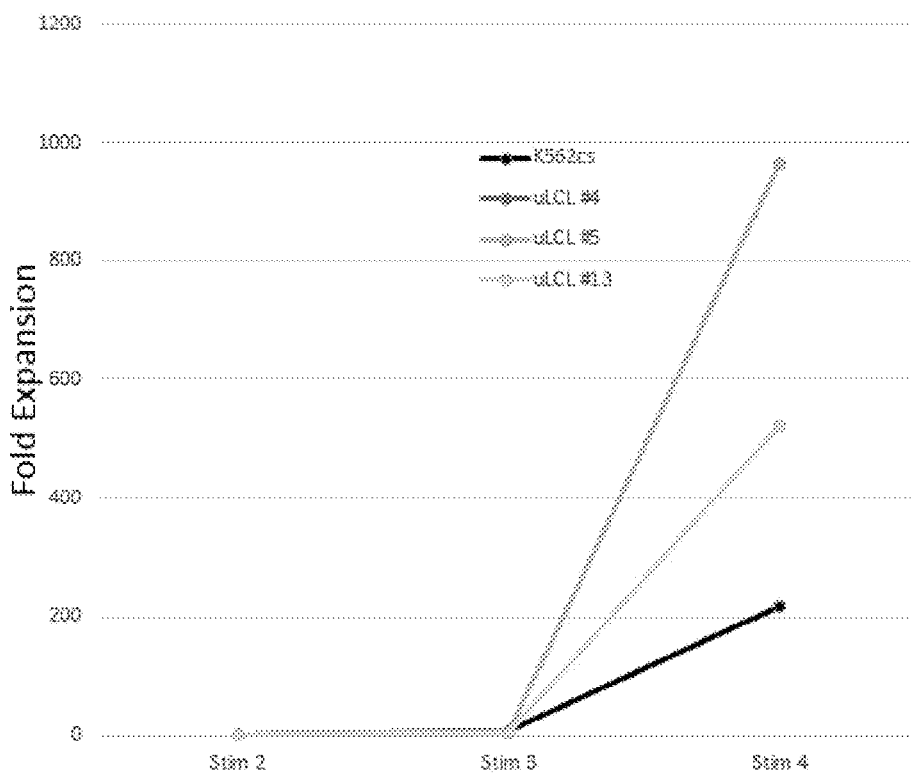
Figure 28C:
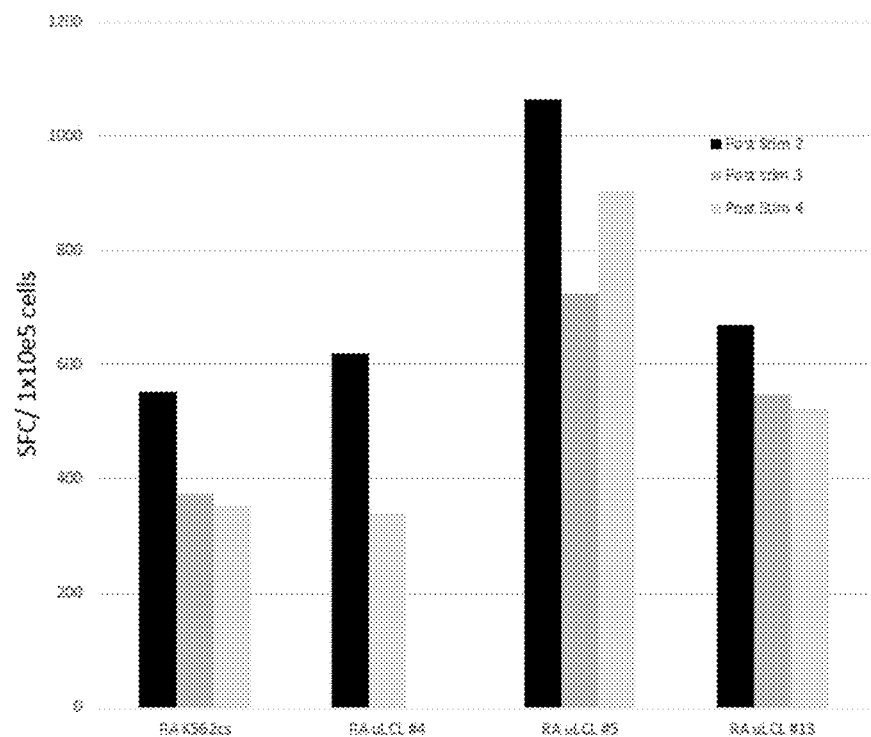
Figure 28D:
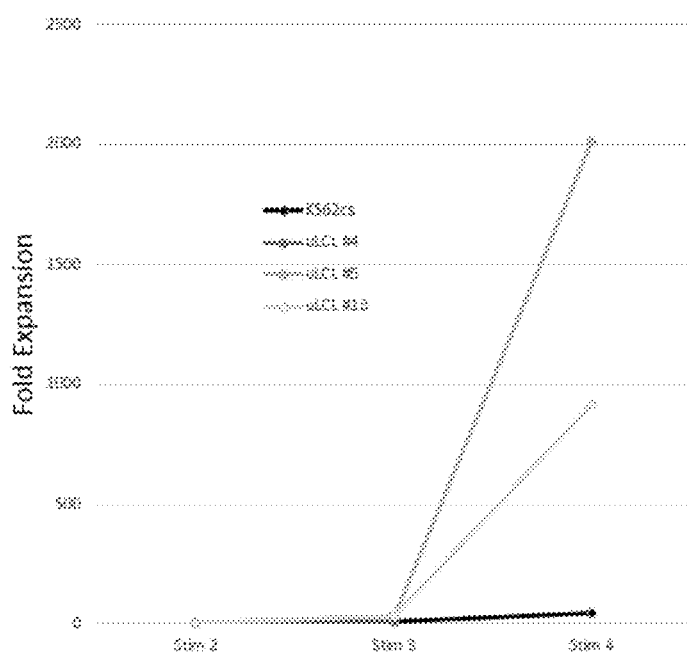

The inventors next analyzed the frequency of antigen-specific T-cells in the populations of cells expanded by stimulations using ULCL clone #5 or #13, or K562cs cells by ELISPOT analysis of IFNγ production at the end of the second and third stimulations. The results obtained from two different donors are shown in FIGS. 26A and 26B. More virus-specific cells were detected where cells had been expanded by stimulation using ULCL cells as costimulatory cells. FIGS. 27A to 27D show the number of cells per 100,000 cells specific for the indicated EBV antigens for four different donors after the indicated number of stimulations using K562cs cells, ULCL clone #5 or LCLs as costimulatory cells, as determined by ELISPOT analysis.

Figure 29A:
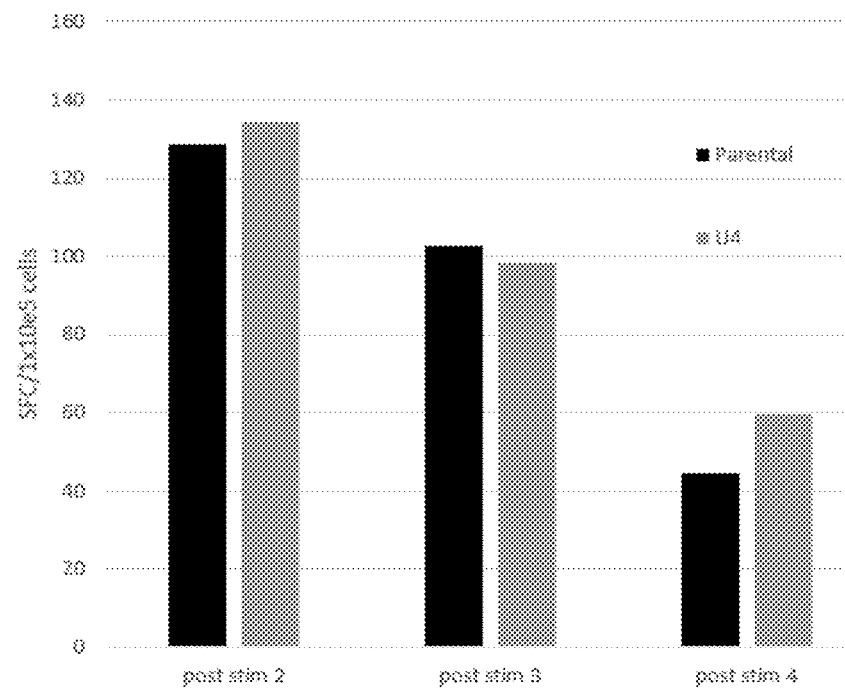
FIGS. 29A and 29B are bar charts showing the frequency of virus-specific T cells in populations expanded using ULCL clone #4 or parental ULCL cells as costimulatory cells, after the indicated number of stimulations, as determined by ELISPOT analysis of the number of IFNγ producing cells.
Figure 29B:
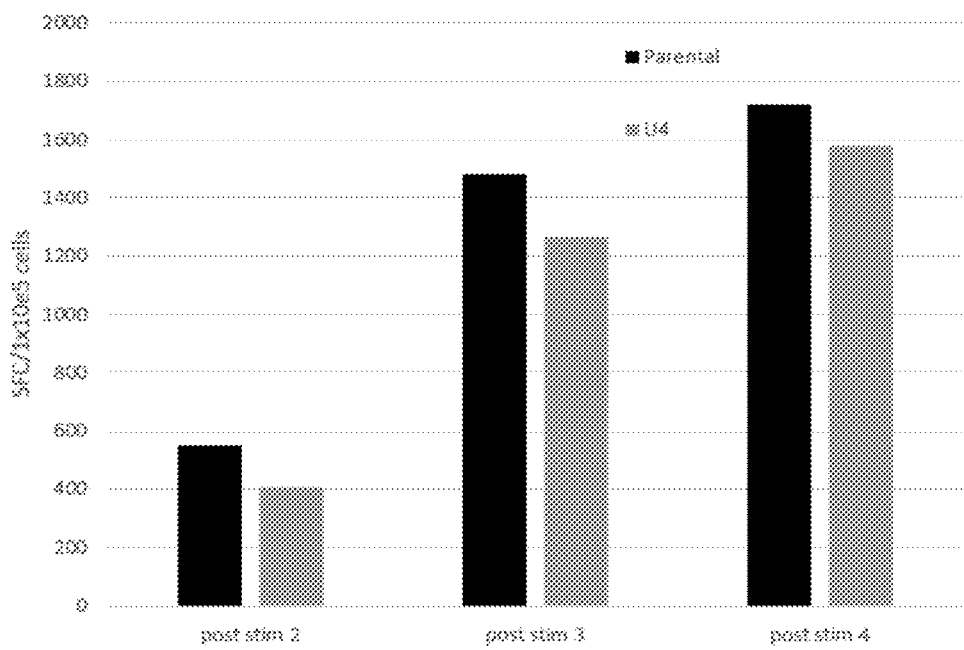

The inventors extended the analysis of virus-specific T cell expansion to four stimulations, and found that stimulations employing ULCLs as costimulatory cells expanded populations containing higher proportions of virus-specific cells as compared to stimulations performed using K562cs cells (FIGS. 28A to 28D). ULCL clone#4 cells were found not to differ significantly from cells of the parental ULCL clone in relation to ability to expand IFNγ producing virus-specific T cells (FIGS. 29A and 29B).

Figure 30A:
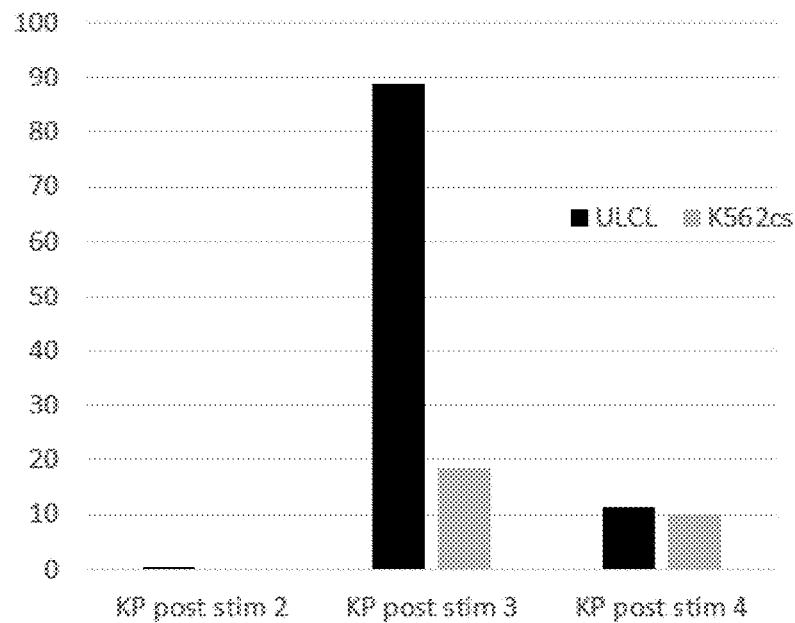
FIGS. 30A and 30B are bar charts for two different donors showing the frequency of virus-specific T cells in populations expanded using ULCL clone #5 or K562cs cells as costimulatory cells, after the indicated number of stimulations, as determined by ELISPOT analysis of the number of IFNγ producing cells.
Figure 30B:
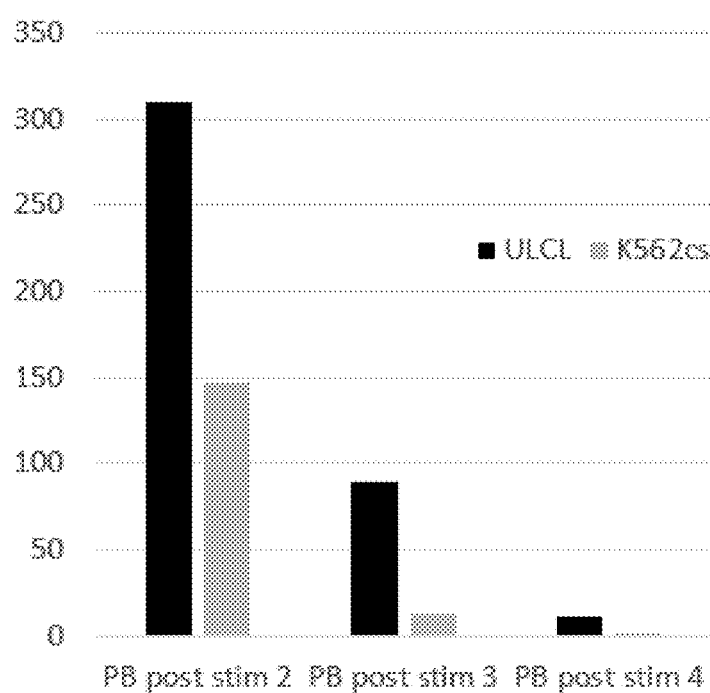
Figure 31A:
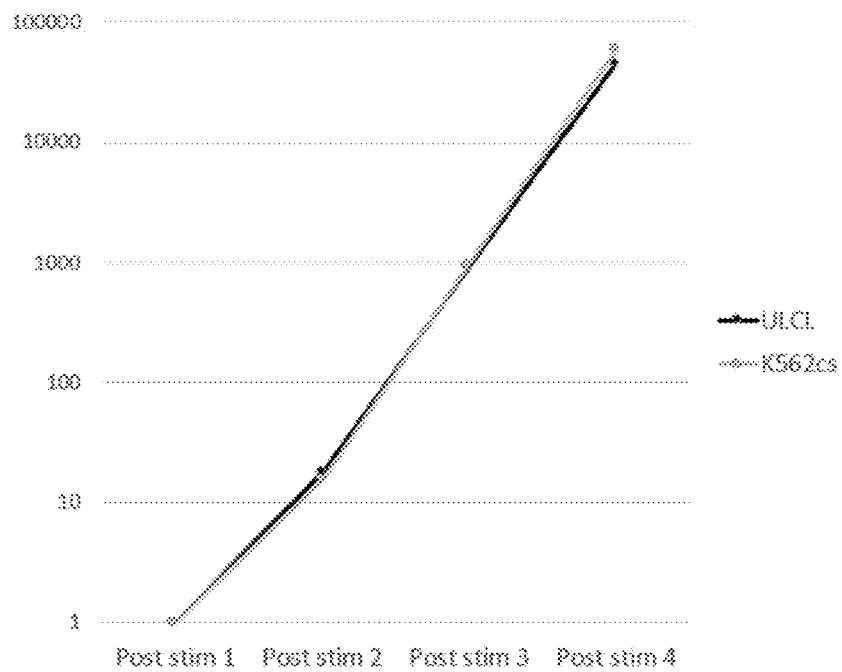
FIGS. 31A and 31B are bar charts for two different donors showing the fold expansion of virus-specific T cells in populations expanded using ULCL clone #5 or K562cs cells as costimulatory cells, after the indicated number of stimulations, as determined by ELISPOT analysis of the number of IFNγ producing cells.
Figure 31B:
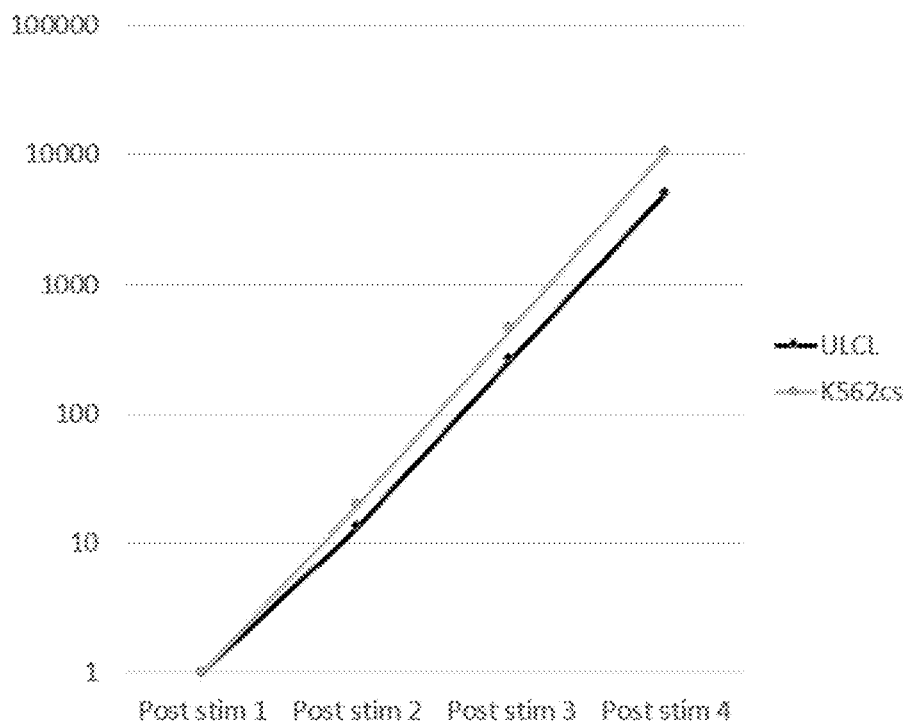
Figure 32:
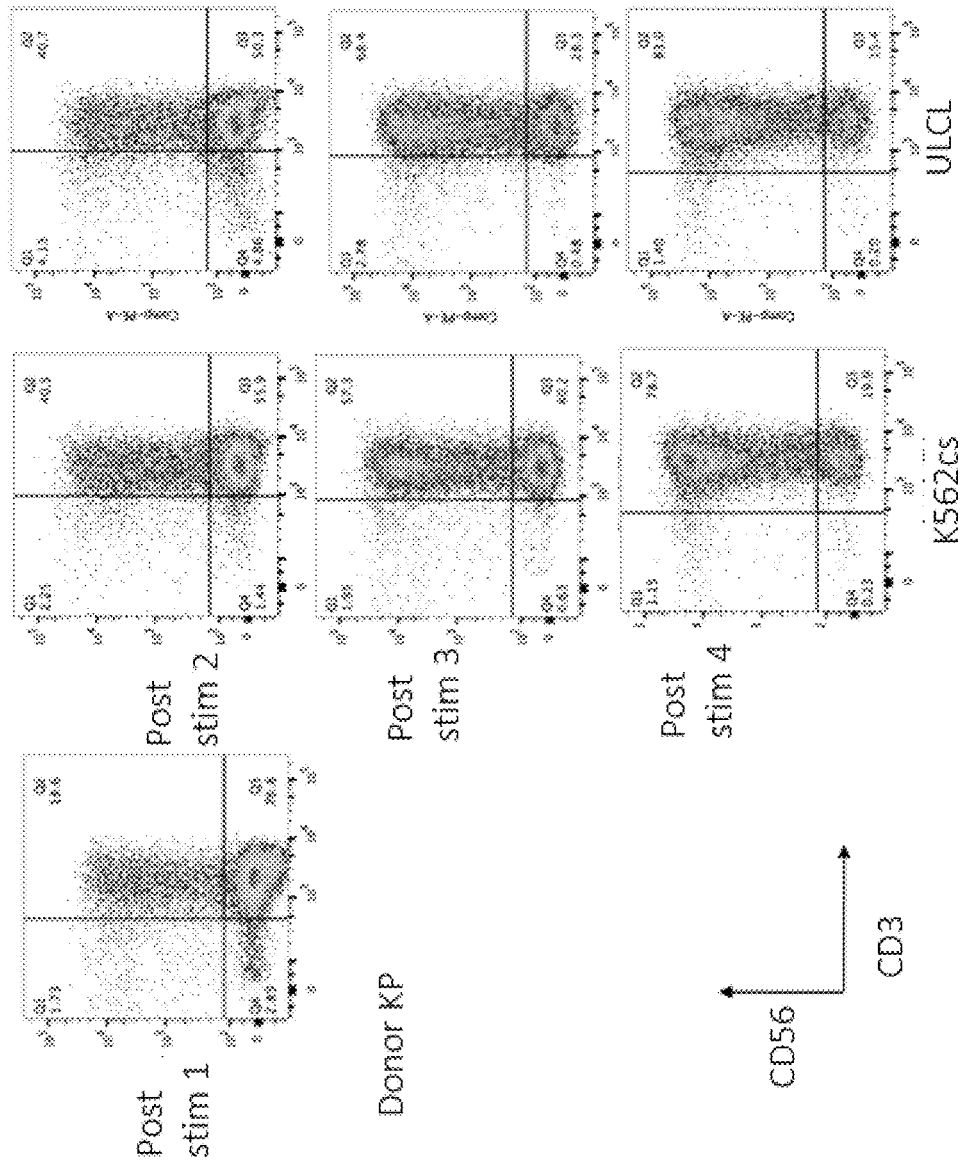
FIG. 32 provides scatterplots showing surface expression of CD3 and CD56 by cells expanded using ULCL clone #5 or K562cs cells as costimulatory cells, after the indicated number of stimulations, as determined by flow cytometry, for donor PB.
Figure 33:
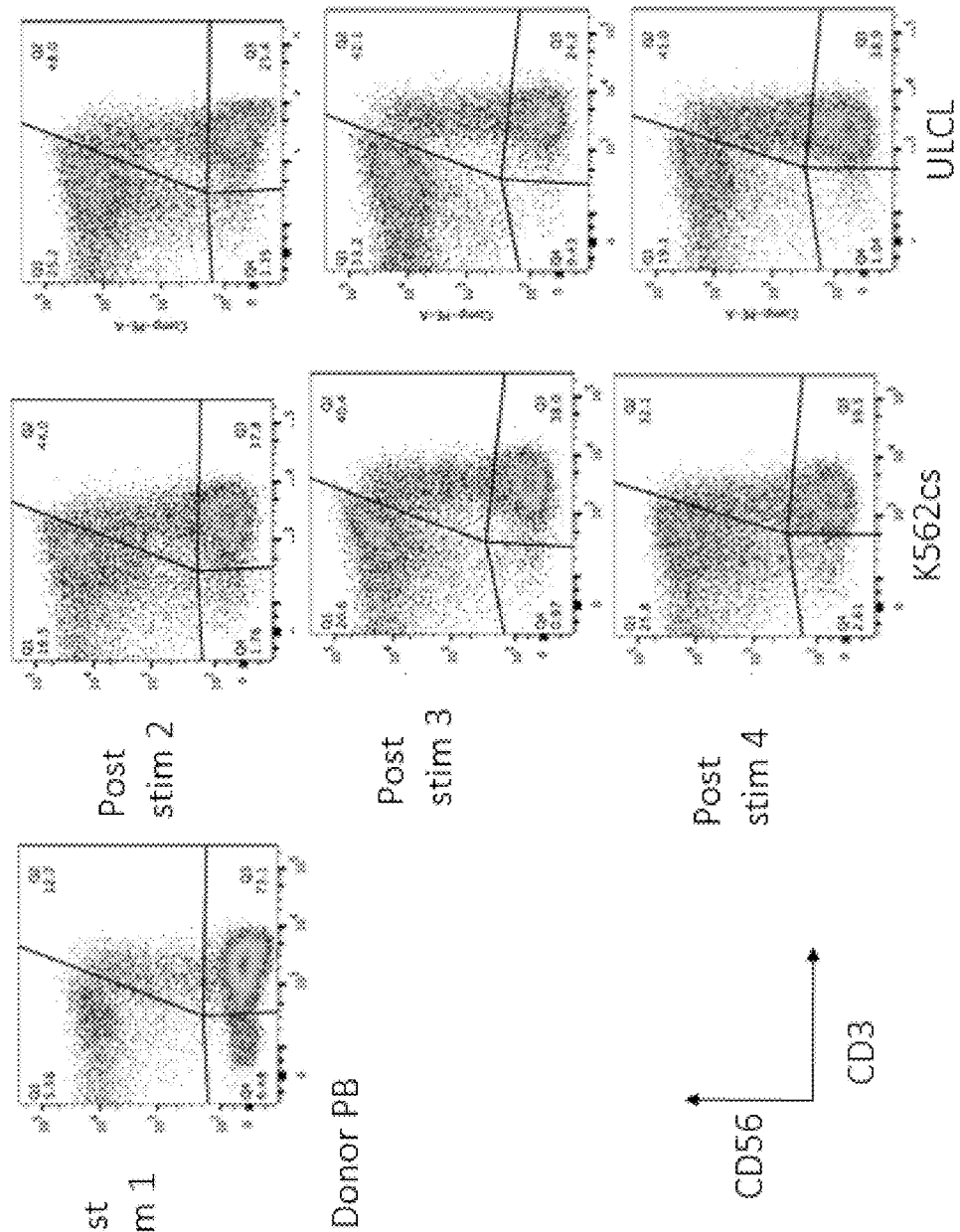
FIG. 33 provides scatterplots showing surface expression of CD3 and CD56 by cells expanded using ULCL clone #5 or K562cs cells as costimulatory cells, after the indicated number of stimulations, as determined by flow cytometry, for donor KP.
Figure 34:
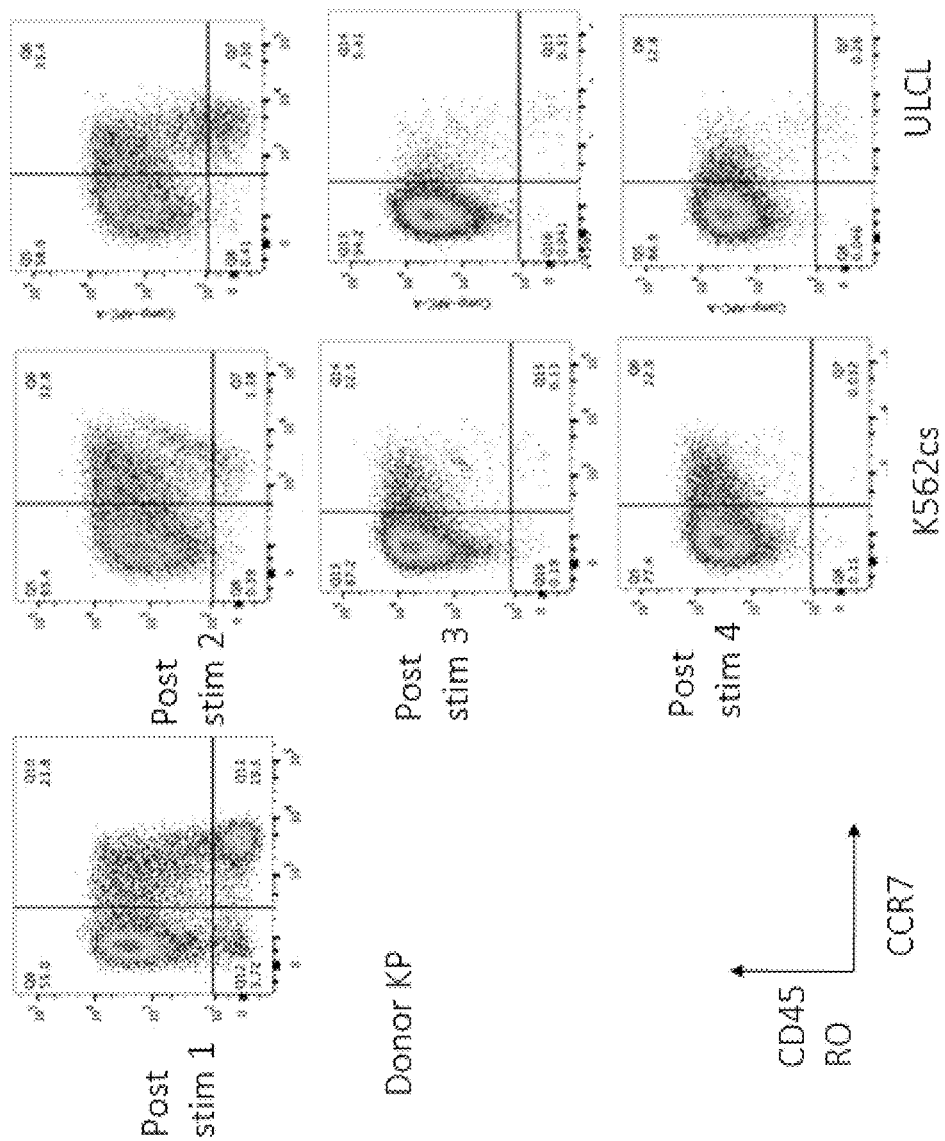
FIG. 34 provides scatterplots showing surface expression of CD45RO and CCR7 by cells expanded using ULCL clone #5 or K562cs cells as costimulatory cells, after the indicated number of stimulations, as determined by flow cytometry, for donor PB.
Figure 35:
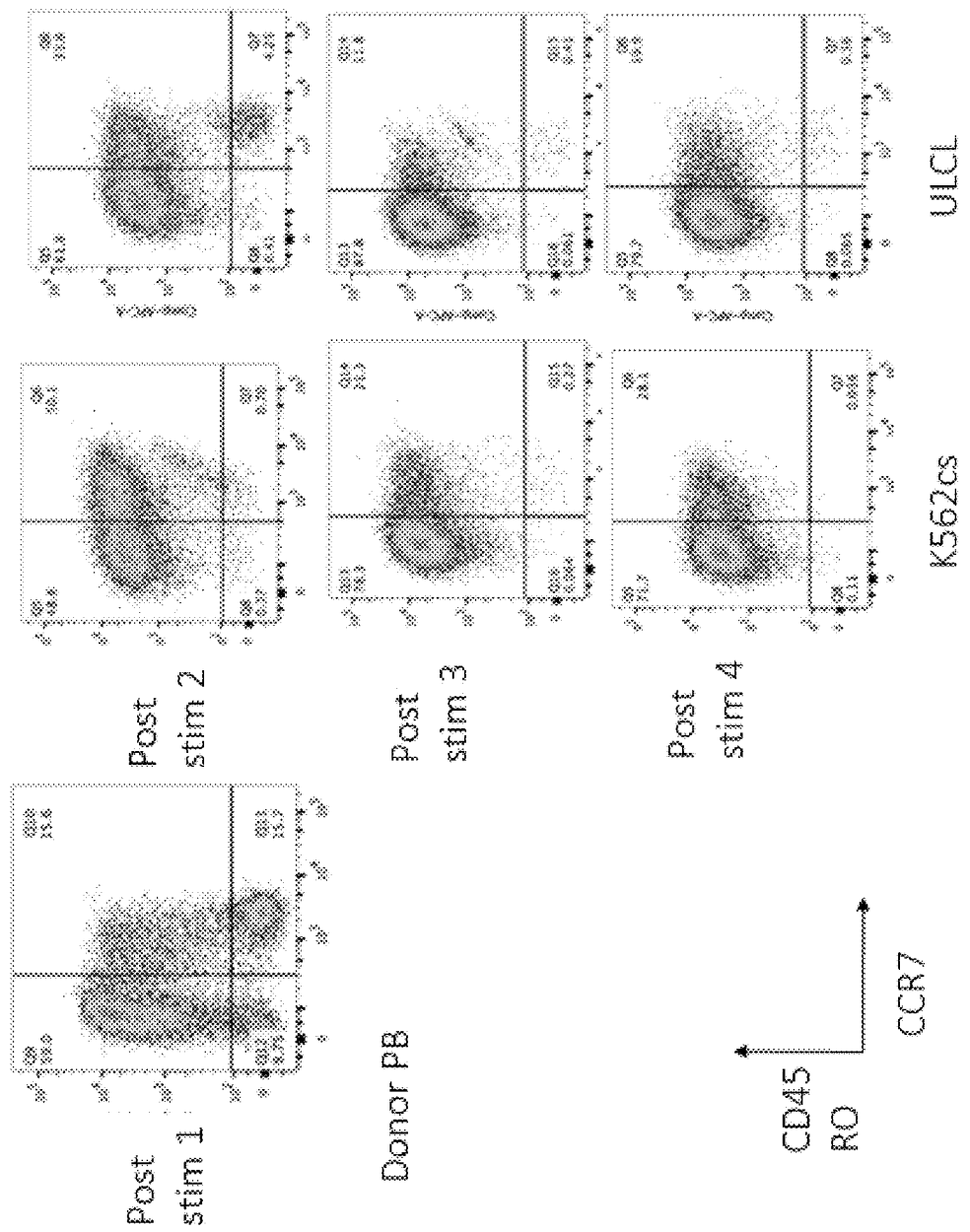
FIG. 35 provides scatterplots showing surface expression of CD45RO and CCR7 by cells expanded using ULCL clone #5 or K562cs cells as costimulatory cells, after the indicated number of stimulations, as determined by flow cytometry, for donor KP.

In further experiments using PBMCs obtained from two different donors, stimulations using ULCL clone #5 yielded populations of cells comprising IFNγ producing virus-specific T cells at a higher frequency as compared to the frequency in populations expanded using K562cs cells in stimulations (FIGS. 30A and 30B), with similar fold expansion (FIGS. 31A and 31B). FIGS. 32 and 33 show that the proportions of CD3+ and CD56+ cells in the expanded populations did not differ significantly in populations expanded using ULCL clone #5 as compared to populations expanded using K562cs cells, and FIGS. 34 and 35 show that populations expanded using K562cs cells expanded slightly greater proportion of central memory cells.

Figure 36A:
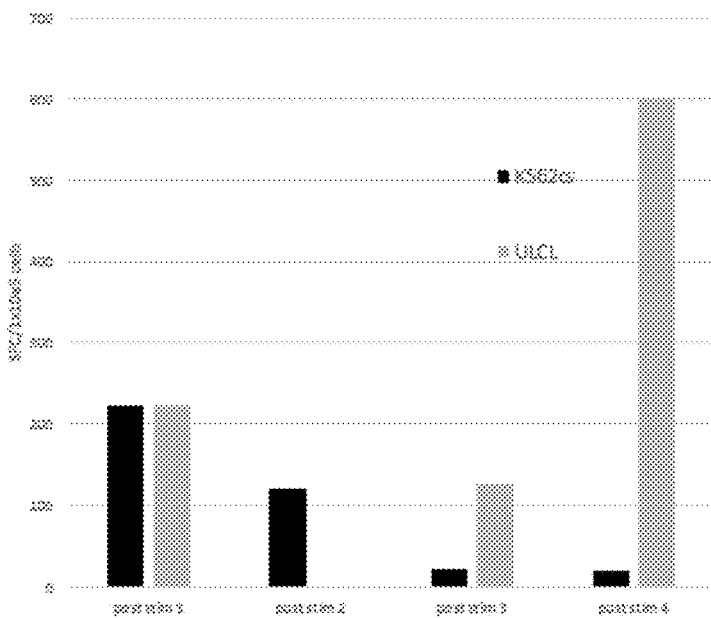
FIGS. 36A and 36B are bar charts for two different donors showing the frequency of virus-specific T cells in populations expanded using ULCL clone #5 or K562cs cells as costimulatory cells, after the indicated number of stimulations, as determined by ELISPOT analysis of the number of IFNγ producing cells.
Figure 36B:
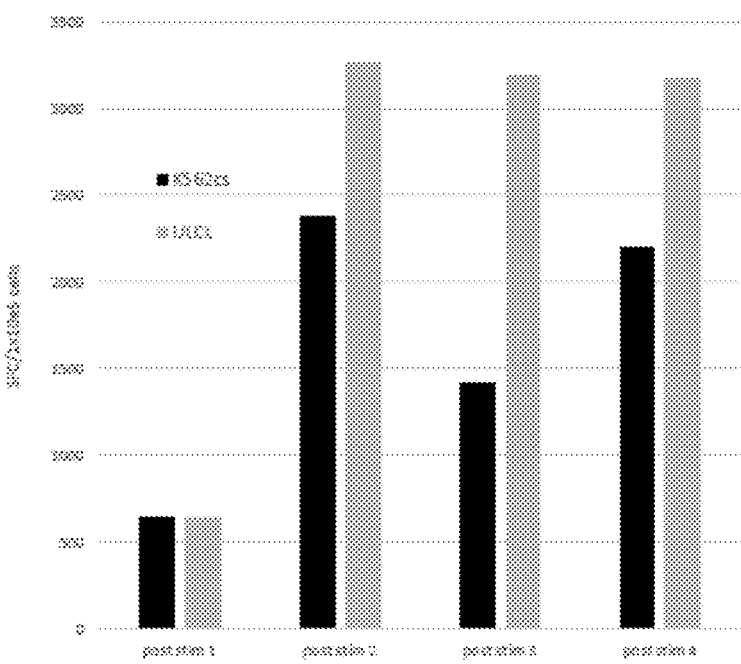
Figure 37A:
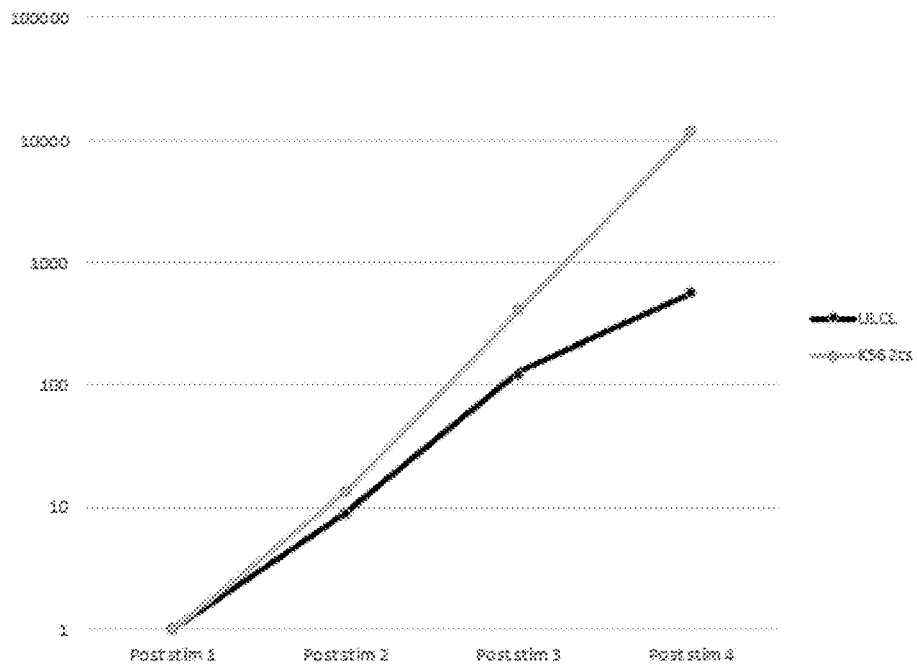
FIGS. 37A and 37B are bar charts for two different donors showing the fold expansion of virus-specific T cells in populations expanded using ULCL clone #5 or K562cs cells as costimulatory cells, after the indicated number of stimulations, as determined by ELISPOT analysis of the number of IFNγ producing cells.
Figure 37B:
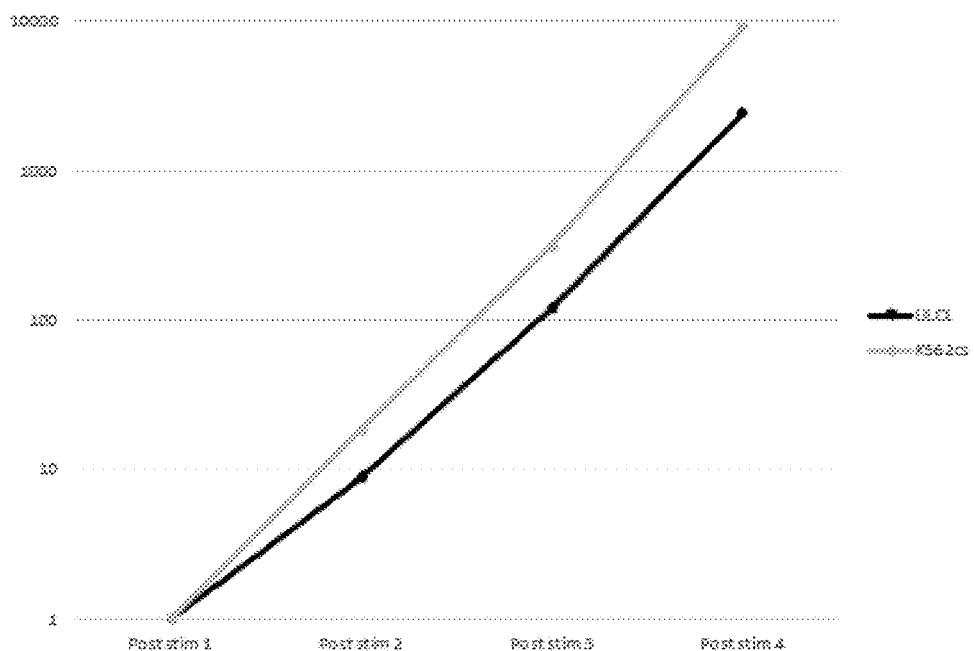
Figure 38:
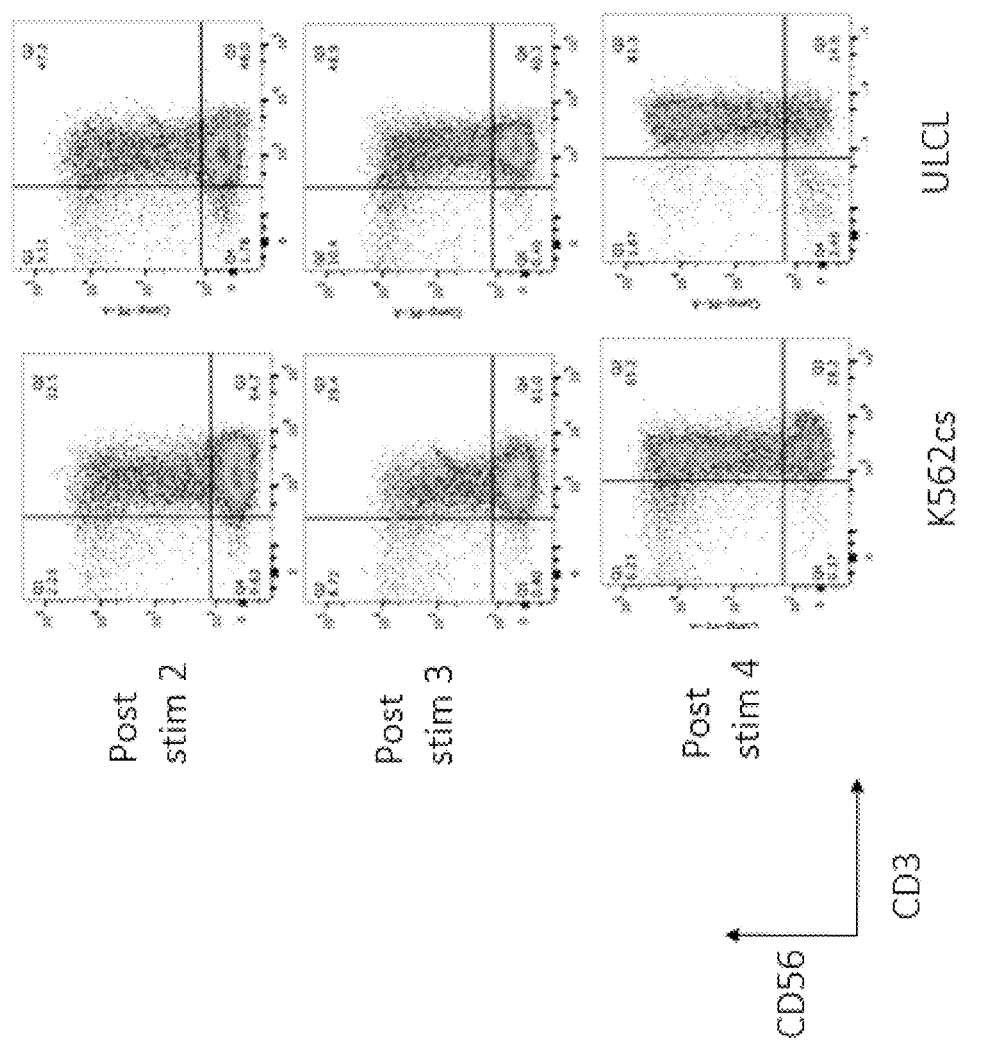
FIG. 38 provides scatterplots showing surface expression of CD3 and CD56 by cells expanded using ULCL clone #5 or K562cs cells as costimulatory cells, after the indicated number of stimulations, as determined by flow cytometry, for one donor.
Figure 39:
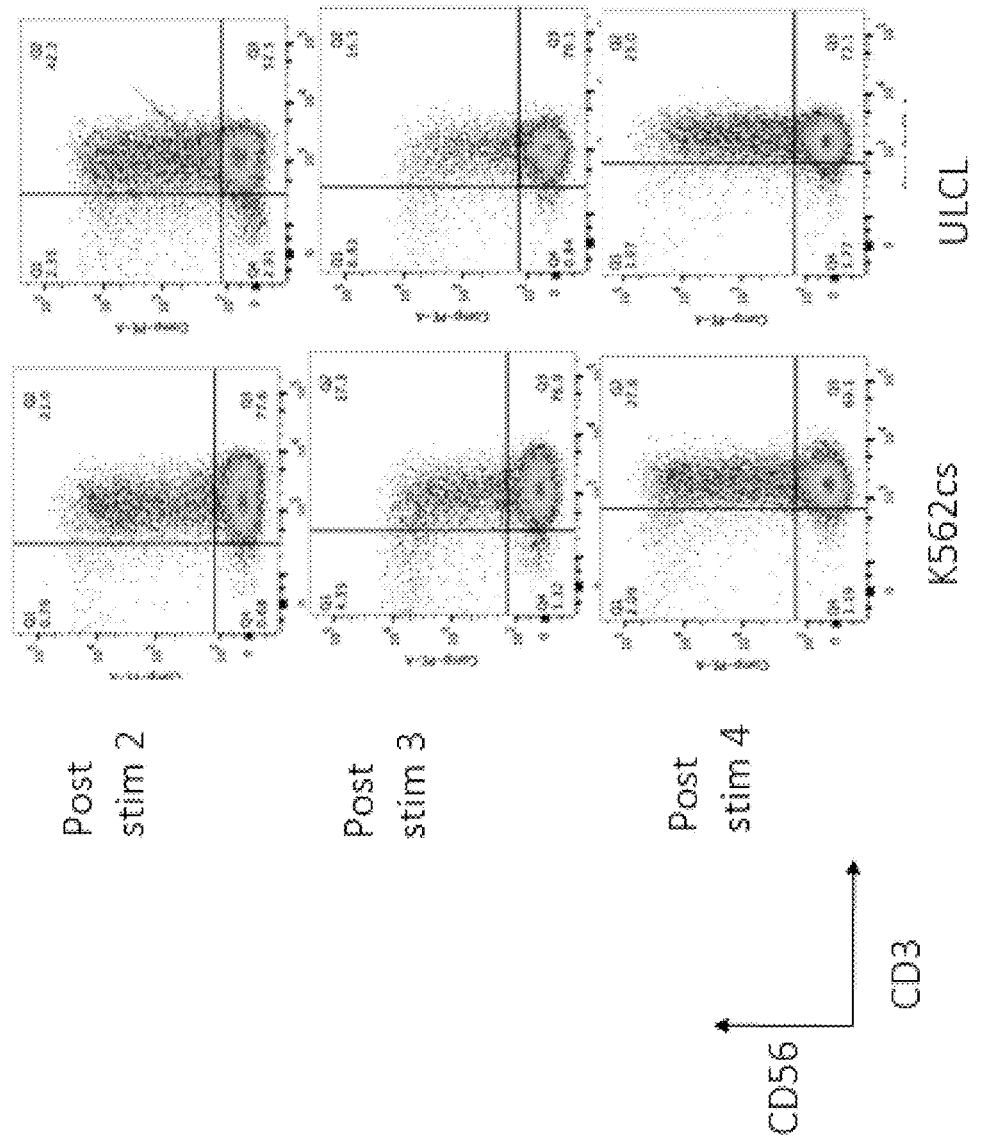
FIG. 39 provides scatterplots showing surface expression of CD3 and CD56 by cells expanded using ULCL clone #5 or K562cs cells as costimulatory cells, after the indicated number of stimulations, as determined by flow cytometry, for one donor.
Figure 40:
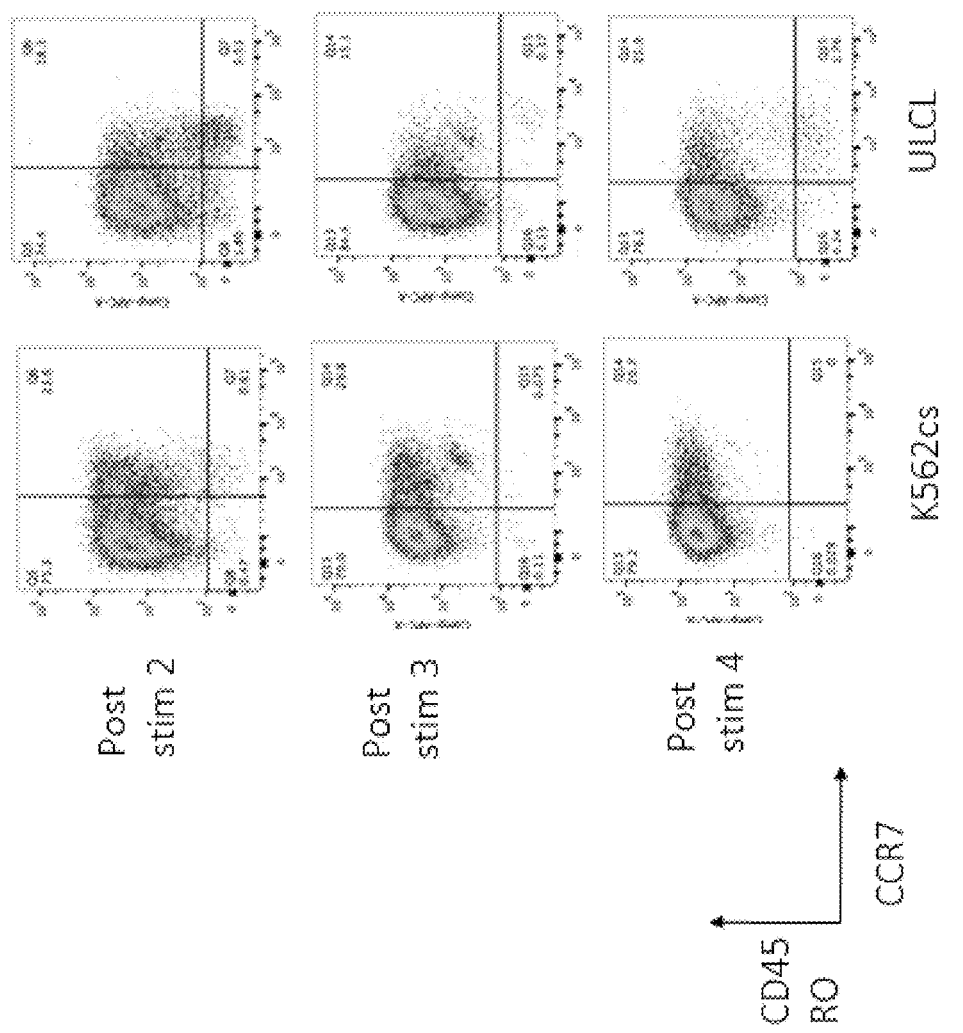
FIG. 40 provides scatterplots showing surface expression of CD45RO and CCR7 by cells expanded using ULCL clone #5 or K562cs cells as costimulatory cells, after the indicated number of stimulations, as determined by flow cytometry, for one donor.
Figure 41:
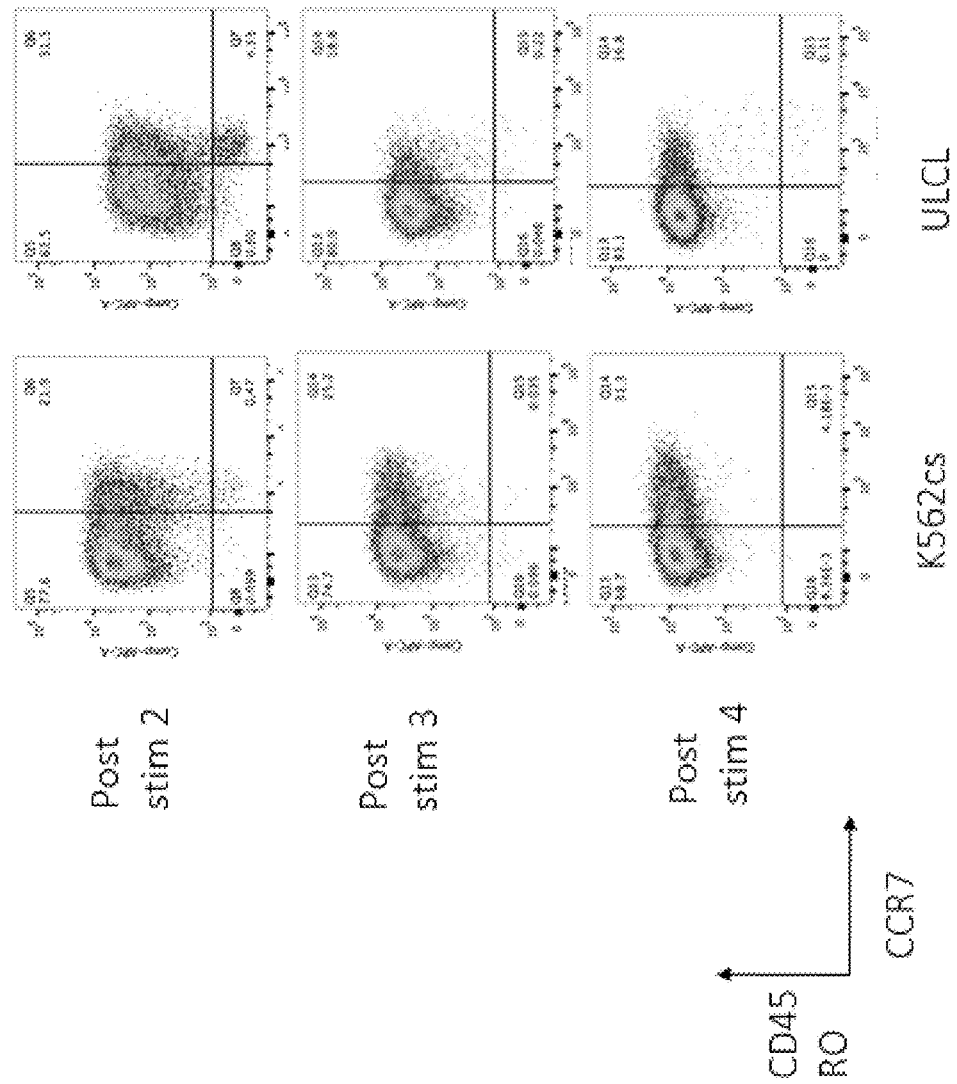
FIG. 41 provides scatterplots showing surface expression of CD45RO and CCR7 by cells expanded using ULCL clone #5 or K562cs cells as costimulatory cells, after the indicated number of stimulations, as determined by flow cytometry, for one donor.

FIGS. 36A and 36B show results from experiments obtained using PBMCs obtained from two further donors, demonstrating that stimulations using ULCL clone #5 yielded populations of cells comprising IFNγ producing virus-specific T cells at a higher frequency as compared to the frequency in populations expanded using K562cs cells in stimulations. In these experiments overall fold expansion was higher when K562cs cells were used in stimulations (FIGS. 37A and 37B). FIGS. 38 and 39 show that the proportions of CD3+ and CD56+ cells in the expanded populations did not differ significantly in populations expanded using ULCL clone #5 as compared to populations expanded using K562cs cells, and FIGS. 40 and 41 show that populations expanded using K562cs cells expanded slightly greater proportion of central memory cells.

Example 7

Further Characterization of HPV-Specific T Cells Expanded by Stimulation Culture in the Presence of Different Combinations of Cytokines and with Different Costimulatory Cells HPV stimulated T-cells (HPVST) were first activated by HPV E6/E7 peptide-pulsed autologous dendritic cells (DCs) at 10-20:1 PBMC:DC ratio, and cultured for 8 days in culture medium containing IL-6 (100 ng/ml), IL-7 (10 ng/ml), IL-12 (10 ng/ml), IL-15 (10 ng/ml) (e.g. per the first stimulation step described by Ramos et al., (J Immunother 2013; 36:66-76)).

Subsequent weekly restimulation steps were then carried out as shown in Table 6, four a total of four stimulations:

different cell types in the expanded populations, and analyzed by ELISPOT to determine the frequency IFNγ producing, virus-specific cells in the expanded populations.

Figure 42:
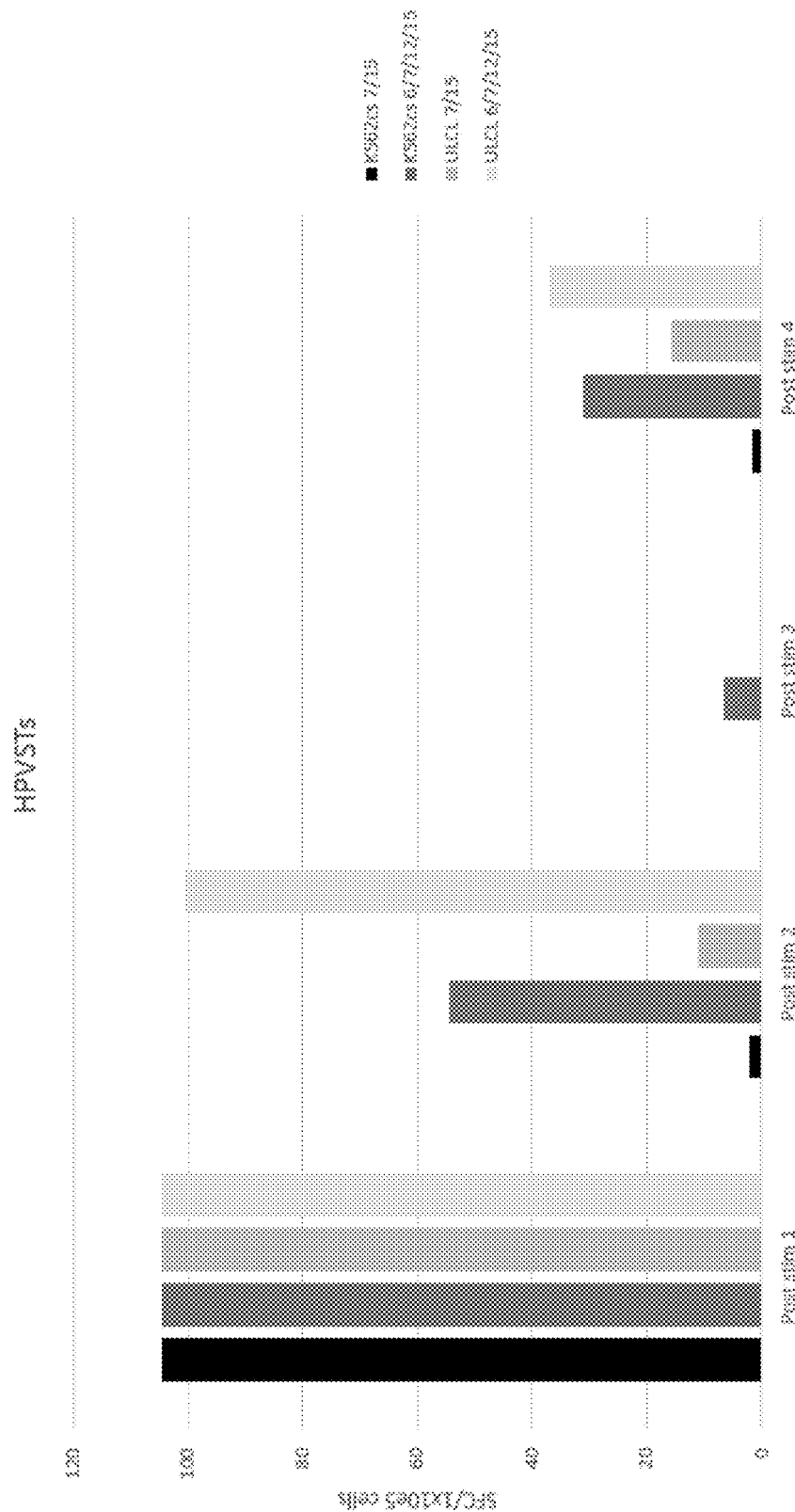
FIG. 42 is a bar chart showing the frequency of HPV-specific T cells in populations expanded using ULCL clone #5 or K562cs cells as costimulatory cells in stimulations comprising the indicated cytokines, and after the indicated number of stimulations, as determined by ELISPOT analysis of the number of IFNγ producing cells.

FIG. 42 shows that HPV-specific T cells were present at a higher frequency in populations of cells expanded by methods employing stimulations in the presence of IL-6, IL-7, IL-12 and IL-15 as compared to stimulations in the presence of IL-7 and IL-15 only. HPV-specific T cells were also present at a higher frequency in populations of cells expanded by methods using ULCLs as costimulatory cells as compared to methods using K562cs cells as costimulatory cells.

Figure 43:
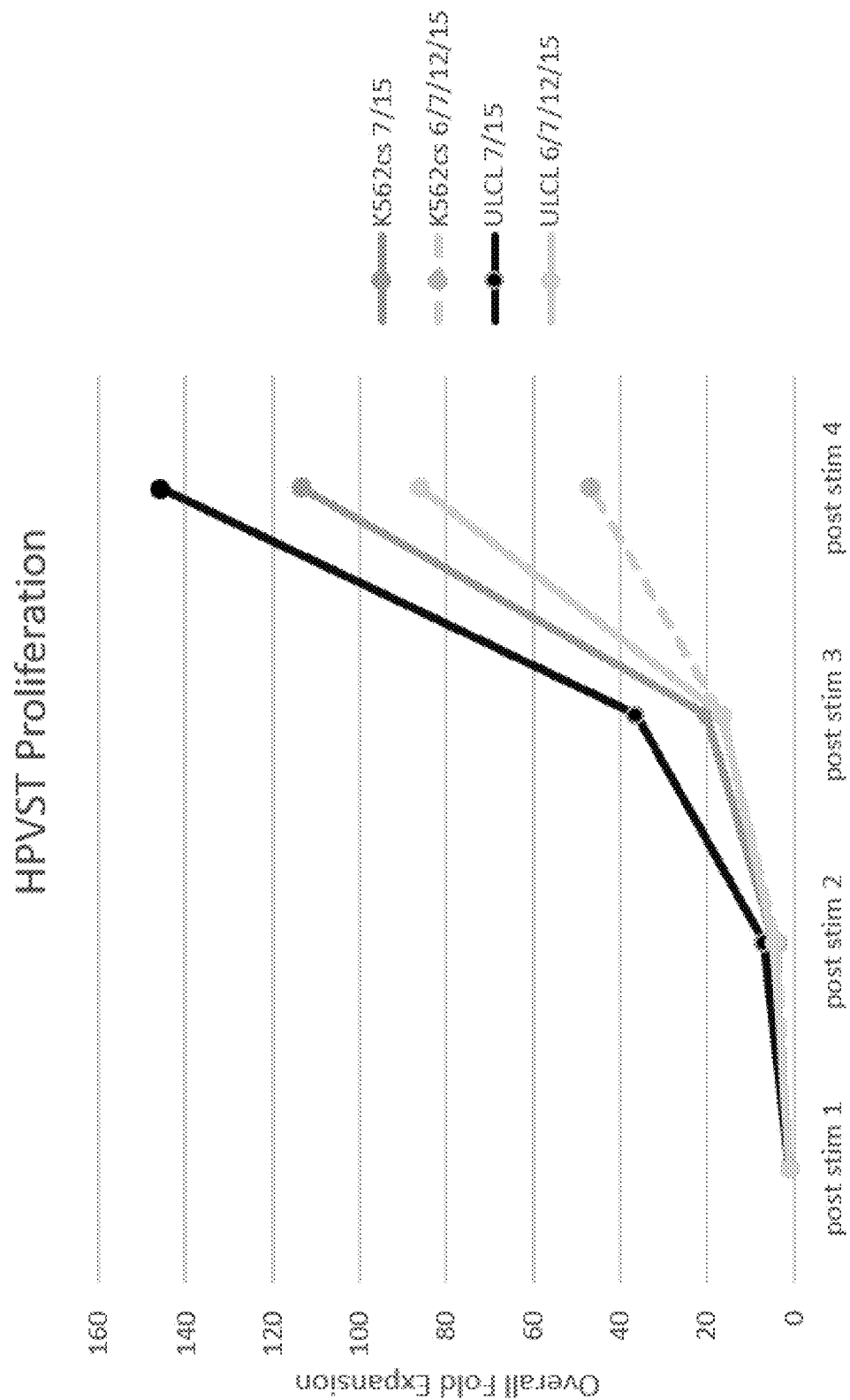
FIG. 43 is a graph showing the fold expansion of cells in populations expanded using ULCL clone #5 or K562cs cells as costimulatory cells in stimulations comprising the indicated cytokines, and after the indicated number of stimulations.

FIG. 43 shows the overall fold expansion of cells expanded according to the different protocols. Methods comprising stimulation in the presence of IL-7 and IL-15 only were found to expand more HPV-specific T cells as compared to methods comprising stimulation in the presence of IL-6, IL-7, IL-12 and IL-15. Methods comprising stimulations using ULCLs as costimulatory cells were shown to expand more HPV-specific T cells as compared methods comprising stimulations using K562cs cells as costimulatory cells.

Figure 44:
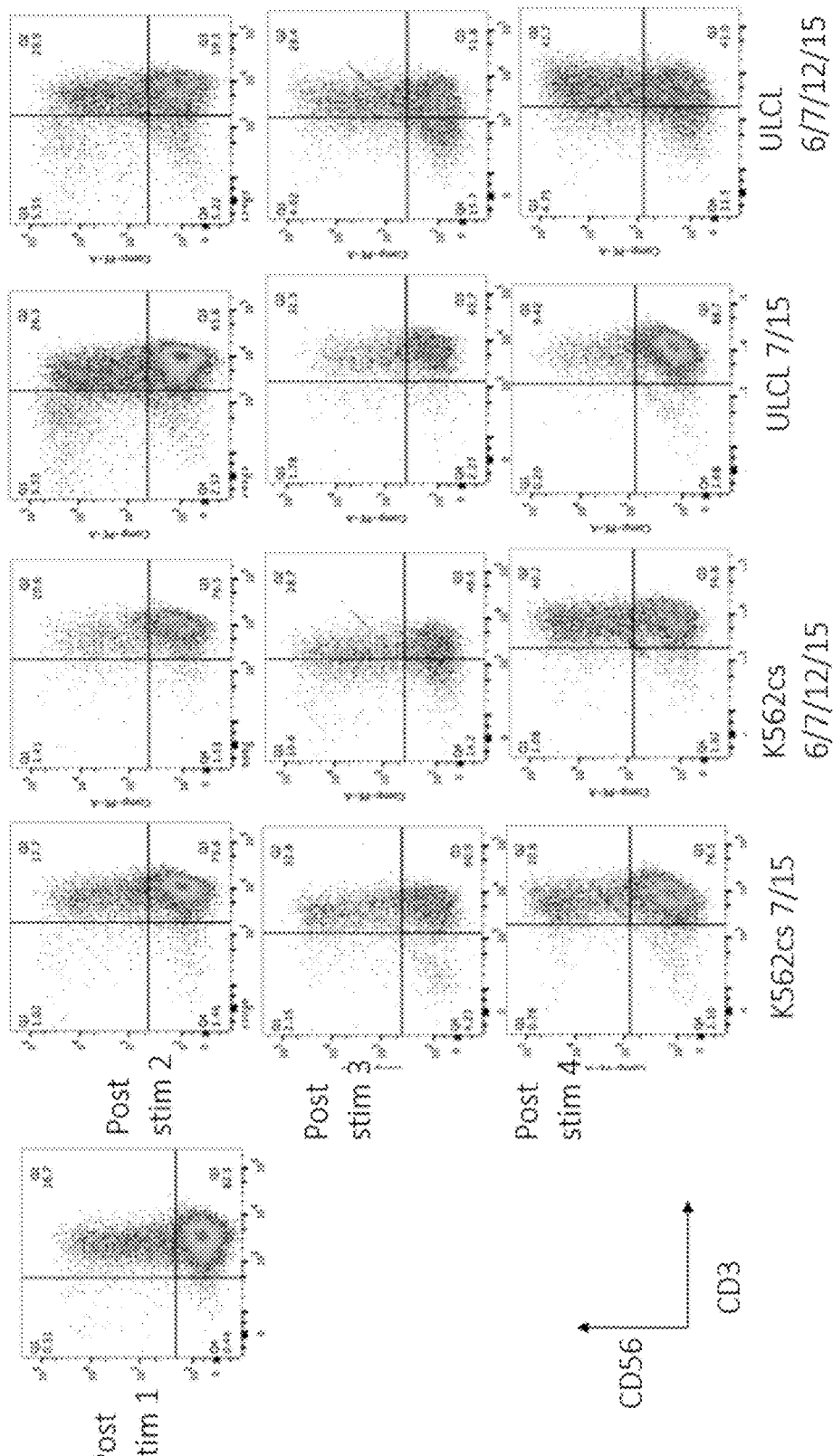
FIG. 44 provides scatterplots showing surface exsspression of CD3 and CD56 by cells expanded using ULCL clone #5 or K562cs cells as costimulatory cells in stimulations comprising the indicated cytokines, and after the indicated number of stimulations, as determined by flow cytometry.

FIG. 44 shows the expression of CD3 and CD56 by cells stimulated according to the different protocols, after the indicated number of stimulations. Cells expanded by stimulation in the presence of IL-7 and IL-15 only were shown to have a greater proportion of CD3+CD56− cells as compared to cells expanded by stimulation in the presence of IL-6, IL-7, IL-12 and IL-15. Cells expanded by stimulations using HLA-negative LCLs as costimulatory cells were shown have a greater proportion of CD3+CD56− cells as compared to cells expanded by stimulations using K562cs as costimulatory cells.

Figure 45:
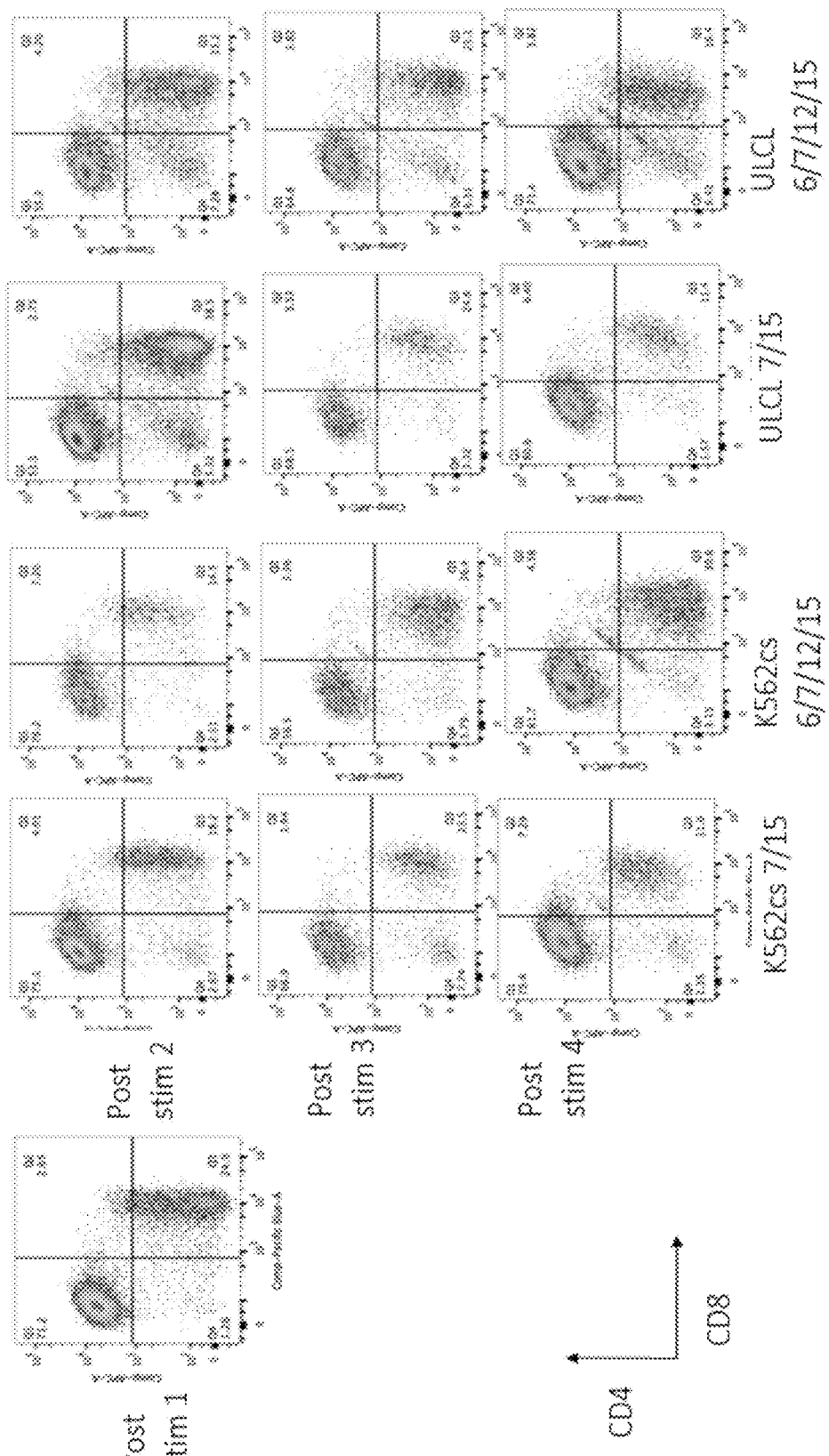
FIG. 45 provides scatterplots showing surface expression of CD4 and CD8 by cells expanded using ULCL clone #5 or K562cs cells as costimulatory cells in stimulations comprising the indicated cytokines, and after the indicated number of stimulations, as determined by flow cytometry.

FIG. 45 shows the expression of CD4 and CD8 by cells stimulated according to the different protocols, after the indicated number of stimulations. Cells expanded by stimulation in the presence of IL-6, IL-7, IL-12 and IL-15 were shown to have a greater proportion of CD8+ cells as compared to cells expanded by stimulation in the presence of IL-7 and IL-15 only.

Figure 46:
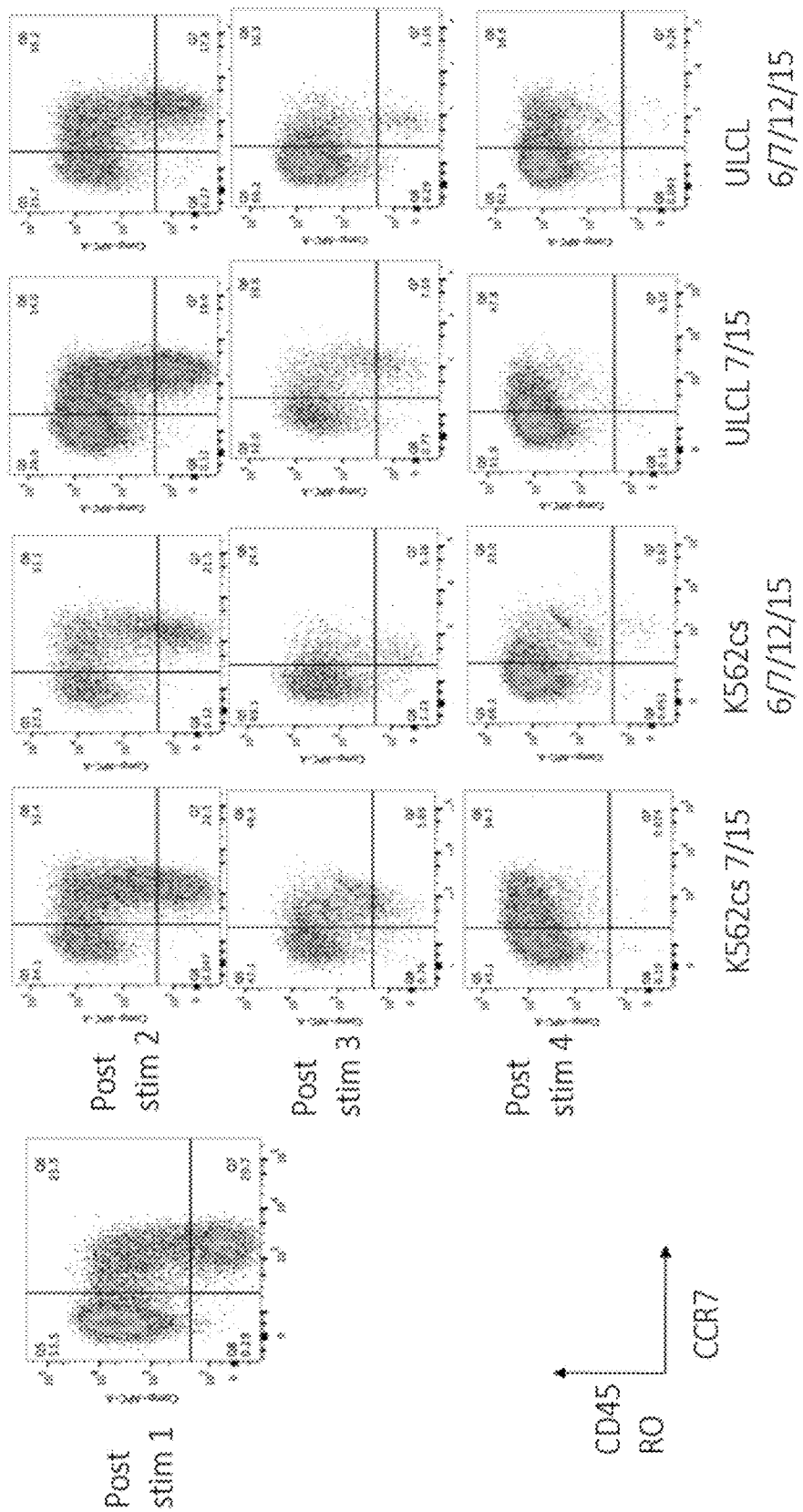
FIG. 46 provides scatterplots showing surface expression of CD45RO and CCR7 by cells expanded using ULCL clone #5 or K562cs cells as costimulatory cells in stimulations comprising the indicated cytokines, and after the indicated number of stimulations, as determined by flow cytometry.

FIG. 46 shows the expression of CD45RO and CCR7 by cells stimulated according to the different protocols, after the indicated number of stimulations. Cells expanded by stimu-

TABLE 6

Second and subsequent stimulations

| Condition | Conditions |
|---|---|
| K562cs 7/15 | HPV E6/E7 peptide-pulsed autologous T-APC at 1:1 ratio, in the presence of equal number of irradiated allogeneic K562-cs co-stimulatory cells, in cell culture media containing IL-7 (10 ng/ml) and IL-15 (100 ng/ml). |
| ULCL 7/15 | HPV E6/E7 peptide-pulsed autologous T-APC at 1:1 ratio, in the presence of equal number of irradiated HLA-negative LCLs, in cell culture media containing IL-7 (10 ng/ml) and IL-15 (100 ng/ml). |
| K562cs 6/7/12/15 | HPV E6/E7 peptide-pulsed autologous T-APC at 1:1 ratio, in the presence of equal number of irradiated allogeneic K562-cs co-stimulatory cells, in cell culture media containing IL-6 (100 ng/ml), IL-7 (10 ng/ml), IL-12 (10 ng/ml) and IL-15 (10 ng/ml). |
| ULCL 6/7/12/15 | HPV E6/E7 peptide-pulsed autologous T-APC at 1:1 ratio, in the presence of equal number of irradiated HLA-negative LCLs, in cell culture media containing IL-6 (100 ng/ml), IL-7 (10 ng/ml), IL-12 (10 ng/ml) and IL-15 (10 ng/ml). |

At the end of each stimulation the cells were counted, and analysed by flow cytometry to determine the proportions of lation in the presence of IL-7 and IL-15 only were shown to have a greater proportion of central memory (i.e. CD45RO+

CCR7+) cells as compared to cells expanded by stimulation in the presence of IL-6, IL-7, IL-12 and IL-15.

Example 8

Generation of Virus-Specific T Cells from PBMCs Depleted of CD45RA+ Cells

The inventors investigated modifications to the methods for expanding virus-specific T cells to increase the frequency of viral-specific antigen-specific T-cells and to reduce the frequency of NK cells in expanded populations.

Figure 47:
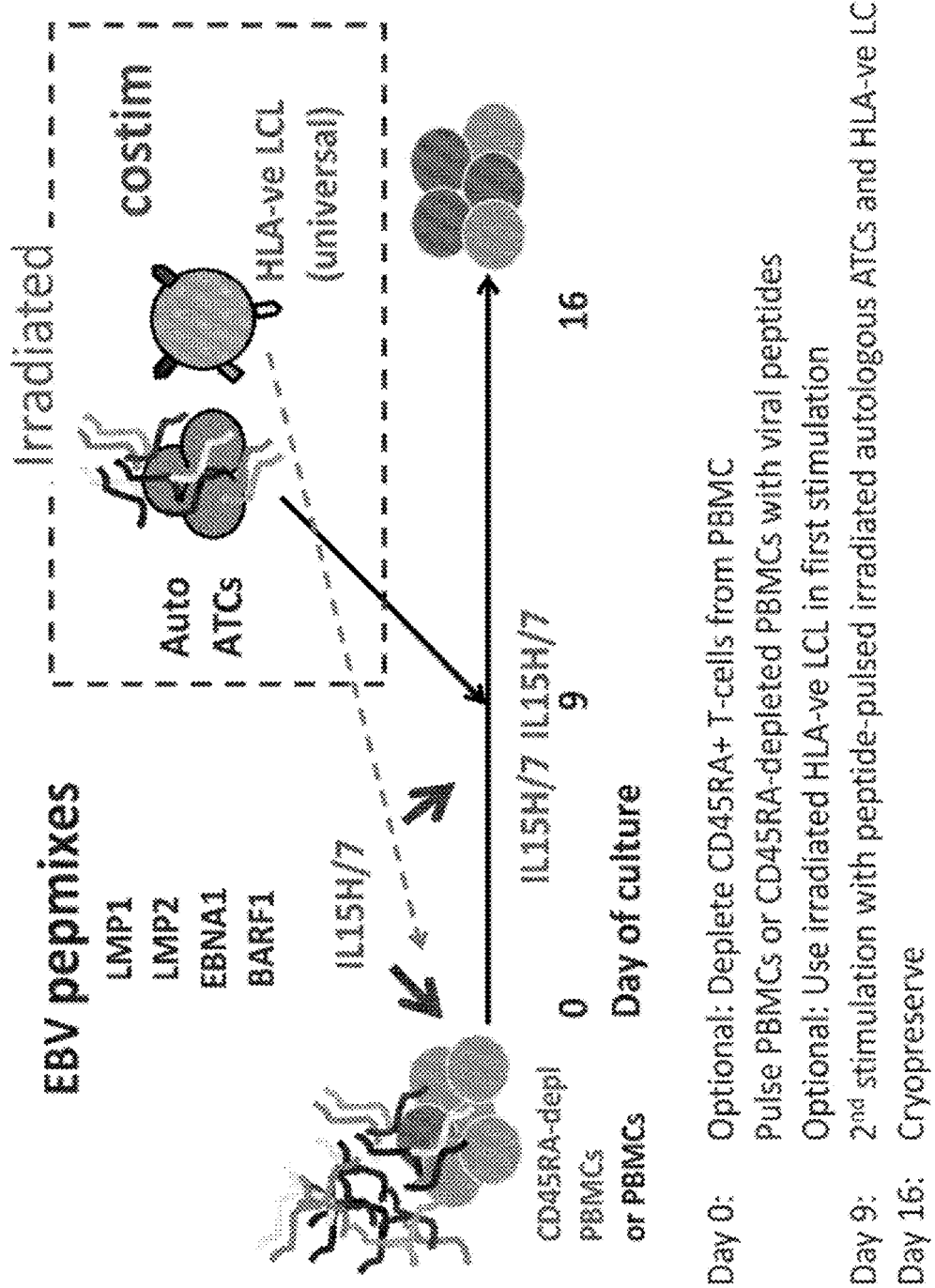
FIG. 47 is a schematic illustration of general embodiments of virus-specific T-cell (VST) generation methods of the disclosure.

FIG. 47 provides a schematic representation of steps of the method used to generate virus-specific T-cells in this Example. Briefly, on day 0 PBMCs (which were either depleted of CD45RA+ cells, or which were not depleted of CD45RA+ cells) were pulsed with viral peptides in the presence of IL-7 (10 ng/ml) and IL-15 (100 ng/ml or 5 ng/ml), or in the presence of IL-4 and IL-7. At day 9, the cells were re-stimulated using peptide-pulsed irradiated autologous antigen-presenting activated T-cells (ATCs) in the presence of irradiated HLA-negative LCLs as costimulatory cells, and in the presence of IL-7 (10 ng/ml) and IL-15 (100 ng/ml or 5 ng/ml), or in the presence of IL-4 and IL-7. At day 16 cells were harvested and analyzed.

Figure 48:
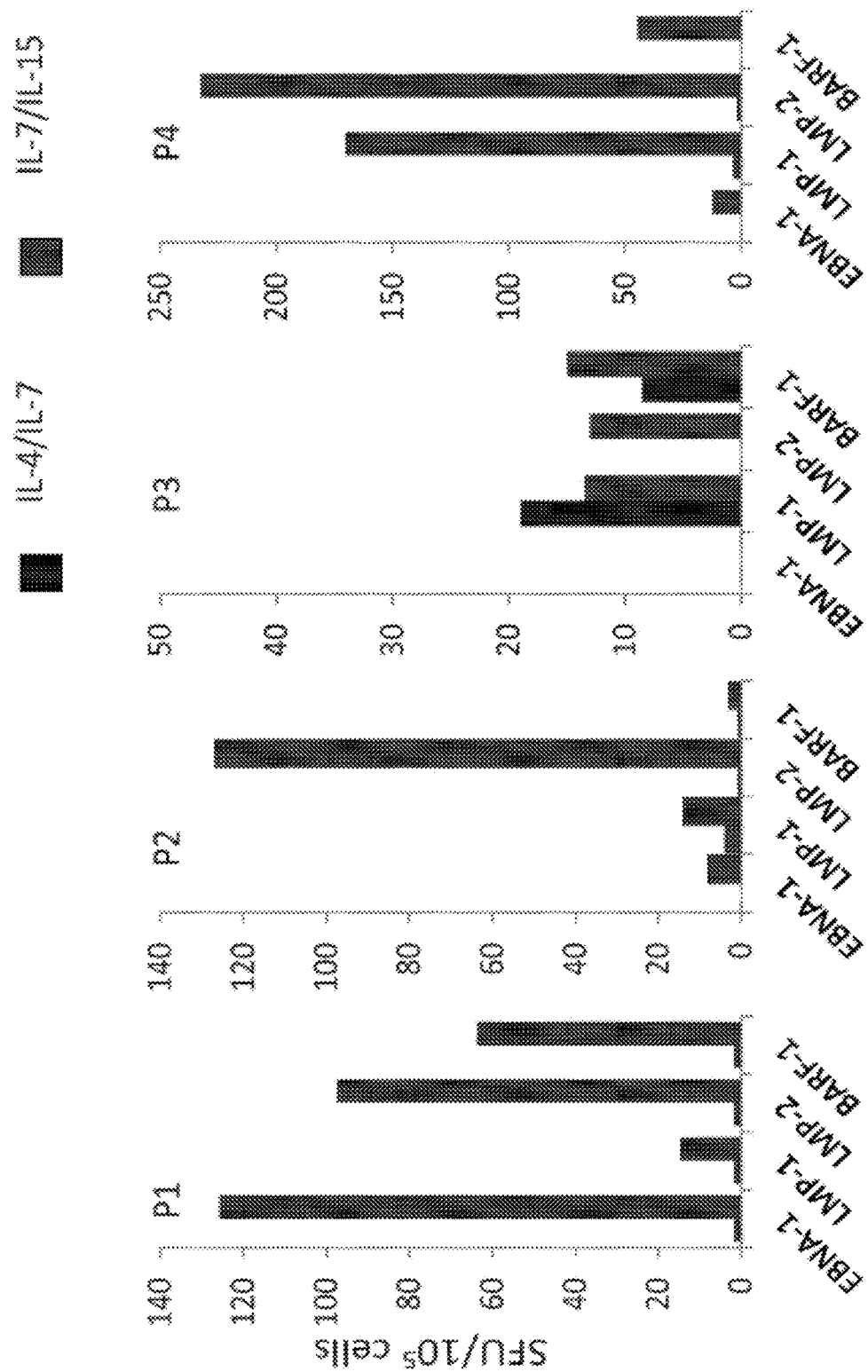
FIG. 48 provides bar charts demonstrating improved specificity of methods of the disclosure that employ IL-7 and IL-15 as compared to known methods that employ IL-4 and IL-7.

FIG. 48 shows results of ELISPOT analysis showing that methods using IL-7 and IL-15 in stimulations expanded virus-specific T cells at a higher frequency as compared to methods using IL-4 and IL-7 in stimulations.

Figure 49:
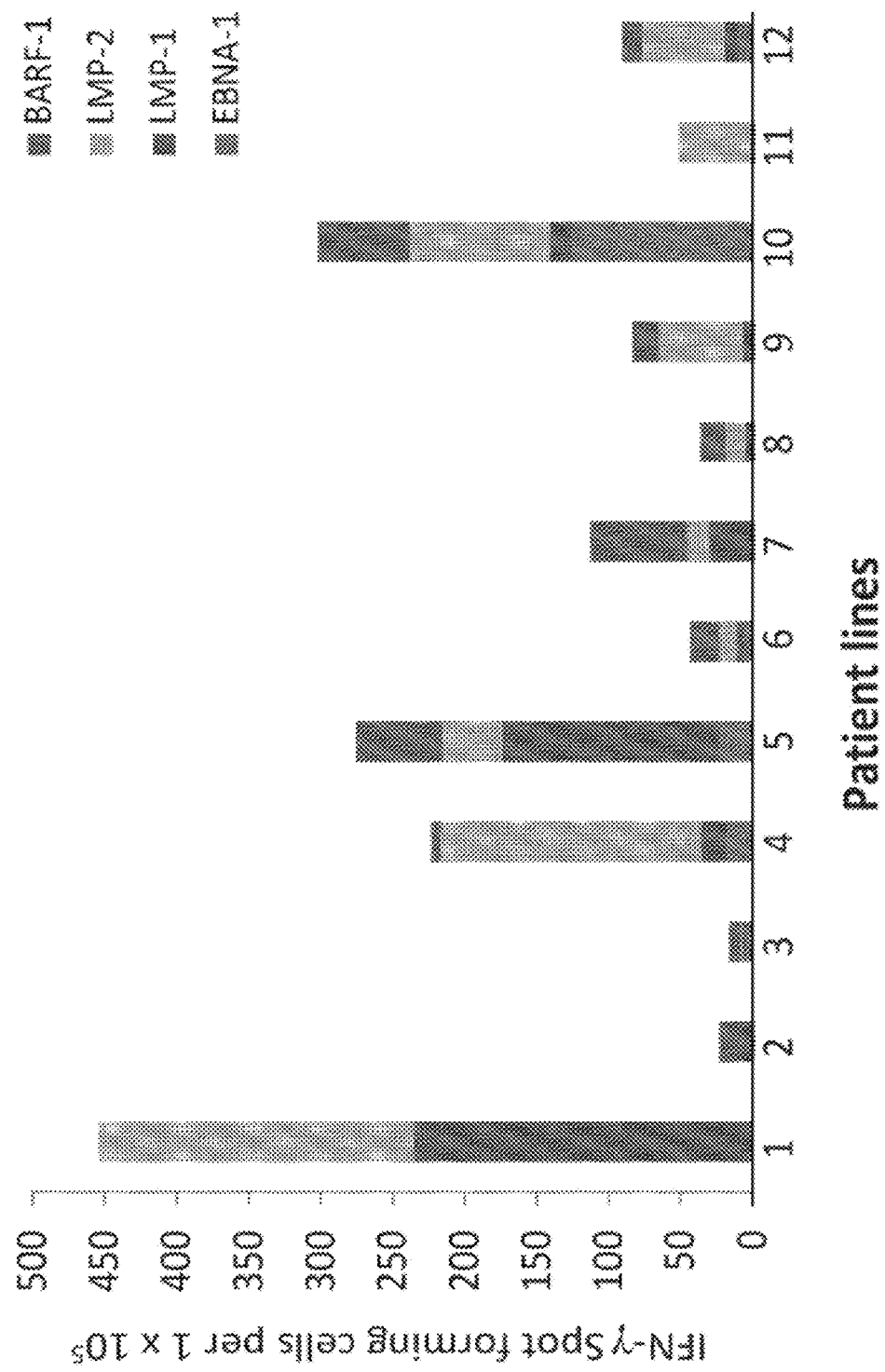
FIG. 49 is a bar chart showing improved EBV antigen specificity of lymphoma patient EBVSTs obtained by stimulations performed in the presence of IL-7 and IL-15, as determined by ELISPOT.

Methods comprising stimulation in the presence of IL-7 and IL-15 were found to be able to expand viral antigen-specific T cells from PBMCs obtained from lymphoma patients (FIG. 49). Using IL-15 instead of IL-4 was found to increase the frequency of antigen-specific T-cells in patient EBV-specific T cells.

Figure 50:
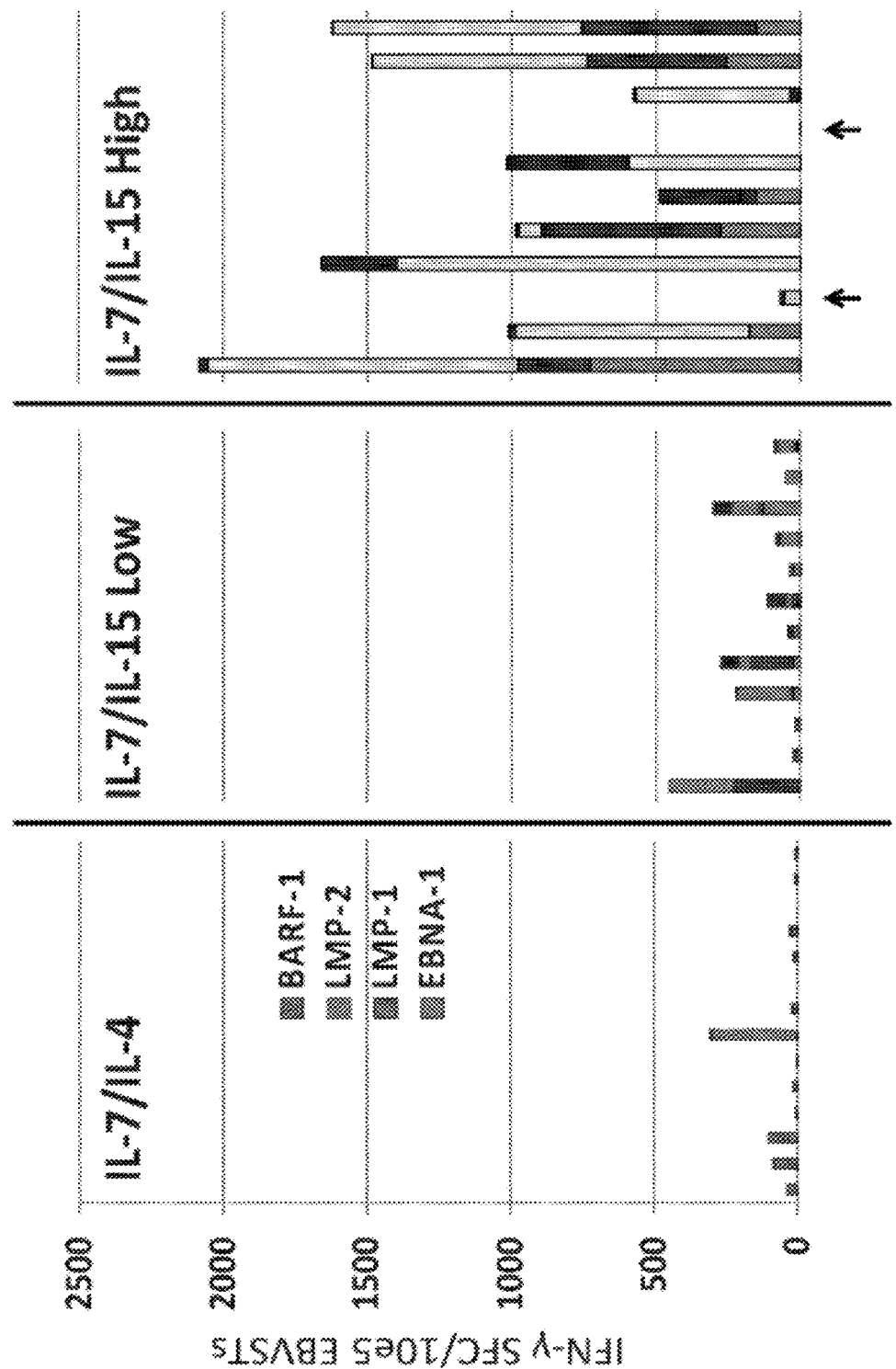
FIG. 50 is a bar chart demonstrating that stimulation in the presence of high doses of IL-15 increases frequency of VSTs.
Figure 51:
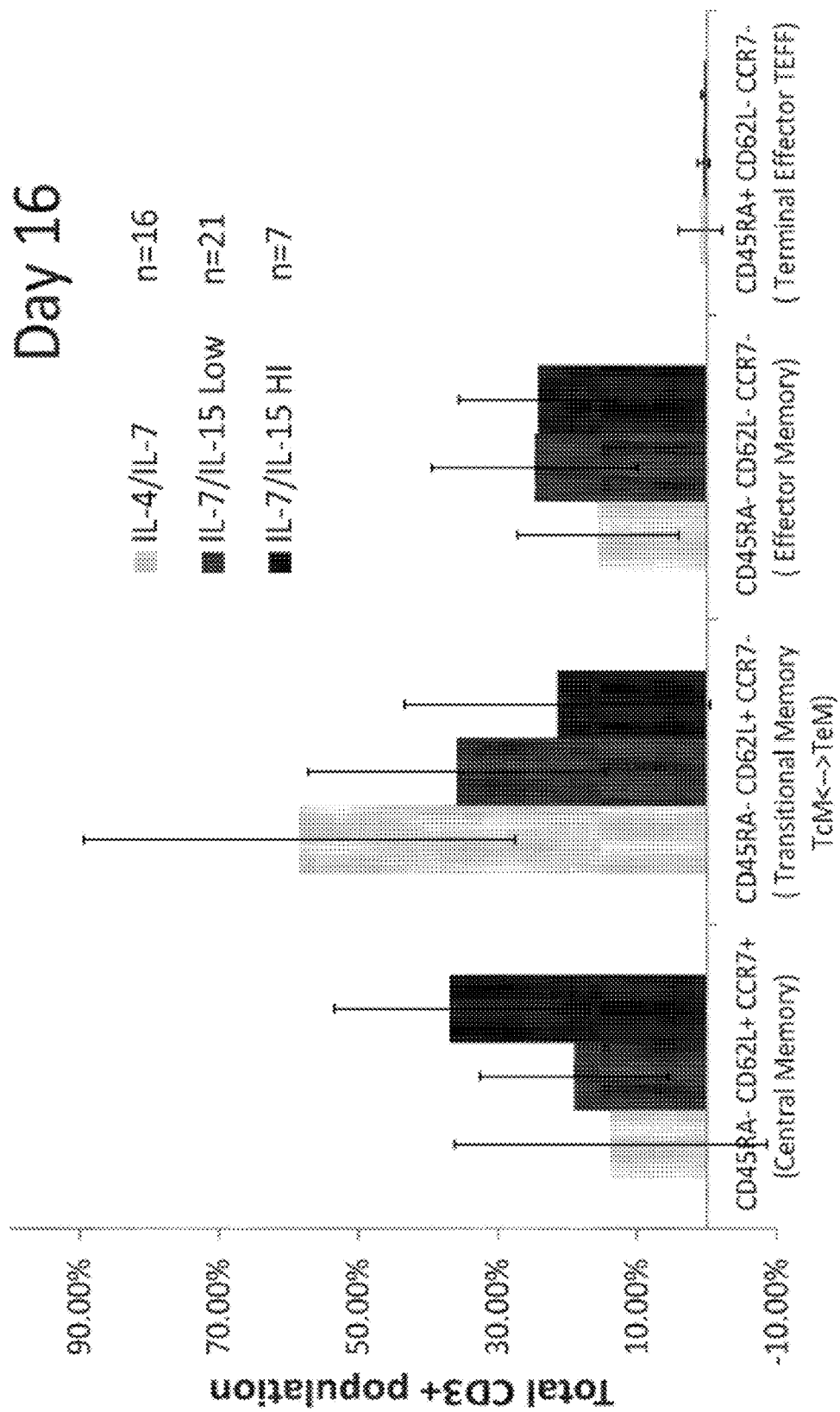
FIG. 51 is a bar chart showing shows that stimulation in the presence of high doses of IL-15 increases the proportion of central memory EBVSTs.
Figure 52:
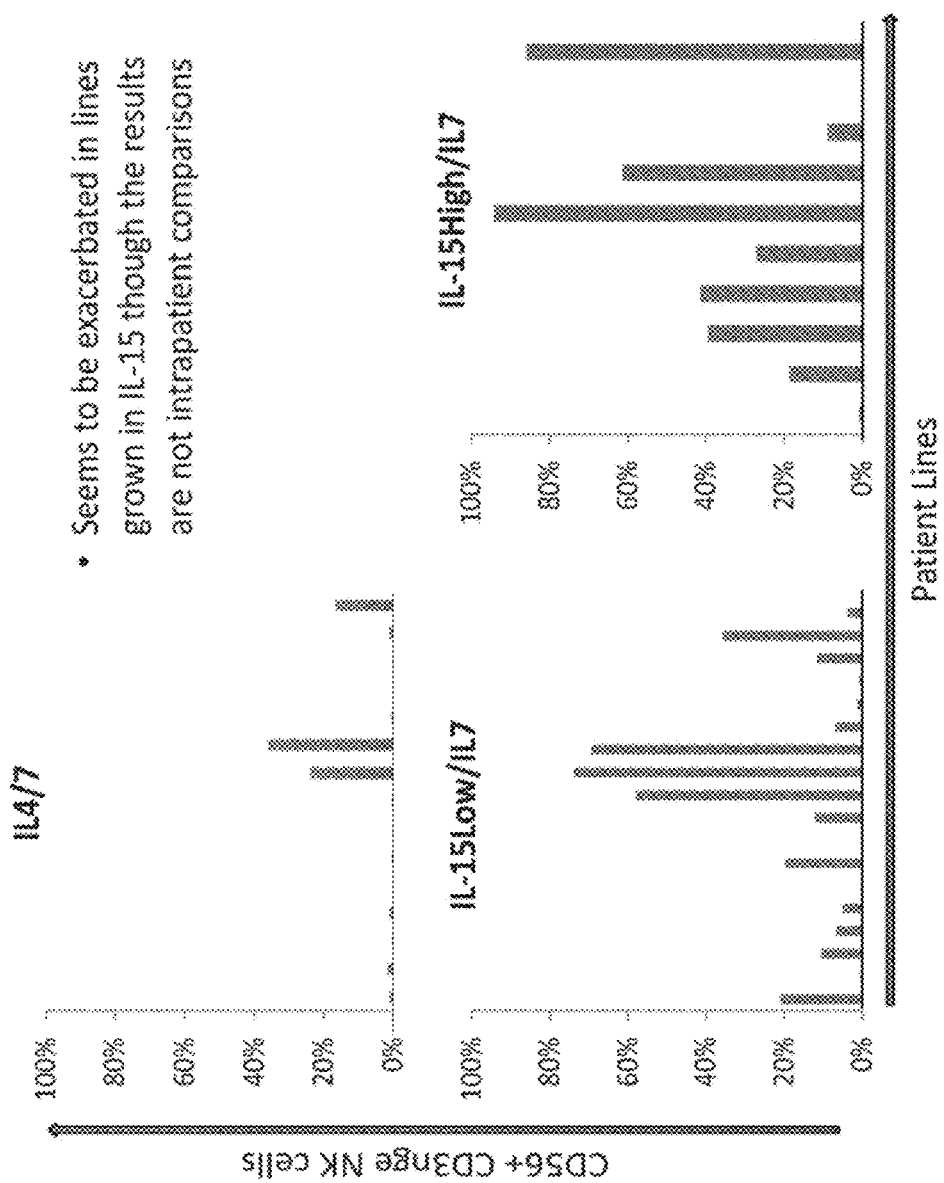
FIG. 52 provides bar charts showing excessive NK-cell outgrowth in EBVSTs from some patients.

Investigation of the optimal concentration of IL-15 to be used in stimulations revealed that a higher dose of IL-15 (100 ng/ml) was best for increasing the frequency of virus-specific T cells (100 ng per mL compared to standard dose of 5 ng per mL)—see FIG. 50. FIG. 51 demonstrates that high doses of IL-15 increased the proportion of central memory EBV-specific T cells in the expanded cell population.

The inventors next investigated how to minimize NK cell outgrowth in populations of expanded cells generated from healthy donor and lymphoma patient PBMCs. Preferential outgrowth of NK cells was found to be higher in methods using IL-15 in stimulations (NK cell populations appear to be larger in populations obtained by stimulations using IL-15 and IL-7). To address this, conditions were developed to avoid excessive NK cell outgrowth. Depletion of CD45RA+ cells from the PBMCs prior to stimulations was investigated. CD45RA is a naïve T-cell marker that is also expressed on natural T-regulatory cells and NK cells, so it was reasoned that depletion of CD45RA+ cells would remove the NK cells from the starting PBMC population. Depletion of CD45RA+cells also removes T regulatory cells that can inhibit the outgrowth of antigen-specific T-cells, especially in cancer patients, and also removes naïve cells that can grow as bystander cells and dilute the antigen-specific T-cells. Depletion can be achieved by any suitable method, e.g. using magnetic labeling and separation (for example, using Miltenyi® Biotec columns). Use of antibody to deplete cells using magnetic beads or nanobubbles may also occur.

Figure 53:
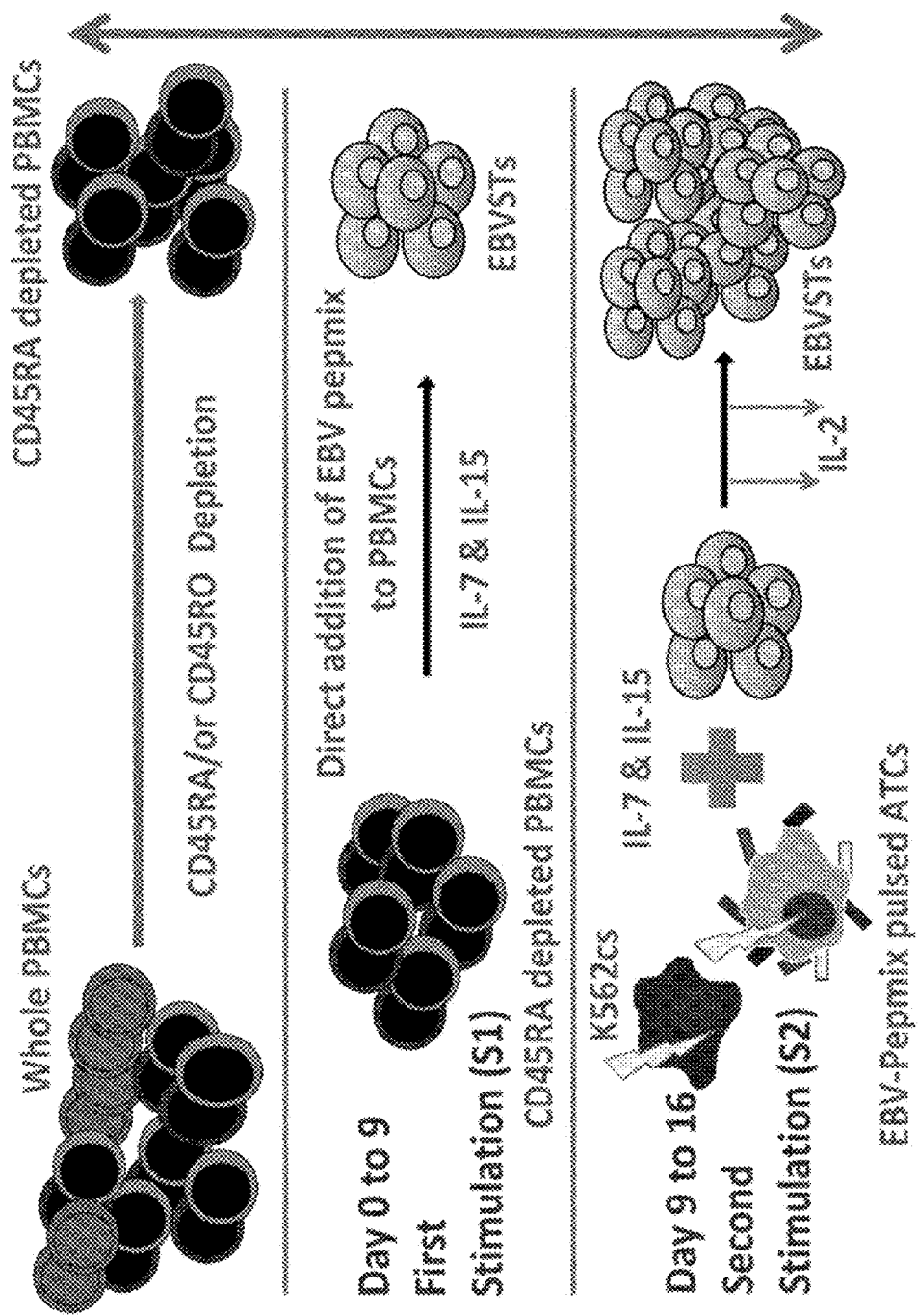
FIG. 53 is a schematic illustration of the generation of pepmix-activated EBVSTs from CD45RA+ cell-depleted PBMCs.
Figure 54:
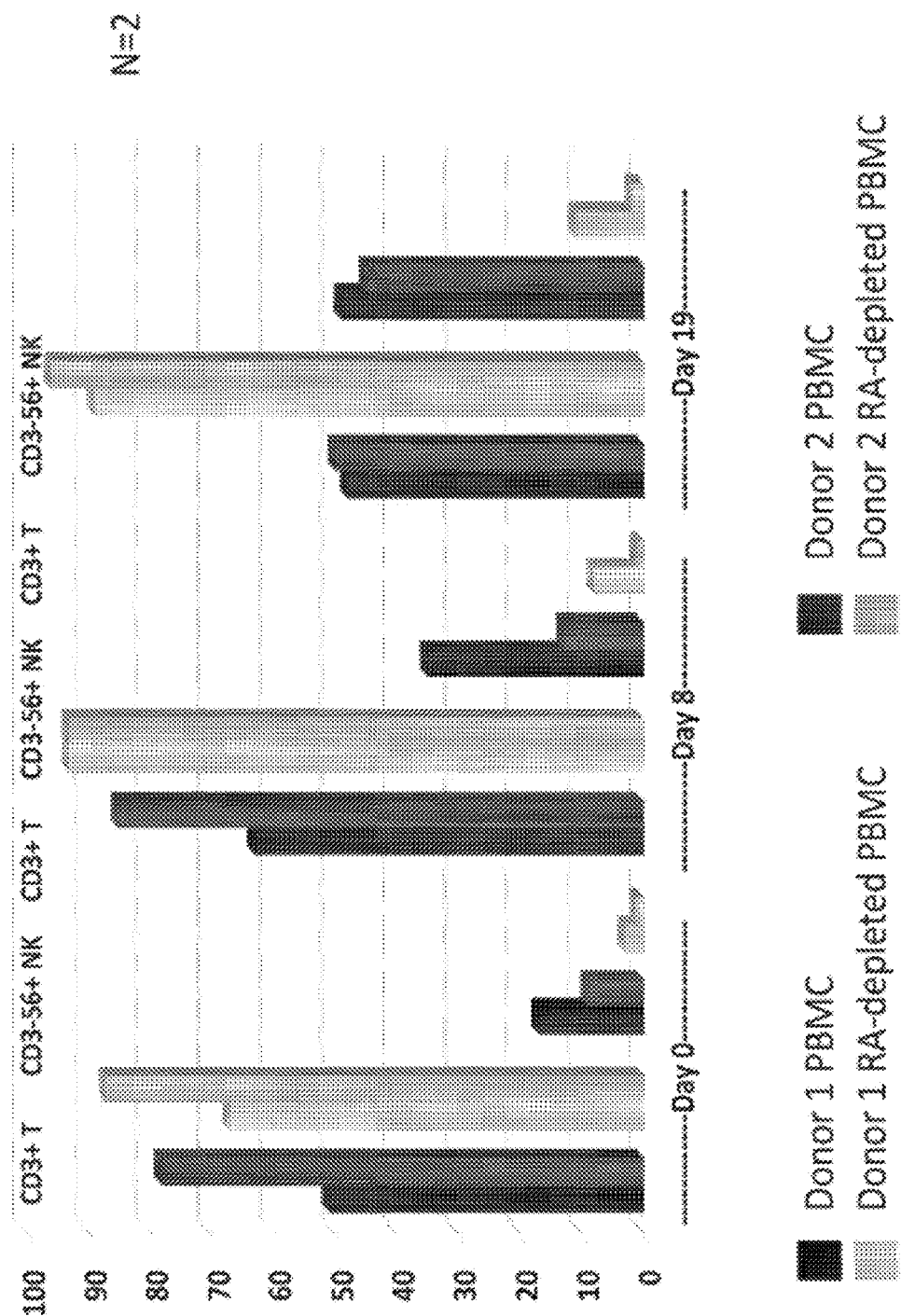
FIG. 54 is a bar chart showing that CD45RA depletion decreases the frequency of CD3-CD56+ NK cells in EBVSTs expanded from healthy donors.
Figure 55:
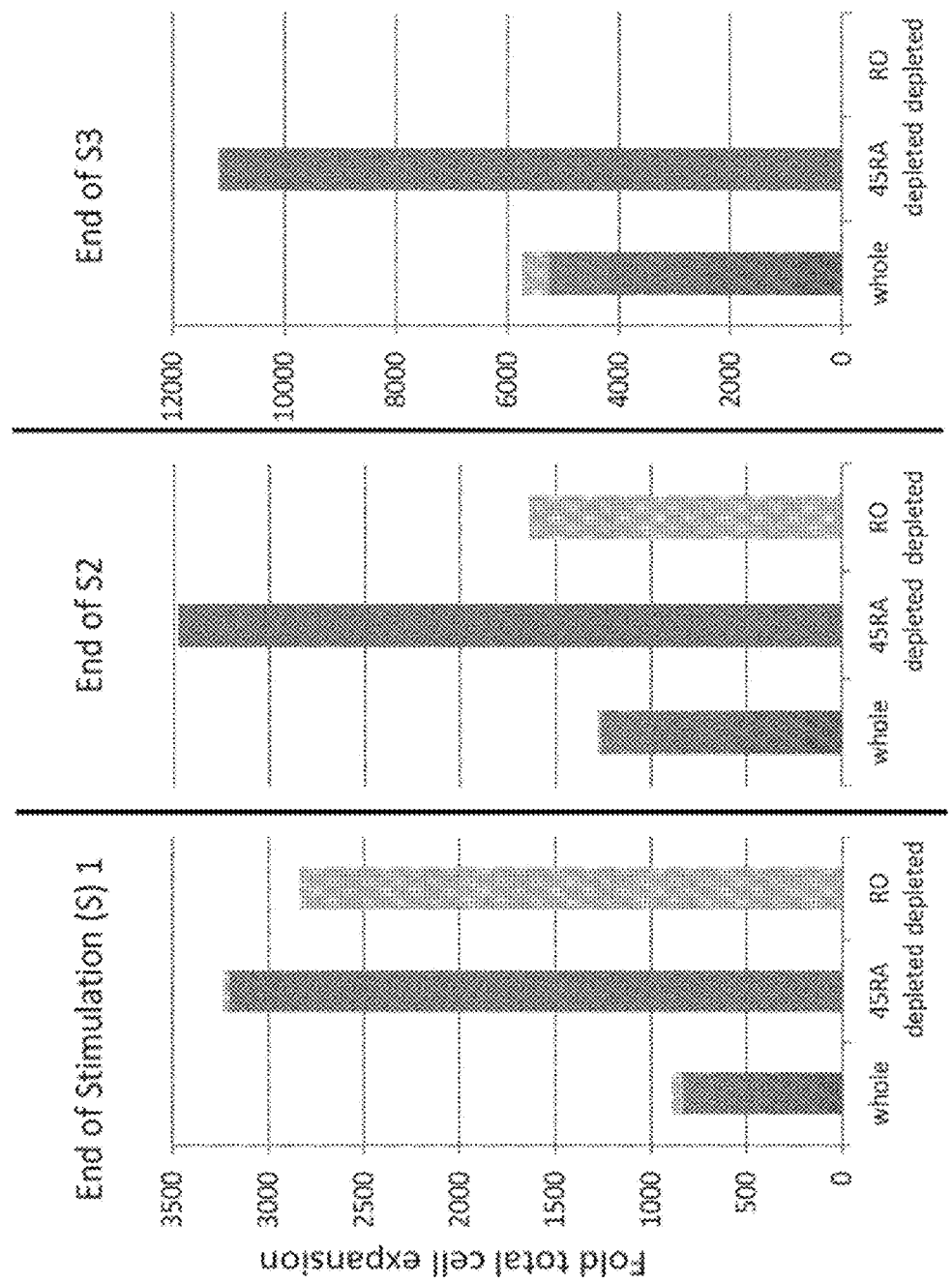
FIG. 55 is a bar chart showing that removal of CD45RA+ cells increases proliferation of EBVSTs.
Figure 56:
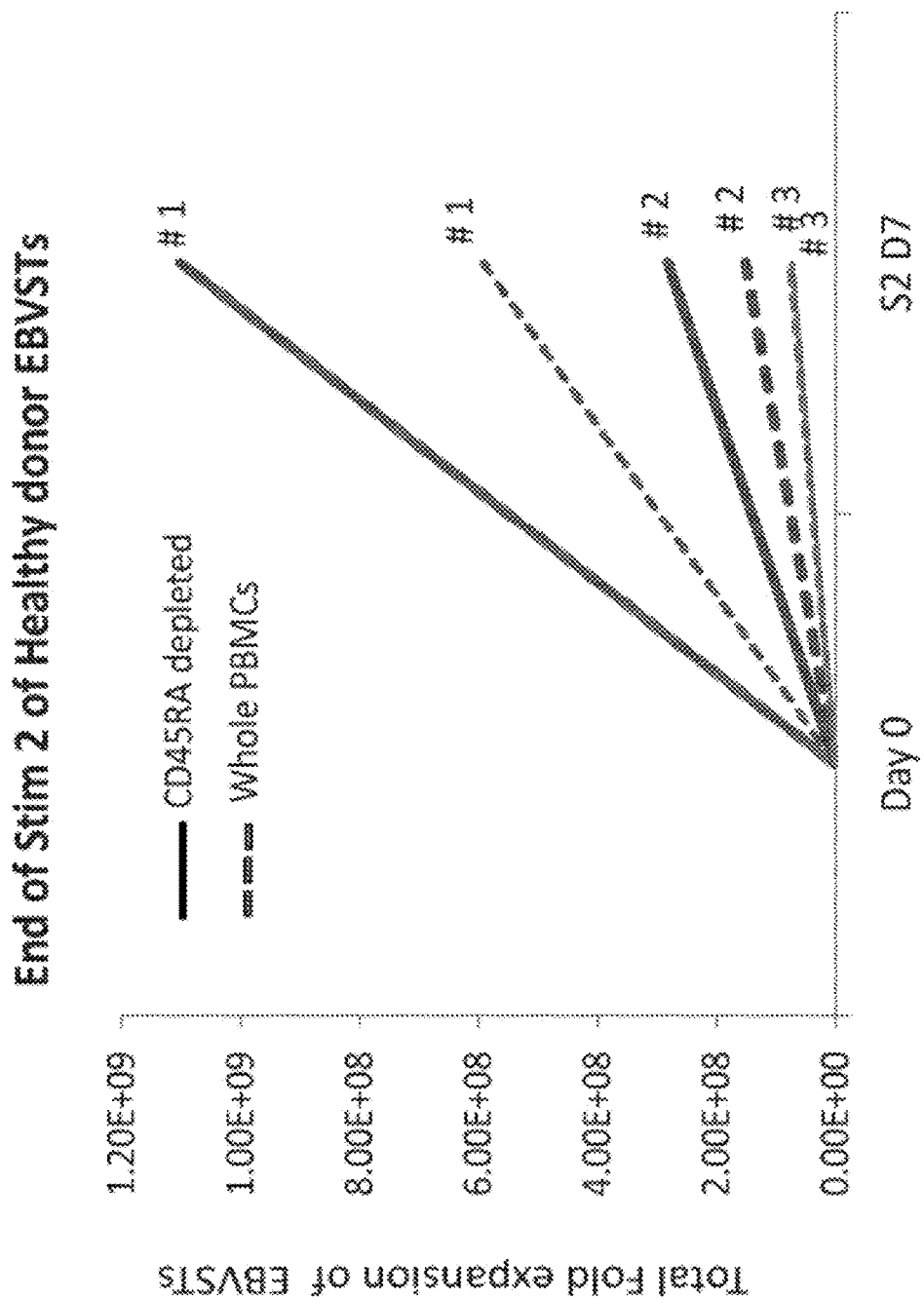
FIG. 56 is a graph that demonstrates that CD45RA depletion enhances the fold expansion of EBVSTs.
Figure 57:
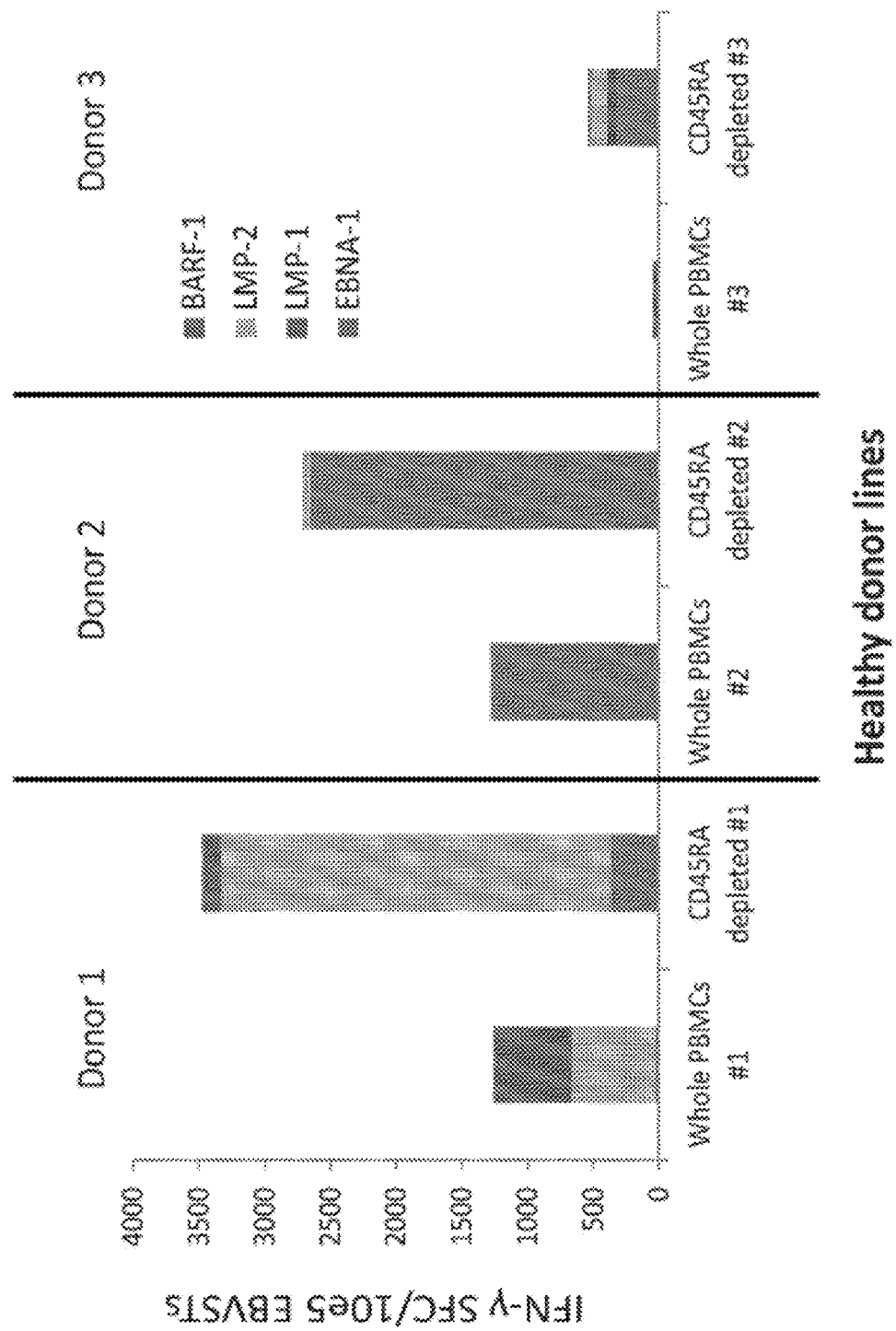
FIG. 57 is a bar chart showing that CD45RA depletion enhances antigen specificity of EBVSTs at the end of a second stimulation (at day 16).
Figure 58:
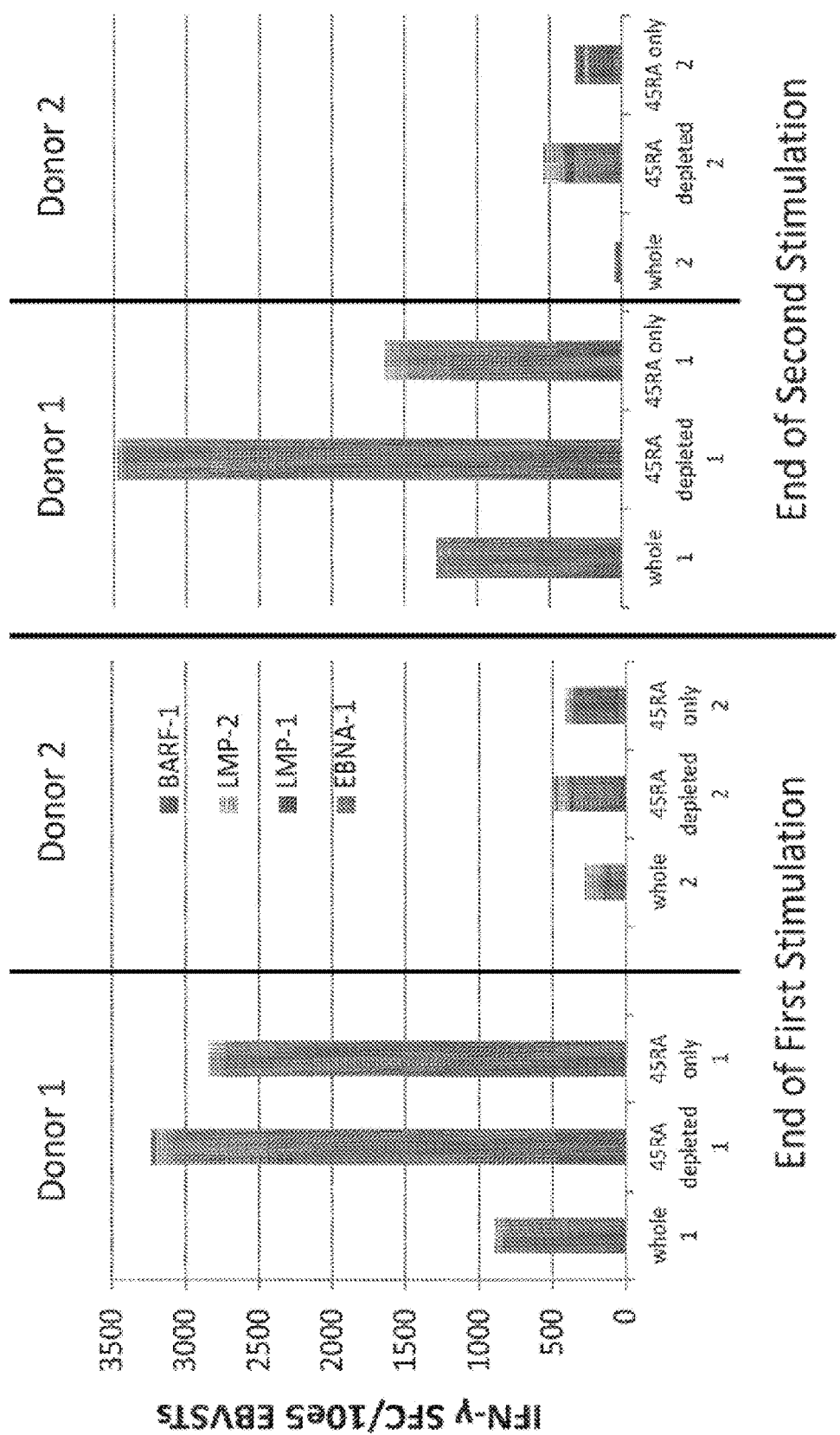
FIG. 58 is a bar chart which demonstrates that CD45RA depletion enhances antigen specificity of EBVSTs.
Figure 59:
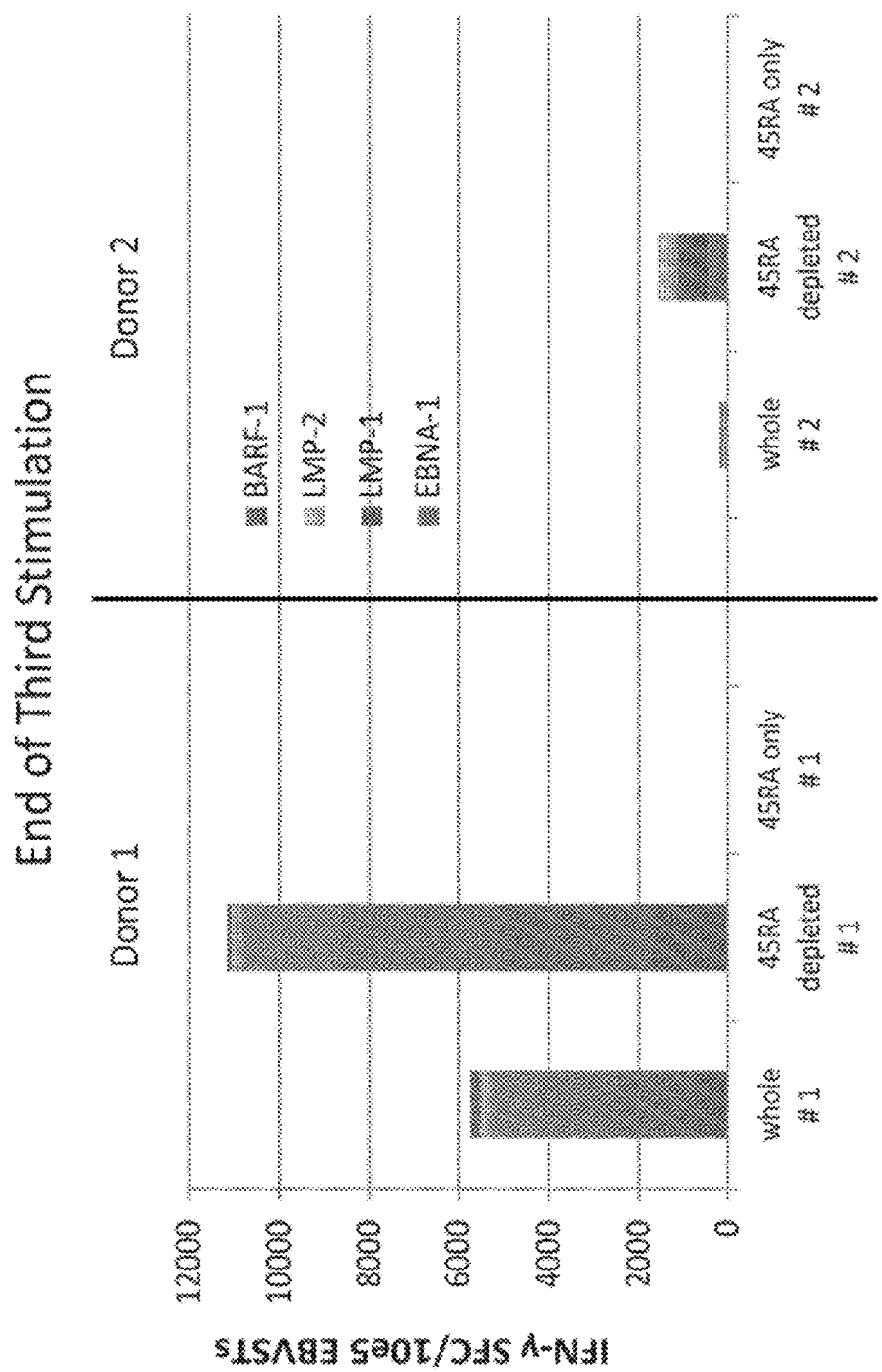
FIG. 59 is a bar chart which demonstrates increased antigen specificity of CD45RA depleted EBVSTs is sustained after a third stimulation.

The process used to generation of pepmix-activated EBV-specific T cells from CD45RA-depleted PBMCs is illustrated schematically in FIG. 53. As shown therein, whole PBMCs populations were depleted of CD45RA (or CD45RO for comparative purposes), and beginning day 0 or day 1 the first stimulation (S1) EBVpepmix was added to the depleted cells in the presence of IL-7 and IL-15 to produce EBVSTs. At the end of S1 and beginning of the second stimulation S2 (for example, between day 8 and day 10), the EBVSTs were exposed to sufficient amounts of EBV-Pepmix pulsed ATCs and sufficient amounts of costimulatory cells (such as K562cs cells) in the presence of IL-7 and IL-15, but in the absence of IL-2, to produce the desired pepmix-activated EBVSTs. FIG. 54 demonstrates the results that CD45RA depletion (CD45RA+ PBMC from healthy donors were depleted using Miltenyi® columns and GMP grade CD45RA-conjugated beads) was found to decrease the frequency of CD3-CD56+ NK cells in the expanded population, which was associated with increased proliferation of EBVSTs (FIG. 55). FIG. 56 illustrates the enhanced fold expansion of EBVSTs following CD45RA depletion from healthy donors at the end of a second stimulation step. In addition, the CD45RA depletion was found to enhance antigen specificity of EBVSTs at the end of a second stimulation (for example, day 16) (see FIGS. 57 and 58, both showing data for healthy donors). The increased antigen specificity of EBVSTs generated by expansion from CD45RA+ cell depleted PBMCs was found to be sustained after a third stimulation (FIG. 59).

Figure 60:
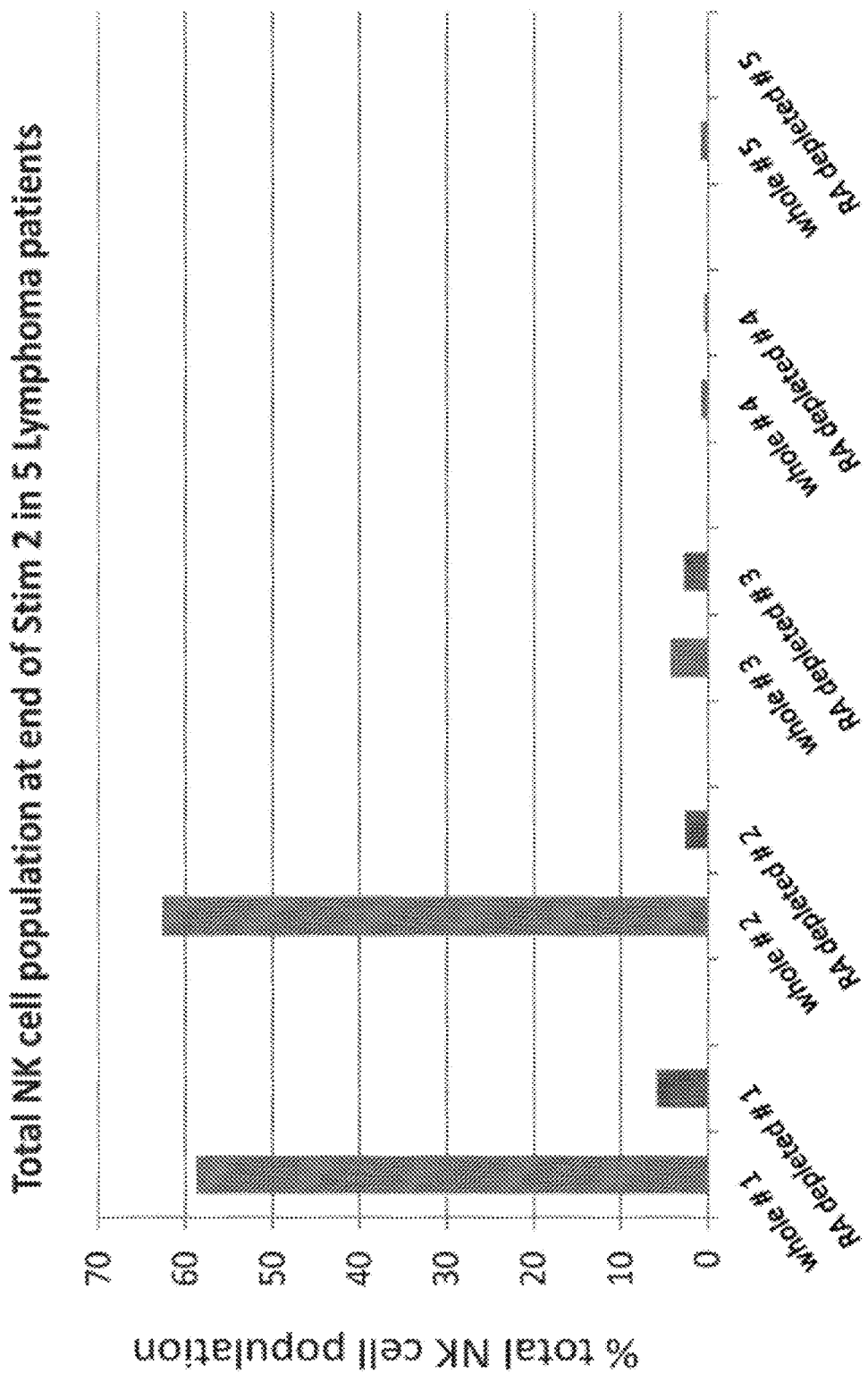
FIG. 60 is a bar chart which demonstrates that CD45RA depletion decreases NK cell population outgrowth in lymphoma patient EBVSTs.
Figure 61:
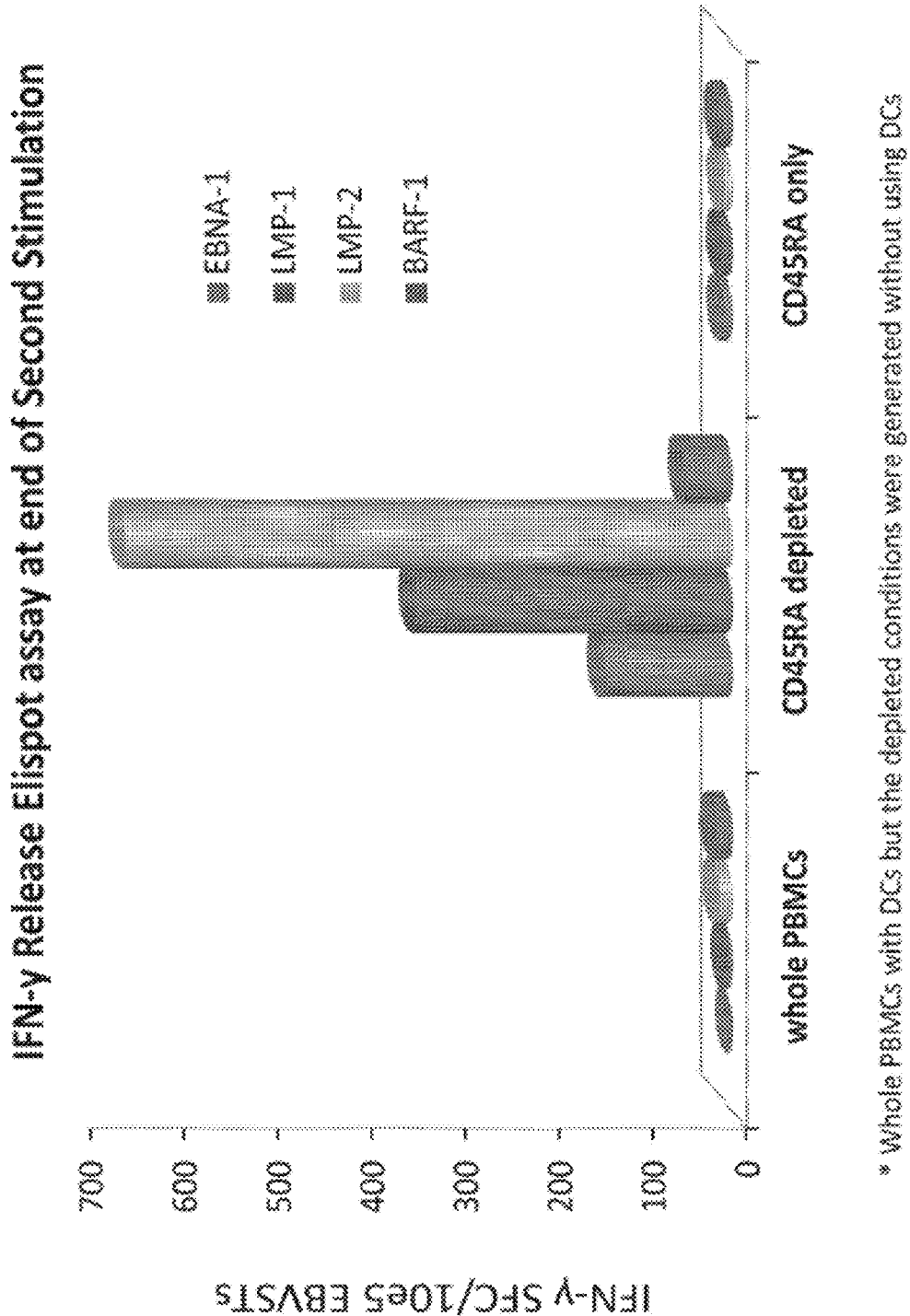
FIG. 61 is a bar chart showing that CD45RA depletion increases the frequency of antigen specific T-cells in lymphoma patient EBVSTs.
Figure 62:
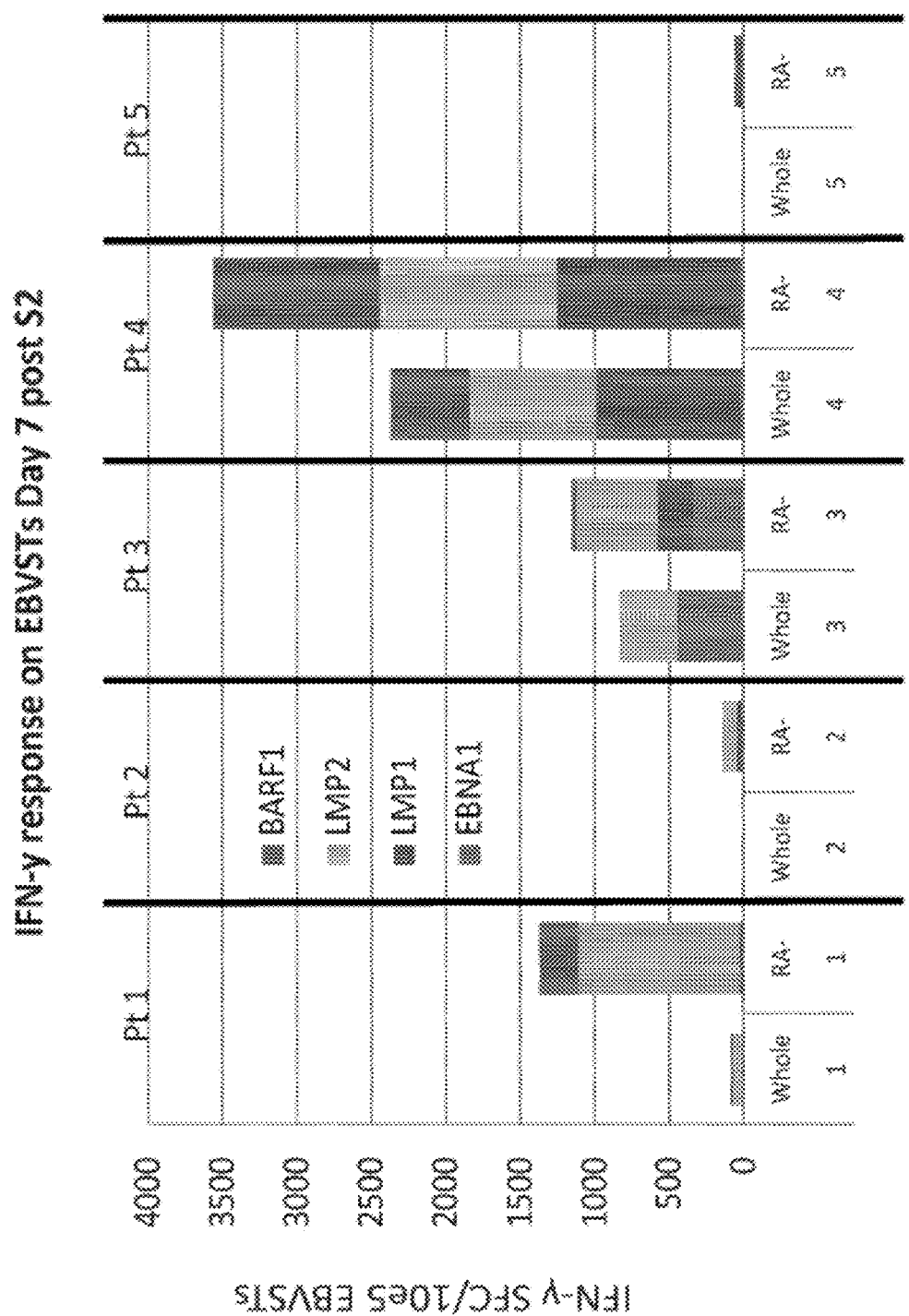
FIG. 62 is a bar chart demonstrating that CD45RA depletion increases antigen specificity in EBVSTs from lymphoma patients.
Figure 63:
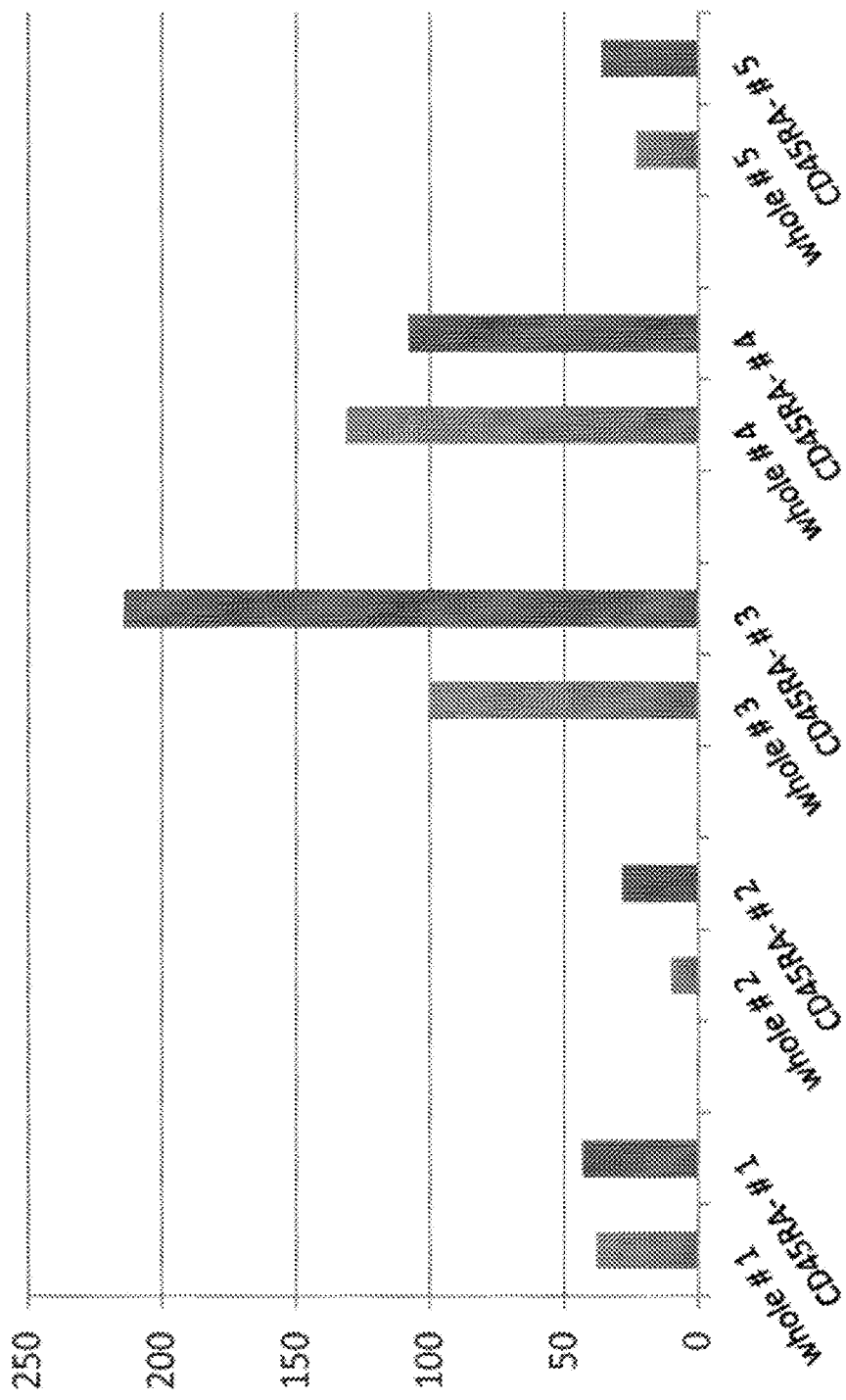
FIG. 63 is a bar chart showing the effect of CD45RA depletion on proliferation of lymphoma patients' EBVSTs.
Figure 64:
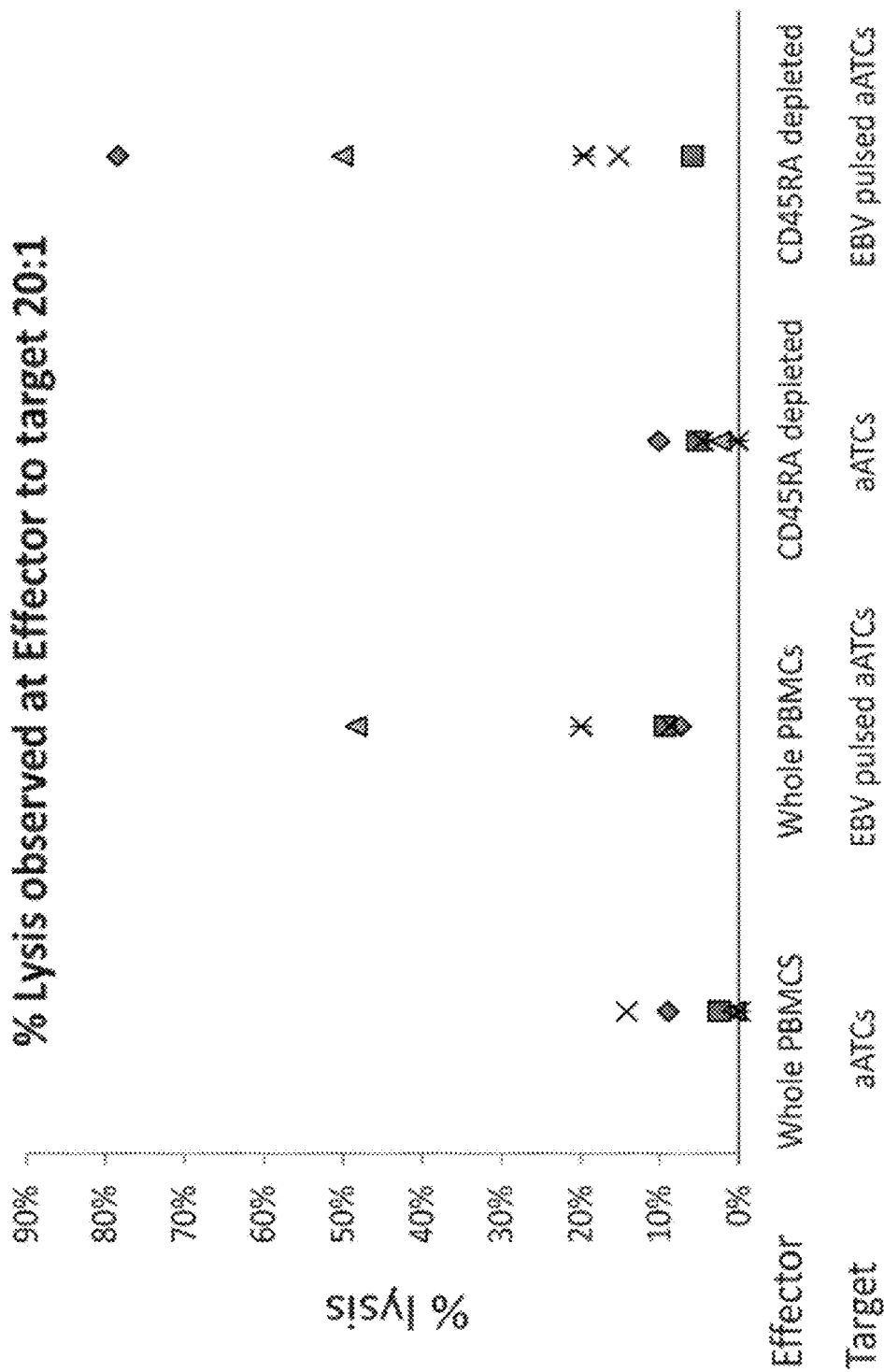
FIG. 64 is a chart which demonstrates that CD45RA-depletion enhances cytolytic activity against pepmix-pulsed autologous activated T-cells (aATCs).

The effects of CD45RA depletion was then characterized in virus-specific T cells obtained by expansion from PBMCs obtain from lymphoma patients, chosen either because their EBVSTs grown without depletion showed high frequencies of NK cells or because they failed to grow or show antigen-specificity. FIG. 60 shows the total NK cell population at the end of a second stimulation step in five lymphoma patients, demonstrating that CD45RA depletion decreased NK cell population outgrowth in lymphoma patient EBVSTs, and that this depletion increased the frequency of the antigen-specific T-cells (illustrated by IFN-y release ELIspot assay at the end of a second stimulation; FIG. 61). This experiment was performed in the absence of dendritic cells for the first stimulation (i.e. CD45RA+ cell depleted PBMCs were contacted directly with EBVPepmix). Similar to the results observed in methods using PBMCs from healthy donors, CD45RA depletion was found to increase antigen specificity in EBVSTs from lymphoma patients (FIG. 62). Proliferation of the lymphoma patients' EBVSTs is demonstrated in FIG. 63. Furthermore, CD45RA depletion enhanced cytolytic activity against pepmix-pulsed autologous activated T-cells (aATCs); percentage lysis was observed at effector to target ratio of 20:1 (FIG. 64).

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of generating or expanding a population of immune cells specific for human papillomavirus (HPV), comprising a step of stimulating a population of immune cells by culture in the presence of antigen-presenting cells (APCs) presenting a peptide of a HPV antigen, in the presence of human leucocyte antigen (HLA)-negative lymphoblastoid cell line cells (LCLs).

2. The method according to claim 1, wherein the HLA-negative LCLs are Epstein-Barr virus (EBV) replication defective.

3. The method according to claim 1, wherein the APCs are activated T cells (ATCs), dendritic cells (DCs) or B-Blasts (BBs).

4. The method according to claim 3, wherein the DCs are derived from CD14+ cells isolated from a population of peripheral blood mononuclear cells (PBMCs).

5. The method according to claim 3, wherein the DCs are derived from CD14+ cells by a method comprising culturing the CD14+ cells in the presence of IL-4 and GM-CSF to produce immature DCs (iDCs).

6. The method according to claim 5, wherein the method by which the DCs are derived from CD14+ cells further comprises culturing the iDCs to produce mature DCs by culture in the presence of: (a) GM-CSF, IL-4, IL-1β, IL-6, TNFα and CD40L; (b) GM-CSF, IL-4, MPLA and IFNγ; (c) GM-CSF, IFNα; or (d) GM-CSF, IL-4, AmpB and IFNγ.

7. The method according to claim 3, wherein the DCs are derived from immature DCs (iDCs) by a method comprising culture in the presence of: (a) GM-CSF, IL-4, IL-1β, IL-6, TNFα and CD40L; (b) GM-CSF, IL-4, MPLA and IFNγ; (c) GM-CSF, IFNα; or (d) GM-CSF, IL-4, AmpB and IFNγ.

8. The method according to claim 1, wherein the population of immune cells stimulated is depleted of CD45RA+ cells.

9. The method according to claim 1, wherein the stimulation is performed by culture in the presence of IL-7 and IL-15, optionally wherein the IL-15 is present in the culture at a final concentration greater than 15 ng/ml.

10. The method according to claim 1, wherein the stimulation is performed by culture in the presence of IL-4, IL-6, IL-7 and IL-15.

11. The method according to claim 1, wherein the APCs or DCs have been pulsed with one or more peptides corresponding to one or more HPV antigens.

12. The method according to claim 11, wherein the one or more HPV antigens are selected from E1, E2, E3, E4, E5, E6 and E7.

13. The method according to claim 11, wherein the one or more HPV antigens are antigens of HPV16, HPV18, HPV1, HPV2 and/or HPV3.

14. The method according to claim 1, wherein the population of immune cells stimulated is obtained from a prior stimulation of immune cells by culture in the presence of APCs presenting a peptide of a HPV antigen, optionally from within a population of PBMCs.

15. The method according to claim 1, wherein the method further comprises one or more further steps comprising stimulating a population of immune cells by culture in the presence of APCs presenting a peptide of a HPV antigen.

16. A method of treating or preventing a HPV-associated disease in a subject, the method comprising administering to a subject a therapeutically or prophylactically effective quantity of a population of immune cells specific for HPV generated or expanded by a method comprising a step of stimulating a population of immune cells by culture in the presence of antigen-presenting cells (APCs) presenting a peptide of a HPV antigen, in the presence of HLA-negative LCLs.

17. A method of treating or preventing a HPV-associated disease in a subject, the method comprising:
   (a) generating or expanding a population of immune cells specific for HPV by a method comprising a step of stimulating a population of immune cells by culture in the presence of antigen-presenting cells (APCs) presenting a peptide of a HPV antigen, in the presence of HLA-negative LCLs, and
   (b) administering a therapeutically or prophylactically effective quantity of the population of immune cells specific for HPV obtained at step (a) to a subject.

18. The method according to claim 17, wherein the HPV-associated disease is a cancer.

19. The method according to claim 18 wherein the cancer is selected from cervical cancer, anal cancer, vulvar cancer, vaginal cancer, penile cancer, oropharyngeal cancer, nasopharyngeal carcinoma, laryngeal papillomatosis, laryngeal cancer, head and neck cancer, or a dysplasia of any of site thereof.

20. The method according to claim 1, wherein the immune cells are peripheral blood mononuclear cells (PBMCs).

21. The method according to claim 16, wherein the immune cells are peripheral blood mononuclear cells (PBMCs).

22. The method according to claim 17, wherein the immune cells are peripheral blood mononuclear cells (PBMCs).

* * * * *